(12) United States Patent
Coats et al.

(10) Patent No.: US 8,685,990 B2
(45) Date of Patent: Apr. 1, 2014

(54) PYRIMIDINE COMPOUNDS AS DELTA OPIOID RECEPTOR MODULATORS

(71) Applicant: Janssen Pharmaceutica, NV, Beerse (BE)

(72) Inventors: Steven J. Coats, Mc Donough, GA (US); Haiyan Bian, Princeton, NJ (US); Peter J. Connolly, New Providence, NJ (US); Gilles Bignan, Bridgewater, NJ (US); Chaozhong Cai, North Wales, PA (US); Scott L. Dax, Landenberg, PA (US); Bart L. DeCorte, Southampton, PA (US); Shu-Chen Lin, Doylestown, PA (US); Li Liu, Germantown, MD (US); Mark J. Macielag, Gwynedd Valley, PA (US); Philip M. Pitis, North Wales, PA (US); Yue-Mei Zhang, Belle Mead, NJ (US); Bin Zhu, Newtown, PA (US); Wei He, Audubon, PA (US)

(73) Assignee: Janssen Pharmaceutica, NV (BE)

(*) Notice: Subject to any disclaimer, the term of this patent is extended or adjusted under 35 U.S.C. 154(b) by 0 days.

(21) Appl. No.: 13/950,952

(22) Filed: Jul. 25, 2013

(65) Prior Publication Data
US 2013/0310358 A1    Nov. 21, 2013

Related U.S. Application Data

(62) Division of application No. 12/913,966, filed on Oct. 28, 2013, now Pat. No. 8,513,271.

(60) Provisional application No. 61/256,405, filed on Oct. 30, 2009.

(51) Int. Cl.
  *A01N 43/54*    (2006.01)

(52) U.S. Cl.
  USPC .......................................... 514/269; 544/319

(58) Field of Classification Search
  USPC ................................................ 544/319, 269
  See application file for complete search history.

(56) References Cited

U.S. PATENT DOCUMENTS

| | | | |
|---|---|---|---|
| 6,465,467 B1 | 10/2002 | Nilsson et al. | |
| 6,787,539 B2 | 9/2004 | Stadler | |
| 7,015,227 B2 | 3/2006 | Darrow et al. | |
| 7,071,180 B2 | 7/2006 | Nilsson et al. | |
| 7,132,546 B2 | 11/2006 | Kato et al. | |
| 7,534,794 B2 | 5/2009 | Nilsson et al. | |
| 8,129,395 B2 | 3/2012 | Maynard et al. | |
| 2003/0199511 A1 | 10/2003 | Li et al. | |
| 2006/0058308 A1* | 3/2006 | Norman et al. | 514/249 |
| 2006/0142307 A1 | 6/2006 | Hellberg et al. | |

FOREIGN PATENT DOCUMENTS

| | | |
|---|---|---|
| CN | 1481238 A | 3/2004 |
| CN | 1628103 A | 6/2005 |
| CN | 1976918 A | 6/2007 |
| WO | WO 2007/769984 A2 | 12/2000 |
| WO | WO 02/42280 A2 | 5/2002 |
| WO | WO 03/051366 A3 | 6/2003 |
| WO | WO 04/000318 A2 | 12/2003 |
| WO | WO 2004/071426 A2 | 8/2004 |
| WO | WO 2005/110416 A2 | 11/2005 |
| WO | WO 2008/046226 A1 | 4/2008 |

OTHER PUBLICATIONS

A. Stefanachi et al., 51 Tetrahedron Letters, 1702-1705 (2010).*
C. Cai, et al., 96 Pharmacology, Biochemistry and Behavior, 130-135 (2010).*
Evans, C.J.(1993), "Diversity Among the Opioid Receptors", in Biological Basis of Substance Abuse, eds. Korenman SG and Barchas J.D. (Oxford University Press, New York), p. 31-48.
Gilbert, P. E. & Martin, W. R., "The Effects of Morphine- and Nalorphine-Like Drugs in the Nondependent, Morphine-Dependent and Cyclazocine-Dependent Chronic Spinal Dog", *J Pharmacol Exp Ther*, 1976, vol. 198, p. 66-82.
Gross, R.A., et al., "Dynorphin A and cAMP-dependent protein kinase independently regulate neuronal calcium currents", *Proc Nati Acad Sci USA*, 1990, vol. 87, p. 7025-29.
Lord, J. A., et al., "Endogenous opioid peptides: multiple agonists and receptors", *Nature*, 1977, vol. 267, p. 495-499.
Mansour, A., et al., "Anatomy of CNS Opioid Receptors", *Trends in Neurosci*, 1988, vol. 11, p. 308-14.
Pert, C. B. and Snyder, S. H., "Opiate Receptor: Demonstration in Nervous Tissue", Science (1973) 179:1011-1014.
Sharma, S. K., et al., "Dual regulation of adenylate cyclase accounts for narcotic dependence and tolerance" *Proc Natl Acad Sci USA*, 1975, vol. 72, p. 3092-96.
Wollemann, M., "Recent Developments in the Research of Opioid Receptor Subtype Molecular Characterization", *J Neurochem*, 1990, vol. 54, p. 1095-1101.
International Search Report and Written Opinion, PCT/US2010/054489, dated Jan. 24, 2011, 10 pages.

* cited by examiner

*Primary Examiner* — James O Wilson
*Assistant Examiner* — Alexander R Pagano

(57) ABSTRACT

Disclosed are compounds, compositions and methods for treating various diseases, syndromes, conditions and disorders, including pain. Such compounds are represented by Formula I as follows:

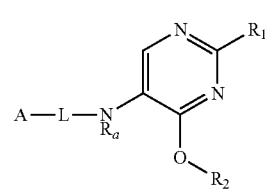

Formula I wherein $R_1$, $R_2$, $R_3$, and L, A, and $R_a$ are defined herein.

3 Claims, No Drawings

PYRIMIDINE COMPOUNDS AS DELTA OPIOID RECEPTOR MODULATORS

CROSS REFERENCE TO RELATED APPLICATIONS

The present application is a divisional application of U.S. application Ser. No. 12/913,966, filed on Oct. 28, 2010 which claims the benefit of the filing of U.S. Provisional Application No. 61/256,405, filed on Oct. 30, 2009. The complete disclosures of the aforementioned related patent applications are hereby incorporated herein by reference for all purposes.

FIELD OF THE INVENTION

The present invention is directed to novel opioid receptor modulators of Formula (I). The invention further relates to methods for preparing such compounds, pharmaceutical compositions containing them, and their use in the treatment of opioid modulated disorders.

BACKGROUND OF THE INVENTION

The term "opiate" has been used to designate pharmacologically active alkaloids derived from opium, e.g., morphine, codeine, and many semi-synthetic congeners of morphine. After the isolation of peptide compounds with morphine-like actions, the term opioid was introduced to refer generically to all drugs with morphine-like actions. Included among opioids are various peptides that exhibit morphine-like activity, such as endorphins, enkephalins and dynorphins. However, some sources use the term "opiate" in a generic sense, and in such contexts, opiate and opioid are interchangeable. Additionally, the term opioid has been used to refer to antagonists of morphine-like drugs as well as to characterize receptors or binding sites that combine with such agents.

Opioids are generally employed as analgesics, but they may have many other pharmacological effects as well. Morphine and related opioids produce certain of their major effects on the central nervous and digestive systems. The effects are diverse, including analgesia, drowsiness, mood changes, respiratory depression, dizziness, mental clouding, dysphoria, pruritus, increased pressure in the biliary tract, decreased gastrointestinal motility, nausea, vomiting, and alterations of the endocrine and autonomic nervous systems.

When therapeutic doses of morphine are given to patients with pain, they report that the pain is less intense, less discomforting, or entirely gone. In addition to experiencing relief of distress, some patients experience euphoria. However, when morphine in a selected pain-relieving dose is given to a pain-free individual, the experience is not always pleasant; nausea is common, and vomiting may also occur. Drowsiness, inability to concentrate, difficulty in mentation, apathy, lessened physical activity, reduced visual acuity, and lethargy may ensue.

Two distinct classes of opioid molecules can bind opioid receptors: the opioid peptides (e.g., the enkephalins, dynorphins, and endorphins) and the alkaloid opiates (e.g., morphine, etorphine, diprenorphine and naloxone). Subsequent to the initial demonstration of opiate binding sites (Pert, C. B. and Snyder, S. H., Science (1973) 179:1011-1014), the differential pharmacological and physiological effects of both opioid peptide analogues and alkaloid opiates served to delineate multiple opioid receptors. Accordingly, three molecularly and pharmacologically distinct opioid receptor types have been described: delta, kappa and mu. Furthermore, each type is believed to have sub-types (Wollemann, M., J Neurochem (1990) 54:1095-1101; Lord, J. A., et al., Nature (1977) 267:495-499).

All three of these opioid receptor types appear to share the same functional mechanisms at a cellular level. For example, the opioid receptors cause inhibition of adenylate cyclase, and inhibition of neurotransmitter release via both potassium channel activation and inhibition of $Ca^{2+}$ channels (Evans, C. J., In: Biological Basis of Substance Abuse, S. G. Korenman & J. D. Barchas, eds., Oxford University Press (in press); North, A. R., et al., Proc Natl Acad Sci USA (1990) 87:7025-29; Gross, R. A., et al., Proc Natl Acad Sci USA (1990) 87:7025-29; Sharma, S. K., et al., Proc Natl Acad Sci USA (1975) 72:3092-96). Although the functional mechanisms are the same, the behavioral manifestations of receptor-selective drugs differ greatly (Gilbert, P. E. & Martin, W. R., J Pharmacol Exp Ther (1976) 198:66-82). Such differences may be attributable in part to the anatomical location of the different receptors.

Delta receptors have a more discrete distribution within the mammalian CNS than either mu or kappa receptors, with high concentrations in the amygdaloid complex, striatum, substantia nigra, olfactory bulb, olfactory tubercles, hippocampal formation, and the cerebral cortex (Mansour, A., et al., Trends in Neurosci (1988) 11:308-14). The rat cerebellum is remarkably devoid of opioid receptors including delta opioid receptors.

There is a continuing need for new delta opioid receptor modulators as analgesics. There is a further need for delta opioid receptor selective agonists as analgesics having reduced side effects. There is also a need for delta opioid receptor antagonists as immunosuppressants, antiinflammatory agents, agents for the treatment of neurological and psychiatric conditions, agents for the treatment of urological and reproductive conditions, medicaments for drug and alcohol abuse, agents for treating gastritis and diarrhea, cardiovascular agents and agents for the treatment of respiratory diseases, having reduced side effects.

There is a continuing need for new opioid receptor modulators as analgesics. There is a further need for delta and mu opioid receptor agonists as analgesics having reduced side effects. There is a further need for mu opioid receptor agonists as analgesics having reduced side effects for the treatment of pain, immune function, esophageal reflux, and cough. There is also a need for delta opioid receptor agonists as analgesic agents, agents for the treatment of respiratory diseases, cardiovascular agents, agents for treating urological dysfunction, and agents for the treatment of neurological and psychiatric conditions. There is further need for dual delta opioid receptor/mu opioid receptor agonists.

SUMMARY OF THE INVENTION

The present invention is directed to a compound of Formula I

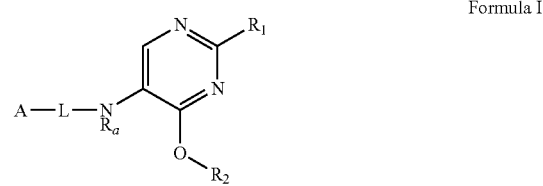

Formula I wherein

R₁ is selected from the group consisting of
i) phenyl optionally substituted with one to two substituents independently selected from the group consisting of $C_{1-4}$alkyl, $C_{2-4}$alkenyl, $C_{2-4}$alkynyl, $C_{1-4}$alkoxy, $C_{1-4}$alkylthio, hydroxy, chloro, and fluoro; in addition, phenyl is optionally substituted with a single amino, $C_{1-4}$alkylamino, di($C_{1-4}$alkyl)amino, di($C_{1-4}$alkyl)aminocarbonyl, $C_{1-4}$alkylaminocarbonyl, hydroxy($C_{1-4}$)alkyl, aminocarbonyl, $C_{1-4}$alkylcarbonylamino, $C_{1-4}$alkoxycarbonylamino, ureido, $C_{1-4}$alkylureido, di($C_{1-4}$alkyl)ureido, cyano, trifluoromethoxy, $C_{1-4}$alkylsulfonyl, nitro, trifluoromethyl, bromo, piperazin-1-yl optionally substituted with 4-$C_{1-4}$alkyl, morpholin-4-yl, phenyl, formamido, or pyridinyl substituent;

and wherein the phenyl and pyridinyl substituents of the R₁-phenyl are each optionally substituted with one substituent selected from the group consisting of $C_{1-4}$alkyl, $C_{1-4}$alkoxy, $C_{1-4}$alkylthio, fluoro, chloro, cyano, amino, and hydroxy;

ii) pyrimidinyl optionally substituted with one to two substituents independently selected from the group consisting of $C_{1-4}$alkyl, $C_{1-4}$alkoxy, $C_{1-4}$alkylthio, and hydroxy; in addition, pyrimidinyl is optionally substituted with a single amino, $C_{1-4}$alkylamino, di($C_{1-4}$alkyl)amino, di($C_{1-4}$alkyl)aminocarbonyl, $C_{1-4}$alkylaminocarbonyl, hydroxy($C_{1-4}$)alkyl, aminocarbonyl, $C_{1-4}$alkylcarbonylamino, $C_{1-4}$alkoxycarbonylamino, ureido, $C_{1-4}$alkylureido, di($C_{1-4}$alkyl)ureido, cyano, trifluoromethoxy, $C_{1-4}$alkylsulfonyl, nitro, trifluoromethyl, bromo, piperazin-1-yl optionally substituted with 4-$C_{1-4}$alkyl, morpholin-4-yl, formamido, pyrrol-1-yl, phenyl, pyridinyl, or piperidin-1-yl substituent;

and, wherein the phenyl and pyridinyl substituents of the R₁-pyrimidinyl are optionally independently substituted with one to two substituents selected from the group consisting of $C_{1-4}$alkyl, $C_{1-4}$alkoxy, $C_{1-4}$alkylthio, fluoro, chloro, cyano, amino, and hydroxy;

iii) pyridinyl optionally substituted with one to two substituents independently selected form the group consisting of $C_{1-4}$alkyl, $C_{1-4}$alkoxy, $C_{1-4}$alkylthio, hydroxy, fluoro, chloro, and cyano; in addition, pyridinyl is optionally substituted with a single hydroxymethyl, amino, $C_{1-4}$alkylamino, di($C_{1-4}$alkyl)amino, $C_{1-4}$alkylsulfonyl, aminocarbonyl, $C_{1-4}$alkylaminocarbonyl, di($C_{1-4}$alkyl)aminocarbonyl, $C_{1-4}$alkylcarbonylamino, $C_{1-4}$alkoxyaminocarbonyl, ureido, $C_{1-4}$alkylureido, di($C_{1-4}$alkyl)ureido, piperazin-1-yl, morpholin-4-yl, phenyl, or pyridinyl substituent;

and, wherein the phenyl and pyridinyl substituents of the R₁-pyridinyl are optionally independently substituted with one to two substituents selected from the group consisting of $C_{1-4}$alkyl, $C_{1-4}$alkoxy, $C_{1-4}$alkylthio, fluoro, chloro, cyano, amino, and hydroxy; and iv) a G-substituent selected from the group consisting of naphthyl, pyrazolyl, thienyl, benzothiazolyl, benzimidazolyl, quinolinyl, indolyl, thiazolyl, furanyl, dihydrobenzofuranyl, pyrazinyl, isoquinolinyl, quinoxalinyl, quinazolinyl, isoxazolyl, oxazolyl, pyrrolopyridinyl, benzo[1,3]dioxol-5-yl, benzo[1,2,5]oxadiazolyl, dibenzothiophenyl, 4H-[1,2,4]oxadiazol-5-on-yl, benzothiophenyl, indazolyl, and 2,3-dihydrobenzo[1,4]dioxinyl;

wherein G is optionally independently substituted with one to two substituents selected from the group consisting of $C_{1-4}$alkyl, $C_{1-4}$alkoxy, fluoro, chloro, bromo, cyano, $C_{1-4}$alkylcarbonyl, amino, $C_{1-4}$alkylamino, and di($C_{1-4}$alkyl)amino;

R₂ is
(i) phenyl optionally substituted with one to three substituents independently selected from the group consisting of $C_{1-4}$alkyl, $C_{1-4}$alkoxy, $C_{1-4}$alkylthio, fluoro, chloro, and hydroxy; in addition, phenyl of R₂ is optionally substituted with a single amino, $C_{1-4}$alkylamino, di($C_{1-4}$alkyl)amino, fluoromethyl, difluoromethyl, trifluoromethyl, fluoromethoxy, difluoromethoxy, trifluoromethoxy, formamidino, aminocarbonyl, $C_{1-4}$alkylaminocarbonyl, di($C_{1-4}$)alkylaminocarbonyl, $C_{1-4}$alkylcarbonylamino, 2,2,2-trifluoroethoxy, cyano, $C_{3-7}$cycloalkylcarbonylamino, hydroxy($C_{1-4}$)alkyl, $C_{1-4}$alkoxy($C_{1-4}$)alkyl, $C_{1-4}$alkoxy($C_{1-4}$)alkoxy, $C_{1-4}$alkylcarbonyloxy, $C_{1-4}$alkylsulfonylamino, $C_{1-4}$alkylsulfonyl, pyridinyl($C_{1-4}$)alkyl, benzyloxycarbonylamino, 4-methyl-piperazin-1-ylcarbonyl, pyrrolidin-1-ylcarbonyl, carboxy, piperidin-1-ylcarbonyl, morpholin-4-ylcarbonyl, $C_{3-7}$cycloalkyl, $C_{3-7}$cycloalkyl-($C_{1-3}$)alkyl, or $C_{3-7}$cycloalkyl-($C_{1-3}$)alkoxy substituent;

(ii) 1,2-dihydrobenzofuranyl, bound to O of Formula (I) at the benzo portion of the ring; and wherein the benzo portion of 1,2-dihydrobenzofuranyl is optionally independently substituted with one to two substituents selected from the group consisting of $C_{1-4}$alkyl, fluoro, chloro, bromo, cyano, $C_{1-4}$alkylcarbonyl, amino, $C_{1-4}$alkylamino, and di($C_{1-4}$alkylamino;

or (iii) heteroaryl selected from the group consisting of benzothiazolyl, benzooxazolyl, pyridinyl, pyrimidinyl, indazolyl, quinolinyl, quinazolinyl, benzimidazolyl, pyrazinyl, triazinyl, benzothiophenyl, benzofuranyl, and isoquinolinyl;

wherein heteroaryl of R₂ is optionally independently substituted with one to two substituents selected from the group consisting of $C_{1-4}$alkyl, fluoro, chloro, bromo, cyano, $C_{1-4}$alkylcarbonyl, amino, $C_{1-4}$alkylamino, and di($C_{1-4}$alkylamino;

A-L- is selected from the group consisting of $a_1$-$L_1$-; $a_2$-$L_2$-; $a_3$-$L_3$-; $a_4$-$L_4$-; and $a_5$-$L_5$-; wherein $L_1$ is absent or $C_{1-4}$alkyl;

$a_1$ is bound through a carbon atom to $L_1$ and is selected from the group consisting of i) pyrrolidinyl optionally substituted at carbon with $C_{1-4}$alkyl, amino, $C_{1-4}$alkylamino, di($C_{1-4}$alkyl)amino, aminomethyl, hydroxy, cyano, $C_{1-4}$alkoxy, $C_{1-4}$alkoxycarbonyl, or one to two fluoro substituents; and wherein pyrrolidinyl is optionally substituted at nitrogen with $C_{1-4}$alkyl, phenyl($C_{1-4}$)alkyl, $C_{1-4}$alkylcarbonyl, $C_{1-4}$alkoxycarbonyl, or phenyl($C_{1-4}$alkoxycarbonyl;

ii) piperidinyl optionally substituted with $C_{1-4}$alkyl, phenyl, amino, $C_{1-4}$alkylamino, di($C_{1-4}$alkyl)amino, aminomethyl, hydroxy, cyano, $C_{1-4}$alkoxy, $C_{1-4}$alkoxycarbonyl, phenyl($C_{1-4}$)alkyl, $C_{1-4}$alkylcarbonyl, or phenyl($C_{1-4}$)alkoxycarbonyl;

and iii) azetidinyl optionally substituted with 3-amino, 3-hydroxy, 3-$C_{1-4}$alkoxy, $C_{1-4}$alkyl, or aminomethyl;

provided that when $L_1$ is absent, $a_1$ is attached to N($R_a$) via a carbon atom other than that which is alpha to a nitrogen atom of $a_1$;

and provided that when $a_1$ is substituted with a substituent containing an oxygen or nitrogen radical as a point of attachment to $a_1$, the substitution is at a carbon atom other than that alpha to a nitrogen atom of $a_1$;

$L_2$ is $C_{1-4}$alkyl;

$a_2$ is bound through a carbon atom to $L_2$ and is selected from the group consisting of
i) piperazinyl optionally substituted at carbon with $C_{1-4}$alkyl, aminomethyl, cyano, or $C_{1-4}$alkoxycarbonyl; and wherein piperazinyl is optionally substituted at nitrogen with $C_{1-4}$alkyl, phenyl($C_{1-4}$)alkyl, $C_{1-4}$alkylcarbonyl, $C_{1-4}$alkoxycarbonyl, or phenyl($C_{1-4}$)alkoxycarbonyl; and
ii) morpholinyl optionally independently substituted with phenyl($C_{1-4}$)alkyl or one to two $C_{1-4}$alkyl substituents;

$L_3$ is methylene;

$a_3$ is imidazolyl optionally independently substituted with one to two $C_{1-4}$alkyl substituents;

$L_4$ is ($C_{2-6}$)alkyl; and when $L_4$ is $C_{3-6}$alkyl, $L_4$ is optionally substituted with chloro, hydroxy or $C_{1-4}$alkoxy; provided that the chloro, hydroxy, and $C_{1-4}$alkoxy substituents are not alpha to a nitrogen-bearing carbon atom;

$a_4$ is selected from the group consisting of amino and $C_{1-4}$alkylamino;

provided that $a_4$ is attached at a carbon atom other than that alpha to $N(R_a)$;

$L_5$ is absent or $C_{1-4}$alkyl;

$a_5$ is $C_{3-7}$cycloalkyl substituted with $R_B$; wherein $R_B$ is selected from the group consisting of amino, $C_{1-4}$alkylamino, di($C_{1-4}$alkyl)amino, aminomethyl, $C_{1-4}$alkylamino-methyl, and di($C_{1-4}$alkyl)amino-methyl;

provided that when $R_B$ contains a nitrogen radical as the point of attachment to $C_{3-7}$cycloalkyl, the attachment is at a carbon atom other than that alpha to $N(R_a)$;

or,

A-L- is taken with $R_a$ and the nitrogen atom to which they are both attached to form a nitrogen-bound heterocyclyl selected from the group consisting of
i) pyrrolidinyl wherein pyrrolidinyl is optionally substituted with $C_{1-4}$alkyl, amino, $C_{1-4}$alkylamino, di($C_{1-4}$alkyl)amino, aminomethyl, cyano, $C_{1-4}$alkoxy, $C_{1-4}$alkoxycarbonyl, or phenyl;
ii) piperazinyl optionally substituted with 4-$C_{1-4}$alkyl; and wherein piperazinyl is optionally independently substituted at carbon with one to two $C_{1-4}$alkyl substituents, 2-oxo, 3-oxo, trifluoromethyl, aminomethyl, or hydroxymethyl;
iii) piperidinyl optionally substituted with one to two $C_{1-4}$alkyl substituents, amino, $C_{1-4}$alkylamino, di($C_{1-4}$alkyl)amino, aminomethyl, hydroxy, cyano, $C_{1-4}$alkoxy, $C_{1-4}$alkoxycarbonyl, phenyl, phenyl($C_{1-4}$)alkyl, or one to two fluoro substituents;
and, wherein the phenyl and the phenyl portion of phenyl($C_{1-4}$)alkyl are optionally substituted with $C_{1-4}$alkyl, $C_{1-4}$alkoxy, $C_{1-4}$alkylthio, fluoro, chloro, cyano, amino, or hydroxy;
iv) azetidinyl optionally substituted with 3-amino or 3-aminomethyl;
v) [1,4]diazepan-1-yl optionally substituted with one to two $C_{1-4}$alkyl substituents;
and
vi) 3,6-diazoabicyclo[3.1.1]hept-3-yl optionally independently substituted with one to two $C_{1-4}$alkyl substituents;

$R_a$ is hydrogen or $C_{1-4}$alkylcarbonyl;

provided that a compound of Formula (I) is other than a compound selected from the group consisting of
a compound wherein $R_1$ is 4-fluoro-phenyl, $R_2$ is 4-methoxy-phenyl, A-L- is $a_1$-$L_1$, $a_1$ is (S)-pyrrolidin-2-yl, $L_1$ is methyl, $R_a$ is H, and X is O;
a compound wherein $R_1$ is pyrimidin-5-yl, $R_2$ is 4-methoxy-phenyl, A-L- is $a_2$-$L_2$, $a_2$ is (S)-morpholin-3-yl, $L_2$ is methyl, $R_a$ is H, and X is O; a compound wherein $R_1$ is 5-fluoro-pyridin-3-yl, $R_2$ is 4-(piperidin-1-ylcarbonyl)-phenyl, A-L- is $a_1$-$L_1$, $a_1$ is (S)-pyrrolidin-2-yl, $L_1$ is methyl, $R_a$ is H, and X is O;
a compound wherein $R_1$ is 5-fluoro-pyridin-3-yl, $R_2$ is 4-(4-methyl-piperazin-1-ylcarbonyl)-phenyl, A-L- is $a_1$-$L_1$, $a_1$ is (S)-pyrrolidin-2-yl, $L_1$ is methyl, $R_a$ is H, and X is O;
a compound wherein $R_1$ is 5-cyano-pyridin-3-yl, $R_2$ is 2-methyl-phenyl, A-L- is $a_1$-$L_1$, $a_1$ is (S)-pyrrolidin-2-yl, $L_1$ is methyl, $R_a$ is H, and X is O;
a compound wherein $R_1$ is pyridin-3-yl, $R_2$ is 4-methoxy-phenyl, A-L- is $a_5$-$L_5$, $a_5$ is cyclohexyl, $L_5$ is absent, $R_B$ is 2-amino, $R_a$ is H, and X is O;
and
a compound wherein $R_1$ is 5-fluoro-pyridin-3-yl, $R_2$ is 4-diethylaminocarbonyl-phenyl, A-L- is $a_1$-$L_1$, $a_1$ is (S)-pyrrolidin-2-yl, $L_1$ is methyl, $R_a$ is H, and X is O;
and enantiomers, diastereomers, solvates, and pharmaceutically acceptable salts thereof.

The present invention is also directed to a pharmaceutical composition comprising a pharmaceutically acceptable carrier and a compound of Formula (I) or a pharmaceutically acceptable salt form thereof.

Also provided are processes for making a pharmaceutical composition comprising mixing a compound of Formula (I) and a pharmaceutically acceptable carrier.

The present invention is further directed to methods for treating or ameliorating an opioid receptor-modulated disorder. In particular, the methods of the present invention are directed to treating or ameliorating a opioid receptor-modulated disorder including, but not limited to, inflammatory pain, centrally mediated pain, peripherally mediated pain, visceral pain, structural related pain, cancer/pain, soft tissue injury related pain, progressive disease related pain, neuropathic pain and acute pain from acute injury, acute pain from trauma, acute pain from surgery, chronic pain from headache, chronic pain from neuropathic conditions, chronic pain from post-stroke conditions and chronic pain from migraine.

The present invention also provides methods for producing the instant compounds and pharmaceutical compositions and medicaments thereof.

DETAILED DESCRIPTION OF THE INVENTION

As used herein, the following terms are intended to have the following meanings:

"$C_{a-b}$" (where a and b are integers) refers to a radical containing from a to b carbon atoms inclusive. For example, $C_{1-3}$ denotes a radical containing 1, 2 or 3 carbon atoms.

With reference to substituents, the term "independently" means that when more than one of such substituent is possible, such substituents may be the same or different from each other. Therefore, designated numbers of carbon atoms (e.g. $C_{1-8}$) shall refer independently to the number of carbon atoms in an alkyl or cycloalkyl moiety or to the alkyl portion of a larger substituent in which alkyl appears as its prefix root.

As used herein, unless otherwise noted, "alkyl" whether used alone or as part of a substituent group refers to straight and branched carbon chains having 1 to 8 carbon atoms or any number within this range. The term "alkoxy" refers to an —Oalkyl substituent group, wherein alkyl is as defined supra. Similarly, the terms "alkenyl" and "alkynyl" refer to straight and branched carbon chains having 2 to 8 carbon atoms or any number within this range, wherein an alkenyl chain has at least one double bond in the chain and an alkynyl chain has at least one triple bond in the chain. An alkyl and alkoxy chain may be substituted on a carbon atom. In substituent groups with multiple alkyl groups such as (C$_{1-6}$alkyl)$_2$amino- the C$_{1-6}$alkyl groups of the dialkylamino may be the same or different.

"Halogenated alkyl" refers to a saturated branched or straight chain alkyl radical derived by removal of 1 hydrogen atom from the parent alkane; the parent alkyl chain contains from 1 to 8 carbon atoms with 1 or more hydrogen atoms replaced with halogen atoms up to and including replacement of all hydrogen atoms with halogen. Preferred halogenated alkyl groups include trifluoromethyl substituted alkyls, difluoromethyl substituted alkyls, and perfluorinated alkyls; more preferred fluorinated alkyls include trifluoromethyl and difluoromethyl.

"Halogenated alkoxy" refers to a radical derived from a halogenated alkyl, radical attached to an oxygen atom with the oxygen atom having one open valence for attachment to a parent structure.

The term "cycloalkyl" refers to saturated or partially unsaturated, moncyclic or polycyclic hydrocarbon of from 3 to 20 carbon atom members (preferably from 3 to 14 carbon atom members). Examples of such groups include, and are not limited to, cyclopropyl, cyclobutyl, cyclopentyl, cyclohexyl, cycloheptyl or adamantyl. The term cycloalkyl includes a cycloalkyl ring fused to a benzene ring (benzo fused cycloalkyl), or a 5 or 6 membered heteroaryl ring (containing one of O, S or N and, optionally, one additional nitrogen) to form a heteroaryl fused cycloalkyl.

The term "heterocyclyl" refers to a nonaromatic monocyclic ring of 5 to 10 members in which 1 to 4 members are nitrogen or a nonaromatic monocyclic ring of 5 to 10 members in which zero, one or two members are nitrogen and up to two members are oxygen or sulfur; wherein, optionally, the ring contains zero, one or two unsaturated bonds. The term heterocyclyl includes a heterocyclyl ring fused to a benzene ring (benzo fused heterocyclyl), a 5 or 6 membered heteroaryl ring (containing one of O, S or N and, optionally, one additional nitrogen), a 5 to 7 membered cycloalkyl or cycloalkenyl ring, a 5 to 7 membered heterocyclyl ring (of the same definition as above but absent the option of a further fused ring) or fused with the carbon of attachment of a cycloalkyl, cycloalkenyl or heterocyclyl ring to form a spiro moiety. For instant compounds of the invention, the carbon atom ring members that form the heterocyclyl ring are fully saturated. Other compounds of the invention may have a partially saturated heterocyclyl ring. Additionally, heterocyclyl includes a heterocyclic ring bridged to form bicyclic rings. Preferred partially saturated heterocyclyl rings may have from one to two double bonds. Such compounds are not considered to be fully aromatic and are not referred to as heteroaryl compounds. Examples of heterocyclyl groups include, and are not limited to, pyrrolinyl (including 2H-pyrrole, 2-pyrrolinyl or 3-pyrrolinyl), pyrrolidinyl, 2-imidazolinyl, imidazolidinyl, 2-pyrazolinyl, pyrazolidinyl, piperidinyl, morpholinyl, thiomorpholinyl and piperazinyl.

The term "aryl" refers to an unsaturated, aromatic monocyclic ring of 6 carbon members or to an unsaturated, aromatic polycyclic ring of from 10 to 14 carbon members. Examples of such aryl rings include, and are not limited to, phenyl, naphthalenyl or anthracenyl. Preferred aryl groups for the practice of this invention are phenyl and naphthalenyl.

The term "heteroaryl" refers to an aromatic ring of 5 or 6 members wherein the ring consists of carbon atoms and has at least one heteroatom member. Suitable heteroatoms include nitrogen, oxygen or sulfur. In the case of 5 membered rings, the heteroaryl ring contains one member of nitrogen, oxygen or sulfur and, in addition, may contain up to three additional nitrogens. In the case of 6 membered rings, the heteroaryl ring may contain from one to three nitrogen atoms. For the case wherein the 6 membered ring has three nitrogens, at most two nitrogen atoms are adjacent. The term heteroaryl includes a heteroaryl ring fused to a benzene ring (benzofused heteroaryl), a 5 or 6 membered heteroaryl ring (containing one of O, S or N and, optionally, one additional nitrogen), a 5 to 7 membered cycloalkyl ring or a 5 to 7 membered heterocyclic ring (as defined supra but absent the option of a further fused ring). Examples of heteroaryl groups include, and are not limited to, furyl, thienyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl or pyrazinyl; fused heteroaryl groups include indolyl, isoindolyl, benzofuryl, benzothienyl, indazolyl, benzimidazolyl, benzothiazolyl, benzoxazolyl, benzisoxazolyl, benzothiadiazolyl, benzotriazolyl, quinoxalinyl, quinolinyl, isoquinolinyl or quinazolinyl.

The term "arylalkyl" means an alkyl group substituted with an aryl group (e.g., benzyl, phenethyl). Similarly, the term "arylalkoxy" indicates an alkoxy group substituted with an aryl group (e.g., benzyloxy).

The term "halogen" refers to fluorine, chlorine, bromine and iodine. Substituents that are substituted with multiple halogens are substituted in a manner that provides compounds, which are stable.

The term "oxo" whether used alone or as part of a substituent group refers to an O═ to either a carbon or a sulfur atom. For example, phthalimide and saccharin are examples of compounds with oxo substituents.

Whenever the term "alkyl" or "aryl" or either of their prefix roots appear in a name of a substituent (e.g., arylalkyl, alkylamino) it shall be interpreted as including those limitations given above for "alkyl" and "aryl." Designated numbers of carbon atoms (e.g., C$_1$-C$_6$) shall refer independently to the number of carbon atoms in an alkyl moiety or to the alkyl portion of a larger substituent in which alkyl appears as its prefix root. For alkyl, and alkoxy substituents the designated number of carbon atoms includes all of the independent member included in the range specified individually and all the combination of ranges within in the range specified. For example C$_{1-6}$ alkyl would include methyl, ethyl, propyl, butyl, pentyl and hexyl individually as well as sub-combinations thereof (e.g. C$_{1-2}$, C$_{1-3}$, C$_{1-4}$, C$_{1-5}$, C$_{2-6}$, C$_{3-6}$, C$_{4-6}$, C$_{5-6}$, C$_{2-5}$, etc.).

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

As used herein, the term "acyl" refers to alkylcarbonyl substituents.

As used herein, the term "a carbon atom which is alpha (α) to a nitrogen atom" is defined as a carbon atom that is adjacent to, and covalently bound to, a nitrogen atom, as illustrated hereinbelow.

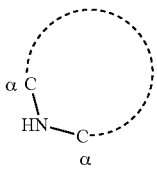

Throughout this disclosure, the terminal portion of the designated side chain is described first, followed by the adjacent functionality toward the point of attachment. Thus, for example, a "phenyl($C_{1-6}$)alkylaminocarbonyl($C_{1-6}$)alkyl" substituent refers to a group of the formula

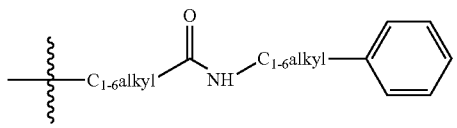

Unless otherwise noted, it is intended that the definition of any substituent or variable at a particular location in a molecule be independent of its definitions elsewhere in that molecule. It is understood that substituents and substitution patterns on the compounds of formula (I) can be selected by one of ordinary skill in the art to provide compounds that are chemically stable and that can be readily synthesized by techniques known in the art as well as those methods set forth herein.

For purposes of the present invention, the term "opioid receptor-modulated" is used to refer to the condition of being affected by the modulation of an opioid receptor, including but not limited to, the state of being mediated by the opioid receptor.

DETAILED DESCRIPTION OF THE INVENTION

Embodiments of the present invention include those compounds of Formula (I) wherein a) $R_1$ is selected from the group consisting of
  i) phenyl optionally substituted with one to two substituents independently selected from the group consisting of $C_{1-4}$alkyl, $C_{1-4}$alkoxy, hydroxy, chloro, and fluoro; in addition, phenyl is optionally substituted with a single amino, di($C_{1-4}$alkyl)amino, di($C_{1-4}$alkyl)aminocarbonyl, hydroxy($C_{1-4}$)alkyl, aminocarbonyl, $C_{1-4}$alkylcarbonylamino, cyano, trifluoromethoxy, $C_{1-4}$alkylsulfonyl, nitro, trifluoromethyl, or phenyl substituent;
  ii) pyrimidinyl optionally substituted with one to two substituents independently selected from the group consisting of $C_{1-4}$alkoxy, $C_{1-4}$alkylthio, and hydroxy; in addition, pyrimidinyl is optionally substituted with a single cyano, morpholin-4-yl, amino, di($C_{1-4}$alkyl)amino, or piperazin-1-yl optionally substituted with 4-$C_{1-4}$alkyl substituent;
  iii) pyridinyl optionally substituted with one to two substituents independently selected from the group consisting of $C_{1-4}$alkyl, $C_{1-4}$alkoxy, $C_{1-4}$alkylthio, hydroxy, fluoro, chloro, and cyano; in addition, pyridinyl is optionally substituted with a single hydroxymethyl, amino, aminocarbonyl, $C_{1-4}$alkylsulfonyl, or pyridinyl substituent;
    wherein the pyridinyl substituent of the $R_1$-pyridinyl is optionally independently substituted with one to two substituents selected from the group consisting of chloro and methyl;
  and
  iv) a G-substituent selected from the group consisting of naphthyl, pyrazolyl, thienyl, benzothiazolyl, quinolinyl, indolyl, thiazolyl, furanyl, dihydrobenzofuranyl, pyrazinyl, quinoxalinyl, oxazolyl, pyrrolopyridinyl, benzo[1,3]dioxol-5-yl, benzo[1,2,5]oxadiazolyl, dibenzothiophenyl, 4H-[1,2,4]oxadiazol-5-on-yl, and benzothiophenyl;
    wherein G is optionally independently substituted with one to two substituents selected from the group consisting of $C_{1-4}$alkyl, fluoro, and chloro;
b) $R_1$ is selected from the group consisting of
  i) phenyl optionally substituted with one to two substituents independently selected from the group consisting of $C_{1-4}$alkyl, $C_{1-4}$alkoxy, hydroxy, chloro, and fluoro; in addition, phenyl is optionally substituted with a single amino, di($C_{1-4}$alkyl)amino, di($C_{1-4}$alkyl)aminocarbonyl, hydroxy($C_{1-4}$)alkyl, aminocarbonyl, $C_{1-4}$alkylcarbonylamino, cyano, trifluoromethoxy, $C_{1-4}$alkylsulfonyl, nitro, trifluoromethyl, or phenyl substituent;
  ii) pyrimidinyl optionally substituted with one to two substituents independently selected from the group consisting of $C_{1-4}$alkoxy, $C_{1-4}$alkylthio, and hydroxy; in addition, pyrimidinyl is optionally substituted with a single cyano, morpholin-4-yl, amino, di($C_{1-4}$alkyl)amino, or piperazin-1-yl optionally substituted with 4-$C_{1-4}$alkyl substituent;
  iii) pyridinyl optionally substituted with one to two substituents independently selected from the group consisting of $C_{1-4}$alkyl, $C_{1-4}$alkoxy, $C_{1-4}$alkylthio, hydroxy, fluoro, chloro, and cyano; in addition, pyridinyl is optionally substituted with a single hydroxymethyl, amino, $C_{1-4}$alkylsulfonyl, or pyridinyl substituent;
    wherein the pyridinyl substituent of the $R_1$-pyridinyl is optionally independently substituted with one to two substituents selected from chloro and methyl;
  and
  iv) a G-substituent selected from the group consisting of naphthyl, pyrazolyl, thienyl, benzothiazolyl, quinolinyl, indolyl, thiazolyl, furanyl, dihydrobenzofuranyl, pyrazinyl, quinoxalinyl, oxazolyl, pyrrolopyridinyl, benzo[1,3]dioxol-5-yl, benzo[1,2,5]oxadiazolyl, dibenzothiophenyl, 4H-[1,2,4]oxadiazol-5-on-yl, and benzothiophenyl;
    wherein G is optionally independently substituted with one to two $C_{1-4}$alkyl substituents;
c) $R_1$ is selected from the group consisting of
  i) phenyl optionally substituted with one to two substituents independently selected from the group consisting of $C_{1-4}$alkyl, $C_{1-2}$alkoxy, hydroxy, chloro, and fluoro; in addition, phenyl is optionally substituted with a single amino, di($C_{1-4}$alkyl)amino, di($C_{1-4}$alkyl)aminocarbonyl, hydroxy($C_{1-4}$)alkyl, aminocarbonyl, $C_{1-4}$alkylcarbonylamino, cyano, trifluoromethoxy, $C_{1-4}$alkylsulfonyl, nitro, trifluoromethyl, or phenyl substituent;
  ii) pyrimidinyl optionally substituted with one to two substituents independently selected from the group consisting of $C_{1-4}$alkoxy and $C_{1-4}$alkylthio; in addition, pyrimidinyl is optionally substituted with a single cyano, morpholin-4-yl, di($C_{1-4}$alkyl)amino, or piperazin-1-yl optionally substituted with 4-$C_{1-4}$alkyl substituent;
  iii) pyridinyl optionally substituted with one to two substituents independently selected from the group consisting of $C_{1-4}$alkyl, $C_{1-4}$alkoxy, $C_{1-4}$alkylthio, hydroxy, fluoro, chloro, and cyano; in addition, pyridinyl is optionally substituted with a single hydroxymethyl, amino, $C_{1-4}$alkylsulfonyl, or pyridinyl substituent;

wherein the pyridinyl substituent of the $R_1$-pyridinyl is optionally independently substituted with one to two substituents selected from chloro and methyl;
and
iv) a G-substituent selected from the group consisting of naphthyl, pyrazolyl, thienyl, benzothiazolyl, quinolinyl, indolyl, thiazolyl, furanyl, dihydrobenzofuranyl, pyrazinyl, quinoxalinyl, pyrrolopyridinyl, benzo[1,3]dioxol-5-yl, benzo[1,2,5]oxadiazolyl, dibenzothiophenyl, 4H-[1,2,4]oxadiazol-5-on-yl, and benzothiophenyl;
wherein G is optionally substituted with one $C_{1-4}$alkyl substituent;

d) $R_1$ is selected from the group consisting of
i) phenyl optionally substituted with one to two substituents independently selected from the group consisting of $C_{1-4}$alkyl, $C_{1-2}$alkoxy, hydroxy, and fluoro; in addition, phenyl is optionally substituted with a single amino, di($C_{1-4}$alkyl)amino, di($C_{1-4}$alkyl)aminocarbonyl, hydroxy($C_{1-4}$)alkyl, aminocarbonyl, $C_{1-4}$alkylcarbonylamino, cyano, trifluoromethoxy, $C_{1-4}$alkylsulfonyl, nitro, or trifluoromethyl substituent;
ii) pyrimidinyl optionally substituted with one to two substituents independently selected from the group consisting of $C_{1-4}$alkoxy and $C_{1-4}$alkylthio; in addition, pyrimidinyl is optionally substituted with a single cyano, morpholin-4-yl, di($C_{1-4}$alkyl)amino, or piperazin-1-yl optionally substituted with 4-$C_{1-4}$alkyl substituent;
iii) pyridinyl optionally substituted with one to two substituents independently selected from the group consisting of $C_{1-4}$alkyl, $C_{1-4}$alkoxy, $C_{1-4}$alkylthio, hydroxy, fluoro, chloro, and cyano; in addition, pyridinyl is optionally substituted with a single hydroxymethyl or amino substituent;
and
iv) a G-substituent selected from the group consisting of pyrazolyl, thienyl, benzothiazolyl, quinolinyl, indolyl, thiazolyl, furanyl, dihydrobenzofuranyl, benzo[1,3]dioxol-5-yl, and benzo[1,2,5]oxadiazolyl;
wherein G is optionally independently substituted with one $C_{1-4}$alkyl substituent;

e) $R_1$ is selected from the group consisting of
i) phenyl optionally substituted with a substituent selected from the group consisting of $C_{1-2}$alkyl, $C_{1-2}$alkoxy, hydroxy, and fluoro; or, phenyl is optionally substituted with one substituent selected from the group consisting of amino, di($C_{1-4}$alkyl)amino, di($C_{1-4}$alkyl)aminocarbonyl, hydroxymethyl, aminocarbonyl, $C_{1-4}$alkylcarbonylamino, cyano, trifluoromethoxy, $C_{1-2}$alkylsulfonyl, nitro, and trifluoromethyl;
ii) pyrimidinyl optionally substituted with one to two substituents selected from the group consisting of $C_{1-4}$alkoxy and $C_{1-4}$alkylthio; or, pyrimidinyl is optionally substituted with one substituent selected from the group consisting of morpholin-4-yl, di($C_{1-4}$alkyl) amino, and piperazin-1-y optionally substituted with 4-methyl;
iii) pyridinyl optionally substituted with one to two substituents selected from the group consisting of $C_{1-4}$alkyl, $C_{1-4}$alkoxy, $C_{1-4}$alkylthio, hydroxy, fluoro, and chloro; or, pyridinyl optionally substituted with one substituent selected from the group consisting of cyano, hydroxymethyl, and amino;
and
iv) a G-substituent selected from the group consisting of pyrazolyl, thienyl, benzothiazolyl, quinolinyl, indolyl, thiazolyl, furanyl, dihydrobenzofuranyl, benzo[1,3]dioxol-5-yl, and benzo[1,2,5]oxadiazolyl;

wherein G is optionally independently substituted with one $C_{1-4}$alkyl substituent;

f) $R_2$ is
(i) phenyl optionally substituted with one to two substituents independently selected from the group consisting of $C_{1-4}$alkyl, $C_{1-4}$alkoxy, $C_{1-4}$alkylthio, one to two fluoro substituents, chloro, and hydroxy; in addition, phenyl is optionally substituted with a single amino, fluoromethyl, trifluoromethyl, fluoromethoxy, difluoromethoxy, trifluoromethoxy, formamidino, aminocarbonyl, di($C_{1-4}$)alkylaminocarbonyl, $C_{1-4}$alkylcarbonylamino, 2,2,2-trifluoroethoxy, cyano, $C_{3-7}$cycloalkylcarbonylamino, hydroxy($C_{1-4}$alkyl, $C_{1-4}$alkoxy($C_{1-4}$)alkyl, $C_{1-4}$alkoxy-($C_{1-4}$)alkoxy, $C_{1-4}$alkylcarbonyloxy, $C_{1-4}$alkylsulfonylamino, $C_{1-4}$alkylsulfonyl, pyridinyl ($C_{1-4}$)alkyl, benzyloxycarbonylamino, 4-methyl-piperazin-1-ylcarbonyl, pyrrolidin-1-ylcarbonyl, carboxy, piperidin-1-ylcarbonyl, or morpholin-4-ylcarbonyl substituent;
or
(ii) heteroaryl selected from the group consisting of benzothiazolyl, benzooxazolyl, and pyridinyl; wherein heteroaryl is optionally independently substituted with one to two $C_{1-4}$alkyl substituents;

g) $R_2$ is
(i) phenyl optionally substituted with one to two substituents independently selected from the group consisting of $C_{1-4}$alkyl, $C_{1-2}$alkoxy, $C_{1-4}$alkylthio, one to two fluoro substituents, chloro, and hydroxy; in addition, phenyl is optionally substituted with a single amino, fluoromethyl, trifluoromethyl, fluoromethoxy, difluoromethoxy, trifluoromethoxy, formamidino, aminocarbonyl, $C_{1-4}$alkylcarbonylamino, $C_{1-4}$alkylcarbonyloxy, 2,2,2-trifluoroethoxy, benzyloxycarbonylamino, hydroxy ($C_{1-4}$)alkyl, or $C_{1-4}$alkoxy($C_{1-4}$)alkyl substituent;
or, (ii) heteroaryl selected from the group consisting of benzothiazolyl and benzooxazolyl; wherein heteroaryl is optionally independently substituted with one to two $C_{1-4}$alkyl substituents;

h) $R_2$ is
(i) phenyl optionally substituted with one to two substituents selected from the group consisting of $C_{1-4}$alkyl, $C_{1-2}$alkoxy, $C_{1-4}$alkylthio, one to two fluoro substituents, chloro, and hydroxy; in addition, phenyl is optionally substituted with a single amino, fluoromethoxy, difluoromethoxy, trifluoromethoxy, formamidino, aminocarbonyl, $C_{1-4}$alkylcarbonylamino, $C_{1-4}$alkylcarbonyloxy, 2,2,2-trifluoroethoxy, or $C_{1-4}$alkoxy($C_{1-4}$) alkyl substituent;
or,
(ii) heteroaryl selected from the group consisting of benzothiazolyl and benzooxazolyl; wherein heteroaryl is optionally independently substituted with one to two $C_{1-4}$alkyl substituents;

i) $R_2$ is
(i) phenyl optionally substituted with one to two substituents selected from the group consisting of $C_{1-2}$alkyl, $C_{1-2}$alkoxy, $C_{1-2}$alkylthio, fluoro, 3-chloro, 4-chloro, and hydroxy; or phenyl is optionally substituted with one substituent selected from the group consisting of amino, difluoromethoxy, trifluoromethoxy, aminocarbonyl, $C_{1-4}$alkylcarbonylamino, $C_{1-4}$alkylcarbonyloxy, and 2,2,2-trifluoroethoxy;
or,
(ii) heteroaryl selected from the group consisting of benzothiazolyl and benzooxazolyl; wherein heteroaryl of $R_2$ is optionally independently substituted with one to two $C_{1-2}$alkyl substituents;

j) $R_2$ is
  (i) phenyl optionally substituted with one to two substituents selected from the group consisting of $C_{1-2}$alkyl, $C_{1-2}$alkoxy, $C_{1-2}$alkylthio, one to two fluoro substituents, 3-chloro, 4-chloro, and hydroxy; or, phenyl is optionally substituted with one substituent selected from the group consisting of amino, difluoromethoxy, trifluoromethoxy, aminocarbonyl, $C_{1-4}$alkylcarbonylamino, $C_{1-4}$alkylcarbonyloxy, and 2,2,2-trifluoroethoxy;
  or,
  (ii) $R_2$ is a heteroaryl selected from the group consisting of benzothiazolyl and benzooxazolyl; wherein heteroaryl of $R_2$ is optionally independently substituted with one to two $C_{1-2}$alkyl substituents;
k) A-L- is selected from the group consisting of $a_1$-$L_1$-; $a_2$-$L_2$-; $a_3$-$L_3$-; $a_4$-$L_4$-; and $a_5$-$L_5$-;
  $L_1$ is absent or $C_{1-4}$alkyl;
  $a_1$ is bound through a carbon atom to $L_1$ and is selected from the group consisting of
  i) pyrrolidinyl optionally substituted at carbon with amino, hydroxy, or one to two fluoro substituents;
  ii) piperidinyl;
  and
  iii) azetidinyl;
  provided that when $L_1$ is absent, $a_1$ is attached to $N(R_a)$ via a carbon atom other than that which is alpha to a nitrogen atom of $a_1$;
  and provided that when $a_1$ is substituted with a substituent containing an oxygen or nitrogen radical as a point of attachment to $a_1$, the substitution is at a carbon atom other than that alpha to a nitrogen atom of $a_1$;
  $L_2$ is $C_{1-4}$alkyl;
  $a_2$ is bound through a carbon atom to $L_2$ and $a_2$ is morpholinyl;
  $L_3$ is methylene;
  $a_3$ is imidazolyl optionally independently substituted with one to two $C_{1-4}$alkyl substituents;
  $L_4$ is $(C_{2-6})$alkyl;
  $a_4$ is selected from the group consisting of amino and $C_{1-4}$alkylamino;
  provided that $a_4$ is attached at a carbon atom of $(C_{2-6})$alkyl other than that alpha to $N(R_a)$;
  $L_5$ is absent or $C_{1-4}$alkyl;
  $a_5$ is $C_{3-7}$cycloalkyl substituted with $R_B$; wherein $R_B$ is amino;
  provided that when $R_B$ contains a nitrogen radical as a point of attachment to $C_{3-7}$cycloalkyl, the attachment is at a carbon atom other than that alpha to $N(R_a)$;
  or,
  A-L- is taken with $R_a$ and the nitrogen atom to which they are both attached to form a nitrogen-bound heterocyclyl selected from the group consisting of
  i) pyrrolidin-1-yl wherein pyrrolidin-1-yl is optionally substituted with $C_{1-4}$alkyl, amino, or aminomethyl;
  ii) piperazin-1-yl optionally substituted with 4-$C_{1-4}$alkyl; and wherein piperazin-1-yl is optionally independently substituted at carbon with one to two $C_{1-4}$alkyl substituents, 2-oxo, or 3-oxo;
  iii) piperidin-1-yl optionally substituted with one to two $C_{1-4}$alkyl substituents or amino;
  iv) azetidin-1-yl optionally substituted with 3-amino or 3-aminomethyl;
  v) [1,4]diazepan-1-yl; and
  vi) 3,6-diazabicyclo[3.1.1]hept-3-yl;

l) A-L- is selected from the group consisting of $a_1$-$L_1$-; $a_2$-$L_2$-; $a_3$-$L_3$-; $a_4$-$L_4$-; and $a_5$-$L_5$-;
  $L_1$ is absent or $C_{1-2}$alkyl;
  $a_1$ is bound through a carbon atom to $L_1$ and is selected from the group consisting of
  i) pyrrolidinyl optionally substituted at carbon with hydroxy or one to two fluoro substituents;
  ii) piperidin-3-yl;
  and
  iii) azetidinyl;
  provided that when $L_1$ is absent, $a_1$ is attached to $N(R_a)$ via a carbon atom other than that which is alpha to a nitrogen atom of $a_1$;
  and provided that when $a_1$ is substituted with a substituent containing an oxygen or nitrogen radical as a point of attachment to $a_1$, the substitution is at a carbon atom other than that alpha to a nitrogen atom of $a_1$;
  $L_2$ is $C_{1-2}$alkyl;
  $a_2$ is bound through a carbon atom to $L_2$ and $a_2$ is morpholinyl;
  $L_3$ is methylene;
  $a_3$ is imidazolyl optionally independently substituted with one to two $C_{1-2}$alkyl substituents;
  $L_4$ is $(C_{2-4})$alkyl;
  $a_4$ is selected from the group consisting of amino and $C_{1-4}$alkylamino;
  provided that $a_4$ is attached at a carbon atom other than that alpha to $N(R_a)$;
  $L_5$ is absent or $C_{1-4}$alkyl;
  $a_5$ is $C_{4-6}$cycloalkyl substituted with $R_B$; wherein $R_B$ is amino;
  provided that when $R_B$ contains a nitrogen radical as the point of attachment to $C_{5-6}$cycloalkyl, the attachment is at a carbon atom other than that alpha to $N(R_a)$;
  or,
  A-L- is taken with $R_a$ and the nitrogen atom to which they are both attached to form a nitrogen-bound heterocyclyl selected from the group consisting of
  i) pyrrolidin-1-yl optionally substituted with amino or aminomethyl;
  ii) piperazin-1-yl optionally substituted with 4-$C_{1-4}$alkyl; and wherein piperazin-1-yl is optionally independently substituted at carbon with one to two $C_{1-4}$alkyl substituents;
  iii) piperidin-1-yl optionally substituted with amino;
  iv) azetidin-1-yl optionally substituted with 3-aminomethyl; and
  v) [1,4]diazepan-1-yl;
  provided that the position of a substituent containing a nitrogen radical as a point of attachment to the nitrogen-bound heterocyclyl is at a carbon atom other than that alpha to a heterocyclyl nitrogen atom;
m) A-L- is selected from the group consisting of $a_1$-$L_1$-; $a_2$-$L_2$-; $a_3$-$L_3$-, $a_4$-$L_4$-; and $a_5$-$L_5$-;
  $L_1$ is absent or $C_{1-2}$alkyl;
  $a_1$ is bound through a carbon atom to $L_1$ and is selected from the group consisting of
  i) pyrrolidinyl optionally substituted at carbon with hydroxy or one to two fluoro substituents;
  and
  ii) piperidin-3-yl
  provided that when $L_1$ is absent, $a_1$ is attached to $N(R_a)$ via a carbon atom other than that which is alpha to a nitrogen atom of $a_1$;
  and provided that when $a_1$ is substituted with a substituent containing an oxygen or nitrogen radical as a point of attachment to $a_1$, the substitution is at a carbon atom other than that alpha to a nitrogen atom of $a_1$;

$L_2$ is $C_{1-2}$alkyl;

$a_2$ is bound through a carbon atom to $L_2$ and $a_2$ is morpholinyl;

$L_3$ is methylene;

$a_3$ is imidazolyl optionally substituted with one to two methyl substituents;

$L_4$ is $(C_{2-3})$alkyl;

$a_4$ is amino, provided that $a_4$ is attached at a carbon atom other than that alpha to $N(R_a)$; $L_2$ is methylene;

$L_5$ is absent or $C_{1-2}$alkyl;

$a_5$ is $C_{4-6}$cycloalkyl substituted with $R_B$; wherein $R_B$ is amino;

provided that when $R_B$ contains a nitrogen radical as the point of attachment to $C_{5-6}$cycloalkyl, the attachment is at a carbon atom other than that alpha to $N(R_a)$;

or,

A-L- is taken with $R_a$ and the nitrogen atom to which they are both attached to form a nitrogen-bound heterocyclyl selected from the group consisting of
i) pyrrolidin-1-yl optionally substituted with amino;
ii) piperazin-1-yl optionally independently substituted at carbon with one to two $C_{1-4}$alkyl substituents;
iii) piperidin-1-yl optionally substituted with amino; and
iv) [1,4]diazepan-1-yl;

provided that the position of a substituent containing an nitrogen radical as a point of attachment to the nitrogen-bound heterocyclyl is at a carbon atom other than that alpha to the heterocyclyl nitrogen atom n) A-L- is selected from the group consisting of $a_1$-$L_1$-; $a_2$-$L_2$-; $a_3$-$L_3$-; $a_4$-$L_4$-; and $a_5$-$L_5$-;

$L_1$ is absent or $C_{1-2}$alkyl;

$a_1$ is bound through a carbon atom to $L_1$ and is selected from the group consisting of
i) pyrrolidinyl optionally substituted at carbon with hydroxy or one to two fluoro substituents; and
ii) piperidin-3-yl provided that when $L_1$ is absent, $a_1$ is attached to $N(R_a)$ via a carbon atom other than that which is alpha to a nitrogen atom of $a_1$;

and provided that when $a_1$ is substituted with a substituent containing an oxygen or nitrogen radical as a point of attachment to $a_1$, the substitution is at a carbon atom other than that alpha to a nitrogen atom of $a_1$;

$L_2$ is methylene;

$a_2$ is bound through a carbon atom to $L_2$ and $a_2$ is morpholinyl;

$L_3$ is methylene;

$a_3$ is imidazolyl optionally substituted with one to two methyl substituents;

$L_4$ is $(C_{2-3})$alkyl;

$a_4$ is amino, provided that $a_4$ is attached at a carbon atom other than that alpha to $N(R_a)$;

$L_5$ is absent or $C_{1-2}$alkyl;

$a_5$ is $C_{4-6}$cycloalkyl substituted with $R_B$; wherein $R_B$ is amino;

provided that when $R_B$ contains a nitrogen radical as the point of attachment to $C_{5-6}$cycloalkyl, the attachment is at a carbon atom other than that alpha to $N(R_a)$;

or,

A-L- is taken with $R_a$ and the nitrogen atom to which they are both attached to form a nitrogen-bound heterocyclyl selected from the group consisting of
i) pyrrolidin-1-yl optionally substituted with amino;
ii) piperazin-1-yl optionally independently substituted at carbon with one to two $C_{1-2}$alkyl substituents;
iii) piperidin-1-yl optionally substituted with amino; and
iv) [1,4]diazepan-1-yl;

provided that the position of a substituent containing an nitrogen radical as a point of attachment to the nitrogen-bound heterocyclyl is at a carbon atom other than that alpha to the heterocyclyl nitrogen atom;

o) $R_a$ is hydrogen;

provided that a compound of Formula (I) is other than a compound selected from the group consisting of
a compound wherein $R_1$ is 4-fluoro-phenyl, $R_2$ is 4-methoxy-phenyl, A-L- is $a_1$-$L_1$, $a_1$ is (S)-pyrrolidin-2-yl, $L_1$ is methyl, $R_a$ is H, and X is O;
a compound wherein $R_1$ is pyrimidin-5-yl, $R_2$ is 4-methoxy-phenyl, A-L- is $a_2$-$L_2$, $a_2$ is (S)-morpholin-3-yl, $L_2$ is methyl, $R_a$ is H, and X is O; a compound wherein $R_1$ is 5-fluoro-pyridin-3-yl, $R_2$ is 4-(piperidin-1-ylcarbonyl)-phenyl, A-L- is $a_1$-$L_1$, $a_1$ is (S)-pyrrolidin-2-yl, $L_1$ is methyl, $R_a$ is H, and X is O;
a compound wherein $R_1$ is 5-fluoro-pyridin-3-yl, $R_2$ is 4-(4-methyl-piperazin-1-ylcarbonyl)-phenyl, A-L- is $a_1$-$L_1$, $a_1$ is (S)-pyrrolidin-2-yl, $L_1$ is methyl, $R_a$ is H, and X is O;
a compound wherein $R_1$ is 5-cyano-pyridin-3-yl, $R_2$ is 2-methyl-phenyl, A-L- is $a_1$-$L_1$, $a_1$ is (S)-pyrrolidin-2-yl, $L_1$ is methyl, $R_a$ is H, and X is O;
a compound wherein $R_1$ is pyridin-3-yl, $R_2$ is 4-methoxy-phenyl, A-L- is $a_5$-$L_5$, $a_5$ is cyclohexyl, $L_5$ is absent, $R_B$ is 2-amino, $R_a$ is H, and X is O;
and
a compound wherein $R_1$ is 5-fluoro-pyridin-3-yl, $R_2$ is 4-diethylaminocarbonyl-phenyl, A-L- is $a_1$-$L_1$, $a_1$ is (S)-pyrrolidin-2-yl, $L_1$ is methyl, $R_a$ is H, and X is O;

and any combination of embodiments a) through o) above, provided that it is understood that combinations in which different embodiments of the same substituent would be combined are excluded;

and enantiomers, diastereomers, solvates, and pharmaceutically acceptable salts thereof.

A further embodiment of the present invention is directed to a compound of Formula (I)

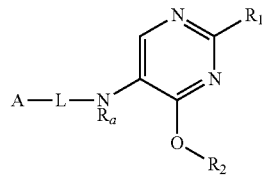

Formula I wherein $R_1$ is selected from the group consisting of
i) phenyl optionally substituted with one to two substituents independently selected from the group consisting of $C_{1-4}$alkyl, $C_{1-4}$alkoxy, hydroxy, chloro, and fluoro; in addition, phenyl is optionally substituted with a single amino, di($C_{1-4}$alkyl)amino, di($C_{1-4}$alkyl)aminocarbonyl, hydroxy($C_{1-4}$alkyl, aminocarbonyl, $C_{1-4}$alkylcarbonylamino, cyano, trifluoromethoxy, $C_{1-4}$alkylsulfonyl, nitro, trifluoromethyl, or phenyl substituent;
ii) pyrimidinyl optionally substituted with one to two substituents independently selected from the group consisting of $C_{1-4}$alkoxy, $C_{1-4}$alkylthio, and hydroxy; in addition, pyrimidinyl is optionally substituted with a single cyano, morpholin-4-yl, amino, di($C_{1-4}$alkyl)amino, or piperazin-1-yl optionally substituted with 4-$C_{1-4}$alkyl substituent;

iii) pyridinyl optionally substituted with one to two substituents independently selected from the group consisting of $C_{1-4}$alkyl, $C_{1-4}$alkoxy, $C_{1-4}$alkylthio, hydroxy, fluoro, chloro, and cyano; in addition, pyridinyl is optionally substituted with a single hydroxymethyl, amino, aminocarbonyl, $C_{1-4}$alkylsulfonyl, or pyridinyl substituent;

wherein the pyridinyl substituent of the $R_1$-pyridinyl is optionally independently substituted with one to two substituents selected from chloro and methyl;

and iv) a G-substituent selected from the group consisting of naphthyl, pyrazolyl, thienyl, benzothiazolyl, quinolinyl, indolyl, thiazolyl, furanyl, dihydrobenzofuranyl, pyrazinyl, quinoxalinyl, oxazolyl, pyrrolopyridinyl, benzo[1,3]dioxol-5-yl, benzo[1,2,5]oxadiazolyl, dibenzothiophenyl, 4H-[1,2,4]oxadiazol-5-on-yl, and benzothiophenyl;

wherein G is optionally independently substituted with one to two substituents selected from the group consisting of $C_{1-4}$alkyl, fluoro, and chloro;

$R_2$ is (i) phenyl optionally substituted with one to two substituents independently selected from the group consisting of $C_{1-4}$alkyl, $C_{1-4}$alkoxy, $C_{1-4}$alkylthio, one to two fluoro substituents, chloro, and hydroxy; in addition, phenyl is optionally substituted with amino, fluoromethyl, trifluoromethyl, fluoromethoxy, difluoromethoxy, trifluoromethoxy, formamidino, aminocarbonyl, di($C_{1-4}$)alkylaminocarbonyl, $C_{1-4}$alkylcarbonylamino, 2,2,2-trifluoroethoxy, cyano, $C_{3-7}$cycloalkylcarbonylamino, hydroxy($C_{1-4}$alkyl), $C_{1-4}$alkoxy($C_{1-4}$)alkyl, $C_{1-4}$alkoxy-($C_{1-4}$)alkoxy, $C_{1-4}$alkylcarbonyloxy, $C_{1-4}$alkylsulfonylamino, $C_{1-4}$alkylsulfonyl, pyridinyl($C_{1-4}$alkyl, benzyloxycarbonylamino, 4-methyl-piperazin-1-ylcarbonyl, pyrrolidin-1-ylcarbonyl, carboxy, piperidin-1-ylcarbonyl, or morpholin-4-ylcarbonyl;

or, (ii) heteroaryl selected from the group consisting of benzothiazolyl, benzooxazolyl, and pyridinyl; wherein heteroaryl is optionally independently substituted with one to two $C_{1-4}$alkyl substituents;

A-L- is selected from the group consisting of $a_1$-$L_1$-; $a_2$-$L_2$-; $a_3$-$L_3$-; $a_4$-$L_4$-; and $a_5$-$L_5$-;

$L_1$ is absent or $C_{1-4}$alkyl;

$a_1$ is bound through a carbon atom to $L_1$ and is selected from the group consisting of i) pyrrolidinyl optionally substituted at carbon with amino, hydroxy, or one to two fluoro substituents;

ii) piperidinyl;

and iii) azetidinyl;

provided that when $L_1$ is absent, $a_1$ is attached to $N(R_a)$ via a carbon atom other than that which is alpha to a nitrogen atom of $a_1$;

and provided that when $a_1$ is substituted with a substituent containing an oxygen or nitrogen radical as a point of attachment to $a_1$, the substitution is at a carbon atom other than that alpha to a nitrogen atom of $a_1$;

$L_2$ is $C_{1-4}$alkyl;

$a_2$ is bound through a carbon atom to $L_2$ and $a_2$ is morpholinyl;

$L_3$ is methylene;

$a_3$ is imidazolyl optionally independently substituted with one to two $C_{1-4}$alkyl substituents;

$L_4$ is ($C_{2-6}$)alkyl;

$a_4$ is selected from the group consisting of amino and $C_{1-4}$alkylamino;

provided that $a_4$ is attached at a carbon atom of ($C_{2-6}$)alkyl other than that alpha to $N(R_a)$;

$L_5$ is absent or $C_{1-4}$alkyl;

$a_5$ is $C_{3-7}$cycloalkyl substituted with $R_B$; wherein $R_B$ is amino;

provided that when $R_B$ contains a nitrogen radical as a point of attachment to $C_{3-7}$cycloalkyl, the attachment is at a carbon atom other than that alpha to $N(R_a)$;

or,

A-L- is taken with $R_a$ and the nitrogen atom to which they are both attached to form a nitrogen-bound heterocyclyl selected from the group consisting of i) pyrrolidin-1-yl wherein pyrrolidin-1-yl is optionally substituted with $C_{1-4}$alkyl, amino, or aminomethyl;

ii) piperazin-1-yl optionally substituted with 4-$C_{1-4}$alkyl; and wherein piperazin-1-yl is optionally independently substituted at carbon with one to two $C_{1-4}$alkyl substituents, 2-oxo, or 3-oxo;

iii) piperidin-1-yl optionally substituted with one to two $C_{1-4}$alkyl substituents or amino;

iv) azetidin-1-yl optionally substituted with 3-amino or 3-aminomethyl;

v) [1,4]diazepan-1-yl; and vi) 3,6-diazoabicyclo[3.1.1]hept-3-yl;

$R_a$ is hydrogen or methylcarbonyl;

provided that a compound of Formula (I) is other than a compound selected from the group consisting of a compound wherein $R_1$ is 4-fluoro-phenyl, $R_2$ is 4-methoxyphenyl, A-L- is $a_1$-$L_1$, $a_1$ is (S)-pyrrolidin-2-yl, $L_1$ is methyl, $R_a$ is H, and X is O;

a compound wherein $R_1$ is pyrimidin-5-yl, $R_2$ is 4-methoxyphenyl, A-L- is $a_2$-$L_2$, $a_2$ is (S)-morpholin-3-yl, $L_2$ is methyl, $R_a$ is H, and X is O;

a compound wherein $R_1$ is 5-fluoro-pyridin-3-yl, $R_2$ is 4-(piperidin-1-ylcarbonyl)-phenyl, A-L- is $a_1$-$L_1$, $a_1$ is (S)-pyrrolidin-2-yl, $L_1$ is methyl, $R_a$ is H, and X is O;

a compound wherein $R_1$ is 5-fluoro-pyridin-3-yl, $R_2$ is 4-(4-methyl-piperazin-1-ylcarbonyl)-phenyl, A-L- is $a_1$-$L_1$, $a_1$ is (S)-pyrrolidin-2-yl, $L_1$ is methyl, $R_a$ is H, and X is O;

a compound wherein $R_1$ is 5-cyano-pyridin-3-yl, $R_2$ is 2-methyl-phenyl, A-L- is $a_1$-$L_1$, $a_1$ is (S)-pyrrolidin-2-yl, $L_1$ is methyl, $R_a$ is H, and X is O;

and a compound wherein $R_1$ is pyridin-3-yl, $R_2$ is 4-methoxyphenyl, A-L- is $a_5$-$L_5$, $a_5$ is cyclohexyl, $L_5$ is absent, $R_B$ is 2-amino, $R_a$ is H, and X is O;

and enantiomers, diastereomers, solvates, and pharmaceutically acceptable salts thereof.

A further embodiment of the present invention is directed to a compound of Formula (I)

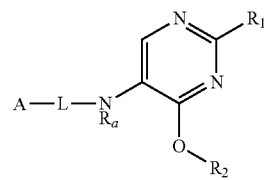

Formula I wherein $R_1$ is selected from the group consisting of i) phenyl optionally substituted with one to two substituents independently selected from the group consisting of $C_{1-4}$alkyl, $C_{1-4}$alkoxy, hydroxy, chloro, and fluoro; in addition, phenyl is optionally substituted with a single amino, di($C_{1-4}$alkyl)amino, di($C_{1-4}$alkyl)aminocarbonyl, hydroxy ($C_{1-4}$alkyl, aminocarbonyl, $C_{1-4}$alkylcarbonylamino, cyano, trifluoromethoxy, $C_{1-4}$alkylsulfonyl, nitro, trifluoromethyl, or phenyl substituent;

ii) pyrimidinyl optionally substituted with one to two substituents independently selected from the group consisting of $C_{1-4}$alkoxy, $C_{1-4}$alkylthio, and hydroxy; in addition, pyrimidinyl is optionally substituted with a single cyano, morpholin-4-yl, amino, di($C_{1-4}$alkyl)amino, or piperazin-1-yl optionally substituted with 4-$C_{1-4}$alkyl substituent;

iii) pyridinyl optionally substituted with one to two substituents independently selected from the group consisting of $C_{1-4}$alkyl, $C_{1-4}$alkoxy, $C_{1-4}$alkylthio, hydroxy, fluoro, chloro, and cyano; in addition, pyridinyl is optionally substituted with a single hydroxymethyl, amino, $C_{1-4}$alkylsulfonyl, or pyridinyl substituent;
wherein the pyridinyl substituent of the $R_1$-pyridinyl is optionally independently substituted with one to two substituents selected from chloro and methyl;
and iv) a G-substituent selected from the group consisting of naphthyl, pyrazolyl, thienyl, benzothiazolyl, quinolinyl, indolyl, thiazolyl, furanyl, dihydrobenzofuranyl, pyrazinyl, quinoxalinyl, oxazolyl, pyrrolopyridinyl, benzo[1,3]dioxol-5-yl, benzo[1,2,5]oxadiazolyl, dibenzothiophenyl, 4H-[1,2,4]oxadiazol-5-on-yl, and benzothiophenyl; wherein G is optionally independently substituted with one to two $C_{1-4}$alkyl substituents;

$R_2$ is (i) phenyl optionally substituted with one to two substituents independently selected from the group consisting of $C_{1-4}$alkyl, $C_{1-2}$alkoxy, $C_{1-4}$alkylthio, one to two fluoro substituents, chloro, and hydroxy; in addition, phenyl is optionally substituted with amino, fluoromethyl, trifluoromethyl, fluoromethoxy, difluoromethoxy, trifluoromethoxy, formamidino, aminocarbonyl, $C_{1-4}$alkylcarbonylamino, $C_{1-4}$alkylcarbonyloxy, 2,2,2-trifluoroethoxy, benzyloxycarbonylamino, hydroxy($C_{1-4}$)alkyl, or $C_{1-4}$alkoxy($C_{1-4}$)alkyl;

or, (ii) heteroaryl selected from the group consisting of benzothiazolyl and benzooxazolyl; wherein heteroaryl is optionally independently substituted with one to two $C_{1-4}$alkyl substituents;

A-L- is selected from the group consisting of $a_1$-$L_1$-; $a_2$-$L_2$-; $a_3$-$L_3$-; $a_4$-$L_4$-; and $a_5$-$L_5$-;

$L_1$ is absent or $C_{1-2}$alkyl;

$a_1$ is bound through a carbon atom to $L_1$ and is selected from the group consisting of i) pyrrolidinyl optionally substituted at carbon with hydroxy or one to two fluoro substituents;

ii) piperidin-3-yl;

and iii) azetidinyl;

provided that when $L_1$ is absent, $a_1$ is attached to N($R_a$) via a carbon atom other than that which is alpha to a nitrogen atom of $a_1$;

and provided that when $a_1$ is substituted with a substituent containing an oxygen or nitrogen radical as a point of attachment to $a_1$, the substitution is at a carbon atom other than that alpha to a nitrogen atom of $a_1$;

$L_2$ is $C_{1-2}$alkyl;

$a_2$ is bound through a carbon atom to $L_2$ and $a_2$ is morpholinyl;

$L_3$ is methylene;

$a_3$ is imidazolyl optionally independently substituted with one to two $C_{1-2}$alkyl substituents;

$L_4$ is ($C_{2-4}$)alkyl;

$a_4$ is selected from the group consisting of amino and $C_{1-4}$alkylamino;

provided that $a_4$ is attached at a carbon atom other than that alpha to N($R_a$);

$L_5$ is absent or $C_{1-4}$alkyl;

$a_5$ is $C_{4-6}$cycloalkyl substituted with $R_B$; wherein $R_B$ is amino;

provided that when $R_B$ contains a nitrogen radical as the point of attachment to $C_{5-6}$cycloalkyl, the attachment is at a carbon atom other than that alpha to N($R_a$);

or,

A-L- is taken with $R_a$ and the nitrogen atom to which they are both attached to form a nitrogen-bound heterocyclyl selected from the group consisting of i) pyrrolidin-1-yl optionally substituted with amino or aminomethyl;

ii) piperazin-1-yl optionally substituted with 4-$C_{1-4}$alkyl; and wherein piperazin-1-yl is optionally independently substituted at carbon with one to two $C_{1-4}$alkyl substituents;

iii) piperidin-1-yl optionally substituted with amino;

iv) azetidin-1-yl optionally substituted with 3-aminomethyl; and v) [1,4]diazepan-1-yl;

provided that the position of a substituent containing a nitrogen radical as a point of attachment to the nitrogen-bound heterocyclyl is at a carbon atom other than that alpha to a heterocyclyl nitrogen atom;

$R_a$ is hydrogen;

provided that a compound of Formula (I) is other than a compound selected from the group consisting of a compound wherein $R_1$ is 4-fluoro-phenyl, $R_2$ is 4-methoxyphenyl, A-L- is $a_1$-$L_1$, $a_1$ is (S)-pyrrolidin-2-yl, $L_1$ is methyl, $R_a$ is H, and X is O;

a compound wherein $R_1$ is pyrimidin-5-yl, $R_2$ is 4-methoxyphenyl, A-L- is $a_2$-$L_2$, $a_2$ is (S)-morpholin-3-yl, $L_2$ is methyl, $R_a$ is H, and X is O;

a compound wherein $R_1$ is 5-cyano-pyridin-3-yl, $R_2$ is 2-methyl-phenyl, A-L- is $a_1$-$L_1$, $a_1$ is (S)-pyrrolidin-2-yl, $L_1$ is methyl, $R_a$ is H, and X is O;

and a compound wherein $R_1$ is pyridin-3-yl, $R_2$ is 4-methoxyphenyl, A-L- is $a_5$-$L_5$, $a_5$ is cyclohexyl, $L_5$ is absent, $R_B$ is 2-amino, $R_a$ is H, and X is O.

and enantiomers, diastereomers, solvates, and pharmaceutically acceptable salts thereof.

A further embodiment of the present invention is directed to a compound of Formula (I)

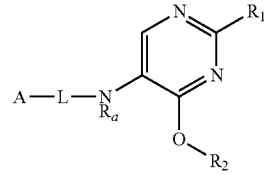

Formula I wherein $R_1$ is selected from the group consisting of i) phenyl optionally substituted with one to two substituents independently selected from the group consisting of $C_{1-4}$alkyl, $C_{1-2}$alkoxy, hydroxy, chloro, and fluoro; in addition, phenyl is optionally substituted with a single amino, di($C_{1-4}$alkyl)amino, di($C_{1-4}$alkyl)aminocarbonyl, hydroxy($C_{1-4}$alkyl, aminocarbonyl, $C_{1-4}$alkylcarbonylamino, cyano, trifluoromethoxy, $C_{1-4}$alkylsulfonyl, nitro, trifluoromethyl, or phenyl substituent;

ii) pyrimidinyl optionally substituted with one to two substituents independently selected from the group consisting of $C_{1-4}$alkoxy and $C_{1-4}$alkylthio; in addition, pyrimidinyl is optionally substituted with a single cyano, morpholin-4-yl, di($C_{1-4}$alkyl)amino, or piperazin-1-yl optionally substituted with 4-$C_{1-4}$alkyl substituent;

iii) pyridinyl optionally substituted with one to two substituents independently selected from the group consisting of $C_{1-4}$alkyl, $C_{1-4}$alkoxy, $C_{1-4}$alkylthio, hydroxy, fluoro, chloro, and cyano; in addition, pyridinyl is optionally substituted with a single hydroxymethyl, amino, $C_{1-4}$alkylsulfonyl, or pyridinyl substituent;
  wherein the pyridinyl substituent of the $R_1$-pyridinyl is optionally independently substituted with one to two substituents selected from chloro and methyl;
and
iv) a G-substituent selected from the group consisting of naphthyl, pyrazolyl, thienyl, benzothiazolyl, quinolinyl, indolyl, thiazolyl, furanyl, dihydrobenzofuranyl, pyrazinyl, quinoxalinyl, pyrrolopyridinyl, benzo[1,3]dioxol-5-yl, benzo[1,2,5]oxadiazolyl, dibenzothiophenyl, 4H-[1,2,4]oxadiazol-5-on-yl, and benzothiophenyl;
wherein G is optionally substituted with one $C_{1-4}$alkyl substituent;

$R_2$ is
(i) phenyl optionally substituted with one to two substituents selected from the group consisting of $C_{1-4}$alkyl, $C_{1-2}$alkoxy, $C_{1-4}$alkylthio, one to two fluoro substituents, chloro, and hydroxy; in addition, phenyl is optionally substituted with a single amino, fluoromethoxy, difluoromethoxy, trifluoromethoxy, formamidino, aminocarbonyl, $C_{1-4}$alkylcarbonylamino, $C_{1-4}$alkylcarbonyloxy, 2,2,2-trifluoroethoxy, or $C_{1-4}$alkoxy($C_{1-4}$)alkyl substituent;
or,
(ii) heteroaryl selected from the group consisting of benzothiazolyl and benzooxazolyl; wherein heteroaryl is optionally independently substituted with one to two $C_{1-4}$alkyl substituents;

A-L- is selected from the group consisting of $a_1$-$L_1$-; $a_2$-$L_2$-; $a_3$-$L_3$-; $a_4$-$L_4$-; and $a_5$-$L_5$-;
$L_1$ is absent or $C_{1-2}$alkyl;
$a_1$ is bound through a carbon atom to $L_1$ and is
i) pyrrolidinyl optionally substituted at carbon with hydroxy or one to two fluoro substituents;
ii) piperidin-3-yl
or
iii) azetidinyl;
provided that when $L_1$ is absent, $a_1$ is attached to N($R_a$) via a carbon atom other than that which is alpha to a nitrogen atom of $a_1$;
and provided that when $a_1$ is substituted with a substituent containing a nitrogen radical as a point of attachment to $a_1$, the substitution is at a carbon atom other than that alpha to a nitrogen atom of $a_1$;
$L_2$ is methylene;
$a_2$ is bound through a carbon atom to $L_2$ and $a_2$ is morpholinyl;
$L_3$ is methylene;
$a_3$ is imidazolyl optionally independently substituted with one to two $C_{1-4}$alkyl substituents;
$L_4$ is ($C_{2-3}$)alkyl;
$a_4$ is amino, provided that $a_4$ is attached at a carbon atom other than that alpha to N($R_a$);
$L_5$ is absent or $C_{1-2}$alkyl;
$a_5$ is $C_{4-6}$cycloalkyl substituted with $R_B$; wherein $R_B$ is amino;
provided that when $R_B$ contains a nitrogen radical as the point of attachment to $C_{5-6}$cycloalkyl, the attachment is at a carbon atom other than that alpha to N($R_a$);

or,
A-L- is taken with $R_a$ and the nitrogen atom to which they are both attached to form a nitrogen-bound heterocyclyl selected from the group consisting of
i) pyrrolidin-1-yl optionally substituted with amino or aminomethyl;
ii) piperazin-1-yl optionally independently substituted at carbon with one to two $C_{1-4}$alkyl substituents;
iii) piperidin-1-yl optionally substituted with amino;
iv) azetidin-1-yl optionally substituted with 3-aminomethyl; and
v) [1,4]diazepan-1-yl;
provided that the position of a substituent containing an nitrogen radical as a point of attachment to the nitrogen-bound heterocyclyl is at a carbon atom other than that alpha to the heterocyclyl nitrogen atom;
$R_a$ is hydrogen;
provided that a compound of Formula (I) is other than a compound selected from the group consisting of
a compound wherein $R_1$ is 4-fluoro-phenyl, $R_2$ is 4-methoxy-phenyl, A-L- is $a_1$-$L_1$, $a_1$ is (S)-pyrrolidin-2-yl, $L_1$ is methyl, $R_a$ is H, and X is O;
a compound wherein $R_1$ is pyrimidin-5-yl, $R_2$ is 4-methoxy-phenyl, A-L- is $a_2$-$L_2$, $a_2$ is (S)-morpholin-3-yl, $L_2$ is methyl, $R_a$ is H, and X is O;
a compound wherein $R_1$ is 5-cyano-pyridin-3-yl, $R_2$ is 2-methyl-phenyl, A-L- is $a_1$-$L_1$, $a_1$ is (S)-pyrrolidin-2-yl, $L_1$ is methyl, $R_a$ is H, and X is O;
and
a compound wherein $R_1$ is pyridin-3-yl, $R_2$ is 4-methoxy-phenyl, A-L- is $a_5$-$L_5$, $a_5$ is cyclohexyl, $L_5$ is absent, $R_B$ is 2-amino, $R_a$ is H, and X is O;
and enantiomers, diastereomers, solvates, and pharmaceutically acceptable salts thereof.

A further embodiment of the present invention is directed to a compound of Formula (I)

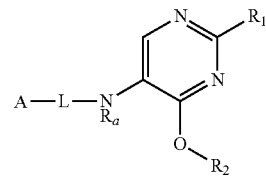

Formula I wherein
$R_1$ is selected from the group consisting of
i) phenyl optionally substituted with one to two substituents independently selected from the group consisting of $C_{1-4}$alkyl, $C_{1-2}$alkoxy, hydroxy, and fluoro; in addition, phenyl is optionally substituted with a single amino, di($C_{1-4}$alkyl)amino, di($C_{1-4}$alkyl)aminocarbonyl, hydroxy($C_{1-4}$)alkyl, aminocarbonyl, $C_{1-4}$alkylcarbonylamino, cyano, trifluoromethoxy, $C_{1-4}$alkylsulfonyl, nitro, or trifluoromethyl substituent;
ii) pyrimidinyl optionally substituted with one to two substituents independently selected from the group consisting of $C_{1-4}$alkoxy and $C_{1-4}$alkylthio; in addition, pyrimidinyl is optionally substituted with a single cyano, morpholin-4-yl, di($C_{1-4}$alkyl)amino, or piperazin-1-yl optionally substituted with 4-$C_{1-4}$alkyl substituent;
iii) pyridinyl optionally substituted with one to two substituents independently selected form the group consisting of $C_{1-4}$alkyl, $C_{1-4}$alkoxy, $C_{1-4}$alkylthio, hydroxy, fluoro, chloro, and cyano; in addition, pyridinyl is optionally substituted with hydroxymethyl or amino;
and
iv) a G-substituent selected from the group consisting of pyrazolyl, thienyl, benzothiazolyl, quinolinyl, indolyl, thiazolyl, furanyl, dihydrobenzofuranyl, benzo[1,3]dioxol-5-yl, and benzo[1,2,5]oxadiazolyl;
wherein G is optionally independently substituted with one $C_{1-4}$alkyl substituent;
$R_2$ is
(i) phenyl optionally substituted with one to two substituents selected from the group consisting of $C_{1-2}$alkyl, $C_{1-2}$alkoxy, $C_{1-2}$alkylthio, fluoro, 3-chloro, 4-chloro, and hydroxy; or phenyl is optionally substituted with one substituent selected from the group consisting of amino, difluoromethoxy, trifluoromethoxy, aminocarbonyl, $C_{1-4}$alkylcarbonylamino, $C_{1-4}$alkylcarbonyloxy, and 2,2,2-trifluoroethoxy;
or,
(ii) heteroaryl selected from the group consisting of benzothiazolyl and benzooxazolyl; wherein heteroaryl of $R_2$ is optionally independently substituted with one to two $C_{1-2}$alkyl substituents;
A-L- is selected from the group consisting of $a_1$-$L_1$-; $a_2$-$L_2$-; $a_3$-$L_3$-, $a_4$-$L_4$-; and $a_5$-$L_5$-;
$L_1$ is absent or $C_{1-2}$alkyl;
$a_1$ is bound through a carbon atom to $L_1$ and is
i) pyrrolidinyl optionally substituted at carbon with hydroxy or one to two fluoro substituents;
or
ii) piperidin-3-yl;
provided that when $L_1$ is absent, $a_1$ is attached to $N(R_a)$ via a carbon atom other than that which is alpha to a nitrogen atom of $a_1$;
and provided that when $a_1$ is substituted with a substituent containing an oxygen or nitrogen radical as a point of attachment to $a_1$, the substitution is at a carbon atom other than that alpha to a nitrogen atom of $a_1$;
$L_2$ is methylene;
$a_2$ is bound through a carbon atom to $L_2$ and $a_2$ is morpholinyl;
$L_3$ is methylene;
$a_3$ is imidazolyl optionally substituted with one to two methyl substituents;
$L_4$ is $(C_{2-3})$alkyl;
$a_4$ is amino, provided that $a_4$ is attached at a carbon atom other than that alpha to $N(R_a)$;
$L_5$ is absent or $C_{1-2}$alkyl;
$a_5$ is $C_{4-6}$cycloalkyl substituted with $R_B$; wherein $R_B$ is amino;
provided that when $R_B$ contains a nitrogen radical as the point of attachment to $C_{5-6}$cycloalkyl, the attachment is at a carbon atom other than that alpha to $N(R_a)$;
or,
A-L- is taken with $R_a$ and the nitrogen atom to which they are both attached to form a nitrogen-bound heterocyclyl selected from the group consisting of
i) pyrrolidin-1-yl optionally substituted with amino;
ii) piperazin-1-yl optionally independently substituted at carbon with one to two $C_{1-4}$alkyl substituents;
iii) piperidin-1-yl optionally substituted with amino;
and
iv) [1,4]diazepan-1-yl;
provided that the position of a substituent containing an nitrogen radical as a point of attachment to the nitrogen-bound heterocyclyl is at a carbon atom other than that alpha to the heterocyclyl nitrogen atom
$R_a$ is hydrogen;

provided that a compound of Formula (I) is other than a compound selected from the group consisting of
a compound wherein $R_1$ is 4-fluoro-phenyl, $R_2$ is 4-methoxy-phenyl, A-L- is $a_1$-$L_1$, $a_1$ is (S)-pyrrolidin-2-yl, $L_1$ is methyl, $R_a$ is H, and X is O;
a compound wherein $R_1$ is pyrimidin-5-yl, $R_2$ is 4-methoxy-phenyl, A-L- is $a_2$-$L_2$, $a_2$ is (S)-morpholin-3-yl, $L_2$ is methyl, $R_a$ is H, and X is O;
a compound wherein $R_1$ is 5-cyano-pyridin-3-yl, $R_2$ is 2-methyl-phenyl, A-L- is $a_1$-$L_1$, $a_1$ is (S)-pyrrolidin-2-yl, $L_1$ is methyl, $R_a$ is H, and X is O;
and
a compound wherein $R_1$ is pyridin-3-yl, $R_2$ is 4-methoxy-phenyl, A-L- is $a_5$-$L_5$, $a_5$ is cyclohexyl, $L_5$ is absent, $R_B$ is 2-amino, $R_a$ is H, and X is O;
and enantiomers, diastereomers, solvates, and pharmaceutically acceptable salts thereof.

A further embodiment of the present invention is directed to a compound of Formula (I)

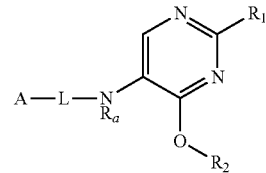

Formula I wherein
$R_1$ is selected from the group consisting of
i) phenyl optionally substituted with a substituent selected from the group consisting of $C_{1-2}$alkyl, $C_{1-2}$alkoxy, hydroxy, and fluoro; or, phenyl is optionally substituted with one substituent selected from the group consisting of amino, di($C_{1-4}$alkyl)amino, di($C_{1-4}$alkyl)aminocarbonyl, hydroxymethyl, aminocarbonyl, $C_{1-4}$alkylcarbonylamino, cyano, trifluoromethoxy, $C_{1-2}$alkylsulfonyl, nitro, and trifluoromethyl;
ii) pyrimidinyl optionally substituted with one to two substituents selected from the group consisting of $C_{1-4}$alkoxy and $C_{1-4}$alkylthio; or, pyrimidinyl is optionally substituted with one substituent selected from the group consisting of morpholin-4-yl, di($C_{1-4}$alkyl)amino, and piperazin-1-yl optionally substituted with 4-methyl;
iii) pyridinyl optionally substituted with one to two substituents selected from the group consisting of $C_{1-4}$alkyl, $C_{1-4}$alkoxy, $C_{1-4}$alkylthio, hydroxy, fluoro, and chloro; or, pyridinyl optionally substituted with one substituent selected from the group consisting of cyano, hydroxymethyl, and amino;
and
iv) a G-substituent selected from the group consisting of pyrazolyl, thienyl, benzothiazolyl, quinolinyl, indolyl, thiazolyl, furanyl, dihydrobenzofuranyl, benzo[1,3]dioxol-5-yl, and benzo[1,2,5]oxadiazolyl;
wherein G is optionally independently substituted with one $C_{1-4}$alkyl substituent;
$R_2$ is
(i) phenyl optionally substituted with one to two substituents selected from the group consisting of $C_{1-2}$alkyl, $C_{1-2}$alkoxy, $C_{1-2}$alkylthio, one to two fluoro substituents, 3-chloro, 4-chloro, and hydroxy; or, phenyl is optionally substituted with one substituent selected from the group consisting of amino, difluoromethoxy, trifluoromethoxy, aminocarbonyl, $C_{1-4}$alkylcarbonylamino, $C_{1-4}$alkylcarbonyloxy, and 2,2,2-trifluoroethoxy;
or,
(ii) heteroaryl selected from the group consisting of benzothiazolyl and benzooxazolyl; wherein heteroaryl of $R_2$ is optionally independently substituted with one to two $C_{1-2}$alkyl substituents;

A-L- is selected from the group consisting of $a_1$-$L_1$-; $a_2$-$L_2$-; $a_3$-$L_3$-, $a_4$-$L_4$-; and $a_5$-$L_5$-;

$L_1$ is absent or $C_{1-2}$alkyl;
$a_1$ is bound through a carbon atom to $L_1$ and is
i) pyrrolidinyl optionally substituted at carbon with hydroxy or one to two fluoro substituents;
or
ii) piperidin-3-yl;
provided that when $L_1$ is absent, $a_1$ is attached to $N(R_a)$ via a carbon atom other than that which is alpha to a nitrogen atom of $a_1$;
and provided that when $a_1$ is substituted with a substituent containing an oxygen or nitrogen radical as a point of attachment to $a_1$, the substitution is at a carbon atom other than that alpha to a nitrogen atom of $a_1$;
$L_2$ is methylene;
$a_2$ is bound through a carbon atom to $L_2$ and $a_2$ is morpholinyl;
$L_3$ is methylene;
$a_3$ is imidazolyl optionally substituted with one to two methyl substituents;
$L_4$ is $(C_{2-3})$alkyl;
$a_4$ is amino, provided that $a_4$ is attached at a carbon atom other than that alpha to $N(R_a)$;
$L_5$ is absent or $C_{1-2}$alkyl;
$a_5$ is $C_{4-6}$cycloalkyl substituted with $R_B$; wherein $R_B$ is amino;
provided that when $R_B$ contains a nitrogen radical as the point of attachment to $C_{5-6}$cycloalkyl, the attachment is at a carbon atom other than that alpha to $N(R_a)$;
or,
A-L- is taken with $R_a$ and the nitrogen atom to which they are both attached to form a nitrogen-bound heterocyclyl selected from the group consisting of
i) pyrrolidin-1-yl optionally substituted with amino;
ii) piperazin-1-yl optionally independently substituted at carbon with one to two $C_{1-2}$alkyl substituents;
iii) piperidin-1-yl optionally substituted with amino; and
iv) [1,4]diazepan-1-yl;
provided that the position of a substituent containing an nitrogen radical as a point of attachment to the nitrogen-bound heterocyclyl is at a carbon atom other than that alpha to the heterocyclyl nitrogen atom
$R_a$ is hydrogen;
provided that a compound of Formula (I) is other than a compound selected from the group consisting of
a compound wherein $R_1$ is 4-fluoro-phenyl, $R_2$ is 4-methoxy-phenyl, A-L- is $a_1$-$L_1$, $a_1$ is (S)-pyrrolidin-2-yl, $L_1$ is methyl, $R_a$ is H, and X is O;
a compound wherein $R_1$ is pyrimidin-5-yl, $R_2$ is 4-methoxy-phenyl, A-L- is $a_2$-$L_2$, $a_2$ is (S)-morpholin-3-yl, $L_2$ is methyl, $R_a$ is H, and X is O;
a compound wherein $R_1$ is 5-cyano-pyridin-3-yl, $R_2$ is 2-methyl-phenyl, A-L- is $a_1$-$L_1$, $a_1$ is (S)-pyrrolidin-2-yl, $L_1$ is methyl, $R_a$ is H, and X is O;
and
a compound wherein $R_1$ is pyridin-3-yl, $R_2$ is 4-methoxy-phenyl, A-L- is $a_5$-$L_5$, $a_5$ is cyclohexyl, $L_5$ is absent, $R_B$ is 2-amino, $R_a$ is H, and X is O;
and enantiomers, diastereomers, solvates, and pharmaceutically acceptable salts thereof.

A further embodiment of the present invention is directed to a compound of Formula (I)

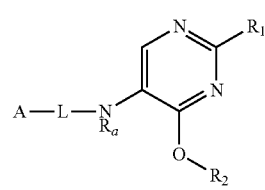

Formula (I)

selected from the group consisting of:
a compound of Formula (I) wherein $R_1$ is 4-methoxy-phenyl, $R_2$ is 4-methoxy-phenyl, A-L- is $a_1$-$L_1$, $a_1$ is pyrrolidin-2-yl, $L_1$ is methyl, and $R_a$ is H; (2S)
a compound of Formula (I) wherein $R_1$ is phenyl, $R_2$ is 4-methoxy-phenyl, A-L- is $a_1$-$L_1$, $a_1$ is pyrrolidin-2-yl, $L_1$ is methyl, and $R_a$ is H; (2S)
a compound of Formula (I) wherein $R_1$ is 3-methoxy-phenyl, $R_2$ is 4-methoxy-phenyl, A-L- is $a_1$-$L_1$, $a_1$ is pyrrolidin-2-yl, $L_1$ is methyl, and $R_a$ is H; (2S)
a compound of Formula (I) wherein $R_1$ is 2-methoxy-phenyl, $R_2$ is 4-methoxy-phenyl, A-L- is $a_1$-$L_1$, $a_1$ is pyrrolidin-2-yl, $L_1$ is methyl, and $R_a$ is H; (2S)
a compound of Formula (I) wherein $R_1$ is naphth-1-yl, $R_2$ is 4-methoxy-phenyl, A-L- is $a_1$-$L_1$, $a_1$ is pyrrolidin-2-yl, $L_1$ is methyl, and $R_a$ is H; (2S)
a compound of Formula (I) wherein $R_1$ is naphth-2-yl, $R_2$ is 4-methoxy-phenyl, A-L- is $a_1$-$L_1$, $a_1$ is pyrrolidin-2-yl, $L_1$ is methyl, and $R_a$ is H; (2S)
a compound of Formula (I) wherein $R_1$ is pyridin-4-yl, $R_2$ is 4-methoxy-phenyl, A-L- is $a_1$-$L_1$, $a_1$ is pyrrolidin-2-yl, $L_1$ is methyl, and $R_a$ is H; (2S)
a compound of Formula (I) wherein $R_1$ is pyridin-3-yl, $R_2$ is 4-methoxy-phenyl, A-L- is $a_1$-$L_1$, $a_1$ is pyrrolidin-2-yl, $L_1$ is methyl, and $R_a$ is H; (2S)
a compound of Formula (I) wherein $R_1$ is thien-3-yl, $R_2$ is 4-methoxy-phenyl, A-L- is $a_1$-$L_1$, $a_1$ is pyrrolidin-2-yl, $L_1$ is methyl, and $R_a$ is H; (2S)
a compound of Formula (I) wherein $R_1$ is furan-3-yl, $R_2$ is 4-methoxy-phenyl, A-L- is $a_1$-$L_1$, $a_1$ is pyrrolidin-2-yl, $L_1$ is methyl, and $R_a$ is H; (2S)
a compound of Formula (I) wherein $R_1$ is pyridin-3-yl, $R_2$ is 4-trifluoromethoxy-phenyl, A-L- is $a_1$-$L_1$, $a_1$ is pyrrolidin-2-yl, $L_1$ is methyl, and $R_a$ is H; (2S)
a compound of Formula (I) wherein $R_1$ is pyridin-3-yl, $R_2$ is 4-aminocarbonyl-phenyl, A-L- is $a_1$-$L_1$, $a_1$ is pyrrolidin-2-yl, $L_1$ is methyl, and $R_a$ is H; (2S)
a compound of Formula (I) wherein $R_1$ is pyridin-3-yl, $R_2$ is 4-methylcarbonylamino-phenyl, A-L- is $a_1$-$L_1$, $a_1$ is pyrrolidin-2-yl, $L_1$ is methyl, and $R_a$ is H; (2S)
a compound of Formula (I) wherein $R_1$ is pyridin-3-yl, $R_2$ is phenyl, A-L- is $a_1$-$L_1$, $a_1$ is pyrrolidin-2-yl, $L_1$ is methyl, and $R_a$ is H; (2S)
a compound of Formula (I) wherein $R_1$ is 3-hydroxy-phenyl, $R_2$ is 4-methoxy-phenyl, A-L- is $a_1$-$L_1$, $a_1$ is pyrrolidin-2-yl, $L_1$ is methyl, and $R_a$ is H; (2S)
a compound of Formula (I) wherein $R_1$ quinolin-5-yl, $R_2$ is 4-methoxy-phenyl, A-L- is $a_1$-$L_1$, $a_1$ is pyrrolidin-2-yl, $L_1$ is methyl, and $R_a$ is H; (2S)
a compound of Formula (I) wherein $R_1$ is quinolin-8-yl, $R_2$ is 4-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 2-methyl-quinolin-5-yl, $R_2$ is 4-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 4-biphenyl, $R_2$ is 4-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is quinolin-3-yl, $R_2$ is 4-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is dibenzothiophen-2-yl, $R_2$ is 4-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 6-methoxy-pyridin-3-yl, $R_2$ is 4-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is pyrimidin-5-yl, $R_2$ is 4-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 2-fluoro-pyridin-3-yl, $R_2$ is 4-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 6-fluoro-pyridin-3-yl, $R_2$ is 4-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 2-methoxy-pyridin-3-yl, $R_2$ is 4-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 2,6-dihydroxy-pyrimidin-5-yl, $R_2$ is 4-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 3-cyano-phenyl, $R_2$ is 4-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 3-nitro-phenyl, $R_2$ is 4-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 3-aminocarbonyl-phenyl, $R_2$ is 4-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 3-N,N-diethylaminocarbonyl-phenyl, $R_2$ is 4-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 3-methanesulfonyl-phenyl, $R_2$ is 4-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 4-hydroxy-phenyl, $R_2$ is 4-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is indol-5-yl, $R_2$ is 4-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 4H-[1,2,4]oxadiazol-5-on-3-yl, $R_2$ is 4-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is pyridin-3-yl, $R_2$ is 4-fluoro-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 6-methoxy-pyridin-3-yl, $R_2$ is 4-fluoro-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 3-fluoro-phenyl, $R_2$ is 4-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 6-methoxy-pyridin-3-yl, $R_2$ is 2-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is pyridin-3-yl, $R_2$ is 2-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 3-diethylamino-phenyl, $R_2$ is 4-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 3-methylcarbonylamino-phenyl, $R_2$ is 4-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 4-methylcarbonylamino-phenyl, $R_2$ is 4-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 6-methoxy-pyridin-3-yl, $R_2$ is 4-amino-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 3-amino-phenyl, $R_2$ is 4-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is pyridin-3-yl, $R_2$ is 4-amino-phenyl, A-L- is $a_1$-$L_1$, $a_1$ is pyrrolidin-2-yl, $L_1$ is methyl, and $R_a$ is H; (2S)

a compound of Formula (I) wherein $R_1$ is benzothiazol-2-yl, $R_2$ is 4-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is thiazol-2-yl, $R_2$ is 4-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is benzothiophen-2-yl, $R_2$ is 4-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 3-trifluoromethyl-phenyl, $R_2$ is 4-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 3-trifluoromethoxy-phenyl, $R_2$ is 4-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 2-methylthio-pyrimidin-5-yl, $R_2$ is 4-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 2-methoxy-pyrimidin-5-yl, $R_2$ is 4-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 5-fluoro-pyridin-3-yl, $R_2$ is 4-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 3,5-difluoro-phenyl, $R_2$ is 4-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 3,4-difluoro-phenyl, $R_2$ is 4-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 3,5-difluoro-4-hydroxymethyl-phenyl, $R_2$ is 4-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 2,4-dimethoxy-pyrimidin-5-yl, $R_2$ is 4-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 6-methoxy-pyridin-3-yl, $R_2$ is 4-hydroxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 2-ethoxy-pyrimidin-5-yl, $R_2$ is 4-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is pyrazol-5-yl, $R_2$ is 4-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 3,5-dimethyl-isoxazol-4-yl, $R_2$ is 4-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 2,3-dihydrobenzofuran5-yl, $R_2$ is 4-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 3-fluoro-4-methoxy-phenyl, $R_2$ is 4-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is pyrazol-4-yl, $R_2$ is 4-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 2-methylthio-pyrimidin-4-yl, $R_2$ is 4-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 1-methyl-pyrazol-4-yl, $R_2$ is 4-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 5-methoxy-pyridin-3-yl, $R_2$ is 4-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 5-cyano-pyridin-3-yl, $R_2$ is 4-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 3-fluoro-5-methoxy-phenyl, $R_2$ is 4-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 3-fluoro-5-methyl-phenyl, $R_2$ is 4-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 6-amino-pyridin-3-yl, $R_2$ is 4-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 5-fluoro-6-methoxy-pyridin-3-yl, $R_2$ is 4-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 6-hydroxy-pyridin-3-yl, $R_2$ is 4-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 6-hydroxy-pyridin-3-yl, $R_2$ is 4-hydroxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is quinoxalin-6-yl, $R_2$ is 4-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 1H-pyrrolo[2,3-b]pyridin-5-yl, $R_2$ is 4-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is benzo[1,2,5]oxadiazol-5-yl, $R_2$ is 4-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is pyrimidin-5-yl, $R_2$ is 4-methoxy-phenyl, A-L- is $a_1$-$L_1$, $a_1$ is 4,4-difluoro-pyrrolidin-2-yl, $L_1$ is methyl, and $R_a$ is H; (2S)

a compound of Formula (I) wherein $R_1$ is pyrimidin-5-yl, $R_2$ is 4-methoxy-phenyl, A-L- is $a_1$-$L_1$, $a_1$ is 4-fluoro-pyrrolidin-2-yl, $L_1$ is methyl, and $R_a$ is H; (2S,4R)

a compound of Formula (I) wherein $R_1$ is 2-amino-pyrimidin-5-yl, $R_2$ is 4-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 2-dimethylamino-pyrimidin-5-yl, $R_2$ is 4-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 2-(morpholin-4-yl)-pyrimidin-5-yl, $R_2$ is 4-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 2-(4-methyl-pyrazin-1-yl)-pyrimidin-5-yl, $R_2$ is 4-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is pyrimidin-5-yl, $R_2$ is benzothiazol-6-yl, A-L- is $a_1$-$L_1$, $a_1$ is pyrrolidin-2-yl, $L_1$ is methyl, and $R_a$ is H; (2S)

a compound of Formula (I) wherein $R_1$ is 5-cyano-pyridin-3-yl, $R_2$ is benzothiazol-6-yl, A-L- is $a_1$-$L_1$, $a_1$ is pyrrolidin-2-yl, $L_1$ is methyl, and $R_a$ is H; (2S)

a compound of Formula (I) wherein $R_1$ is pyrimidin-5-yl, $R_2$ is 2-methyl-benzoxazol-6-yl, A-L- is $a_1$-$L_1$, $a_1$ is pyrrolidin-2-yl, $L_1$ is methyl, and $R_a$ is H; (2S)

a compound of Formula (I) wherein $R_1$ is 5-cyano-pyridin-3-yl, $R_2$ is 2-methyl-benzoxazol-6-yl, A-L- is $a_1$-$L_1$, $a_1$ is pyrrolidin-2-yl, $L_1$ is methyl, and $R_a$ is H; (2S)

a compound of Formula (I) wherein $R_1$ is pyrimidin-5-yl, $R_2$ is 4-methoxy-phenyl, A-L- is $a_1$-$L_1$, $a_1$ is 4-fluoro-pyrrolidin-2-yl, $L_1$ is methyl, and $R_a$ is H; (2S,4S)

a compound of Formula (I) wherein $R_1$ is 5-cyano-pyridin-3-yl, $R_2$ is 2-methyl-benzothiazol-6-yl, A-L- is $a_1$-$L_1$, $a_1$ is pyrrolidin-2-yl, $L_1$ is methyl, and $R_a$ is H; (2S)

a compound of Formula (I) wherein $R_1$ is pyrimidin-5-yl, $R_2$ is 2-methyl-benzothiazol-6-yl, A-L- is $a_1$-$L_1$, $a_1$ is pyrrolidin-2-yl, $L_1$ is methyl, and $R_a$ is H; (2S)

a compound of Formula (I) wherein $R_1$ is 3,5-dimethyl-phenyl, $R_2$ is 4-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is benzo[1,3]dioxol-5-yl, $R_2$ is 4-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 3,5-dichloro-phenyl, $R_2$ is 4-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 6-cyano-pyridin-3-yl, $R_2$ is 4-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 5-cyano-pyridin-3-yl, $R_2$ is 3,5-difluoro-4-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is pyrimidin-5-yl, $R_2$ is 3,5-difluoro-4-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 5-cyano-pyridin-3-yl, $R_2$ is 3-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is pyrimidin-5-yl, $R_2$ is 3-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is pyridin-3-yl, $R_2$ is 3-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 5-cyano-pyridin-3-yl, $R_2$ is 2,3-difluoro-4-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 5-fluoro-pyridin-3-yl, $R_2$ is 2,3-difluoro-4-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is pyrimidin-5-yl, $R_2$ is 2,3-difluoro-4-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 5-cyano-pyridin-3-yl, $R_2$ is 4-ethoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is pyrimidin-5-yl, $R_2$ is 4-ethoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 5-fluoro-pyridin-3-yl, $R_2$ is 4-ethoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 5-methylthio-pyridin-3-yl, $R_2$ is 4-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 5-methanesulfonyl-pyridin-3-yl, $R_2$ is 4-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is pyrimidin-5-yl, $R_2$ is 4-methoxy-phenyl, A-L- is $a_1$-$L_1$, $a_1$ is piperidin-3-yl, $L_1$ is absent, and $R_a$ is H; (racemic)

a compound of Formula (I) wherein $R_1$ is 5-cyano-pyridin-3-yl, $R_2$ is 4-difluoromethoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is pyrimidin-5-yl, $R_2$ is 4-difluoromethoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 5-fluoro-pyridin-3-yl, $R_2$ is 4-difluoromethoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 5-cyano-pyridin-3-yl, $R_2$ is 4-n-propyloxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is pyrimidin-5-yl, $R_2$ is 4-n-propyloxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 5-fluoro-pyridin-3-yl, $R_2$ is 4-n-propyloxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is indol-4-yl, $R_2$ is 4-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is indol-6-yl, $R_2$ is 4-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is indol-7-yl, $R_2$ is 4-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is pyrazin-2-yl, $R_2$ is 4-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 2-cyano-pyrimidin-5-yl, $R_2$ is 4-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 5-cyano-pyridin-3-yl, $R_2$ is 4-(2,2,2-trifluoro-ethoxy)-phenyl, A-L- is $a_1$-$L_1$, $a_1$ is pyrrolidin-2-yl, $L_1$ is methyl, and $R_a$ is H; (2S)

a compound of Formula (I) wherein $R_1$ is pyrimidin-5-yl, $R_2$ is 4-(2,2,2-trifluoro-ethoxy)-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 5-fluoro-pyridin-3-yl, $R_2$ is 4-(2,2,2-trifluoro-ethoxy)-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 5-cyano-pyridin-3-yl, $R_2$ is 4-n-butoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is pyrimidin-5-yl, $R_2$ is 4-n-butoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 5-fluoro-pyridin-3-yl, $R_2$ is 4-n-butoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 5-fluoro-pyridin-3-yl, $R_2$ is 4-chloro-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 5-cyano-pyridin-3-yl, $R_2$ is 4-chloro-phenyl, A-L- is $a_1$-$L_1$, $a_1$ is pyrrolidin-2-yl, $L_1$ is methyl, and $R_a$ is H; (2S)

a compound of Formula (I) wherein $R_1$ is pyrimidin-5-yl, $R_2$ is 4-chloro-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 5-fluoro-pyridin-3-yl, $R_2$ is 3-fluoro-4-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 5-cyano-pyridin-3-yl, $R_2$ is 3-fluoro-4-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is pyrimidin-5-yl, $R_2$ is 3-fluoro-4-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 5-cyano-pyridin-3-yl, $R_2$ is 4-methoxy-phenyl, A-L- is $a_1$-$L_1$, $a_1$ is 4-fluoro-pyrrolidin-2-yl, $L_1$ is methyl, and $R_a$ is H; (2S,4R)

a compound of Formula (I) wherein $R_1$ is pyridin-3-yl, $R_2$ is 3-cyano-phenyl, A-L- is $a_1$-$L_1$, $a_1$ is pyrrolidin-2-yl, $L_1$ is methyl, and $R_a$ is H; (2S)

a compound of Formula (I) wherein $R_1$ is pyridin-3-yl, $R_2$ is 4-cyano-phenyl, A-L- is $a_1$-$L_1$, $a_1$ is pyrrolidin-2-yl, $L_1$ is methyl, and $R_a$ is H; (2S)

a compound of Formula (I) wherein $R_1$ is pyridin-3-yl, $R_2$ is 3-fluoro-4-cyano-phenyl, A-L- is $a_1$-$L_1$, $a_1$ is pyrrolidin-2-yl, $L_1$ is methyl, and $R_a$ is H; (2S)

a compound of Formula (I) wherein $R_1$ is pyridin-3-yl, $R_2$ is 4-cyclopropylcarbonylamino-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 5-cyano-pyridin-3-yl, $R_2$ is 4-isopropyloxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is pyrimidin-5-yl, $R_2$ is 4-isopropyloxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is pyridin-3-yl, $R_2$ is 4-isopropyloxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 3-cyano-5-fluoro-phenyl, $R_2$ is 4-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 5-cyano-pyridin-3-yl, $R_2$ is 4-hydroxymethyl-phenyl, A-L- is $a_1$-$L_1$, $a_1$ is pyrrolidin-2-yl, $L_1$ is methyl, and $R_a$ is H; (2S)

a compound of Formula (I) wherein $R_1$ is pyrimidin-5-yl, $R_2$ is 4-hydroxymethyl-phenyl, A-L- is $a_1$-$L_1$, $a_1$ is pyrrolidin-2-yl, $L_1$ is methyl, and $R_a$ is H; (2S)

a compound of Formula (I) wherein $R_1$ is pyridin-3-yl, $R_2$ is 4-hydroxymethyl-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 5-cyano-pyridin-3-yl, $R_2$ is 4-fluoro-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 5-cyano-pyridin-3-yl, $R_2$ is 4-methyl-phenyl, A-L- is $a_1$-$L_1$, $a_1$ is pyrrolidin-2-yl, $L_1$ is methyl, and $R_a$ is H; (2S)

a compound of Formula (I) wherein $R_1$ is pyrimidin-5-yl, $R_2$ is 4-methyl-phenyl, A-L- is $a_1$-$L_1$, $a_1$ is pyrrolidin-2-yl, $L_1$ is methyl, and $R_a$ is H; (2S)

a compound of Formula (I) wherein $R_1$ is pyridin-3-yl, $R_2$ is 4-methyl-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 5-cyano-pyridin-3-yl, $R_2$ is 4-methylthio-phenyl, A-L- is $a_1$-$L_1$, $a_1$ is pyrrolidin-2-yl, $L_1$ is methyl, and $R_a$ is H; (2S)

a compound of Formula (I) wherein $R_1$ is pyrimidin-5-yl, $R_2$ is 4-methylthio-phenyl, A-L- is $a_1$-$L_1$, $a_1$ is pyrrolidin-2-yl, $L_1$ is methyl, and $R_a$ is H; (2S)

a compound of Formula (I) wherein $R_1$ is pyridin-3-yl, $R_2$ is 4-methylthio-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 5-cyano-pyridin-3-yl, $R_2$ is 4-methoxymethyl-phenyl, A-L- is $a_1$-$L_1$, $a_1$ is pyrrolidin-2-yl, $L_1$ is methyl, and $R_a$ is H; (2S)

a compound of Formula (I) wherein $R_1$ is pyrimidin-5-yl, $R_2$ is 4-methoxymethyl-phenyl, A-L- is $a_1$-$L_1$, $a_1$ is pyrrolidin-2-yl, $L_1$ is methyl, and $R_a$ is H; (2S)

a compound of Formula (I) wherein $R_1$ is pyridin-3-yl, $R_2$ is 4-methoxymethyl-phenyl, A-L- is $a_1$-$L_1$, $a_1$ is pyrrolidin-2-yl, $L_1$ is methyl, and $R_a$ is H; (2S)

a compound of Formula (I) wherein $R_1$ is pyrimidin-5-yl, $R_2$ is 4-hydroxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is pyridin-3-yl, $R_2$ is 3-diethylaminocarbonyl-phenyl, A-L- is $a_1$-$L_1$, $a_1$ is pyrrolidin-2-yl, $L_1$ is methyl, and $R_a$ is H; (2S)

a compound of Formula (I) wherein $R_1$ is pyridin-3-yl, $R_2$ is 4-pyrrolidin-1-ylcarbonyl-phenyl, A-L- is $a_1$-$L_1$, $a_1$ is pyrrolidin-2-yl, $L_1$ is methyl, and $R_a$ is H; (2S)

a compound of Formula (I) wherein $R_1$ is pyridin-3-yl, $R_2$ is 4-carboxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is pyridin-3-yl, $R_2$ is 4-piperidin-1-ylcarbonyl-phenyl, A-L- is $a_1$-$L_1$, $a_1$ is pyrrolidin-2-yl, $L_1$ is methyl, and $R_a$ is H; (2S)

a compound of Formula (I) wherein $R_1$ is pyridin-3-yl, $R_2$ is 4-(morpholin-4-ylcarbonyl)-phenyl, A-L- is $a_1$-$L_1$, $a_1$ is pyrrolidin-2-yl, $L_1$ is methyl, and $R_a$ is H; (2S)

a compound of Formula (I) wherein $R_1$ is pyridin-3-yl, $R_2$ is 4-(4-methyl-piperazin-1-ylcarbonyl)-phenyl, A-L- is $a_1$-$L_1$, $a_1$ is pyrrolidin-2-yl, $L_1$ is methyl, and $R_a$ is H; (2S)

a compound of Formula (I) wherein $R_1$ is pyridin-3-yl, $R_2$ is 3-carboxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 5-fluoro-pyridin-3-yl, $R_2$ is 3-carboxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 5-fluoro-pyridin-3-yl, $R_2$ is 4-carboxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is pyridin-3-yl, $R_2$ is 3-(pyrrolidin-1-ylcarbonyl)-phenyl, A-L- is $a_1$-$L_1$, $a_1$ is pyrrolidin-2-yl, $L_1$ is methyl, and $R_a$ is H; (2S)

a compound of Formula (I) wherein $R_1$ is pyridin-3-yl, $R_2$ is 3-(piperidin-1-ylcarbonyl)-phenyl, A-L- is $a_1$-$L_1$, $a_1$ is pyrrolidin-2-yl, $L_1$ is methyl, and $R_a$ is H; (2S)

a compound of Formula (I) wherein $R_1$ is pyridin-3-yl, $R_2$ is 3-(morpholin-4-ylcarbonyl)-phenyl, A-L- is $a_1$-$L_1$, $a_1$ is pyrrolidin-2-yl, $L_1$ is methyl, and $R_a$ is H; (2S)

a compound of Formula (I) wherein $R_1$ is pyridin-3-yl, $R_2$ is 3-(4-methyl-piperazin-1-ylcarbonyl)-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 5-fluoro-pyridin-3-yl, $R_2$ is 3-diethylaminocarbonyl-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 5-fluoro-pyridin-3-yl, $R_2$ is 3-(pyrrolidin-1-ylcarbonyl)-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 5-fluoro-pyridin-3-yl, $R_2$ is 3-(piperidin-1-ylcarbonyl)-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 5-fluoro-pyridin-3-yl, $R_2$ is 3-(morpholin-4-ylcarbonyl)-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 5-fluoro-pyridin-3-yl, $R_2$ is 3-(4-methyl-piperazin-1-ylcarbonyl)-phenyl, A-L- is $a_1$-$L_1$, $a_1$ is pyrrolidin-2-yl, $L_1$ is methyl, and $R_a$ is H; (2S)

a compound of Formula (I) wherein $R_1$ is pyridin-3-yl, $R_2$ is 4-diethylaminocarbonyl-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 5-fluoro-pyridin-3-yl, $R_2$ is 4-(pyrrolidin-1-ylcarbonyl)-phenyl, A-L- is $a_1$-$L_1$, $a_1$ is pyrrolidin-2-yl, $L_1$ is methyl, and $R_a$ is H; (2S)

a compound of Formula (I) wherein $R_1$ is pyridin-3-yl, $R_2$ is 4-benzyloxycarbonylamino-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 5-fluoro-pyridin-3-yl, $R_2$ is 4-methyl-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 5-cyano-pyridin-3-yl, $R_2$ is 4-ethyl-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 5-chloro-pyridin-3-yl, $R_2$ is 4-ethyl-phenyl, A-L- is $a_1$-$L_1$, $a_1$ is pyrrolidin-2-yl, $L_1$ is methyl, and $R_a$ is H; (2S)

a compound of Formula (I) wherein $R_1$ is pyrimidin-5-yl, $R_2$ is 4-methoxy-phenyl, A-L- is $a_1$-$L_1$, $a_1$ is pyrrolidin-2-yl, $L_1$ is methyl, $R_a$ is methylcarbonyl; (2S)

a compound of Formula (I) wherein $R_1$ is 5-fluoro-pyridin-3-yl, $R_2$ is 4-ethyl-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 5-cyano-pyridin-3-yl, $R_2$ is 3-fluoro-4-methyl-phenyl, A-L- is $a_1$-$L_1$, $a_1$ is pyrrolidin-2-yl, $L_1$ is methyl, and $R_a$ is H; (2S)

a compound of Formula (I) wherein $R_1$ is pyridin-3-yl, $R_2$ is 4-ethyl-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 5-fluoro-pyridin-3-yl, $R_2$ is 3-fluoro-4-methyl-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 5-chloro-pyridin-3-yl, $R_2$ is 3-fluoro-4-methyl-phenyl, A-L- is $a_1$-$L_1$, $a_1$ is pyrrolidin-2-yl, $L_1$ is methyl, and $R_a$ is H; (2S)

a compound of Formula (I) wherein $R_1$ is pyridin-3-yl, $R_2$ is 3-fluoro-4-methyl-phenyl, A-L- is $a_1$-$L_1$, $a_1$ is pyrrolidin-2-yl, $L_1$ is methyl, and $R_a$ is H; (2S)

a compound of Formula (I) wherein $R_1$ is pyridin-3-yl, $R_2$ is 3-benzyloxycarbonylamino-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 5-cyano-pyridin-3-yl, $R_2$ is 2,3-difluoro-4-methyl-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 5-chloro-pyridin-3-yl, $R_2$ is 2,3-difluoro-4-methyl-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 5-fluoro-pyridin-3-yl, $R_2$ is 2,3-difluoro-4-methyl-phenyl, A-L- is $a_1$-$L_1$, $a_1$ is pyrrolidin-2-yl, $L_1$ is methyl, and $R_a$ is H; (2S)

a compound of Formula (I) wherein $R_1$ is pyridin-3-yl, $R_2$ is 2,3-difluoro-4-methyl-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 5-fluoro-pyridin-3-yl, $R_2$ is 4-methoxy-phenyl, A-L- is $a_1$-$L_1$, $a_1$ is 4-fluoro-pyrrolidin-2-yl, $L_1$ is methyl, and $R_a$ is H; (2S,4R)

a compound of Formula (I) wherein $R_1$ is 5-chloro-pyridin-3-yl, $R_2$ is 4-methoxy-phenyl, A-L- is $a_1$-$L_1$, $a_1$ is 4-fluoro-pyrrolidin-2-yl, $L_1$ is methyl, and $R_a$ is H; (2S,4R)

a compound of Formula (I) wherein $R_1$ is 5-cyano-pyridin-3-yl, $R_2$ is 4-ethyl-phenyl, A-L- is $a_1$-$L_1$, $a_1$ is 4-fluoro-pyrrolidin-2-yl, $L_1$ is methyl, and $R_a$ is H; (2S,4R)

a compound of Formula (I) wherein $R_1$ is pyridin-3-yl, $R_2$ is 4-methoxy-phenyl, A-L- is $a_1$-$L_1$, $a_1$ is 4-fluoro-pyrrolidin-2-yl, $L_1$ is methyl, and $R_a$ is H; (2S,4R)

a compound of Formula (I) wherein $R_1$ is 5-fluoro-pyridin-3-yl, $R_2$ is 4-benzyloxycarbonylamino-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 5-fluoro-pyridin-3-yl, $R_2$ is 4-amino-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 5-cyano-pyridin-3-yl, $R_2$ is 4-methoxy-phenyl, A-L- is $a_1$-$L_1$, $a_1$ is piperidin-3-yl, $L_1$ is absent, and $R_a$ is H; (3S)

a compound of Formula (I) wherein $R_1$ is 5-cyano-pyridin-3-yl, $R_2$ is 3-methyl-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 5-chloro-pyridin-3-yl, $R_2$ is 3-methyl-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 5-fluoro-pyridin-3-yl, $R_2$ is 3-methyl-phenyl, A-L- is $a_1$-$L_1$, $a_1$ is pyrrolidin-2-yl, $L_1$ is methyl, and $R_a$ is H; (2S)

a compound of Formula (I) wherein $R_1$ is pyridin-3-yl, $R_2$ is 3-methyl-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 5-cyano-pyridin-3-yl, $R_2$ is 3-methyl-4-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 5-fluoro-pyridin-3-yl, $R_2$ is 3-methyl-4-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 5-cyano-pyridin-3-yl, $R_2$ is 4-fluoromethyl-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 5-cyano-pyridin-3-yl, $R_2$ is 4-methoxy-phenyl, A-L- is $a_1$-$L_1$, $a_1$ is piperidin-3-yl, $L_1$ is absent, and $R_a$ is H; (3S)

a compound of Formula (I) wherein $R_1$ is 5-cyano-pyridin-3-yl, $R_2$ is 4-methoxy-phenyl, A-L- is $a_1$-$L_1$, $a_1$ is piperidin-4-yl, $L_1$ is absent, and $R_a$ is H;

a compound of Formula (I) wherein $R_1$ is pyridin-3-yl, $R_2$ is 4-(pyridin-3-ylmethyl)-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 5-chloro-pyridin-3-yl, $R_2$ is 3-methyl-4-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is pyridin-3-yl, $R_2$ is 3-methyl-4-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 5-cyano-pyridin-3-yl, $R_2$ is 4-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 5-fluoro-pyridin-3-yl, $R_2$ is 4-methylcarbonylamino-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 5-fluoro-pyridin-3-yl, $R_2$ is 4-methanesulfonylamino-phenyl, A-L- is $a_1$-$L_1$, $a_1$ is pyrrolidin-2-yl, $L_1$ is methyl, and $R_a$ is H; (2S)

a compound of Formula (I) wherein $R_1$ is pyridin-3-yl, $R_2$ is 4-methanesulfonylamino-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 5-cyano-pyridin-3-yl, $R_2$ is 4-methoxy-phenyl, A-L- is $a_1$-$L_1$, $a_1$ is azetidin-3-yl, $L_1$ is methyl, and $R_a$ is H; (2S)

a compound of Formula (I) wherein $R_1$ is pyridin-3-yl, $R_2$ is 4-formamido-phenyl, A-L- is $a_1$-$L_1$, $a_1$ is pyrrolidin-2-yl, $L_1$ is methyl, and $R_a$ is H; (2S)

a compound of Formula (I) wherein $R_1$ is pyridin-3-yl, $R_2$ is 4-fluoromethyl-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 5-cyano-pyridin-3-yl, $R_2$ is 3-methyl-4-fluoro-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 5-fluoro-pyridin-3-yl, $R_2$ is 3-methyl-4-fluoro-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 5-cyano-pyridin-3-yl, $R_2$ is 4-trifluoromethyl-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 5-fluoro-pyridin-3-yl, $R_2$ is 4-trifluoromethyl-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 5-fluoro-pyridin-3-yl, $R_2$ is 4-methanesulfonyl-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 5-fluoro-pyridin-3-yl, $R_2$ is 4-formamido-phenyl, A-L- is $a_1$-$L_1$, $a_1$ is pyrrolidin-2-yl, $L_1$ is methyl, and $R_a$ is H; (2S)

a compound of Formula (I) wherein $R_1$ is pyridin-3-yl, $R_2$ is 4-methoxy-phenyl, A-L- is $a_1$-$L_1$, $a_1$ is pyrrolidin-3-yl, $L_1$ is absent, and $R_a$ is H; (3R)

a compound of Formula (I) wherein $R_1$ is pyridin-3-yl, $R_2$ is 4-methoxy-phenyl, A-L- is $a_1$-$L_1$, $a_1$ is piperidin-2-yl, $L_1$ is methyl, and $R_a$ is H; (2S)

a compound of Formula (I) wherein $R_1$ is pyridin-3-yl, $R_2$ is 4-methoxy-phenyl, A-L- is $a_1$-$L_1$, $a_1$ is azetidin-3-yl, $L_1$ is absent, and $R_a$ is H;

a compound of Formula (I) wherein $R_1$ is 5-cyano-pyridin-3-yl, $R_2$ is 4-methoxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 5-chloro-pyridin-3-yl, $R_2$ is 2-methyl-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 5-cyano-pyridin-3-yl, $R_2$ is 3-methylcarbonyloxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 5-chloro-pyridin-3-yl, $R_2$ is 2-chloro-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 5-cyano-pyridin-3-yl, $R_2$ is 2-chloro-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 5-cyano-pyridin-3-yl, $R_2$ is 3-hydroxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 5-methoxy-pyridin-3-yl, $R_2$ is 2-chloro-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 5-methylthio-pyridin-3-y, $R_2$ is 2-chloro-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 5-methylthio-pyridin-3-y, $R_2$ is 4-methoxy-phenyl, A-L- is $a_1$-$L_1$, $a_1$ is 4-fluoro-pyrrolidin-2-yl, $L_1$ is methyl, and $R_a$ is H; (2S,4R)

a compound of Formula (I) wherein $R_1$ is 5-methoxy-pyridin-3-yl, $R_2$ is 4-methoxy-phenyl, A-L- is $a_1$-$L_1$, $a_1$ is 4-fluoro-pyrrolidin-2-yl, $L_1$ is methyl, and $R_a$ is H; (2S,4R)

a compound of Formula (I) wherein $R_1$ is pyridin-3-yl, $R_2$ is 4-methoxy-phenyl, A-L- is $a_1$-$L_1$, $a_1$ is piperidin-3-yl, $L_1$ is absent, and $R_a$ is H; (3S)

a compound of Formula (I) wherein $R_1$ is pyridin-3-yl, $R_2$ is 4-methoxy-phenyl, A-L- is $a_1$-$L_1$, $a_1$ is pyrrolidin-3-yl, $L_1$ is absent, and $R_a$ is H; (3S)

a compound of Formula (I) wherein $R_1$ is 5-methyl-pyridin-3-yl, $R_2$ is 4-methoxy-phenyl, A-L- is $a_1$-$L_1$, $a_1$ is 4-fluoro-pyrrolidin-2-yl, $L_1$ is methyl, and $R_a$ is H; (2S,4R)

a compound of Formula (I) wherein $R_1$ is 5-methyl-pyridin-3-yl, $R_2$ is 4-methoxy-phenyl, A-L- is $a_1$-$L_1$, $a_1$ is 4-fluoro-pyrrolidin-2-yl, $L_1$ is methyl, and $R_a$ is H; (2S,4S)

a compound of Formula (I) wherein $R_1$ is 5-methoxy-pyridin-3-yl, $R_2$ is 4-methoxy-phenyl, A-L- is $a_1$-$L_1$, $a_1$ is 4-fluoro-pyrrolidin-2-yl, $L_1$ is methyl, and $R_a$ is H; (2S,4S)

a compound of Formula (I) wherein $R_1$ is 5-methylthio-pyridin-3-y, $R_2$ is 4-(2-methoxy-ethoxy)-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 5-methyl-pyridin-3-yl, $R_2$ is 4-(2-methoxy-ethoxy)-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 5-methoxy-pyridin-3-yl, $R_2$ is 4-(2-methoxy-ethoxy)-phenyl, A-L- is $a_1$-$L_1$, $a_1$ is pyrrolidin-2-yl, $L_1$ is methyl, and $R_a$ is H; (2S)

a compound of Formula (I) wherein $R_1$ is pyridin-3-yl, $R_2$ is 4-(2-methoxy-ethoxy)-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 5-methoxy-pyridin-3-yl, $R_2$ is 4-methoxy-phenyl, A-L- is $a_1$-$L_1$, $a_1$ is piperidin-3-yl, $L_1$ is absent, and $R_a$ is H; (3S)

a compound of Formula (I) wherein $R_1$ is 5-methoxy-pyridin-3-yl, $R_2$ is 4-methoxy-phenyl, A-L- is $a_1$-$L_1$, $a_1$ is piperidin-3-yl, $L_1$ is absent, and $R_a$ is H; (3R)

a compound of Formula (I) wherein $R_1$ is 5-methoxy-pyridin-3-yl, $R_2$ is 4-methoxy-phenyl, A-L- is $a_1$-$L_1$, $a_1$ is piperidin-3-yl, $L_1$ is absent, $R_a$ is H; (3S)

a compound of Formula (I) wherein $R_1$ is 5-methylthio-pyridin-3-y, $R_2$ is 3-methylcarbonyloxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 5-methoxy-pyridin-3-yl, $R_2$ is 3-hydroxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 5-methoxy-pyridin-3-yl, $R_2$ is 3-methylcarbonyloxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 5-methyl-pyridin-3-yl, $R_2$ is 3-methylcarbonyloxy-phenyl, A-L- is $a_1$-$L_1$, $a_1$ is pyrrolidin-2-yl, $L_1$ is methyl, and $R_a$ is H; (2S)

a compound of Formula (I) wherein $R_1$ is 5-methylthio-pyridin-3-y, $R_2$ is 4-methoxy-phenyl, A-L- is $a_1$-$L_1$, $a_1$ is piperidin-3-yl, $L_1$ is absent, and $R_a$ is H; (3S)

a compound of Formula (I) wherein $R_1$ is 5-methyl-pyridin-3-yl, $R_2$ is 4-methoxyphenyl, A-L- is $a_1$-$L_1$, $a_1$ is pyrrolidin-2-yl, $L_1$ is methyl, and $R_a$ is H; (2S)

a compound of Formula (I) wherein $R_1$ is 5-methylthiopyridin-3-yl, $R_2$ is 4-methoxyphenyl, A-L- is $a_1$-$L_1$, $a_1$ is piperidin-3-yl, $L_1$ is absent, $R_a$ is H; (3R)

a compound of Formula (I) wherein $R_1$ is 5-methylthiopyridin-3-yl, $R_2$ is 4-methoxyphenyl, A-L- is $a_1$-$L_1$, $a_1$ is pyrrolidin-3-yl, $L_1$ is absent, $R_a$ is H; (3S)

a compound of Formula (I) wherein $R_1$ is 5-methoxypyridin-3-yl, $R_2$ is 4-methoxyphenyl, A-L- is $a_1$-$L_1$, $a_1$ is pyrrolidin-3-yl, $L_1$ is absent, $R_a$ is H; (3S)

a compound of Formula (I) wherein $R_1$ is 5-methyl-pyridin-3-yl, $R_2$ is 4-methoxyphenyl, A-L- is $a_1$-$L_1$, $a_1$ is pyrrolidin-3-yl, $L_1$ is absent, $R_a$ is H; (3S)

a compound of Formula (I) wherein $R_1$ is 5-methyl-pyridin-3-yl, $R_2$ is 4-methoxyphenyl, A-L- is $a_1$-$L_1$, $a_1$ is piperidin-3-yl, $L_1$ is absent, $R_a$ is H; (3R)

a compound of Formula (I) wherein $R_1$ is 5-methyl-pyridin-3-yl, $R_2$ is 4-methoxyphenyl, A-L- is $a_1$-$L_1$, $a_1$ is piperidin-3-yl, $L_1$ is absent, $R_a$ is H; (3S)

a compound of Formula (I) wherein $R_1$ is 5-methyl-pyridin-3-yl, $R_2$ is 4-fluoromethoxyphenyl, A-L- is $a_1$-$L_1$, $a_1$ is pyrrolidin-2-yl, $L_1$ is methyl, and $R_a$ is H; (2S)

a compound of Formula (I) wherein $R_1$ is pyridin-3-yl, $R_2$ is 4-methoxyphenyl, A-L- is $a_1$-$L_1$, $a_1$ is piperidin-3-yl, $L_1$ is absent, $R_a$ is H; (3R)

a compound of Formula (I) wherein $R_1$ is 6-fluoro-5-methylpyridin-3-yl, $R_2$ is 4-methoxyphenyl, A-L- is $a_1$-$L_1$, $a_1$ is pyrrolidin-2-yl, $L_1$ is methyl, and $R_a$ is H; (2S)

a compound of Formula (I) wherein $R_1$ is 2,5-dimethyl-pyridin-3-yl, $R_2$ is 4-methoxyphenyl, A-L- is $a_1$-$L_1$, $a_1$ is pyrrolidin-2-yl, $L_1$ is methyl, and $R_a$ is H; (2S)

a compound of Formula (I) wherein $R_1$ is 6'-chloro-3,5'-dimethyl-[2,3']bipyridinyl-5-yl, $R_2$ is 4-methoxyphenyl, A-L- is $a_1$-$L_1$, $a_1$ is pyrrolidin-2-yl, $L_1$ is methyl, and $R_a$ is H; (2S)

a compound of Formula (I) wherein $R_1$ is 6-chloro-4-methylpyridin-3-yl, $R_2$ is 4-methoxyphenyl, A-L- is $a_1$-$L_1$, $a_1$ is pyrrolidin-2-yl, $L_1$ is methyl, and $R_a$ is H; (2S)

a compound of Formula (I) wherein $R_1$ is 6-chloro-5-methyl-pyridin-3-yl, $R_2$ is 4-methoxyphenyl, A-L- is $a_1$-$L_1$, $a_1$ is pyrrolidin-2-yl, $L_1$ is methyl, and $R_a$ is H; (2S)

a compound of Formula (I) wherein $R_1$ is pyridin-3-yl, $R_2$ is 4-methoxyphenyl, A-L- is $a_1$-$L_1$, $a_1$ is piperidin-2-yl, $L_1$ is methyl, and $R_a$ is H; (2R)

a compound of Formula (I) wherein $R_1$ is 2-chloro-5-methylpyridin-3-yl, $R_2$ is 4-methoxyphenyl, A-L- is $a_1$-$L_1$, $a_1$ is pyrrolidin-2-yl, $L_1$ is methyl, and $R_a$ is H; (2S)

a compound of Formula (I) wherein $R_1$ is 5-hydroxymethyl-pyridin-3-yl, $R_2$ is 4-methoxyphenyl, A-L- is $a_1$-$L_1$, $a_1$ is pyrrolidin-2-yl, $L_1$ is methyl, and $R_a$ is H; (2S)

a compound of Formula (I) wherein $R_1$ is pyridin-3-yl, $R_2$ is 4-methoxyphenyl, A-L- is $a_1$-$L_1$, $a_1$ is 4-hydroxy-pyrrolidin-2-yl, $L_1$ is methyl, $R_a$ is H; (trans 2S,4R)

a compound of Formula (I) wherein $R_1$ is pyridin-3-yl, $R_2$ is 4-methoxyphenyl, A-L- is $a_1$-$L_1$, $a_1$ is -hydroxypyrrolidin-2-yl, $L_1$ is methyl, and $R_a$ is H; (cis 2R,4R)

a compound of Formula (I) wherein $R_1$ is pyridin-3-yl, $R_2$ is 4-methoxyphenyl, A-L- is $a_1$-$L_1$, $a_1$ is 4-hydroxy-pyrrolidin-2-yl, $L_1$ is methyl, and $R_a$ is H; (cis 2S,4S)

a compound of Formula (I) wherein $R_1$ is 5-methoxypyridin-3-yl, $R_2$ is 4-methoxyphenyl, A-L- is $a_1$-$L_1$, $a_1$ is 4-hydroxy-pyrrolidin-2-yl, $L_1$ is methyl, $R_a$ is H, (trans 2S,4R)

a compound of Formula (I) wherein $R_1$ is 5-methoxypyridin-3-yl, $R_2$ is 4-methoxyphenyl, A-L- is $a_1$-$L_1$, $a_1$ is 4-hydroxy-pyrrolidin-2-yl, $L_1$ is methyl, and $R_a$ is H; (cis 2R,4R)

a compound of Formula (I) wherein $R_1$ is 5-cyano-pyridin-3-yl, $R_2$ is 4-methoxy-phenyl, A-L- is $a_2$-$L_2$, $a_2$ is morpholin-2-yl, $L_2$ is methyl, and $R_a$ is H; (racemic)

a compound of Formula (I) wherein $R_1$ is 5-fluoro-pyridin-3-yl, $R_2$ is 4-methoxy-phenyl, A-L- is $a_2$-$L_2$, $a_2$ is morpholin-2-yl, $L_2$ is methyl, and $R_a$ is H;

a compound of Formula (I) wherein $R_1$ is pyrimidin-5-yl, $R_2$ is 4-methoxy-phenyl, A-L- is $a_2$-$L_2$, $a_2$ is morpholin-2-yl, $L_2$ is methyl, and $R_a$ is H;

a compound of Formula (I) wherein $R_1$ is pyrimidin-5-yl, $R_2$ is 4-methoxy-phenyl, A-L- is $a_2$-$L_2$, $a_2$ is morpholin-3-yl, $L_2$ is methyl, and $R_a$ is H; (racemic)

a compound of Formula (I) wherein $R_1$ is 5-cyano-pyridin-3-yl, $R_2$ is 4-methoxy-phenyl, A-L- is $a_2$-$L_2$, $a_2$ is morpholin-3-yl, $L_2$ is methyl, and $R_a$ is H; (racemic)

a compound of Formula (I) wherein $R_1$ is 5-cyano-pyridin-3-yl, $R_2$ is 4-methoxy-phenyl, A-L- is $a_2$-$L_2$, $a_2$ is morpholin-3-yl, $L_2$ is methyl, and $R_a$ is H; (3S)
a compound of Formula (I) wherein $R_1$ is 5-fluoro-pyridin-3-yl, $R_2$ is 4-methoxy-phenyl, A-L- is $a_2$-$L_2$, $a_2$ is morpholin-3-yl, $L_2$ is methyl, and $R_a$ is H; (3S)
a compound of Formula (I) wherein $R_1$ is pyridin-3-yl, $R_2$ is 4-methoxy-phenyl, A-L- is $a_2$-$L_2$, $a_2$ is morpholin-3-yl, $L_2$ is methyl, and $R_a$ is H; (3S)
a compound of Formula (I) wherein $R_1$ is 5-cyano-pyridin-3-yl, $R_2$ is 4-methoxy-phenyl, A-L- is $a_3$-$L_3$, $a_3$ is imidazol-2-yl, $L_3$ is methyl, and $R_a$ is H;
a compound of Formula (I) wherein $R_1$ is 5-cyano-pyridin-3-yl, $R_2$ is 4-methoxy-phenyl, A-L- is $a_3$-$L_3$, $a_3$ is 3H-imidazol-4-yl, $L_3$ is methyl, and $R_a$ is H;
a compound of Formula (I) wherein $R_1$ is 5-cyano-pyridin-3-yl, $R_2$ is 4-methoxy-phenyl, A-L- is $a_3$-$L_3$, $a_3$ is 5-methyl-3H-imidazol-4-yl, $L_3$ is methyl, R and $R_a$ is H;
a compound of Formula (I) wherein $R_1$ is 5-cyano-pyridin-3-yl, $R_2$ is 4-methoxy-phenyl, A-L- is $a_3$-$L_3$, $a_3$ is 3-methyl-3H-imidazol-4-yl, $L_3$ is methyl, and $R_a$ is H;
a compound of Formula (I) wherein $R_1$ is 5-cyano-pyridin-3-yl, $R_2$ is 4-methoxy-phenyl, A-L- is $a_3$-$L_3$, $a_3$ is 2-ethyl-5-methyl-3H-imidazol-4-yl, $L_3$ is methyl, and $R_a$ is H;
a compound of Formula (I) wherein $R_1$ is pyridin-3-yl, $R_2$ is 4-methoxy-phenyl, A-L- is $a_3$-$L_3$, $a_3$ is 3H-imidazol-4-yl, $L_3$ is methyl, and $R_a$ is H;
a compound of Formula (I) wherein $R_1$ is 5-methylthio-pyridin-3-y, $R_2$ is 4-methoxy-phenyl, A-L- is $a_3$-$L_3$, $a_3$ is 3H-imidazol-4-yl, $L_3$ is methyl, and $R_a$ is H;
a compound of Formula (I) wherein $R_1$ is 5-methoxy-pyridin-3-yl, $R_2$ is 4-methoxy-phenyl, A-L- is $a_3$-$L_3$, $a_3$ is 3H-imidazol-4-yl, $L_3$ is methyl, and $R_a$ is H;
a compound of Formula (I) wherein $R_1$ is 5-methyl-pyridin-3-yl, $R_2$ is 4-methoxy-phenyl, A-L- is $a_3$-$L_3$, $a_3$ is 3H-imidazol-4-yl, $L_3$ is methyl, and $R_a$ is H;
a compound of Formula (I) wherein $R_1$ is 5-cyano-pyridin-3-yl, $R_2$ is 4-methoxy-phenyl, A-L- is $a_4$-$L_4$, $a_4$ is 2-amino, $L_4$ is propyl, and $R_a$ is H; (2S)
a compound of Formula (I) wherein $R_1$ is 5-cyano-pyridin-3-yl, $R_2$ is 4-methoxy-phenyl, A-L- is $a_4$-$L_4$, $a_4$ is 2-amino, $L_4$ is ethyl, and $R_a$ is H;
a compound of Formula (I) wherein $R_1$ is 5-cyano-pyridin-3-yl, $R_2$ is 4-methoxy-phenyl, A-L- is $a_4$-$L_4$, $a_4$ is 2-amino, $L_4$ is 4-methyl-pentyl, and $R_a$ is H; (2S)
a compound of Formula (I) wherein $R_1$ is pyrimidin-5-yl, $R_2$ is 4-methoxy-phenyl, A-L- is $a_4$-$L_4$, $a_4$ is 2-amino, $L_4$ is 4-methyl-pentyl, and $R_a$ is H; (2S)
a compound of Formula (I) wherein $R_1$ is 5-methyl-pyridin-3-yl, $R_2$ is 4-methoxyphenyl, A-L- is $a_4$-$L_4$, $a_4$ is 2-amino, $L_4$ is ethyl, and $R_a$ is H;
a compound of Formula (I) wherein $R_1$ is pyridin-3-yl, $R_2$ is 4-methoxyphenyl, A-L- is $a_4$-$L_4$, $a_4$ is 2-methylamino, $L_4$ is ethyl, and $R_a$ is H;
a compound of Formula (I) wherein $R_1$ is 5-cyano-pyridin-3-yl, $R_2$ is 4-methoxy-phenyl, A-L- is $a_5$-$L_5$, $a_5$ is cyclohexyl, $L_5$ is absent, and $R_a$ is H; (cis/trans mixture)
a compound of Formula (I) wherein $R_1$ is 5-cyano-pyridin-3-yl, $R_2$ is 4-methoxy-phenyl, A-L- is $a_5$-$L_5$, $a_5$ is cyclohexyl, $L_5$ is methyl, and $R_a$ is H; (2S,1R)
a compound of Formula (I) wherein $R_1$ is pyrimidin-5-yl, $R_2$ is 4-methoxy-phenyl, A-L- is $a_5$-$L_5$, $a_5$ is cyclohexyl, $L_5$ is methyl, and $R_a$ is H; (2S,1R)
a compound of Formula (I) wherein $R_1$ is 5-cyano-pyridin-3-yl, $R_2$ is 4-methoxy-phenyl, A-L- is $a_5$-$L_5$, $a_5$ is cyclobutyl, $L_5$ is methyl, and $R_a$ is H; (trans)
a compound of Formula (I) wherein $R_1$ is pyrimidin-5-yl, $R_2$ is 4-methoxy-phenyl, A-L- is $a_5$-$L_5$, $a_5$ is cyclobutyl, $L_5$ is methyl, and $R_a$ is H; (trans)
a compound of Formula (I) wherein $R_1$ is 5-cyano-pyridin-3-yl, $R_2$ is 4-methoxy-phenyl, A-L- is $a_5$-$L_5$, $a_5$ is cyclobutyl, $L_5$ is absent, and $R_a$ is H; (cis/trans mixture)
a compound of Formula (I) wherein $R_1$ is pyrimidin-5-yl, $R_2$ is 4-methoxy-phenyl, A-L- is $a_5$-$L_5$, $a_5$ is cyclobutyl, $L_5$ is absent, and $R_a$ is H; (cis/trans mixture)
a compound of Formula (I) wherein $R_1$ is pyridin-3-yl, $R_2$ is 4-methoxy-phenyl, A-L- is $a_5$-$L_5$, $a_5$ is cyclohexyl, $L_5$ is absent, and $R_a$ is H; (cis)
a compound of Formula (I) wherein $R_1$ is pyridin-3-yl, $R_2$ is 4-methoxy-phenyl, A-L- is $a_5$-$L_5$, $a_5$ is cyclohexyl, $L_5$ is absent, and $R_a$ is H; (racemic, cis/trans mixture)
a compound of Formula (I) wherein $R_1$ is pyridin-3-yl, $R_2$ is 4-methoxy-phenyl, A-L- is $a_5$-$L_5$, $a_5$ is cyclohexyl, $L_5$ is absent, and $R_a$ is H; (1RS,3SR racemic cis)
a compound of Formula (I) wherein $R_1$ is pyridin-3-yl, $R_2$ is 4-methoxy-phenyl, A-L- is $a_5$-$L_5$, $a_5$ is cyclohexyl, $L_5$ is absent, and $R_a$ is H; (1RS,2SR racemic single stereoisomer, unknown cis/trans)
a compound of Formula (I) wherein $R_1$ is 5-methoxy-pyridin-3-yl, $R_2$ is 4-methoxy-phenyl, A-L- is $a_5$-$L_5$, $a_5$ is cyclohexyl, $L_5$ is absent, and $R_a$ is H; racemic, mixture of cis/trans)
a compound of Formula (I) wherein $R_1$ is 5-methylthiopyridin-3-yl, $R_2$ is 4-methoxyphenyl, A-L- is $a_5$-$L_5$, $a_5$ is cyclohexyl, $L_5$ is absent, and $R_a$ is H; (racemic, mixture of cis and trans)
a compound of Formula (I) wherein $R_1$ is 5-methoxypyridin-3-yl, $R_2$ is 4-methoxyphenyl, A-L- is $a_5$-$L_5$, $a_5$ is cyclohexyl, $L_5$ is absent, and $R_a$ is H; (cis 1R,3S)
a compound of Formula (I) wherein $R_1$ is 5-methoxypyridin-3-yl, $R_2$ is 4-methoxyphenyl, A-L- is $a_5$-$L_5$, $a_5$ is cyclohexyl, $L_5$ is absent, $R_a$ is H; (cis 1S,3R)
a compound of Formula (I) wherein $R_1$ is 5-methoxypyridin-3-yl, $R_2$ is 4-methoxyphenyl, A-L- is $a_5$-$L_5$, $a_5$ is cyclohexyl, $L_5$ is absent, and $R_a$ is H; (trans, one enantiomer, absolute unknown)
a compound of Formula (I) wherein $R_1$ is 5-methoxypyridin-3-yl, $R_2$ is 4-methoxyphenyl, A-L- is $a_5$-$L_5$, $a_5$ is cyclohexyl, $L_5$ is absent, and $R_a$ is H; (trans, one enantiomer, absolute unknown)
a compound of Formula (I) wherein $R_1$ is 5-methyl-pyridin-3-yl, $R_2$ is 4-methoxyphenyl, A-L- is $a_5$-$L_5$, $a_5$ is cyclohexyl, $L_5$ is absent, and $R_a$ is H; (racemic, mixture of cis and trans)
a compound of Formula (I) wherein $R_1$ is 5-methylthiopyridin-3-yl, $R_2$ is 4-methoxyphenyl, A-L- is $a_5$-$L_5$, $a_5$ is cyclohexyl, $L_5$ is absent, and $R_a$ is H; (cis 1S,3R)
a compound of Formula (I) wherein $R_1$ is 5-methylthiopyridin-3-yl, $R_2$ is 4-methoxyphenyl, A-L- is $a_5$-$L_5$, $a_5$ is cyclohexyl, $L_5$ is absent, and $R_a$ is H; (cis 1R,3S)
a compound of Formula (I) wherein $R_1$ is 5-methylthiopyridin-3-yl, $R_2$ is 4-methoxyphenyl, A-L- is $a_5$-$L_5$, $a_5$ is cyclohexyl, $L_5$ is absent, and $R_a$ is H; (trans, one enantiomer, absolute unknown)
a compound of Formula (I) wherein $R_1$ is 5-methylthiopyridin-3-yl, $R_2$ is 4-methoxyphenyl, A-L- is $a_5$-$L_5$, $a_5$ is cyclohexyl, $L_5$ is absent, and $R_a$ is H; (trans, one enantiomer, absolute unknown)
a compound of Formula (I) wherein $R_1$ is pyridin-3-yl, $R_2$ is 4-cyclopropylphenyl, and A-L- and $R_a$ are taken together with the atoms to which they are attached to form piperazin-1-yl;

a compound of Formula (I) wherein $R_1$ is pyridin-3-yl, $R_2$ is 4-methoxyphenyl, A-L- is $a_5$-$L_5$, $a_5$ is cyclohexyl, $L_5$ is absent, and $R_a$ is H; (cis 1S,3R)

a compound of Formula (I) wherein $R_1$ is pyridin-3-yl, $R_2$ is 4-methoxyphenyl, A-L- is $a_5$-$L_5$, $a_5$ is cyclohexyl, $L_5$ is absent, and $R_a$ is H; (cis 1R,3S)

a compound of Formula (I) wherein $R_1$ is pyridin-3-yl, $R_2$ is 4-methoxyphenyl, A-L- is $a_5$-$L_5$, $a_5$ is cyclohexyl, $L_5$ is absent, and $R_a$ is H; (trans, one enantiomer, absolute unknown)

a compound of Formula (I) wherein $R_1$ is phenyl, $R_2$ is 4-methoxy-phenyl, and A-L- and $R_a$ are taken together with the atoms to which they are attached to form piperazin-1-yl;

a compound of Formula (I) wherein $R_1$ is 5-cyano-pyridin-3-yl, $R_2$ is 4-methoxy-phenyl, and A-L- and $R_a$ are taken together with the atoms to which they are attached to form piperazin-1-yl;

a compound of Formula (I) wherein $R_1$ is 5-cyano-pyridin-3-yl, $R_2$ is 4-methoxy-phenyl, and A-L- and $R_a$ are taken together with the atoms to which they are attached to form 3-aminopyrrolidin-1-yl;

a compound of Formula (I) wherein $R_1$ is pyridin-3-yl, $R_2$ is 4-methoxy-phenyl, and A-L- and $R_a$ are taken together with the atoms to which they are attached to form piperazin-1-yl;

a compound of Formula (I) wherein $R_1$ is 5-cyano-pyridin-3-yl, $R_2$ is 4-methoxy-phenyl, A-L- is, A-L- and $R_a$ are taken to form, 3-aminopyrrolidin-1-yl; 3S a compound of Formula (I) wherein $R_1$ is 5-cyano-pyridin-3-yl, $R_2$ is 4-methoxy-phenyl, and A-L- and $R_a$ are taken together with the atoms to which they are attached to form 3-aminopiperidin-1-yl; (3S)

a compound of Formula (I) wherein $R_1$ is 5-cyano-pyridin-3-yl, $R_2$ is 4-methoxy-phenyl, and A-L- and $R_a$ are taken together with the atoms to which they are attached to form 3-aminopiperidin-1-yl; (3R)

a compound of Formula (I) wherein $R_1$ is 5-cyano-pyridin-3-yl, $R_2$ is 4-methoxy-phenyl, and A-L- and $R_a$ are taken together with the atoms to which they are attached to form 3-aminomethylazetidin-1-yl;

a compound of Formula (I) wherein $R_1$ is 5-cyano-pyridin-3-yl, $R_2$ is 4-methoxy-phenyl, and A-L- and $R_a$ are taken together with the atoms to which they are attached to form 2-aminomethylpyrrolidin-1-yl; (2R)

a compound of Formula (I) wherein $R_1$ is 5-cyano-pyridin-3-yl, $R_2$ is 4-methoxy-phenyl, and A-L- and $R_a$ are taken together with the atoms to which they are attached to form 4-aminopiperidin-1-yl;

a compound of Formula (I) wherein $R_1$ is 5-cyano-pyridin-3-yl, $R_2$ is 4-methoxy-phenyl, and A-L- and $R_a$ are taken together with the atoms to which they are attached to form 2-aminomethylpyrrolidin-1-yl; (2R)

a compound of Formula (I) wherein $R_1$ is 5-cyano-pyridin-3-yl, $R_2$ is 4-methoxy-phenyl, and A-L- and $R_a$ are taken together with the atoms to which they are attached to form 3-oxopiperazin-1-yl;

a compound of Formula (I) wherein $R_1$ is pyridin-3-yl, $R_2$ is 4-methoxy-phenyl, and A-L- and $R_a$ are taken together with the atoms to which they are attached to form [1,4]diazepan-1-yl;

a compound of Formula (I) wherein $R_1$ is 5-cyano-pyridin-3-yl, $R_2$ is 4-methoxy-phenyl, and A-L- and $R_a$ are taken together with the atoms to which they are attached to form 2-oxopiperazin-1-yl;

a compound of Formula (I) wherein $R_1$ is 5-cyano-pyridin-3-yl, $R_2$ is 4-methoxy-phenyl, and A-L- and $R_a$ are taken together with the atoms to which they are attached to form 3,6-diaza-bicyclo[3.1.1]hept-3-ylamino;

a compound of Formula (I) wherein $R_1$ is pyridin-3-yl, $R_2$ is 4-methoxy-phenyl, v 3-aminopyrrolidin-1-yl; (3R)

a compound of Formula (I) wherein $R_1$ is pyridin-3-yl, $R_2$ is 4-methoxy-phenyl, and A-L- and $R_a$ are taken together with the atoms to which they are attached to form 3-amino-azetidin-1-yl;

a compound of Formula (I) wherein $R_1$ is 5-methylthio-pyridin-3-y, $R_2$ is 4-methoxy-phenyl, and A-L- and $R_a$ are taken together with the atoms to which they are attached to form piperazin-1-yl;

a compound of Formula (I) wherein $R_1$ is 5-methoxy-pyridin-3-yl, $R_2$ is 4-methoxy-phenyl, and A-L- and $R_a$ are taken together with the atoms to which they are attached to form piperazin-1-yl;

a compound of Formula (I) wherein $R_1$ is 5-cyano-pyridin-3-yl, $R_2$ is 4-methoxy-phenyl, and A-L- and $R_a$ are taken together with the atoms to which they are attached to form 3-methyl-piperazin-1-yl; (racemic)

a compound of Formula (I) wherein $R_1$ is 5-cyano-pyridin-3-yl, $R_2$ is 4-methoxy-phenyl, and A-L- and $R_a$ are taken together with the atoms to which they are attached to form 2-methyl-piperazin-1-yl; (2R)

a compound of Formula (I) wherein $R_1$ is 5-cyano-pyridin-3-yl, $R_2$ is 4-methoxy-phenyl, and A-L- and $R_a$ are taken together with the atoms to which they are attached to form 2-methyl-piperazin-1-yl; (2S)

a compound of Formula (I) wherein $R_1$ is 5-methoxy-pyridin-3-yl, $R_2$ is 4-methoxy-phenyl, and A-L- and $R_a$ are taken together with the atoms to which they are attached to form [1,4]-diazepan-1-yl;

a compound of Formula (I) wherein $R_1$ is 5-methylthiopyridin-3-yl, $R_2$ is 4-methoxyphenyl, and A-L- and $R_a$ are taken together with the atoms to which they are attached to form [1,4]-diazepan-1-yl;

a compound of Formula (I) wherein $R_1$ is 5-methylthiopyridin-3-yl, $R_2$ is 4-methoxyphenyl, and A-L- and $R_a$ are taken together with the atoms to which they are attached to form 3-amino-pyrrolidin-1-yl; (3R)

a compound of Formula (I) wherein $R_1$ is 5-methoxypyridin-3-yl, $R_2$ is 4-methoxyphenyl, and A-L- and $R_a$ are taken together with the atoms to which they are attached to form 3-amino-pyrrolidin-1-yl; (3R)

a compound of Formula (I) wherein $R_1$ is 5-methylthiopyridin-3-yl, $R_2$ is 4-methoxyphenyl, and A-L- and $R_a$ are taken together with the atoms to which they are attached to form 3,3-dimethyl-piperazin-1-yl;

a compound of Formula (I) wherein $R_1$ is 5-methyl-pyridin-3-yl, $R_2$ is 4-methoxyphenyl, and A-L- and $R_a$ are taken together with the atoms to which they are attached to form piperazin-1-yl;

a compound of Formula (I) wherein $R_1$ is 5-methyl-pyridin-3-yl, $R_2$ is 4-methoxyphenyl, and A-L- and $R_a$ are taken together with the atoms to which they are attached to form 3-amino-pyrrolidin-1-yl; (3R)

a compound of Formula (I) wherein $R_1$ is pyridin-3-yl, $R_2$ is 4-methoxyphenyl, and A-L- and $R_a$ are taken together with the atoms to which they are attached to form 4-methyl-piperazin-1-yl;

a compound of Formula (I) wherein $R_1$ is pyridin-3-yl, $R_2$ is 4-methoxyphenyl, and A-L- and $R_a$ are taken together with the atoms to which they are attached to form 2-methyl-piperazin-1-yl; (2S)

a compound of Formula (I) wherein $R_1$ is pyridin-3-yl, $R_2$ is 4-methoxyphenyl, and A-L- and $R_a$ are taken together with the atoms to which they are attached to form 3,3-dimethyl-piperazin-1-yl;

a compound of Formula (I) wherein $R_1$ is pyridin-3-yl, $R_2$ is 4-methoxyphenyl, and A-L- and $R_a$ are taken together with the atoms to which they are attached to form 3-methyl-piperazin-1-yl; (3S)

a compound of Formula (I) wherein $R_1$ is pyridin-3-yl, $R_2$ is 4-methoxyphenyl, and A-L- and $R_a$ are taken together with the atoms to which they are attached to form 3-methyl-piperazin-1-yl; (3R)

a compound of Formula (I) wherein $R_1$ is 5-methyl-pyridin-3-yl, $R_2$ is 4-methoxyphenyl, and A-L- and $R_a$ are taken together with the atoms to which they are attached to form [1,4]diazepan-1-yl;

a compound of Formula (I) wherein $R_1$ is pyridin-3-yl, $R_2$ is 4-methoxyphenyl, and A-L- and $R_a$ are taken together with the atoms to which they are attached to form 3,5-dimethyl-piperazin-1-yl; (cis)

a compound of Formula (I) wherein $R_1$ is 5-methoxypyridin-3-yl, $R_2$ is 4-methoxyphenyl, and A-L- and $R_a$ are taken together with the atoms to which they are attached to form 2-ethyl-piperazin-1-yl; (2S)

a compound of Formula (I) wherein $R_1$ is 5-methoxypyridin-3-yl, $R_2$ is 4-methoxyphenyl, and A-L- and $R_a$ are taken together with the atoms to which they are attached to form 3-ethyl-piperazin-1-yl; (3R).

For use in medicine, salts of compounds of formula (I) refer to non-toxic "pharmaceutically acceptable salts." Other salts may, however, be useful in the preparation of compounds of formula (I) or of their pharmaceutically acceptable salts thereof. Suitable pharmaceutically acceptable salts of compounds of formula (I) include acid addition salts which can, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid.

Furthermore, where the compounds of formula (I) carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include the following: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids and bases which may be used in the preparation of pharmaceutically acceptable salts include the following: acids including acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hippuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid;

and bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, sodium hydroxide, triethanolamine, tromethamine and zinc hydroxide.

Embodiments of the present invention include prodrugs of compounds of formula (I). In general, such prodrugs will be functional derivatives of the compounds that are readily convertible in vivo into the required compound. Thus, in the methods of treatment of embodiments of the present invention, the term "administering" encompasses the treatment of the various disorders described with the compound specifically disclosed or with a compound which may not be specifically disclosed, but which converts to the specified compound in vivo after administration to a patient. Conventional procedures for the selection and preparation of suitable prodrug derivatives are described, for example, in "Design of Prodrugs", ed. H. Bundgaard, Elsevier, 1985.

Where the compounds according to embodiments of this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention. The skilled artisan will understand that the term compound as used herein, is meant to include solvated compounds of Formula I.

Where the processes for the preparation of the compounds according to certain embodiments of the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

One embodiment of the present invention is directed to a composition comprising the (+)-enantiomer of a compound of formula (I) wherein said composition is substantially free from the (−)-isomer of said compound. In the present context, substantially free means less than 25%, preferably less than 10%, more preferably less than 5%, even more preferably less than 2% and even more preferably less than 1% of the (−)-isomer calculated as.

$$\%(+)\text{-enantiomer} = \frac{(\text{mass}(+)\text{-enantiomer})}{(\text{mass}(+)\text{-enantiomer}) + (\text{mass}(-)\text{-enantiomer})} \times 100$$

Another embodiment of the present invention is a composition comprising the (−)-enantiomer of a compound of formula (I) wherein said composition is substantially free from the (+)-isomer of said compound. In the present context, substantially free from means less than 25%, preferably less than 10%, more preferably less than 5%, even more preferably less than 2% and even more preferably less than 1% of the (+)-isomer calculated as $$\%(-)\text{-enantiomer} = \frac{(\text{mass}(-)\text{-enantiomer})}{(\text{mass}(+)\text{-enantiomer}) + (\text{mass}(-)\text{-enantiomer})} \times 100.$$

During any of the processes for preparation of the compounds of embodiments of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

Even though the compounds of embodiments of the present invention (including their pharmaceutically acceptable salts and pharmaceutically acceptable solvates) can be administered alone, they will generally be administered in admixture with a pharmaceutical carrier, excipient or diluent selected with regard to the intended route of administration and standard pharmaceutical practice. Thus, particular embodiments of the present invention are directed to pharmaceutical compositions comprising compounds of formula (I) and one or more than one pharmaceutically acceptable carrier, excipient or diluent.

By way of example, in the pharmaceutical and veterinary compositions of embodiments of the present invention, the compounds of formula (I) may be admixed with any suitable binder(s), lubricant(s), suspending agent(s), coating agent(s), and/or solubilizing agent(s).

Tablets or capsules of the compounds may be administered one or two or more at a time, as appropriate. It is also possible to administer the compounds in sustained release formulations.

Alternatively, compounds of formula (I) can be administered by inhalation (intratracheal or intranasal) or in the form of a suppository or pessary, or they may be applied topically in the form of a lotion, solution, cream, ointment or dusting powder. For example, they can be incorporated into a cream consisting of an aqueous emulsion of polyethylene glycols or liquid paraffin. They can also be incorporated, at a concentration of between 1% and 10% by weight, into an ointment consisting of a white wax or white soft paraffin base together with such stabilizers and preservatives as may be required. An alternative means of transdermal administration is by use of a skin patch.

For some applications, preferably the compositions are administered orally in the form of tablets containing excipients such as starch or lactose, or in capsules or ovules either alone or in admixture with excipients, or in the form of elixirs, solutions or suspensions containing flavoring or coloring agents.

The compositions (as well as the compounds alone) can also be injected parenterally, for example intracavernosally, intravenously, intramuscularly, subcutaneously, intradermally or intrathecally. In this case, the compositions will comprise a suitable carrier or diluent.

For parenteral administration, the compositions are best used in the form of a sterile aqueous solution which may contain other substances, for example, enough salts or monosaccharides to make the solution isotonic with blood.

For buccal or sublingual administration, the compositions may be administered in the form of tablets or lozenges, which can be formulated in a conventional manner.

By way of further example, pharmaceutical and veterinary compositions containing one or more of the compounds of formula (I) as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral, etc.). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations also may be coated with substances such as sugars or be enterically-coated so as to modulate the major site of absorption. For parenteral administration, the carrier will usually consist of sterile water, and other ingredients may be added to increase solubility or preservation. Injectable suspensions or solutions may also be prepared utilizing aqueous carriers along with appropriate additives.

A therapeutically effective amount of compounds of formula (I) or a pharmaceutical composition thereof comprises a dose range from about 0.1 mg to about 3000 mg, in particular from about 1 mg to about 1000 mg or, more particularly, from about 10 mg to about 500 mg of active ingredient in a regimen of about 1 to 4 times per day for an average (70 kg) human; although, it is apparent to one skilled in the art that the therapeutically effective amount for active compounds of the invention will vary as will the conditions being treated.

For oral administration, a pharmaceutical composition is preferably provided in the form of tablets containing 0.01, 10.0, 50.0, 100, 150, 200, 250, and 500 milligrams of the active ingredient for the symptomatic adjustment of the dosage to the subject to be treated.

Advantageously, compounds of formula (I) may be administered in a single daily dose, or the total daily dosage may be administered in divided doses of two, three or four times daily. Furthermore, compounds of formula (I) can be administered in intranasal form via topical use of suitable intranasal vehicles, or via transdermal skin patches well known to those skilled in that art.

It is also apparent to one skilled in the art that the therapeutically effective dose for active compounds of formula (I) or a pharmaceutical composition thereof will vary according to the desired effect. Therefore, optimal dosages to be administered may be readily determined and will vary with the particular compound used, the mode of administration, the strength of the preparation, and the advancement of the disease condition. In addition, factors associated with the particular subject being treated, including subject age, weight, diet and time of administration, will result in the need to adjust the dose to achieve an appropriate therapeutic level. The above dosages are thus exemplary of the average case. There can be, of course, individual instances wherein higher or lower dosage ranges are merited, and such are within the scope of this invention.

Compounds of formula (I) may be administered in any of the foregoing compositions and dosage regimens or by means of those compositions and dosage regimens established in the art whenever use of the compounds of formula (I) as analgesics is required for a subject in need thereof.

Examples of pain intended to be within the scope of the present invention include, but are not limited to, inflammatory pain, centrally mediated pain, peripherally mediated pain, visceral pain, structural or soft tissue injury related pain, progressive disease related pain, neuropathic pain and acute pain such as caused by acute injury, trauma or surgery and chronic pain such as headache and that caused by neuropathic conditions, post-stroke conditions, cancer, and migraine.

Compounds of the present invention are also useful as immunosuppressants, antiinflammatory agents, agents for the treatment and prevention of neurological and psychiatric conditions, for instance, depression and Parkinson's disease, agents for the treatment of urological and reproductive conditions, for instance, urinary incontinence and premature ejaculation, medicaments for drug and alcohol abuse, agents for treating gastritis and diarrhea, cardiovascular agents and cardioprotective agents and agents for the treatment of respiratory diseases.

The compounds of the present invention are also useful in treating pain caused by osteoarthritis, rheumatoid arthritis, fibromyalgia, migraine, headache, toothache, burn, sunburn, snake bite (in particular, venomous snake bite), spider bite, insect sting, neurogenic bladder, benign prostatic hypertrophy, interstitial cystitis, rhinitis, contact dermatitis/hypersensitivity, itch, eczema, pharyngitis, mucositis, enteritis, cellulites, causalgia, sciatic neuritis, mandibular joint neuralgia, peripheral neuritis, polyneuritis, stump pain, phantom limb pain, post-operative ileus, cholecystitis, postmastectomy pain syndrome, oral neuropathic pain, Charcot's pain, reflex sympathetic dystrophy, Guillain-Barre syndrome, meralgia paresthetica, burning-mouth syndrome, cluster headache, migraine headache, peripheral neuropathy, bilateral peripheral neuropathy, diabetic neuropathy, optic neuritis, postfebrile neuritis, migrating neuritis, segmental neuritis, Gombault's neuritis, neuronitis, cervicobrachial neuralgia, cranial neuralgia, geniculate neuralgia, glossopharyngial neuralgia, migrainous neuralgia, idiopathic neuralgia, intercostals neuralgia, mammary neuralgia, Morton's neuralgia, nasociliary neuralgia, occipital neuralgia, red neuralgia, Sluder's neuralgia, splenopalatine neuralgia, supraorbital neuralgia, vidian neuralgia, inflammatory bowel disease, irritable bowel syndrome, sinus headache, tension headache, labor, childbirth, menstrual cramps, and cancer.

In regard to the use of the present compounds in treatment of the diseases or conditions such as those listed above, a therapeutically effective dose can be determined by persons skilled in the art by the use of established animal models. The therapeutically effective dose of the compounds of Formula (I) exemplified in such a treatment is from about 0.001 mg/kg/day to about 300 mg/kg/day. Particularly, the range is from about 0.5 to about 5.0 mg/kg of body weight per day; and more particularly, from about 1.0 to about 3.0 mg/kg of body weight per day. The compounds may be administered on a regimen of 1 to 4 times per day.

General Synthetic Methods

Representative compounds of the present invention can be synthesized in accordance with the general synthetic methods described below and illustrated in the schemes and examples that follow. Since the schemes are an illustration, the invention should not be construed as being limited by the chemical reactions and conditions described in the schemes. The various starting materials used in the schemes and examples are commercially available or may be prepared by methods well within the skill of persons versed in the art. The variables are as defined herein.

Abbreviations used in the instant specification, particularly the schemes and examples, are as follows:

| | |
|---|---|
| AcCl | acetyl chloride |
| AcOH | glacial acetic acid |
| aq. | aqueous |
| Bn or Bzl | benzyl |
| conc. | concentrated |
| DBU | 1,8-diazabicyclo[5.4.0]undec-7-ene |
| DCM | dichloromethane |
| DMF | N,N-dimethylformamide |
| DMSO | dimethylsulfoxide |
| dppf | 1,1'-bis(diphenylphosphino)ferrocene |
| ESI | electron-spray ionization |
| EtOAc | ethyl acetate |
| EtOH | ethanol |
| h or hrs | hour(s) |
| HATU | O-(1H-7-azabenzotriazol-1-yl)--1,1,3,3-tetramethyl-uronium-hexafluorophosphate |
| HPLC | high performance liquid chromatography |
| Me | methyl |
| MeOH | methanol |
| MHz | megahertz |
| min | minutes |
| MPLC | medium pressure liquid chromatography |
| MS | mass spectroscopy |
| NMR | nuclear magnetic resonance |
| NT | not tested |
| Ph | phenyl |
| Pd/C | palladium on activated carbon |
| $Ph_3P$ | triphenylphosphine |
| PPA | polyphosphoric acid |
| rt | room temperature |
| TBDMS | tetra-butyldimethylsilane |
| TEA/$Et_3N$ | triethylamine |
| TFA | trifluoroacetic acid |
| THF | tetrahydrofuran |
| TLC | thin layer chromatography |
| TMS | tetramethylsilane or tetramethylsilyl |

Scheme A illustrates a route for the synthesis of compounds of Formula (I)-A wherein A-L is $a_1$-$L_1$- or $a_2$-$L_2$-.

Scheme A

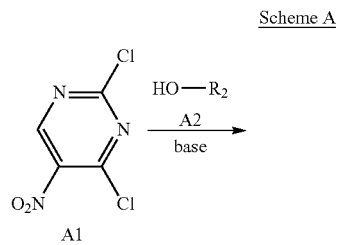

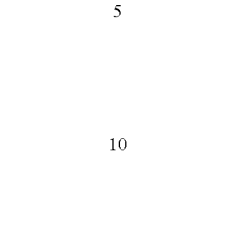

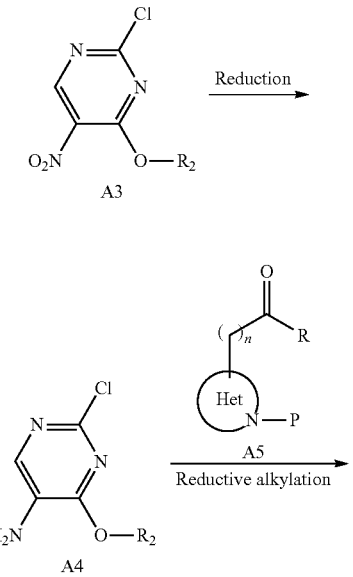

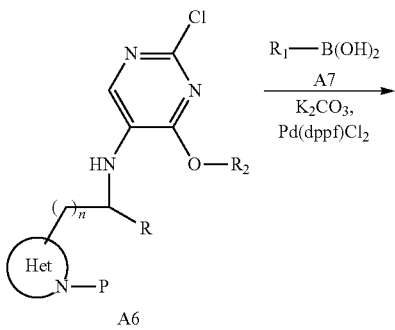

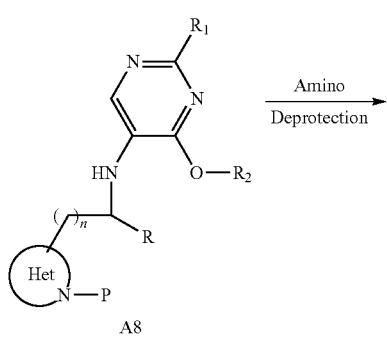

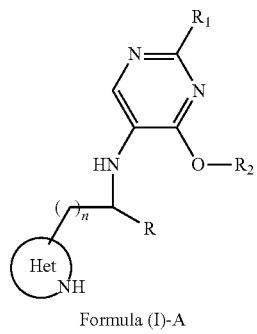

Formula (I)-A

R = H and n = 0 or 1
or R = CH$_3$ and n = 0

The compound of formula A1 is either commercially available or can be made by known methods, including those described in the scientific literature. A compound of formula A1 may be treated with a compound of formula A2 under basic conditions to afford a compound of formula A3. The nitro group of a compound of formula A3 may be reduced to its corresponding primary amino group of formula A4 by the action of a reducing agent such as zinc, tin, or iron in acetic acid, or by catalytic hydrogenation. The resultant amino group of a compound of formula A4 may undergo a reductive alkylation with an amino-protected aldehyde (R is H) or ketone (R is methyl) of formula A5 (wherein P is an amino protecting group) in the presence of a hydride source such as triacetoxysodium borohydride to install the A-L- portion of compounds of the present invention. A compound of formula A6 may be coupled with an $R_1$-substituted boronic acid of formula A7 in the presence of a transition metal catalyst such as Pd(dppf)Cl$_2$ and a base such as potassium carbonate to afford a compound of formula A8. Similarly, $R_1$ substituents may be installed under conventional Stille coupling conditions using appropriately substituted tin reagents. The amine of a compound of formula A8 may be deprotected under appropriate conditions known to those skilled in the art to afford a compound of formula (I)-A of the present invention. For example, Boc-protected amines may be deprotected under acidic conditions using reagents such as HCl, TFA, and the like. Likewise, Cbz-protected amines may be deprotected under acidic conditions or by catalytic hydrogenation.

Scheme B illustrates a route for the synthesis of compounds of Formula (I)-B wherein A-L is $a_1$-$L_1$- or $a_3$-$L_3$- and L is absent.

Scheme B

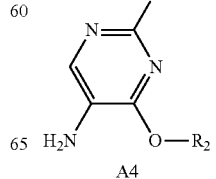

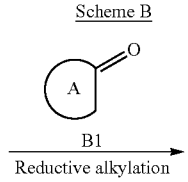

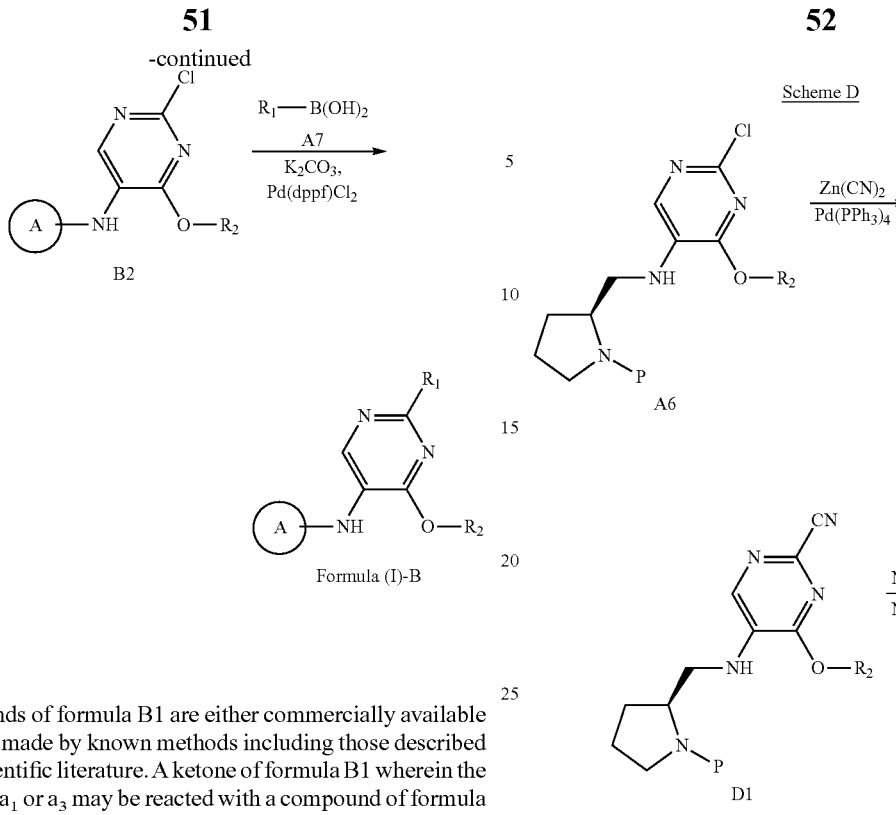

Compounds of formula B1 are either commercially available or can be made by known methods including those described in the scientific literature. A ketone of formula B1 wherein the A-ring is $a_1$ or $a_3$ may be reacted with a compound of formula A4 using the methods described in Scheme A to afford a compound of formula B2.

Scheme C illustrates a route for the synthesis of certain A-L- intermediates useful toward compounds of the present invention wherein A-L- is $a_3$-$L_3$- and $L_3$ is $C_{1-2}$alkyl.

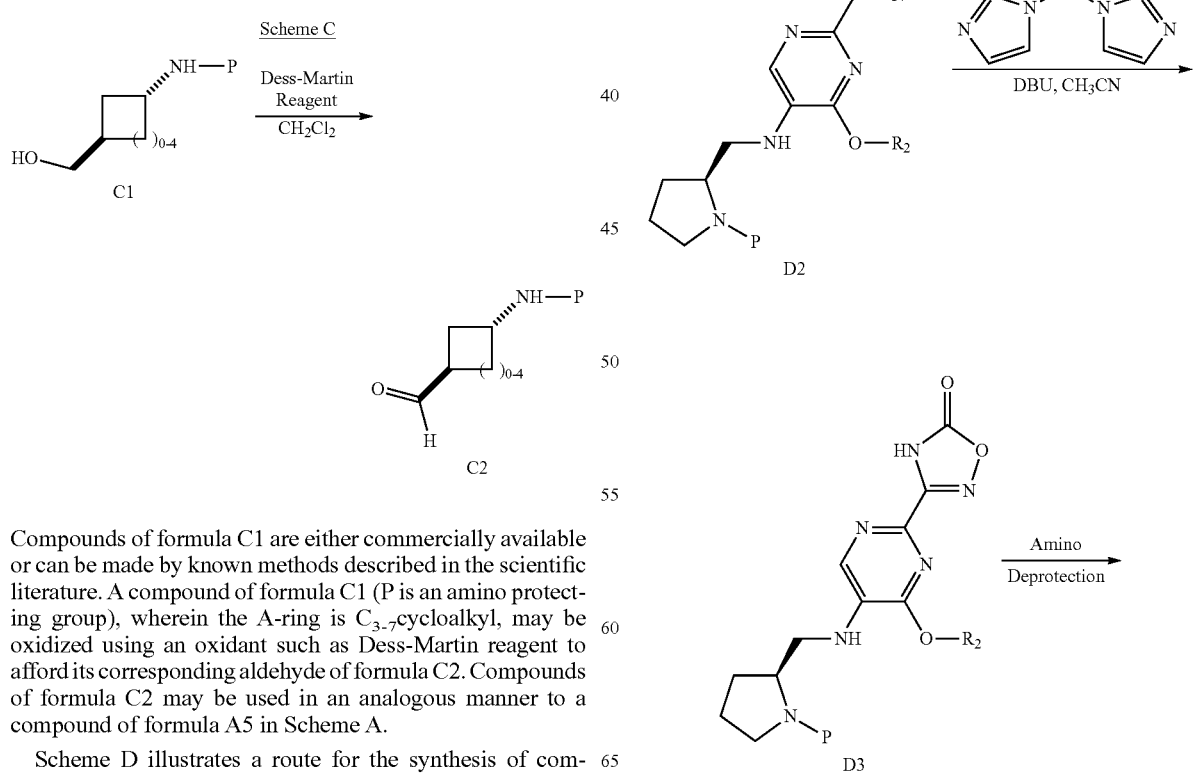

Compounds of formula C1 are either commercially available or can be made by known methods described in the scientific literature. A compound of formula C1 (P is an amino protecting group), wherein the A-ring is $C_{3-7}$cycloalkyl, may be oxidized using an oxidant such as Dess-Martin reagent to afford its corresponding aldehyde of formula C2. Compounds of formula C2 may be used in an analogous manner to a compound of formula A5 in Scheme A.

Scheme D illustrates a route for the synthesis of compounds of formula (I)-D wherein $R_1$ is 4H-[1,2,4]oxadiazol-5-on-yl.

53
-continued

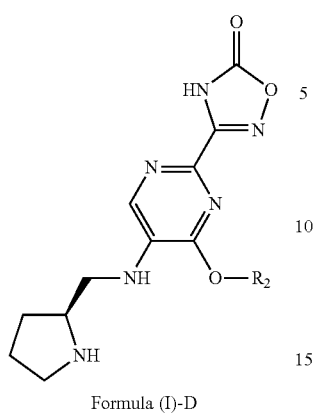

Formula (I)-D

A compound of formula A6 may be converted to its corresponding cyanide of formula D1 by the action of zinc(II) cyanide in the presence of a palladium catalyst and DMF. Subsequent treatment of a compound of formula D1 with hydroxylamine under of microwave irradiation affords a compound of formula D2. A compound of formula D2 may be converted to a compound of formula D3 via condensation with CDI in the presence of an appropriate coupling agent such as DBU and the like. Deprotection of the amino functionality using conventional chemistry affords compounds of formula (I)-D.

Scheme E illustrates a route for the synthesis of compounds of formula (I)-E wherein $R_a$ is $C_{1-4}$alkylcarbonyl.

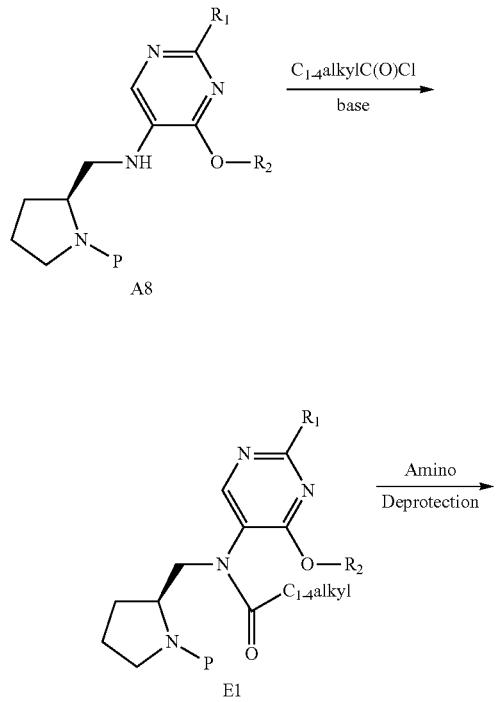

54
-continued

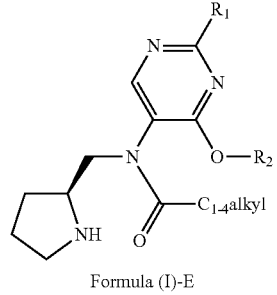

Formula (I)-E

A compound of formula A8 may by acylated by the action of a suitable acylating agent, such as an acid chloride, anhydride, or the like to afford a compound of formula E1. Amino deprotection by the standard methods discussed herein affords a compound of formula (I)-E.

Scheme F illustrates a route for the synthesis of compounds of formula (I)-F wherein $R_2$ is phenyl substituted with amino or a derivative thereof.

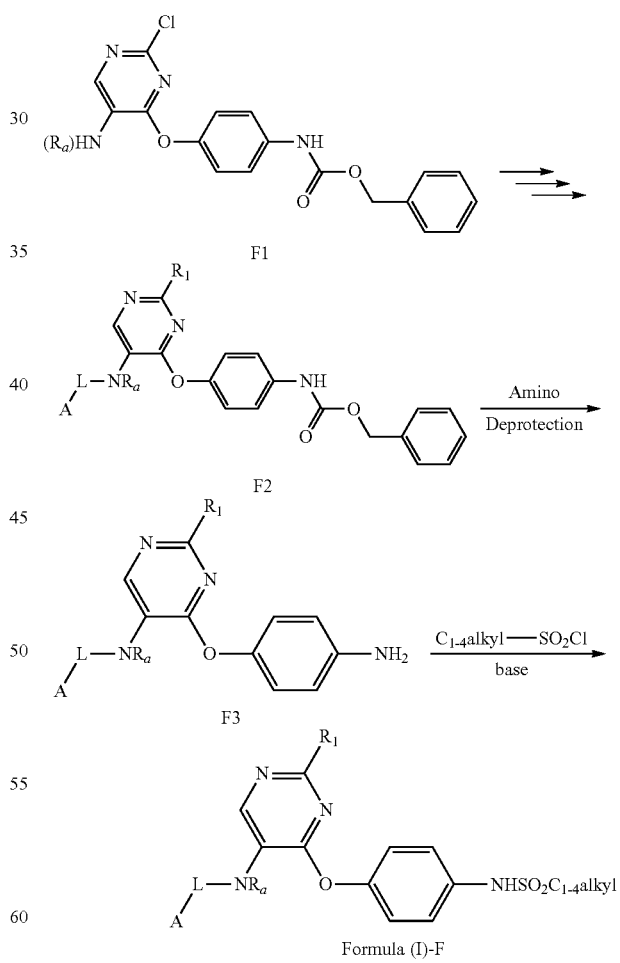

The compounds of formula F1 can be made in an analogous manner to a compound of formula A4 together with known methods described in the scientific literature. A compound of formula F1 may be converted to a compound of formula F2 via the synthetic sequences presented in Scheme A. The Cbz-amino protecting group may be removed with palladium catalyzed hydrogenation to afford the corresponding primary amino compound of formula F3. At this stage, the amino group may be treated with a variety of electrophilic reagents to afford desirable $R_2$ substitutions of the present invention. For example, treatment with a $C_{1-4}$alkylsulfonyl chloride affords a compound of formula (I)-F. Likewise, the amino group of F3 may be acylated using conventional acylating agents or treated with an alkylating agent to make additional amino derivatives.

Scheme G illustrates an alternate route for the synthesis of intermediates of formula A8.

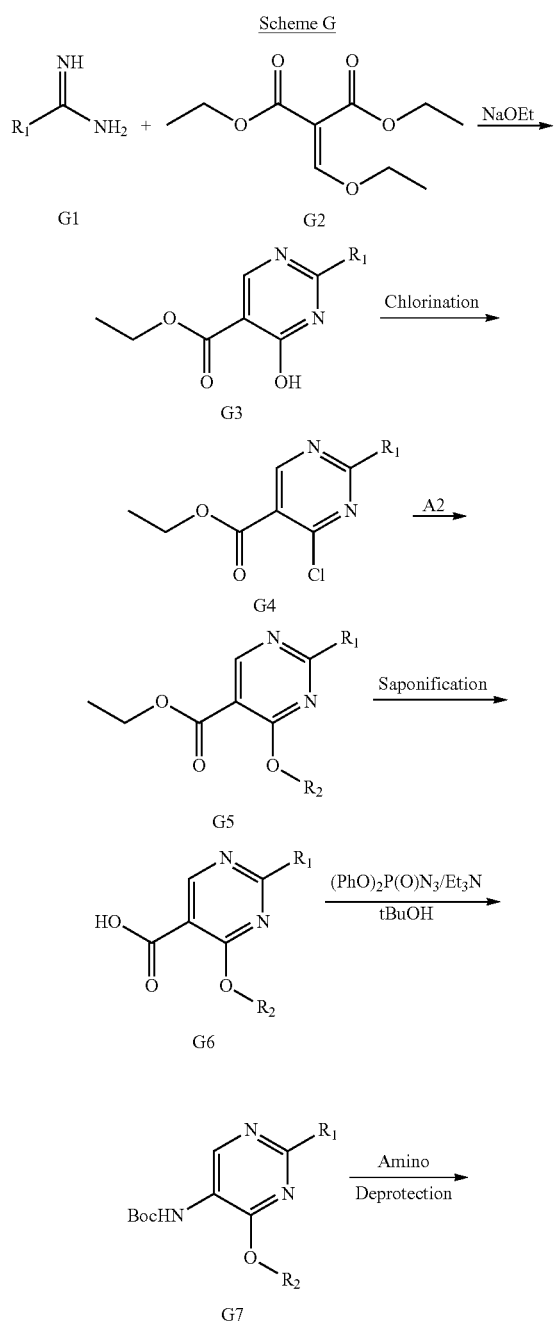

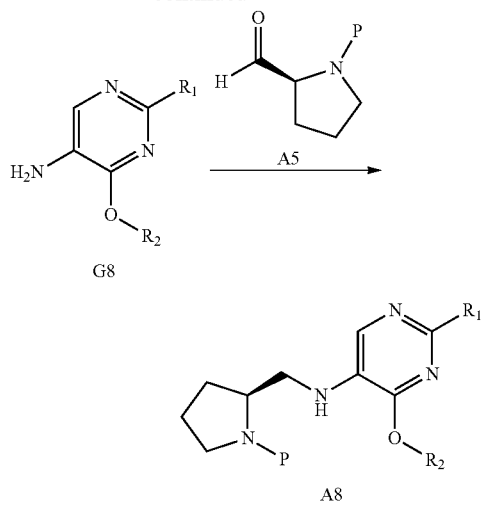

Compounds of formula G1 are either commercially available or can be made by known methods described in the scientific literature. A compound of formula G1 may be condensed with a compound of formula G2 in the presence of alkoxide to afford a pyrimidine of formula G3. The hydroxy group may be converted to its corresponding chloride of formula G4 by the action of a chlorinating agent such as thionyl chloride, phosphorus trichloride, or the like. Nucleophilic addition of a compound of formula A2 affords a compound of formula G5, which may be saponified by treatment with hydroxide to afford a carboxylic acid of formula G6. Treatment with diphenylphosphorylazide in t-butanol leads to a Curtius arrangement to afford a Boc-protected amine of formula G7. Removal of the Boc protecting group provides the amine of formula G8 which may subsequently undergo a reductive alkylation with a compound of formula A5 to afford a compound of formula A8.

Scheme H illustrates a route for the synthesis of intermediates of formula H5 that may be useful for the preparation of compounds of formula (I) wherein $R_2$ is di($C_{1-4}$alkyl)aminocarbonyl-substituted phenyl.

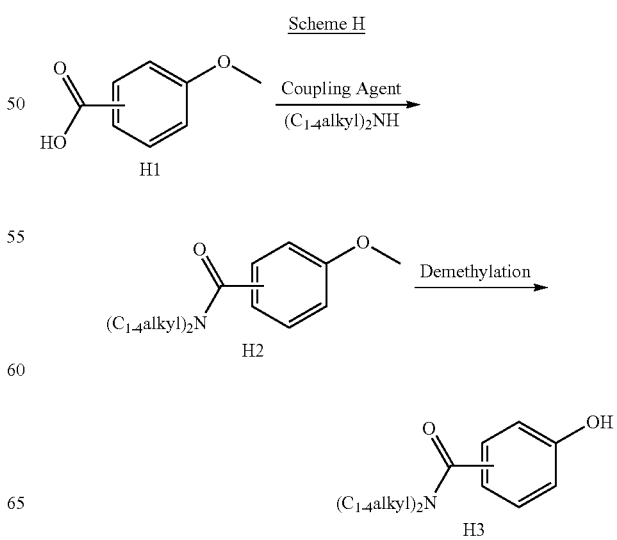

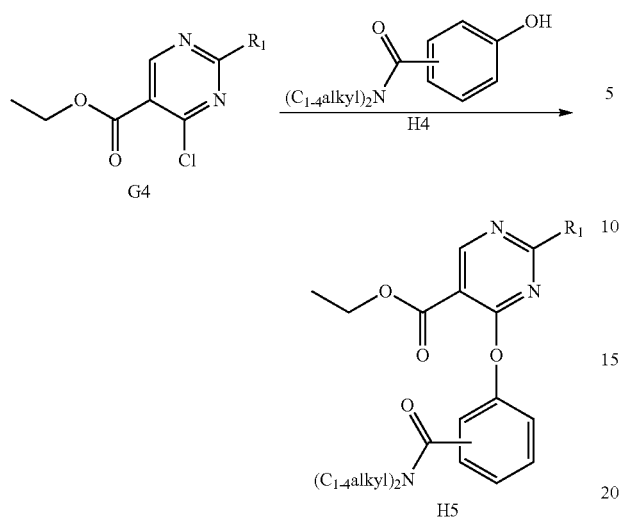

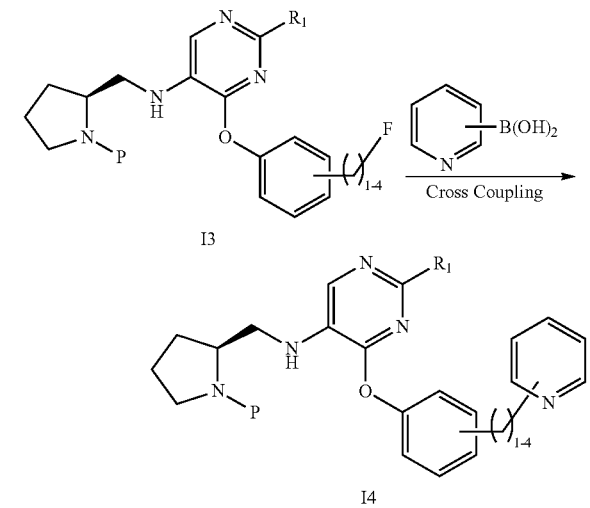

Compounds of formula H1 are either commercially available or can be made by known methods described in the scientific literature. A compound of formula I1 may be coupled with an appropriately substituted amine in the presence of a suitable coupling agent such as HATU to afford an amide of formula H2. Upon conventional deprotection of the phenolic group, a compound of formula H3 may be reacted with a compound of formula G4 to afford a compound of formula H4 wherein $R_2$ is an aminocarbonyl-substituted phenyl ring. In a manner analogous to that of intermediate G5, a compound of formula H4 may be converted to a desired compound of formula H5 using the methods of Scheme G.

Scheme I illustrates a route for the preparation of compounds of Formulae-I2, I3, and I4 wherein $R_2$ is phenyl substituted with hydroxy($C_{1-4}$)alkyl, fluoro($C_{1-4}$)alkyl, or pyridinyl($C_{1-4}$)alkyl, respectively.

A compound of formula I1 may be prepared according to the methods taught herein using conventional reagents. A compound of formula I1 may be coupled with a compound of formula A7 as described herein to afford an $R_1$-substituted compound of formula I2. A compound of formula I2 may be treated with appropriate reagents to afford amino-deprotected compounds of Formula (I) wherein $R_2$ is phenyl substituted with hydroxy($C_{1-4}$)alkyl. A compound of formula I2 may be converted to a fluoro-alkyl substituted compound of formula I3 by the action of DAST. Subsequent removal of protecting group P affords desired compounds of Formula (I) wherein $R_2$ is phenyl substituted with fluoro$C_{1-4}$)alkyl.

Furthermore, a compound of formula I3 may undergo a palladium-catalyzed cross coupling reaction with a pyridine boronic acid to afford compounds of formula I4, which upon removal of protecting group P result in compounds of Formula (I) wherein $R_2$ is phenyl substituted with pyridinyl($C_{1-4}$)alkyl.

Scheme J illustrates a route for the preparation of compounds of formula (I)-J wherein A-L- is taken with $R_a$ and the nitrogen atom to which they are both attached to form a nitrogen-bound heterocyclyl as defined herein.

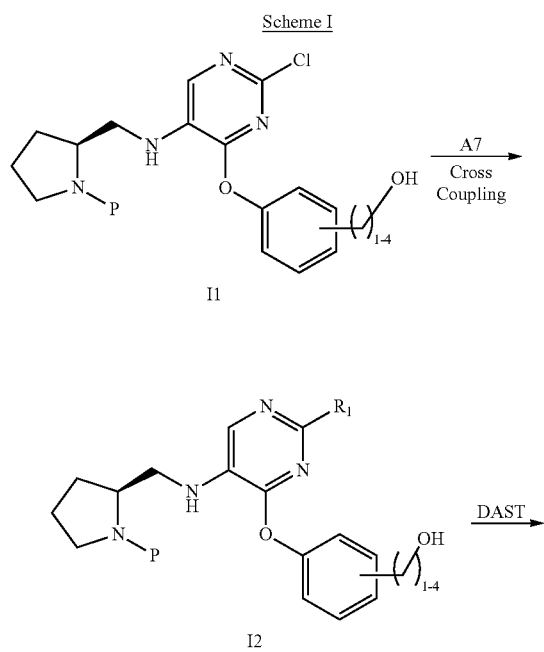

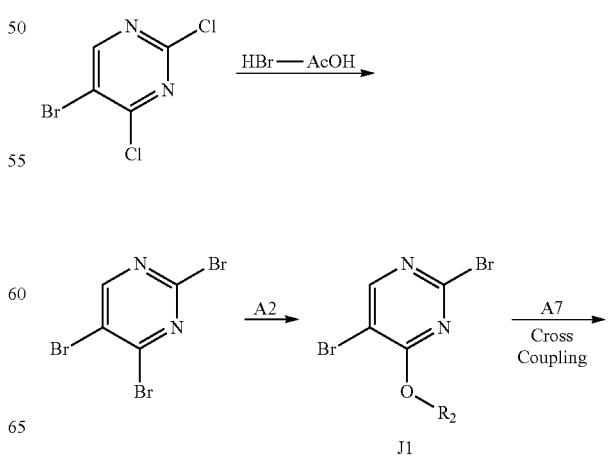

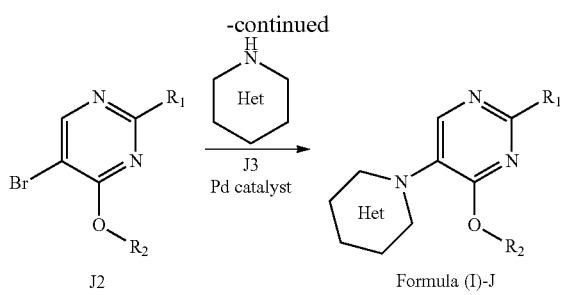

Commercially available 2,4-dichloro-5-bromo-pyrimidine may be treated with HBr solution under acidic conditions to form 2,4,5-tribromo-pyrimidine, which may then be reacted with a compound of formula A2 to afford a compound of formula J1. A compound of formula J1 may undergo a palladium catalyzed substitution with a compound of formula A7 under conditions described herein to afford a compound of formula J2. A compound of formula J2 may undergo a second palladium catalyzed substitution with an amino-containing heterocycle (Het), as defined herein, to afford a compound of Formula (I)-J.

Scheme K illustrates a route for the preparation of compounds of formula (I)-K wherein A-L- is $a_3$-$L_3$ and $L_3$ is absent.

A compound mixture of formula K1 is either commercially available or can be made by known methods described in the scientific literature. The free amine of a compound of formula K1 may be Cbz-protected using conventional synthetic methods and subsequently separated into its diastereomeric pairs, of formulae K2-a and K2-b, using normal phase column chromatography. A diastereomeric pair of formula K2-a may be further separated into its individual enantiomers, K2-a1 and K2-a2, using chiral column chromatography. At this stage, each enantiomer (a compound of formula K2-a1 is illustrated) may be Cbz-deprotected using standard palladium catalyzed hydrogenation to afford a compound of formula K3. A compound of formula K3 may be coupled with a compound of formula J2 as described herein to afford a compound of formula K4 which, upon deprotection of its amino group, affords a compound of formula (I)-K.

SPECIFIC EXAMPLES

Reagents were purchased from commercial sources. Nuclear magnetic resonance (NMR) spectra for hydrogen atoms were measured in the indicated solvent with tetramethylsilane (TMS) as the internal standard on a Bruker Avance or Varian (300 or 400 MHz) spectrometer. The values are expressed in parts per million downfield from TMS. The mass spectra (MS) were determined on a Micromass Platform LC

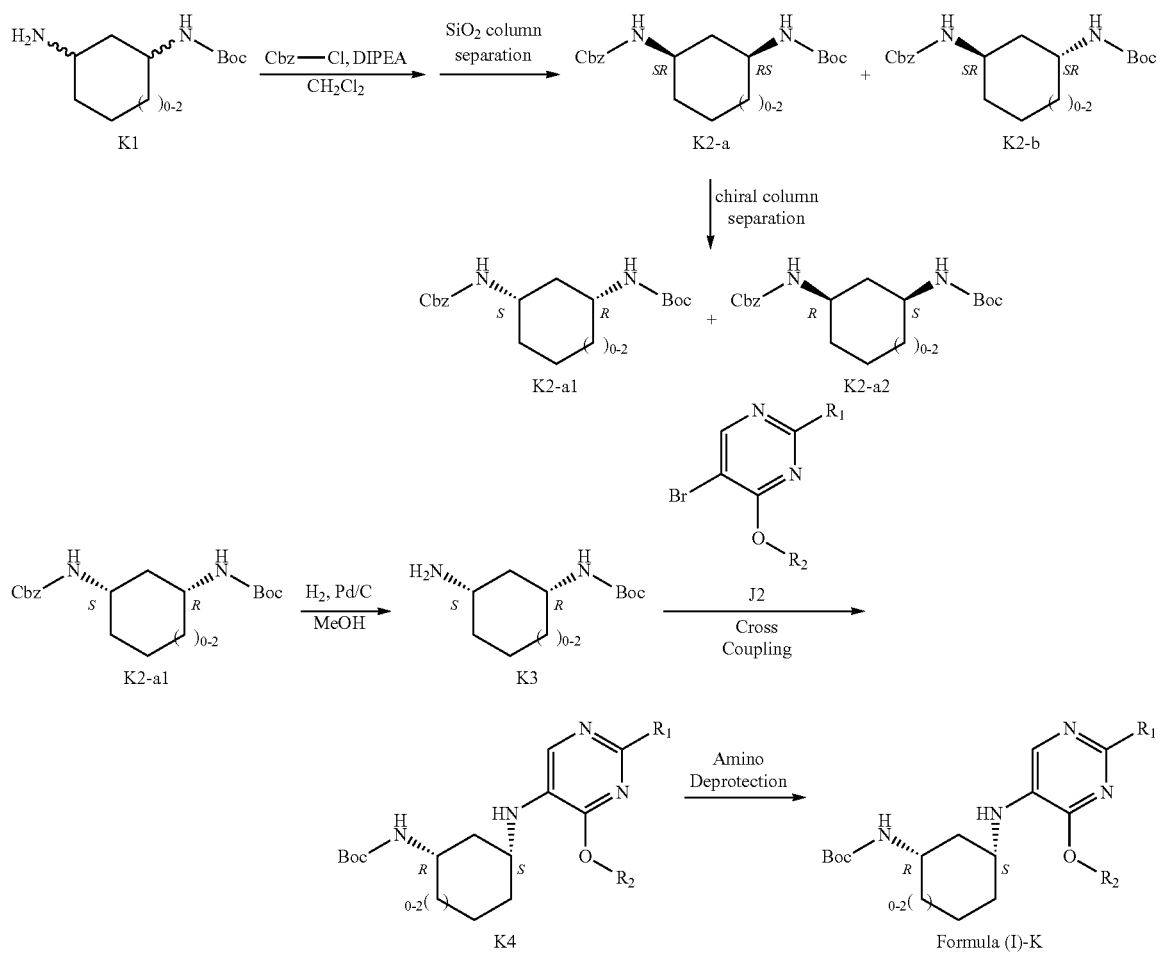

or Agilent 1100 LCMS spectrometer as (ESI) m/z (M+H)+ using an electrospray technique. Microwave accelerated reactions were performed using a CEM Discover or Biotage microwave instrument, and were contained in a sealed pressure vessel unless otherwise noted. Stereoisomeric compounds may be characterized as racemic mixtures or as separate diastereomers and enantiomers thereof using X-ray crystallography and other methods known to one skilled in the art. Unless otherwise noted, the materials used in the examples were obtained from readily available commercial suppliers or synthesized by standard methods known to one skilled in the art of chemical synthesis. The substituent groups, which vary between examples, are hydrogen unless otherwise noted.

Example 1

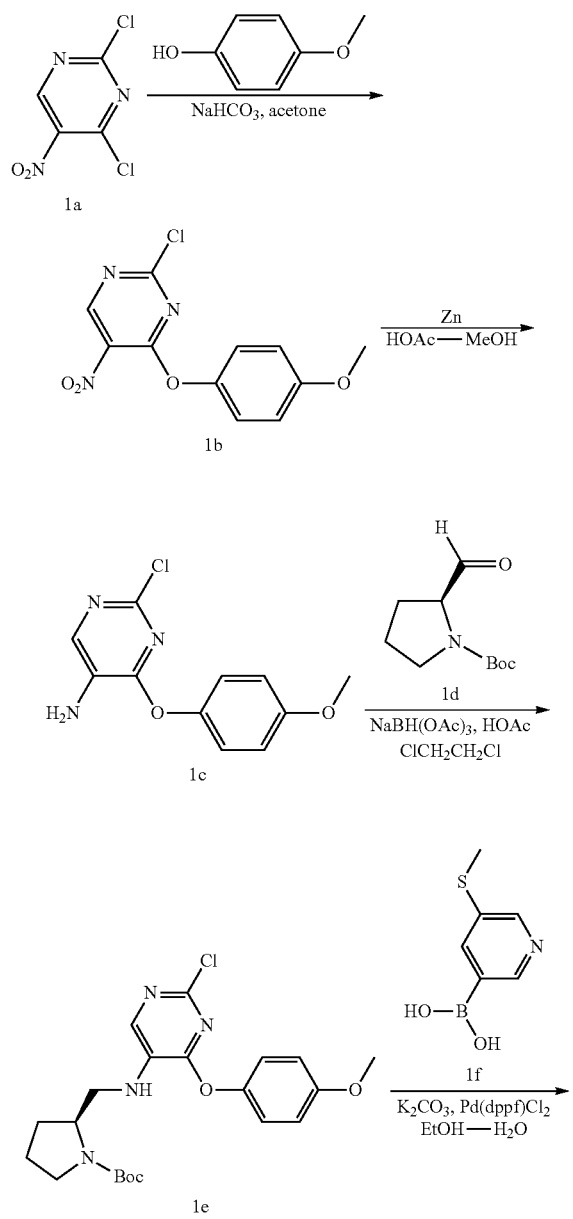

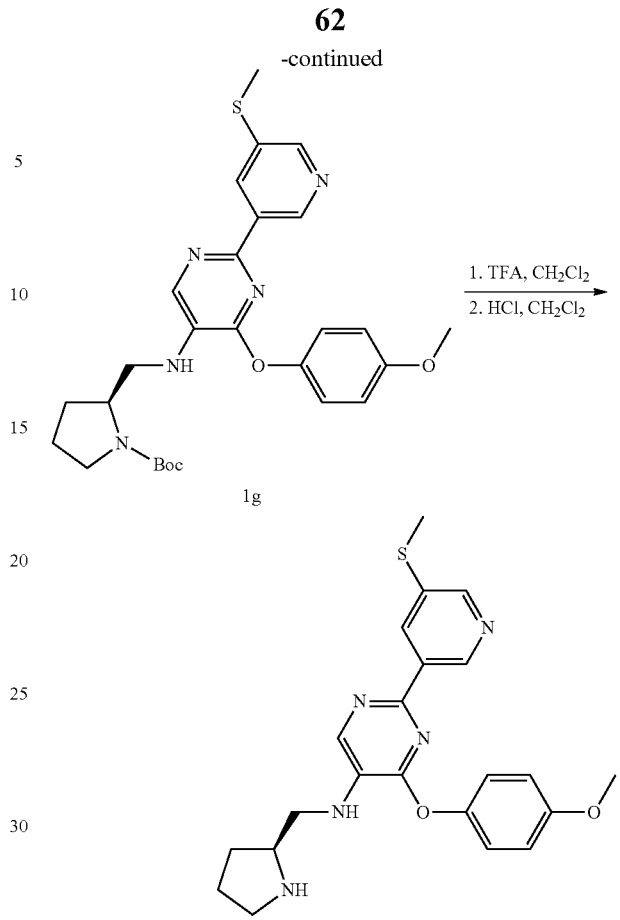

A. 2-Chloro-4-(4-methoxy-phenoxy)-5-nitro-pyrimidine (1b)

To a solution of 2,4-dichloro-5-nitro-pyrimidine (Compound 1a) (5.82 g; 30.0 mmol) in acetone (480 mL), cooled to 0° C., was added a solution of 4-methoxy-phenol (3.75 g; 30.0 mmol) in a mixture of 1 N $NaHCO_{3(aq)}$ (30 mL) and $H_2O$ (120 mL) dropwise by an addition funnel. After completion of addition, the reaction mixture was allowed to warm to ambient temperature, and was then stirred at room temperature for 3 h. The resultant mixture was evaporated in vacuo, and the residue was washed sequentially with EtOAc, 1 N $NaOH_{(aq)}$, and $H_2O$. The organic phase was washed sequentially with $H_2O$ and brine, and dried over $Na_2SO_4$. The mixture was filtered and the solvent was evaporated under reduced pressure to give the crude material. The crude material was recrystallized from $Et_2O$-hexanes to afford Compound 1b (7.70 g; 91% yield) as a yellow solid. $^1$H-NMR (400 MHz, $CDCl_3$): δ 9.17 (s, 1H), 7.13-7.15 (m, 2H), 6.98-7.01 (m, 2H), 3.87 (s, 3H); MS: m/z 282.0 (M+H)+.

B. 2-Chloro-4-(4-methoxy-phenoxy)-pyrimidin-5-ylamine (1c)

To a stirred solution of Compound 1b (7.72 g; 27.4 mmol) in a mixture of glacial acetic acid (60 mL) and MeOH (120 mL) was added zinc dust (5.38 g; 82.2 mol) in portions at ambient temperature. The reaction mixture was stirred at room temperature for 20 h. The resultant mixture was filtered through a microglass filter and the filtrate was neutralized to pH 7 with 2 N KOH$_{(aq)}$. The mixture was partitioned between CH$_2$Cl$_2$ and H$_2$O. The organic phase was washed sequentially with H$_2$O and brine, and dried over Na$_2$SO$_4$. The mixture was filtered and the solvent was removed under reduced pressure to give the crude material. The crude material was purified by flash column chromatography (SiO$_2$), eluting with a heptane-EtOAc gradient to afford Compound 1c (5.52 g; 80% yield) as an orange-red solid. $^1$H-NMR (400 MHz, CDCl$_3$): δ 7.94 (s, 1H), 7.12-7.14 (m, 2H), 6.95-6.97 (m, 2H), 3.85 (s, 3H); MS: m/z 252.0 (M+H)$^+$.

C. 2-(S)-{[2-Chloro-4-(4-methoxy-phenoxy)-pyrimidin-5-ylamino]-methyl}-pyrrolidine-1-carboxylic acid tert-butyl ester (1e)

To a solution of Compound 1c (4.45 g, 17.7 mmol) in 1,2-dichloroethane (80 mL) was added Boc-L-prolinal (Compound 1d) (5.0 g; 24.4 mmol) and glacial acetic acid (4.5 mL) at ambient temperature, and the mixture was stirred under a nitrogen atmosphere for 3 h. The mixture was then treated with NaB(OAc)$_3$H (9.37 g; 44.2 mmol) and continually stirred at room temperature for 20 h. The resultant mixture was diluted with CH$_2$Cl$_2$, and washed with saturated NaHCO$_{3(aq)}$ and H$_2$O. The organic phase was washed sequentially with H$_2$O and brine, and then dried over Na$_2$SO$_4$. The mixture was filtered and the filtrate was evaporated under reduced pressure to give the crude material. The crude material was purified by flash column chromatography (SiO$_2$), eluting with a Et$_2$O—CH$_2$Cl$_2$ gradient to afford Compound 1e (6.54 g; 85% yield) as a pale-yellow solid. $^1$H-NMR (400 MHz, CDCl$_3$): δ 7.73-7.79 (m, 1H), 7.07-7.14 (m, 2H), 6.91-6.98 (m, 2H), 5.73 (br. s, 0.6H), 4.77 (br. s, 0.4H), 4.20-4.30 (m, 1H), 3.85 (s, 3H), 3.21-3.58 (m, 4H), 1.81-2.11 (m, 4H), 1.46-1.49 (m, 9H); MS: m/z 435.1 (M+H)$^+$.

D. 2-(S)-{[4-(4-Methoxy-phenoxy)-2-(5-methylsulfanyl-pyridin-3-yl)-pyrimidin-5-ylamino]-methyl}-pyrrolidine-1-carboxylic acid tert-butyl ester (1g)

To a teflon-lined septum sealed Schlenk tube, a mixture of Compound 1e (4.0 g; 9.20 mmol), 5-(methylthio)pyridin-3-yl boronic acid (Compound 1f) (2.32 g; 13.7 mmol), K$_2$CO$_3$ (2.50 g; 18.1 mmol) and [1,1'-bis(diphenylphosphino)-ferrocene]dichloro-palladium(II) (0.45 g, 0.55 mmol) in a mixture of ethanol (18 mL) and H$_2$O (4.5 mL) was irradiated in a microwave reactor at 130° C. for 30 min. The resultant mixture was diluted with EtOAc, washed with saturated NH$_4$Cl$_{(aq)}$ and H$_2$O. The organic phase was washed with H$_2$O, and then dried over Na$_2$SO$_4$. The mixture was filtered and the filtrate was evaporated under reduced pressure to give the crude material. The crude material was purified by flash column chromatography (SiO$_2$), eluting with a heptane-EtOAc gradient to afford Compound 1g (3.45 g; 72% yield) as pale-yellow solid. $^1$H-NMR (400 MHz, CDCl$_3$): δ 9.00 (s, 1H), 8.40 (d, 1H), 8.21 (s, 1H), 7.99 (br. s, 1H), 7.12-7.18 (m, 2H), 6.93-6.96 (m, 2H), 5.77 (br. s, 0.6H), 4.90 (br. s, 0.4H), 4.22-4.32 (m, 1H), 3.86 (s, 3H), 3.18-3.56 (m, 4H), 2.47 (s, 3H), 1.80-2.15 (m, 4H), 1.46-1.52 (m, 9H); MS: m/z 524.2 (M+H)$^+$.

E. Cpd 107: [4-(4-Methoxy-phenoxy)-2-(5-methyl-sulfanyl-pyridin-3-yl)-pyrimidin-5-yl]-pyrrolidin-2-(S)-ylmethyl-amine To a solution of Compound 1g (3.45 g; 6.59 mmol) in CH$_2$Cl$_2$ (20 mL) was added trifluoroacetic acid (4.9 mL; 66 mmol) at ambient temperature. The reaction mixture was stirred at room temperature for 20 h. The resultant mixture was adjusted to pH 12 with 1 N NaOH$_{(aq)}$. The resultant mixture was extracted with CH$_2$Cl$_2$ and H$_2$O. The organic phase was washed with H$_2$O, and dried over Na$_2$SO$_4$. The mixture was then filtered, and the filtrate was concentrated under reduced pressure. The residue was dissolved in CH$_2$Cl$_2$ (35 mL), and treated with 1.0 M HCl in Et$_2$O (6.6 mL; 6.6 mmol) at ambient temperature. The reaction mixture was stirred at room temperature for 20 h. The resultant mixture was concentrated in vacuo, before the residue was taken up in a small portion of MeOH/CH$_2$Cl$_2$, and then triturated with Et$_2$O. A solid was collected by filteration and dried to afford an HCl salt of Compound 107 (2.33 g; 77% yield) as a pale-yellow solid. HCl salt-$^1$H-NMR (400 MHz, DMSO-d$_6$): δ 9.06 (br. s, 1H), 8.83 (d, 1H), 8.66 (br. s, 1H), 8.42 (d, 1H), 8.25 (s, 1H), 8.05 (t, 1H), 7.25-7.29 (m, 2H), 7.04-7.09 (m, 2H), 6.36 (t, 1H), 3.83-3.87 (m, 1H), 3.81 (s, 3H), 3.56 (t, 2H), 3.35 (s, 3H), 3.17-3.26 (m, 2H), 2.12-2.18 (m, 1H), 1.87-2.01 (m, 2H), 1.70-1.76 (m, 1H); MS: m/z 424.2 (M+H)$^+$.

Following the procedure described above for Example 1 and substituting the appropriate reagents, starting materials and purification methods known to those skilled in the art, the following compounds of the present invention were prepared:

| Cpd | MS (M + H)$^+$ | Cpd | MS (M + H)$^+$ |
|---|---|---|---|
| 1 | 407.2 | 2 | 377.0 |
| 4 | 407.0 | 3 | 407.0 |
| 6 | 427.0 | 5 | 427.0 |
| 8 | 378.2 | 7 | 378.2 |
| 10 | 367.2 | 9 | 383.0 |
| 12 | 391.0 | 11 | 432.0 |
| 14 | 348.0 | 13 | 405.0 |
| 16 | 428.2 | 15 | 393.0 |
| 18 | 442.2 | 17 | 428.2 |
| 20 | 428.1 | 19 | 453.2 |
| 22 | 408.1 | 21 | 483.2 |
| 24 | 396.2 | 23 | 379.1 |
| 26 | 408.2 | 25 | 396.1 |
| 28 | 402.1 | 27 | 411.1 |
| 30 | 420.1 | 29 | 422.2 |
| 32 | 455.1 | 31 | 476.2 |
| 34 | 416.2 | 33 | 393.1 |
| 37 | 396.2 | 36 | 366.2 |
| 39 | 408.2 | 38 | 395.1 |
| 41 | 420.1 | 40 | 378.2 |
| 43 | 434.1 | 42 | 434.1 |
| 49 | 433.0 | 45 | 392.1 |
| 51 | 461.1 | 50 | 445.0 |
| 53 | 409.1 | 52 | 425.1 |
| 55 | 413.1 | 54 | 396.1 |
| 57 | 443.1 | 56 | 413.1 |
| 59 | 394.2 | 58 | 439.0 |
| 62 | 396.1 | 61 | 367.2 |
| 64 | 425.1 | 63 | 419.1 |
| 67 | 381.1 | 65 | 367.2 |
| 69 | 403.1 | 68 | 408.1 |
| 71 | 409.2 | 70 | 425.1 |
| 73 | 426.1 | 72 | 393.1 |
| 75 | 380.2 | 74 | 394.2 |
| 77 | 417.1 | 76 | 429.1 |
| 81 | 394.2 | 78 | 419.1 |
| 83 | 464.2 | 82 | 422.1 |
| 85 | 406.2 | 84 | 477.1 |
| 87 | 404.2 | 86 | 430.0 |
| 90 | 444.0 | 88 | 428.0 |
| 96 | 439.0 | 91 | 420.2 |
| 98 | 403.0 | 97 | 415.0 |
| 100 | 378.2 | 99 | 379.2 |
| 102 | 432.0 | 101 | 439.2 |
| 104 | 417.2 | 103 | 415.0 |
| 106 | 410.2 | 105 | 393.2 |
| 110 | 439.0 | 108 | 455.0 |
| 112 | 432.0 | 111 | 415.0 |

-continued

| Cpd | MS (M + H)+ | Cpd | MS (M + H)+ |
|---|---|---|---|
| 114 | 407.2 | 113 | 431.2 |
| 117 | 416.2 | 115 | 424.2 |
| 119 | 416.2 | 118 | 416.2 |
| 123 | 447.2 | 122 | 471.2 |
| 125 | 445.2 | 124 | 464.0 |
| 127 | 438.2 | 126 | 421.2 |
| 129 | 407.0 | 128 | 400.0 |
| 131 | 414.2 | 130 | 383.0 |
| 133 | 397.2 | 132 | 421.2 |
| 140 | 407.2 | 139 | 431.2 |
| 142 | 419.1 | 141 | 406.2 |
| 144 | 379.2 | 143 | 403.2 |
| 146 | 391.2 | 145 | 378.2 |
| 148 | 363.2 | 147 | 387.2 |
| 150 | 419.1 | 149 | 362.2 |
| 152 | 394.2 | 151 | 395.2 |
| 154 | 393.2 | 153 | 417.2 |
| 178 | 380.2 | 155 | 392.2 |
| 180 | 410.2 | 179 | 401.2 |
| 183 | 405.2 | 182 | 394.2 |
| 185 | 398.2 | 184 | 376.2 |
| 187 | 380.2 | 186 | 414.0 |
| 190 | 432.0 | 189 | 423.2 |
| 192 | 398.2 | 191 | 416.0 |
| 201 | 396.2 | 200 | 387.2 |
| 203 | 362.2 | 202 | 380.2 |
| 205 | 410.2 | 204 | 417.2 |
| 211 | 392.2 | 210 | 426.2 |
| 219 | 398.2 | 218 | 405.2 |
| 221 | 434.2 | 220 | 441.2 |
| 227 | 396.0 | 222 | 444.1 |
| 229 | 416.0 | 230 | 407.0 |
| 231 | 389.0 | 232 | 412.0 |
| 233 | 428.0 | 241 | 468.0 |
| 242 | 436.0 | 243 | 452.0 |
| 244 | 422.0 | 249 | 394.2 |
| 253 | 392.0 | 262 | 410.0 |
| 263 | 406.0 | 265 | 426.0 |
| 266 | 426.0 | 268 | 426.0 |

Cpd 44

The title compound was prepared in an analogous manner to the preparation of Cpd 107 of Example 1, substituting (4-hydroxy-phenyl)-carbamic acid tert-butyl ester for 4-methoxy-phenol in procedure A, and substituting 4-methoxy-pyridin-3-yl boronic acid for 5-(methylthio)pyridin-3-yl boronic acid in procedure D. MS: m/z 393.2 (M+H)+.

Cpd 46

The title compound was prepared in an analogous manner to the preparation of Cpd 107 of Example 1, substituting (4-hydroxy-phenyl)-carbamic acid tert-butyl ester for 4-methoxy-phenol in procedure A, and substituting pyridin-3-yl boronic acid for 5-(methylthio)pyridin-3-yl boronic acid in Procedure D. MS: m/z 363.2 (M+H)+.

Cpd 60

The title compound was prepared in an analogous manner to the preparation of Cpd 107 of Example 1, substituting 5-(4,4,5,5-tetramethyl-[1,3,2]dioxaborolan-2-yl)-pyrimidine-2-carbonitrile for 5-(methylthio)pyridin-3-yl boronic acid in Procedure D. TFA salt-$^1$H-NMR (400 MHz, DMSO-$d_6$): δ 8.95 (s, 2H), 8.53 (br. s, 1H), 8.21 (s, 1H), 7.23-7.26 (m, 2H), 7.04-7.07 (m, 2H), 6.23 (t, 1H), 4.36 (q, 2H), 3.81-3.86 (m, 1H), 3.81 (s, 3H), 3.48-3.53 (m, 2H), 3.15-3.26 (m, 2H), 2.10-2.17 (m, 1H), 1.87-2.00 (m, 2H), 1.65-1.74 (m, 1H), 1.32 (t, 3H); MS: m/z 423.1 (M+H)+.

Cpd 92

$^1$H-NMR (400 MHz, CDCl$_3$) δ 7.92 (1H, s), 7.60 (2H, s), 7.16-7.14 (2H, m), 6.94 (1H, s), 6.90-6.87 (2H, m), 3.86-3.80 (4H, m), 3.61-3.50 (2H, m), 3.29-3.23 (2H, m), 3.20-2.95 (1H, br s), 2.27 (6H, s), 2.14-2.09 (1H, m), 2.03-2.00 (1H, m), 1.95-1.90 (1H, m), 1.79-1.74 (1H, m); MS: m/z 405.2 (M+H)+.

Cpd 93

$^1$H-NMR (400 MHz, CDCl$_3$) δ 7.90 (1H, s), 7.62-7.60 (1H, m), 7.52-7.51 (1H, m), 7.15-7.13 (2H, m), 6.94-6.91 (2H, m), 6.76-6.74 (1H, m), 5.94 (2H, s), 4.86-4.83 (1H, m), 3.84 (3H, s), 3.68-3.62 (1H, m), 3.42-3.26 (2H, m), 3.12-3.08 (2H, m), 2.10-2.02 (1H, m), 1.97-1.91 (1H, m), 1.89-1.80 (1H, m), 1.69-1.60 (1H, m); MS: m/z 421.2 (M+H)+.

Cpd 94

$^1$H-NMR (400 MHz, CD$_3$OD) δ 8.12 (1H, s), 7.90-7.89 (2H, m), 7.37-7.36 (1H, m), 7.19-7.17 (2H, m), 7.05-7.03 (2H, m), 4.03-3.94 (1H, m), 3.68-3.56 (2H, m), 3.42-3.32 (2H, m), 3.31-3.29 (1H, m), 2.36-2.28 (1H, m), 2.19-2.05 (2H, m), 1.93-1.81 (1H, m); MS: m/z 445.0 & 447.0 (M+H)+.

Cpd 95

$^1$H-NMR (400 MHz, CDCl$_3$) δ 9.33 (1H, s), 8.42-8.40 (1H, m), 8.00 (1H, m), 7.64-7.62 (1H, m), 7.16-7.12 (2H, m), 6.98-6.95 (2H, m), 5.94 (2H, s), 5.03-5.01 (1H, m), 3.87 (3H, s), 3.59-3.55 (1H, m), 3.35-3.29 (1H, m), 3.18-3.10 (1H, m), 3.05-2.94 (2H, m), 2.07-1.99 (1H, m), 1.92-1.79 (2H, m), 1.60-1.54 (1H, m); MS: m/z 403.2 (M+H)+.

Cpd 121

The title compound was prepared in an analogous manner to the preparation of Cpd 107 of Example 1, substituting 5-(4,4,5,5-tetramethyl-[1,3,2]dioxaborolan-2-yl)-pyrimidine-2-carbonitrile for 5-(methylthio)pyridin-3-yl boronic acid and substituting CH$_3$CN for ethanol in Procedure D. TFA salt-$^1$H-NMR (400 MHz, CDCl$_3$): δ 9.33 (s, 2H), 7.98 (s, 1H), 7.09-7.13 (m, 2H), 6.91-6.96 (m, 2H), 5.59 (t, 1H), 3.85-3.88 (m, 1H), 3.85 (s, 3H), 3.60-3.62 (m, 2H), 3.21-3.26 (m, 2H), 2.18-2.24 (m, 1H), 1.95-2.09 (m, 2H), 1.75-1.85 (m, 1H); MS: m/z 404.2 (M+H)+.

Cpd 260

The title compound was prepared in an analogous manner the preparation of Cpd 107 of Example 1, substituting 4-fluoromethoxy-phenol[1] for 4-methoxy-phenol in Procedure A, and substituting 5-methylpyridin-3-yl boronic acid for 5-(methylthio)pyridin-3-yl boronic acid in Procedure D. $^1$H-NMR (400 MHz, DMSO-$d_6$): δ 9.36 (br. s, 1H), 9.02 (br. s, 1H), 8.86 (s, 1H), 8.42-8.43 (m, 1H), 8.24-8.28 (m, 1H), 8.16-8.19 (m, 1H), 6.86-7.38 (m, 4H), 6.34-6.43 (m, 1H), 5.85-5.98 (m, 1H), 5.76 (s, 2H), 3.81-4.14 (m, 1H), 3.52-3.61 (m, 2H), 3.15-3.27 (m, 2H), 2.33 (s, 3H), 2.11-2.19 (m, 1H), 1.84-2.03 (m, 2H), 1.63-1.77 (m, 1H); MS: m/z 410.0 (M+H)+.

[1] 4-Fluoromethoxy-phenol was prepared as illustrated in the following synthetic scheme and procedure.

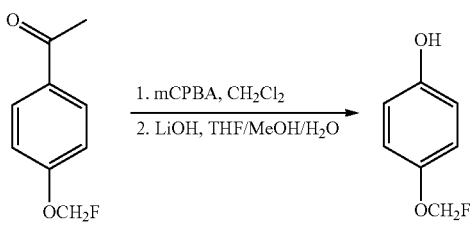

A. 4-Fluoromethoxy-phenol

To a solution of 1-(4-fluoromethoxy-phenyl)-ethanone (1.5 g; 8.9 mmol) in dichloromethane (30 mL) was added mCPBA (4.0 g; 17.8 mmol). The resulting mixture was stirred at room temperature for 4 h, then washed with saturated NaHCO$_3$ (3×). The organic layer was dried over Na$_2$SO$_4$, concentrated under reduced pressure to give the crude material (3.77 g). The crude material (3.77 g) was dissolved in THF/MeOH/H$_2$O (5/5/5 mL), then treated with LiOH (4.0 g; 108 mmol) at room temperature for 4 h. The reaction mixture was acidified with 2N HCl solution to pH 5. The mixture was extracted with EtOAc (3×). The organic phases were combined, dried over Na$_2$SO$_4$ and concentrated under reduced pressure to afford the title compound (1.3 g). This compound was used directly without further purification.

Cpd 264

The title compound was prepared in an analogous manner to the preparation of Cpd 107 of Example 1, substituting 4-chloro-5-methylpyridin-3-yl boronic acid for 5-(methylthio)pyridin-3-yl boronic acid in Procedure D, and the title compound was obtained as a by-product of Cpd 266. $^1$H-NMR (400 MHz, DMSO-d$_6$): δ 9.44 (br. s, 1H), 9.05 (br. s, 1H), 8.96 (d, 1H), 8.46 (d, 1H), 8.27 (s, 1H), 8.23 (d, 1H), 8.04 (d, 1H), 7.27-7.31 (m, 2H), 7.04-7.08 (m, 2H), 6.41 (br. s, 1H), 3.83-3.90 (m, 1H), 3.57-3.94 (m, 2H), 3.15-3.27 (m, 2H), 2.40 (s, 3H), 2.38 (s, 3H), 2.11-2.19 (m, 1H), 1.85-2.03 (m, 2H), 1.67-1.77 (m, 1H); MS: m/z 517.2 (M+H)$^+$.

Example 2

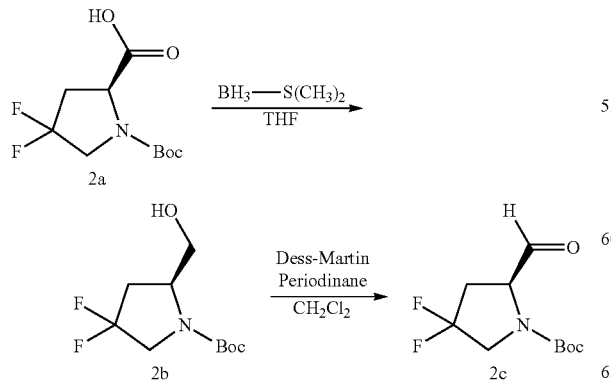

A. 4,4-Difluoro-2-(S)-hydroxymethyl-pyrrolidine-1-carboxylic acid tert-butyl ester (2b)

To a solution of 4,4-difluoro-pyrrolidine-1,2-dicarboxylic acid 1-tert-butyl ester (Compound 2a) (1.5 g; 6.0 mmol) in tetrahydrofuran (15 mL) was added borane-dimethylsulfide complex (3.79 mL; 7.58 mmol) dropwise at ambient temperature. The reaction mixture was refluxed for 2 h. The resultant mixture was allowed to cool to room temperature. The mixture was partitioned between EtOAc and H$_2$O. The organic phase was washed with H$_2$O, and then dried over Na$_2$SO$_4$. The mixture was filtered and the filtrate was evaporated under reduced pressure to give the crude material. The crude material was purified by flash column chromatography (SiO$_2$), eluting with a heptane-EtOAc gradient to afford Compound 2b (1.2 g; 84% yield) as a colorless oil. $^1$H-NMR (400 MHz, CDCl$_3$): δ4.08-4.23 (m, 2H), 3.61-3.87 (m, 4H), 2.45-2.57 (m, 1H), 2.15 (br.s, 1H), 1.49 (s, 9H).

B. 4,4-Difluoro-2-(S)-formyl-pyrrolidine-1-carboxylic acid tert-butyl ester (2c)

To a solution of Compound 2b (1.33 g; 5.61 mmol) in CH$_2$Cl$_2$ (20 mL) was added 3,3,3-triacetoxy-3-iodophthalide (3.56 g; 8.39 mmol) at ambient temperature. The reaction mixture was stirred at room temperature for 2 h. The resultant mixture was diluted with EtOAc, and washed sequentially with saturated NaHCO$_{3(aq)}$ and H$_2$O. The organic phase was washed with H$_2$O, and then dried over Na$_2$SO$_4$. The mixture was filtered and the filtrate was evaporated under reduced pressure to give the crude material. The crude material was purified by flash column chromatography (SiO$_2$), eluting with a heptane-EtOAc gradient to afford Compound 2c (0.58 g; 44% yield) as a colorless oil. $^1$H-NMR (400 MHz, CDCl$_3$): δ 9.59 (d, 1H), 4.28-4.45 (m, 1H), 3.77-3.89 (m, 2H), 2.43-2.63 (m, 2H), 1.46-1.51 (m, 9H).

Following the procedure described above for Example 2 and substituting the appropriate starting materials and purification methods known to those skilled in the art, the following aldehydes were prepared:

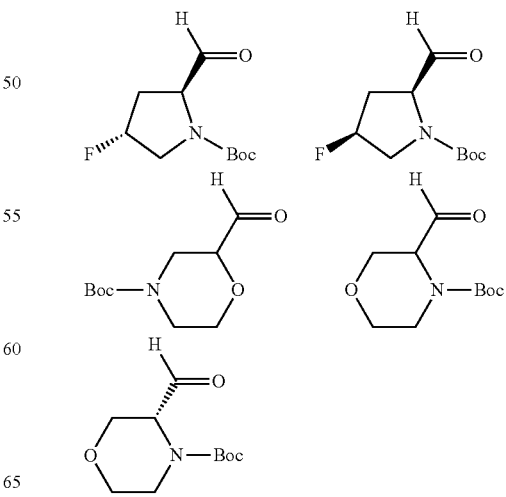

Example 3

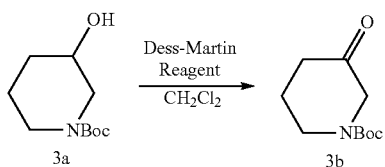

A. 3-Oxo-piperidine-1-carboxylic acid tert-butyl ester (3b)

To a solution of 3-hydroxy-piperidine-1-carboxylic acid tert-butyl ester (Compound 3a) (0.25 g; 1.24 mmol) in anhydrous dichloromethane (9.0 mL) at 0° C. was added 1,1,1-tris(actyloxy)-1,1-dihydro-1,2-benzodioxol-3-(1H)-one (1.58 g; 3.72 mmol). The mixture was allowed to stir at room temperature under nitrogen for 2 h, to which was then added additional 1,1,1-tris(actyloxy)-1,1-dihydro-1,2-benziodoxol-3-(1H)-one (0.5 g; 1.18 mmol). Upon stirring for 20 h at room temperature, the reaction mixture was partitioned between dichloromethane and brine. The organic layer was washed with brine, dried over $Na_2SO_4$, filtered, and the solvent evaporated in vacuo to yield a crude oil. The crude oil was purified via flash column chromatography, eluting with 40% ethyl acetate in hexanes, to yield Compound 3b as an oil (0.24 g; 97% yield). $^1$H NMR (400 MHz, $CDCl_3$): δ 4.0 (2H, br s), 3.60-3.57 (2H, m), 2.49-2.45 (2H, m), 2.01-1.95 (1H, m), 1.46 (9H, s).

Example 4

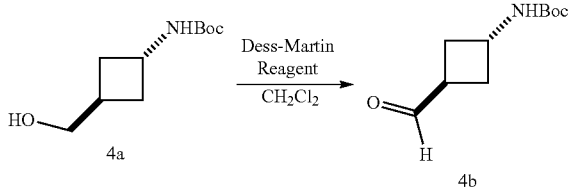 [SMILES: CC(C)(C)OC(=O)N[C@H]1C[C@H](CO)C1 ; "CH2Cl2" ; CC(C)(C)OC(=O)N[C@H]1C[C@H](C=O)C1]

A. trans-(3-Formyl-cyclobutyl)-carbamic acid tert-butyl ester (4b)

To a solution of trans-(3-hydroxymethyl-cyclobutyl)-carbamic acid tert-butyl ester (Compound 4a) (0.2 g; 1.0 mmol) in anhydrous dichloromethane (8.0 mL) at 0° C. was added 1,1,1-tris(acetyloxy)-1,1-dihydro-1,2-benzodioxol-3-(1H)-one (0.84 g; 2.0 mmol). The reaction was allowed to stir at room temperature under nitrogen for 3 h, before partitioning the reaction mixture between dichloromethane and brine. The organic layer was washed with brine, dried over $Na_2SO_4$, filtered, and the solvent evaporated in vacuo to yield a crude oil. The crude oil was purified via flash column chromatography, eluting with 30% ethyl acetate in hexanes, to yield Compound 4b as a foam (0.2 g; 88% yield). $^1$H NMR (400 MHz, $CDCl_3$): δ 9.82 (1H, d), 4.77 (1H, br s), 4.16-4.11 (1H, br s), 3.04-3.03 (1H, m), 2.69-2.64 (2H, m), 2.21-2.13 (2H, m), 1.44 (9H, s).

Following the procedure described above for Example 4 and substituting the appropriate starting materials and purification methods known to those skilled in the art, the following aldehydes were prepared:

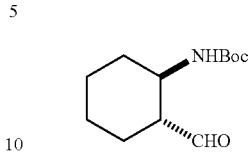

$^1$H NMR (400 MHz, $CDCl_3$): δ 9.58 (1H, d), 4.53 (1H, br s), 3.75 (1H, br s), 2.12-2.0 (2H, m), 1.84-1.73 (2H, m), 1.54-1.15 (13H, m).

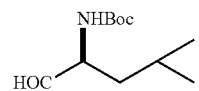

$^1$H NMR (400 MHz, $CDCl_3$): δ 9.59 (1H, br s), 4.9 (1H, br s), 4.26-4.24 (1H, m), 1.79-1.62 (2H, m), 1.45 (9H, s), 1.44-1.36 (1H, m), 0.98-0.96 (6H, m).

Following the procedure described above for Example 1 and substituting the appropriate reagents, starting materials (including the aldehydes or ketones which were prepared in Examples 2, 3, and 4), and purification methods known to those skilled in the art, the following compounds of the present invention were prepared:

| Cpd | MS (M + H)⁺ | Cpd | MS (M + H)⁺ |
| --- | --- | --- | --- |
| 79 | 415.2 | 80 | 397.1 |
| 89 | 397.2 | 277 | 419.2 |
| 278 | 412.2 | 279 | 395.2 |
| 280 | 395.2 | 281 | 419.2 |
| 282 | 419.1 | 134 | 421.0 |
| 283 | 412.2 | 193 | 414.2 |
| 284 | 394.2 | 195 | 419.2 |
| 194 | 430.0 | 235 | 426.0 |
| 234 | 442.0 | 239 | 410.0 |
| 238 | 410.0 | 240 | 426.0 |

Additional compounds with NMR data (below table):

Cpd 109

$^1$H NMR (400 MHz, $CDCl_3$): δ 9.30 (1H, s), 9.12 (2H, s), 8.07 (1H, s), 7.16-7.13 (2H, m), 6.97-6.95 (2H, m), 4.74-4.72 (1H, m), 3.87 (3H, s), 3.63-3.55 (1H, m), 3.30-3.26 (1, m), 2.95-2.91 (1H, m), 2.81-2.71 (2H, m), 2.05-1.99 (1H, m), 1.84-1.77 (1H, m), 1.68-1.57 (2H, m); MS: m/z 379.2 (M+H)⁺.

Cpd 196

HCl salt-$^1$H-NMR (400 MHz, DMSO-$d_6$): δ 9.90 (br, s, 1H), 9.79 (br. s, 1H), 9.06 (d, 1H), 8.59 (dd, 1H), 8.34 (d, 1H), 8.32 (s, 1H), 7.53 (dd, 1H), 7.27-7.32 (m, 2H), 7.04-7.08 (m, 2H), 6.45 (t, 1H), 5.48 (dt, 1H), 4.04-4.11 (m, 1H), 3.81 (s, 3H), 3.42-3.80 (m, 5H), 1.91-2.09 (m, 1H); MS: m/z 396.2 (M+H)⁺.

Cpd 292

$^1$H NMR (400 MHz, $CDCl_3$): δ 9.42 (1H, d), 8.76 (1H, d), 8.57 (1H, t), 7.99 (1H, s), 7.15-7.13 (2H, m), 6.98-6.96 (2H, m), 4.98 (1H, t), 3.87 (3H, s), 3.33-3.26 (2H, m), 3.09-3.04 (1H, m), 1.26 (3H, d); MS m/z 377.0 (M+H)+.

Cpd 293

1H NMR (400 MHz, CDCl3): δ 9.42 (1H, d), 8.76 (1H, d), 8.57 (1H, t), 8.0 (1H, s), 7.15-7.13 (2H, m), 6.98-6.96 (2H, m), 4.93 (1H, t), 3.88 (3H, s), 3.37-3.33 (2H, m), 3.12-3.09 (2H, m); MS: m/z 363.0 (M+H)+.

Cpd 294

1H NMR (400 MHz, CDCl3): δ 9.42 (1H, d), 8.76 (1H, d), 8.58-8.57 (1H, m), 7.98 (1H, s), 7.16-7.14 (2H, m), 6.98-6.96 (2H, m), 5.0 (1H, br s), 3.87 (3H, s), 3.35-3.30 (1H, m), 3.19-3.14 (1H, m), 3.03-2.97 (1H, m), 1.84-1.77 (1H, m), 1.39-1.36 (2H, m), 1.0-0.95 (6H, dd); MS: m/z 419.2 (M+H)+.

Cpd 295

1H NMR (400 MHz, CDCl3): δ 9.31 (2H, s), 9.12 (1H, s), 7.99 (1H, s), 7.16-7.14 (2H, m), 6.97-6.94 (2H, m), 5.0 (1H, br s), 3.87 (3H, s), 3.35-3.31 (1H, m), 3.2-3.14 (1H, m), 3.02-2.97 (1H, m), 1.84-1.77 (1H, m), 1.4-1.35 (2H, m), 1.0-0.95 (6H, dd); MS: m/z 395.2 (M+H)+.

Cpd 298

1H NMR (400 MHz, CDCl3): δ 9.41-9.40 (2H, m), 8.76-8.75 (2H, m), 8.56-8.55 (2H, m), 7.98-7.96 (2H, d), 7.15-7.12 (4H, m), 6.99-6.96 (4H, m), 4.61-4.56 (1H, m), 4.35-4.33 (1H, m), 3.88-3.87 (6H, d), 3.70-3.65 (1H, m), 3.42-3.37 (2H, m), 3.02-2.98 (1H, m), 2.84-2.77 (2H, m), 2.25-2.22 (2H, m), 2.02-1.90 (4H, m), 1.86-1.75 (4H, m), 1.42-1.25 (8H, m); MS: m/z 417.2 (M+H)+.

Cpd 299

1H NMR (400 MHz, CDCl3): δ 9.41 (1H, d), 8.75 (1H, d), 8.57 (1H, t), 7.99 (1H, s), 7.15-7.13 (2H, m), 6.98-6.96 (2H, m), 6.11 (1H, br s), 3.87 (3H, s), 3.37-3.34 (1H, m), 3.29-3.26 (1H, m), 2.54-2.48 (1H, m), 1.92-1.87 (2H, m), 1.77-1.74 (2H, m), 1.55-1.19 (5H, m); MS: m/z 431.0 (M+H)+.

Cpd 300

1H NMR (400 MHz, CDCl3): δ 9.31 (2H, s), 9.11 (1H, s), 8.0 (1H, s), 7.15-7.13 (2H, m), 6.96-6.94 (2H, m), 5.98 (1H, br s), 3.86 (3H, s), 3.39-3.34 (1H, m), 3.29-3.25 (1H, m), 2.54-2.48 (1H, m), 1.91-1.88 (2H, m), 1.76-1.74 (2H, m), 1.55-1.19 (5H, m); MS: m/z 407.0 (M+H)+.

Cpd 301

1H NMR (400 MHz, CDCl3): δ 9.41 (1H, s), 8.76 (1H, s), 8.57 (1H, s), 7.97 (1H, s), 7.14-7.12 (2H, m), 6.98-6.96 (2H, m), 4.43-4.40 (1H, m), 3.87 (3H, s), 3.73-3.69 (1H, br s), 3.36-3.33 (2H, m), 2.61-2.57 (1H, m), 2.30-2.22 (2H, m), 2.01-1.94 (2H, m); MS: m/z 403.2 (M+H)+.

Cpd 302

1H NMR (400 MHz, CDCl3): δ 9.31 (2H, s), 9.12 (1H, s), 7.98 (1H, s), 7.14-7.12 (2H, m), 6.97-6.94 (2H, m), 4.40-4.37 (1H, m), 3.86 (3H, s), 3.71-3.65 (1H, br s), 3.36-3.32 (2H, m), 2.61-2.57 (1H, m), 2.30-2.22 (2H, m), 2.01-1.93 (2H, m); MS: m/z 379.2 (M+H)+.

Cpd 303

1H NMR (400 MHz, CDCl3): δ 9.42 (4H, d), 8.76 (2H, d), 8.57-8.56 (2H, m), 7.88 (1H, s), 7.81 (1H, s), 7.15-7.12 (4H, m), 6.99-6.96 (4H, m), 4.63-4.59 (1H, m), 4.19-4.13 (1H, m), 3.88-3.81 (7H, m), 3.69-3.64 (1H, m), 3.38-3.34 (1H, m), 3.00-2.94 (1H, m), 2.39-2.33 (4H, m), 2.30-2.24 (4H, m); MS: m/z 389.2 (M+H)+.

Cpd 304

1H NMR (400 MHz, CDCl3): δ 9.31 (4H, s), 9.12 (2H, s), 7.88 (1H, s), 7.81 (1H, s), 7.15-7.12 (4H, m), 6.98-6.95 (4H, m), 4.59-4.55 (1H, m), 4.17-4.13 (1H, m), 3.88-3.81 (7H, m), 3.68-3.66 (1H, m), 3.38-3.34 (1H, m), 3.00-2.94 (1H, m), 2.39-2.33 (4H, m), 2.29-2.23 (4H, m); MS: m/z 365.2 (M+H)+.

Example 5

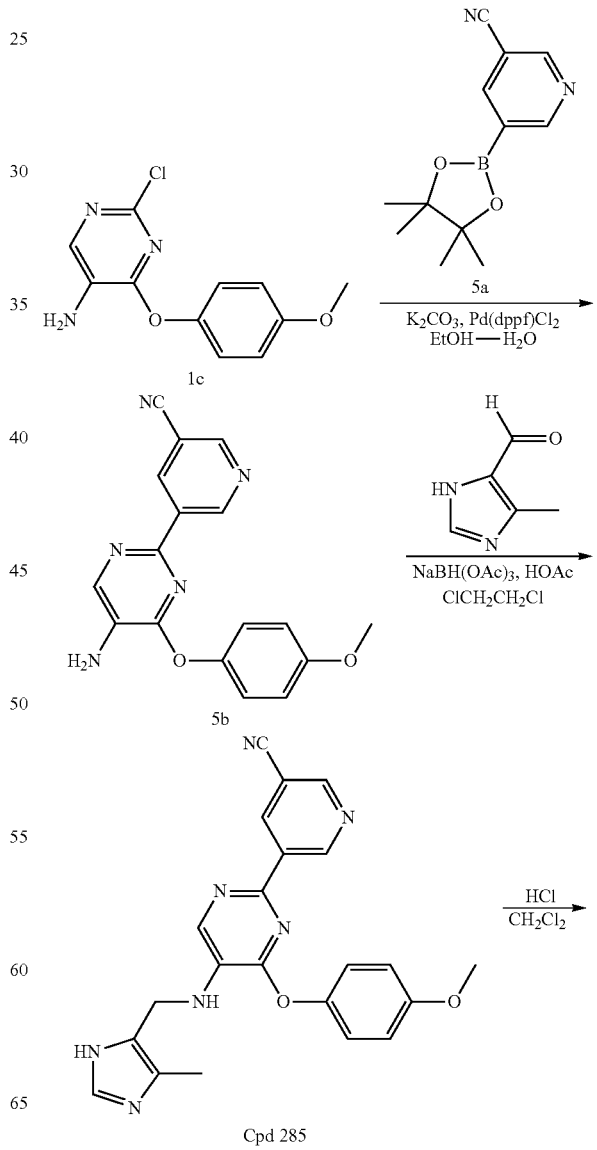

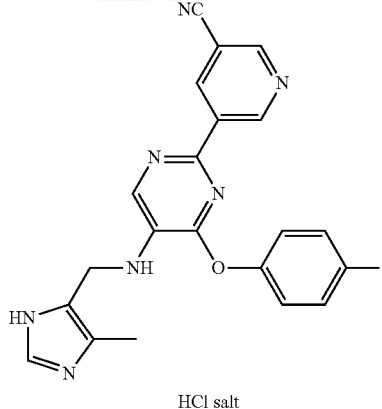

HCl salt

A. 5-[5-Amino-4-(4-methoxy-phenoxy)-pyrimidin-2-yl]-nicotinonitrile (5b)

Using an adaptation of the method described in Procedure D of Example 1, substituting Compound 5a for Compound 1f, the title Compound 5b was obtained. MS: m/z 320.1 (M+H)$^+$.

B. Cpd 285: 5-{4-(4-Methoxy-phenoxy)-5-[(5-methyl-3H-imidazol-4-ylmethyl)-amino]-pyrimidin-2-yl}-nicotinonitrile Using an adaptation of the method described in Procedure C of Example 1, substituting Compound 5b for Compound 1c, and substituting 5-methyl-3H-imidazole-4-carbaldehyde for Compound 1d, the title Compound 285 was obtained as a free base. $^1$H-NMR (400 MHz, DMSO-d$_6$): δ 11.79 (br. s, 1H), 9.21 (s, 1H), 8.94 (s, 1H), 8.51 (s, 1H), 8.31 (s, 1H), 7.47 (s, 1H), 7.27 (d, 2H), 7.05 (d, 2H), 6.44 (br. s, 1H), 4.03 (m, 2H), 3.81 (s, 3H), 2.23 (s, 3H); MS: m/z 414.0 (M+H)$^+$.

Following the procedure described above for Example 5 and substituting the appropriate reagents, starting materials and purification methods known to those skilled in the art, the following compounds of the present invention were prepared:

| Cpd | MS (M + H)$^+$ | Cpd | MS (M + H)$^+$ |
|---|---|---|---|
| 283 | 400.0 | 284 | 400.2 |
| 286 | 414.0 | 287 | 442.0 |
| 288 | 375.0 | 289 | 421.0 |
| 290 | 405.0 | 291 | 389.0 |

Example 6

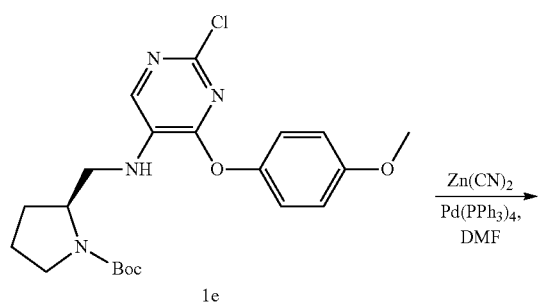

1e

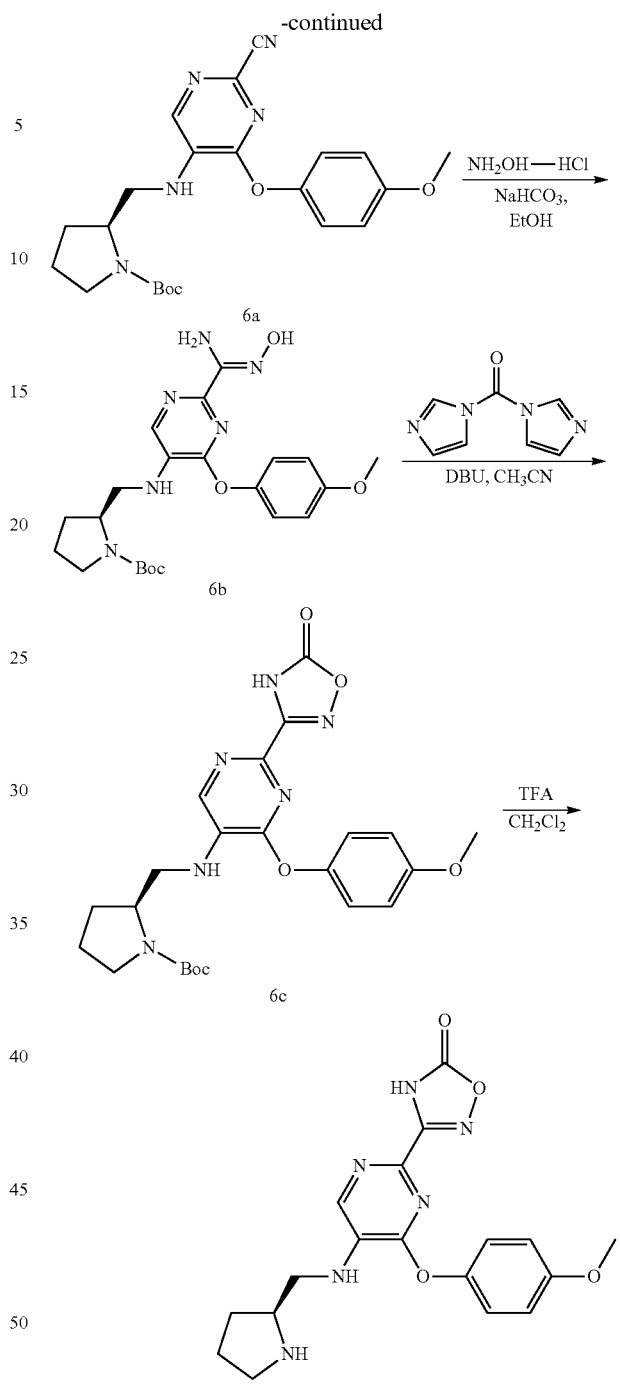

A. 2-(S)-{[2-Cyano-4-(4-methoxy-phenoxy)-pyrimidin-5-ylamino]-methyl}-pyrrolidine-1-carboxylic Acid tert-Butyl Ester (6a)

A mixture of Compound 1e (0.4 g; 0.92 mmol), Zn(CN)$_2$ (0.11 g; 0.92 mmol), and Pd(PPh$_3$)$_4$ (0.106 g; 0.092 mmol) in DMF (2.4 mL) was irradiated at 160° C. in a CEM microwave reactor for 16 min. Purification by preparative TLC, eluting with 1/1 EtOAc/hexanes, gave the product 6a (0.059 g; 15% yield). MS: m/z 426.2 (M+H)$^+$.

B. 2-(S)-{[2-(N-Hydroxycarbamimidoyl)-4-(4-methoxy-phenoxy)-pyrimidin-5-ylamino]-methyl}-pyrrolidine-1-carboxylic Acid tert-Butyl Ester (6b)

To a microwave vessel was added NaHCO$_3$ (0.03 g; 0.354 mmol), hydroxylamine hydrochloride (0.016 g; 0.236 mmol) and H$_2$O (0.2 mL). A suspension of Compound 6a (0.05 g; 0.118 mmol) in EtOH (0.5 mL) was added to the vessel, and the reaction mixture was irradiated at 130° C. in a CEM microwave reactor for 32 min. Purification by preparative TLC, eluting with 1/1 EtOAc/hexanes, gave the product 6b (0.053 g; 98% yield). MS: m/z 456.2 (M+H)$^+$.

C. 2-(S)-{[4-(4-Methoxy-phenoxy)-2-(5-oxo-4,5-dihydro-[1,2,4]oxadiazol-3-yl)-pyrimidin-5-ylamino]-methyl}-pyrrolidine-1-carboxylic Acid tert-Butyl Ester (6c)

To a solution of Compound 6b (0.038 g; 0.0828 mmol) and 1,1'-carbonyldiimidazole (0.015 g; 0.091 mmol) in CH$_3$CN (1 mL) was added 1,8-diazabicyclo[5.4.0]undec-7-ene (0.05 mL, 0.33 mmol) and the resulting mixture was stirred at rt for 20 h. The reaction mixture was washed with water, dried over Na$_2$SO$_4$, filtered, and the solvent evaporated in vacuo to yield Compound 6c. MS: m/z 485.3 (M+H)$^+$.

D. Cpd 35: 3-{4-(4-Methoxy-phenoxy)-5-[(pyrrolidin-2-(S)-ylmethyl)-amino]-pyrimidin-2-yl}-4H-[1,2,4]oxadiazol-5-one To a solution of Compound 6c (150 mg; 0.31 mmol) in CH$_2$Cl$_2$ (4 mL) was added TFA (1 mL) and the mixture was stirred at room temperature for 2 h. The reaction mixture was concentrated and the resultant residue was purified by reverse phase HPLC to afford Compound 35 as a TFA salt. $^1$H-NMR (300 MHz, CD$_3$OD): δ 8.16 (s, 1H), 7.18 (d, 2H), 7.00 (d, 2H), 3.97 (m, 1H), 3.83 (s, 3H), 3.61-3.66 (m, 2H), 3.34-3.40 (m, 2H), 2.27-2.35 (m, 1H), 2.04-2.19 (m, 2H), 1.82-1.92 (m, 1H); MS: m/z 385.2 (M+H)$^+$.

Example 7

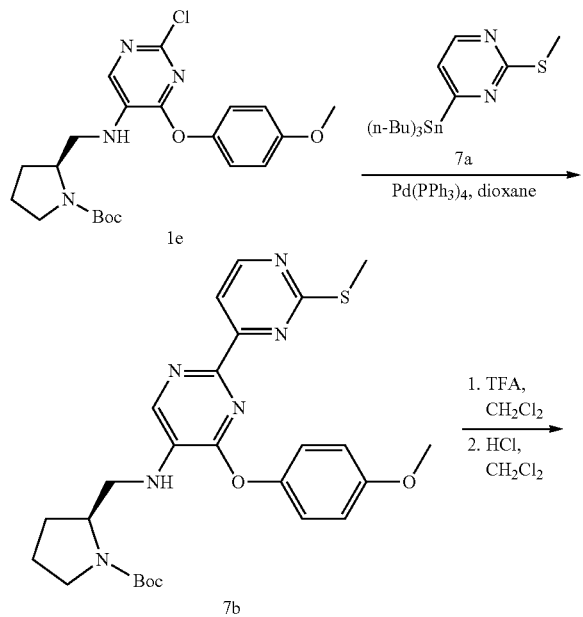

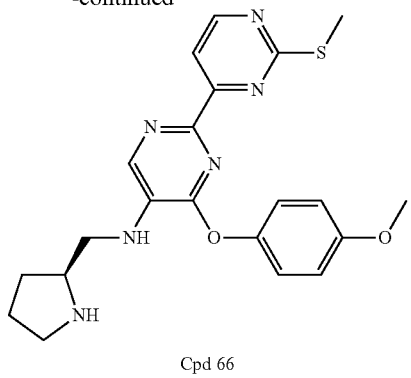

Cpd 66

A. 2-(S)-{[4-(4-Methoxy-phenoxy)-2'-methylsulfanyl-[2,4]bipyrimidin-yl-5-ylamino]-methyl}-pyrrolidine-1-carboxylic acid tert-butyl ester (7b)

To a teflon-lined septum-sealed Schlenk tube, a mixture of Compound 1e (213 mg; 0.49 mmol), 2-methylsulfanyl-4-tributylstannanyl-pyrimidine (Compound 7a) (305 mg; 0.735 mmol) and tetrakis-(triphenylphosphine)palladium(0) (57 mg; 0.049 mmol) in dioxane (1.0 mL) was irradiated in a Microwave reactor at 150° C. for 30 min. The resultant mixture was diluted with EtOAc, and washed with saturated NH$_4$Cl$_{(aq)}$ and H$_2$O. The organic phase was washed with H$_2$O, and then dried over Na$_2$SO$_4$. The mixture was filtered and the filtrate was evaporated under reduced pressure to give the crude material. The crude material was purified by flash column chromatography (SiO$_2$), eluting with a heptane-EtOAc gradient to afford Compound 7b (129 mg; 50% yield). $^1$H-NMR (400 MHz, CDCl$_3$): δ 8.48-8.50 (m, 1H), 8.08-8.12 (m, 1H), 7.54-7.57 (m, 1H), 7.16-7.23 (m, 2H), 6.96-7.01 (m, 2H), 6.27 (br. s, 0.7H), 5.18 (br, 0.3H), 4.25-4.36 (m, 1H), 3.88 (s, 3H), 3.24-3.59 (m, 4H), 2.68 (s, 3H), 1.79-2.16 (m, 4H), 1.44-1.54 (m, 9H); MS: m/z 525.2 (M+H)$^+$.

B. Cpd 66: [4-(4-Methoxy-phenoxy)-2'-methylsulfanyl-[2,4]bipyrimidinyl-5-yl]-pyrrolidin-2-(S)-ylmethyl-amine Using an adaptation of the method described in Procedure E of Example 1, substituting Compound 7b for Compound 1g, the title Compound 66 was obtained as a HCl salt. $^1$H-NMR (400 MHz, DMSO-d$_6$): δ 8.89 (br. s, 1H), 8.62 (d, 1H), 8.31 (s, 1H), 7.59 (d, 1H), 7.29-7.31 (m, 2H), 7.02-7.04 (m, 2H), 6.66 (t, 1H), 3.83 (t, 1H), 3.80 (s, 3H), 3.57-3.60 (m, 2H), 3.11-3.25 (m, 2H), 2.45 (s, 3H), 2.08-2.15 (m, 1H), 1.84-1.99 (m, 2H), 1.66-1.74 (m, 1H); MS: m/z 425.1 (M+H)$^+$.

Following the procedure described above for Example 8 and substituting the appropriate reagents, starting materials and purification methods known to those skilled in the art, the following compounds of the present invention were prepared:

| Cpd | MS (M + H)$^+$ | Cpd | MS (M + H)$^+$ |
|---|---|---|---|
| 47 | 434.1 | 48 | 384.1 |
| 120 | 379.2 | | |

Example 8

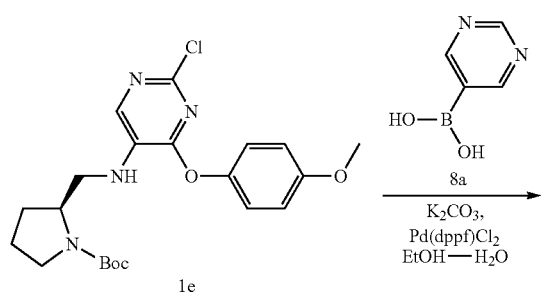

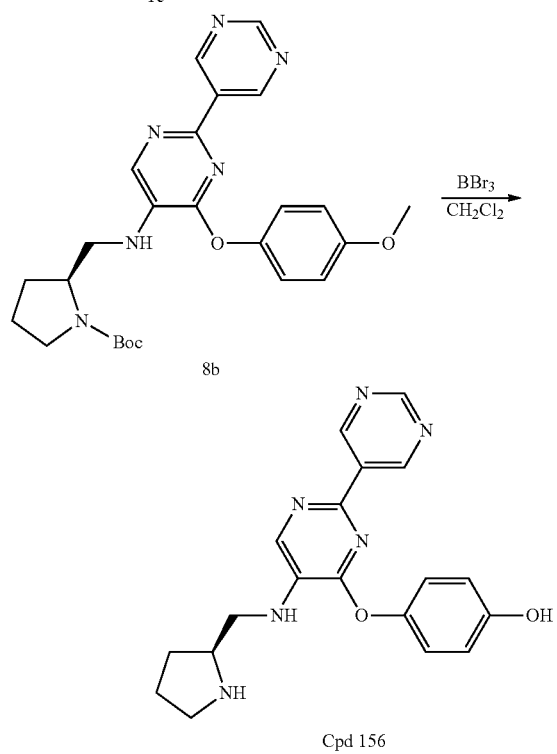

A. 2-(S)-{[4-(4-Methoxy-phenoxy)-[2,5']bipyrimidi- nyl-5-ylamino]-methyl}-pyrrolidine-1-carboxylic acid tert-butyl ester (8b)

Using an adaptation of the method described in Procedure D of Example 1, substituting pyrimidine-5-boronic acid (Compound 8a) for Compound 1f, the title Compound 8b was obtained as a pale-yellow solid. $^1$H-NMR (400 MHz, CDCl$_3$): δ 9.31 (s, 2H), 9.11 (s, 1H), 8.00-8.03 (m, 1H), 7.10-7.15 (m, 2H), 6.93-6.96 (m, 2H), 5.89 (br. s, 0.7H), 4.98 (br. s, 0.3; H), 4.21-4.35 (m, 1H), 3.86 (s, 3H), 3.19-3.56 (m, 4H), 1.80-2.14 (m, 4H), 1.43-1.46 (m, 9H); MS: m/z 479.2 (M+H)$^+$.

B. Cpd 156: 4-{5-[(Pyrrolidin-2-(S)-ylmethyl)- amino]-[2,5]bipyrimidinyl-4-yloxy}-phenol To a solution of Compound 8b (100 mg; 0.21 mmol) in CH$_2$Cl$_2$ (10 mL) cooled to 0° C. was added BBr$_3$—S(CH$_3$)$_2$ in CH$_2$Cl$_2$ (1.0 M, 1.5 mL) dropwise. The mixture was allowed to warm to ambient temperature, and then was refluxed at 70° C. for 5 h. An additional portion of BBr$_3$—S (CH$_3$)$_2$ in CH$_2$Cl$_2$ (1.0 M, 1.5 mL) was added to the reaction mixture upon reaching room temperature. The reaction mixture was refluxed at 70° C. for 20 h. The reaction was adjusted to pH 6 with 1 N NaOH$_{(aq)}$, and the organic phase was concentrated. The resultant residue was purified by reverse phase HPLC, eluting with a CH$_3$CN—H$_2$O gradient to afford Compound 156 (29.7 mg; 27% yield) as a HBr salt. $^1$H-NMR (400 MHz, DMSO-d$_6$): δ 9.54 (s, 1H), 9.17 (s, 1H), 9.16 (s, 1H), 8.97 (br. s, 1H), 8.55 (br. s, 1H), 7.27 (d, 1H), 7.12-7.15 (m, 2H), 6.86-6.89 (m, 2H), 6.42 (t, 1H), 3.85 (br. s, 1H), 3.53-3.57 (m, 2H), 3.18-3.26 (m, 2H), 2.11-2.18 (m, 1H), 1.88-1.98 (m, 2H), 1.67-1.72 (m, 1H); MS: m/z 365.1 (M+H)$^+$.

Example 9

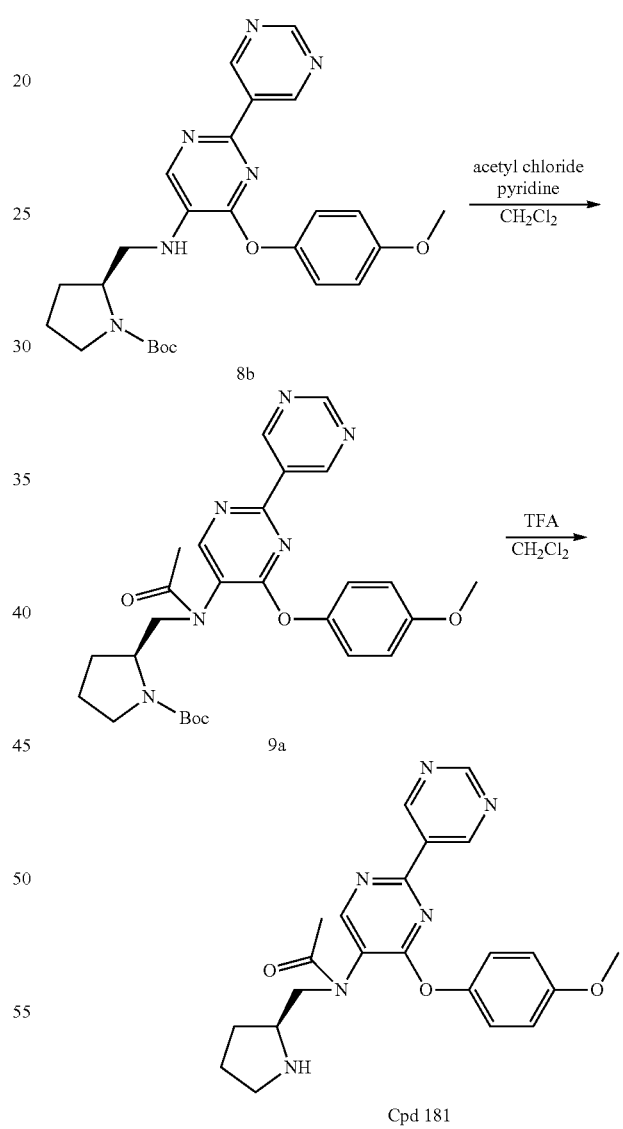

A. 2-(S)-({Acetyl-[4-(4-methoxy-phenoxy)-[2,5'] bipyrimidinyl-5-yl]-amino}-methyl)-pyrrolidine-1- carboxylic acid tert-butyl ester (9a)

To a solution of Compound 8b (89 mg; 0.19 mmol) in CH$_2$Cl$_2$ (7 mL) was added acetyl chloride (0.1 mL) and pyridine (0.1 mL) at ambient temperature. The mixture was stirred at room temperature for 3 h. Diluted the resulted mixture with $CH_2Cl_2$. The organic phase was washed sequentially with $H_2O$ and brine, and then dried over $Na_2SO_4$. The mixture was filtered and the filtrate was evaporated under reduced pressure to afford Compound 9a. The crude product was used in the next reaction without further purification. MS: m/z 521.3 (M+H)+.

B. Cpd 181: N-[4-(4-Methoxy-phenoxy)-[2,5']bipyrimidinyl-5-yl]-N-pyrrolidin-2-(S)-ylmethyl-acetamide To a solution of Compound 9a in $CH_2Cl_2$ (3 mL) was added trifluoroacetic acid (0.4 mL) at ambient temperature. The mixture was stirred at room temperature for 20 h. The solvent was evaporated under reduced pressure. The crude material was purified by reverse phase HPLC, eluting with a $CH_3CN$—$H_2O$ gradient to afford Compound 181 (71.1 mg; 71% yield) as a TFA salt. $^1$H-NMR (400 MHz, DMSO-$d_6$): δ 9.34 (s, 1H), 9.32 (s, 2H), 9.09 (br. s, 0.6H), 9.00 (s, 0.4H), 8.99 (s, 1H), 8.42 (br. s, 1H), 7.32 (d, 2H), 7.08 (d, 2H), 4.25-4.31 (m, 0.6H), 4.10-4.13 (m, 0.4H), 3.82 (s, 3H), 3.64-3.79 (m, 2H), 3.17-3.31 (m, 2H), 1.85-2.14 (m, 6H), 1.61-1.68 (m, 1H); MS: m/z 421.2 (M+H)+.

Example 10

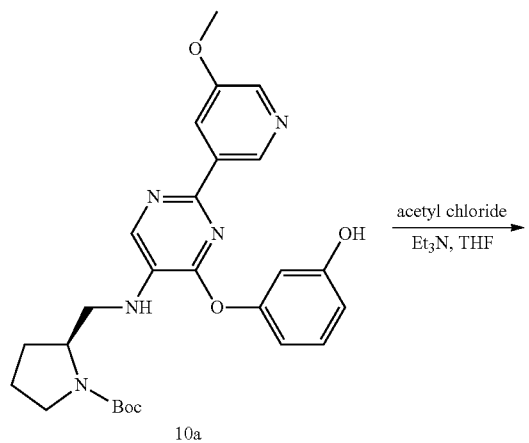

10a

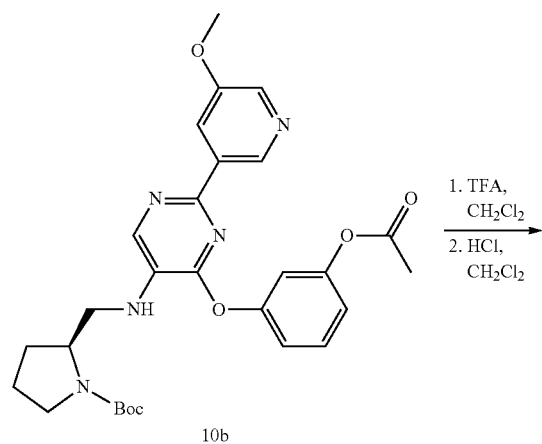

10b

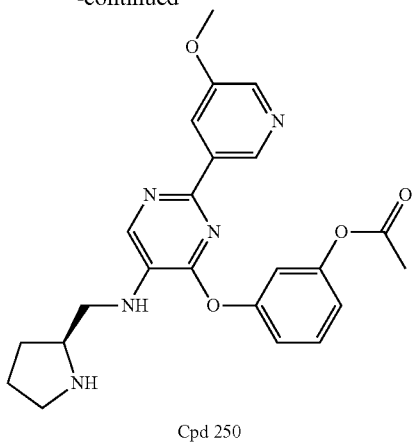

Cpd 250

A. 2-(S)-{[4-(3-Hydroxy-phenoxy)-2-(5-methoxy-pyridin-3-yl)-pyrimidin-5-ylamino]-methyl}-pyrrolidine-1-carbxylic acid tert-butyl ester (10a)

The title compound was prepared in a same manner to Compound 1g in Example 1. Using an adaptation of the method described in Procedure A-D, substituting 3-Hydroxyphenol for 4-Methoxyphenol in Procedure A and substituting 5-Methoxy-pyridin-3-yl boronic acid for Compound 1f in Procedure D, the title Compound 10a was obtained. MS: m/z 494.2 (M+H)+.

B. 2-(S)-{[4-(3-Acetoxy-phenoxy)-2-(5-methoxy-pyridin-3-yl)-pyrimidin-5-ylamino]-methyl}-pyrrolidine-1-carboxylic acid tert-butyl ester (10b)

To a solution of Compound 10a (50 mg; 0.1 mmol) in tetrahydrofuran (5 mL), cooled to −78° C., was added acetyl chloride (0.009 mL; 0.12 mmol) and triethylamine (0.035 mL; 0.25 mmol). The mixture was stirred at −78° C. for 1 hour. Diluted the resulted mixture with EtOAc and $H_2O$. The organic phase was washed sequentially with $H_2O$, and then dried over $Na_2SO_4$. The mixture was filtered and the filtrate was evaporated under reduced pressure to give the crude material. The crude material was purified by flash column chromatography ($SiO_2$), eluting with a EtOAc-heptane gradient to afford Compound 10b (43 mg; 80% yield). MS: m/z 536.0 (M+H)+.

C. Cpd 250: Acetic acid 3-{2-(5-methoxy-pyridin-3-yl)-5-[(pyrrolidin-2-(S)-ylmethyl)-amino]-pyrimidin-4-yloxy}-phenyl ester Using an adaptation of the method described in Procedure E of Example 1, substituting Compound 10b for Compound 1g, the title Compound 250 was obtained as a HCl salt. $^1$H-NMR (400 MHz, DMSO-$d_6$): δ 9.67 (br. s, 1H), 9.37 (br. s, 1H), 8.75 (s, 1H), 8.44 (s, 1H), 8.35 (s, 1H), 7.99 (s, 1H), 7.55 (t, 1H), 7.31 (d, 1H), 7.26 (s, 1H), 7.11 (d, 1H), 6.63 (br. s, 1H), 3.88 (s, 3H), 3.84 (m, 1H), 3.62-3.68 (m, 2H), 3.13-3.25 (m, 2H), 2.28 (s, 3H), 2.10-2.18 (m, 1H), 1.85-2.02 (m, 2H), 1.68-1.76 (m, 1H); MS: m/z 436.0 (M+H)+.

Following the procedure described above for Example 10 and substituting the appropriate reagents, starting materials and purification methods known to those skilled in the art, the following compounds of the present invention were prepared:

| Cpd | MS (M + H)+ | Cpd | MS (M + H)+ |
|---|---|---|---|
| 228 | 431.0 | 248 | 452.0 |
| 251 | 420.0 | | |

Example 11

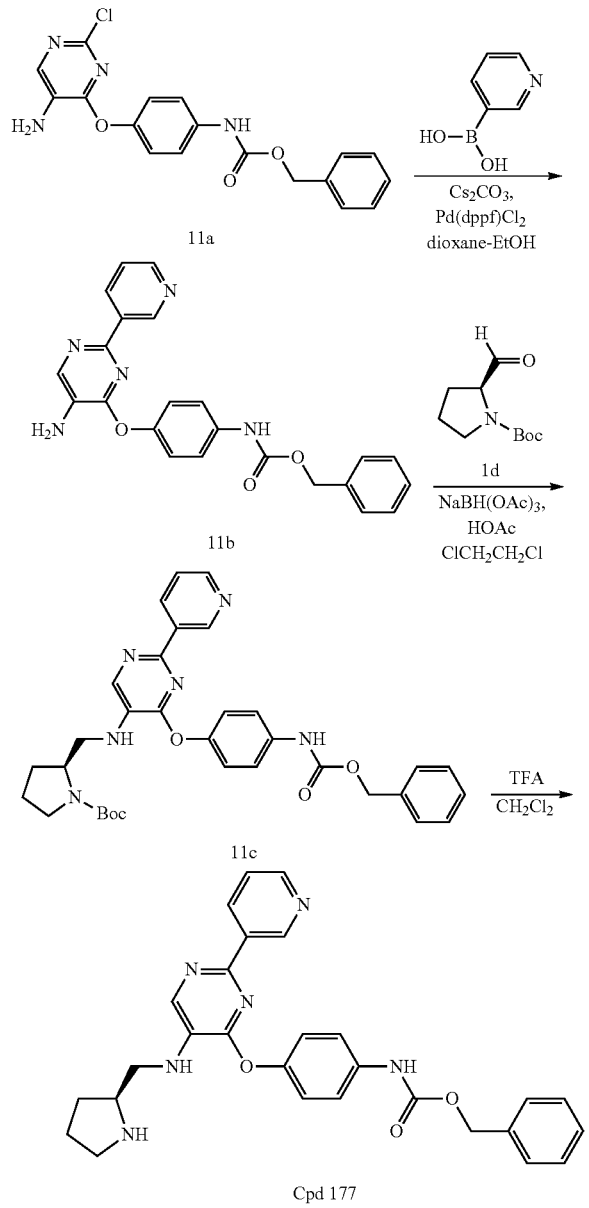

Cpd 177

A. [4-(5-Amino-2-chloro-pyrimidin-4-yloxy)-phenyl]-carbamic acid benzyl ester (11a)

The title compound was prepared in a same manner to Compound 1c in Example 1. Using an adaptation of the method described in Procedures A and B, substituting (4-hydroxy-phenyl)-carbamic acid benzyl ester (prepared according to the procedure disclosed in U.S. Pat. No. 3,933,470) for 4-methoxyphenol in Procedure A, the title Compound 11a was obtained. MS: m/z 371.2 (M+H)+.

B. [4-(5-Amino-2-pyridin-3-yl-pyrimidin-4-yloxy)-phenyl]-carbamic acid benzyl ester (11b)

To a teflon-lined septum sealed Schlenk tube, a mixture of Compound 11a (1.0 g; 2.7 mmol), pyridin-3-yl boronic acid (0.83 g; 6.75 mmol), $Cs_2CO_3$ (2.60 g; 8.1 mmol) and [1,1'-Bis(diphenylphosphino)-ferrocene]dichloro-palladium(II) (0.49 g; 0.6 mmol) in a mixture of dioxane (15 mL) and EtOH (1 mL) was irradiated in a microwave reactor at 150° C. for 55 min. The reaction mixture was poured into water, diluted with EtOAc and the solid was collected by filtration. The organic phase was isolated and dried over $MgSO_4$. and the reaction mixture was concentrated under reduced pressure. The resultant residue was purified by reverse phase HPLC, eluting with a $CH_3CN$—$H_2O$ (0.5% TFA) gradient to afford Compound 11b (0.72 g; 42% yield based on di-TFA). $^1$H-NMR (300 MHz, MeOH-d$_4$): δ 9.2 (s, 1H), 8.9 (d, 1H), 8.7 (d, 1H), 8.2 (s, 1H), 8.0 (m, 1H), 7.5 (d, 2H), 7.5-7.3 (m, 6H), 7.2 (m, 2H), 5.2 (s, 2H); MS: m/z 414.2 (M+H)+.

C. 2-(S)-{[4-(4-Benzyloxycarbonylamino-phenoxy)-2-pyridin-3-yl-pyrimidin-5-ylamino]-methyl}-pyrrolidine-1-carboxylic acid tert-butyl ester (11c)

To a solution of Compound 11b (0.55 g; 1.3 mmol) in 1,2-dichloroethane (25 ml) was added Boc-L-prolinal (0.37 mL; 1.9 mmol). To the reaction mixture was then added $NaBH(OAc)_3$ (0.4 g; 1.9 mmol) portionwise, and the reaction mixture was continually stirred at room temperature for 5 h. The resultant mixture was diluted with water. After stirring for 10 min the organic phase was isolated, washed with brine, and dried over $MgSO_4$. The solvent was evaporated in vacuo to afford Compound 11c. The compound was used in the next step without further purification.

D. Cpd 177: (4-{2-Pyridin-3-yl-5-[(pyrrolidin-2-(S)-ylmethyl)-amino]-pyrimidin-4-yloxy}-phenyl)-carbamic acid benzyl ester (11d)

To a solution of Compound 11c (80 mg; 0.13 mmol) in $CH_2Cl_2$ (3 mL) was added trifluoroacetic acid (0.5 mL). The reaction was stirred at room temperature for 3 h and the solvent was evaporated in vacuo to give a crude residue. The crude material was purified by reverse phase HPLC, eluting with a $CH_3CN$—$H_2O$ gradient to afford Compound 177 (31.6 mg; 46% yield). $^1$H-NMR (300 MHz, MeOH-d$_4$): δ 8.7 (d, 1H), 8.6 (d, 1H), 8.2 (s, 1H), 7.7 (m, 1H), 7.6 (m, 2H), 7.5-7.25 (m, 7H), 7.2 (m, 2H), 5.2 (s, 2H), 4.0 (m, 1H), 3.7 (m, 2H), 3.5-3.3 (m, 4H), 2.4 (m, 1H), 2.2 (m, 2H) 1.9 (m, 1H); MS: m/z 497.2 (M+H)+.

Following the procedure described for Example 11 and substituting the appropriate reagents, starting materials and purification methods known to those skilled in the art, the following compounds of the present invention were prepared:

| Cpd | MS (M + H)+ | Cpd | MS (M + H)+ |
|---|---|---|---|
| 188 | 497.2 | 197 | 515.2 |

Example 12

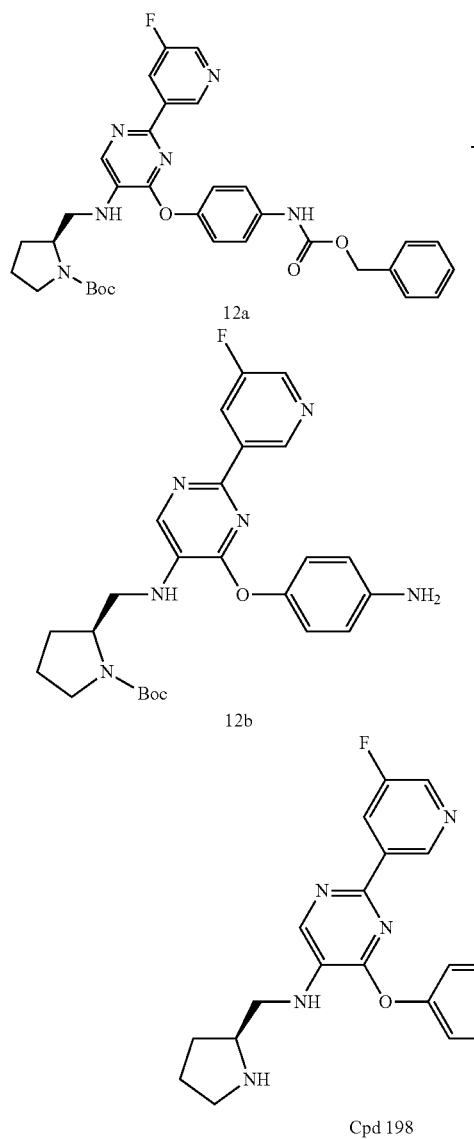

A. 2-(S)-{[4-(4-Benzyloxycarbonylamino-phenoxy)-2-(5-fluoro-pyridin-3-yl)-pyrimidin-5-ylamino]-methyl}-pyrrolidine-1-carboxylic acid tert-butyl ester (12a)

The title compound was prepared according to the method described for Compound 11c in Example 11. Using an adaptation of the method described in Procedures A-C, substituting 5-fluoro-pyridin-3-yl boronic acid for pyridin-3-yl boronic acid in Procedure B, the title Compound 12a was obtained. MS: m/z 615.2 (M+H)$^+$.

B. 2-(S)-{[4-(4-Amino-phenoxy)-2-(5-fluoro-pyridin-3-yl)-pyrimidin-5-ylamino]-methyl}-pyrrolidine-1-carboxylic acid tert-butyl ester (12b)

To a Parr bottle was placed 10% Pd/C (100 mg), Compound 12a (1.2 g; 1.9 mmol) and EtOH (35 mL). The reaction mixture was placed under a 50-psi H$_2$ atmosphere and the reaction was shaken for 20 h. The catalyst was collected by vacuum filtration and the filtrate was evaporated in vacuo to afford Compound 12b. The compound was used in the next step without further purification. MS: m/z 481.0 (M+H)$^+$.

C. Cpd 198: [4-(4-Amino-phenoxy)-2-(5-fluoro-pyridin-3-yl)-pyrimidin-5-yl]-pyrrolidin-2-(S)-ylmethyl-amine Using an adaptation of the method described in Procedure D of Example 11, substituting Compound 12b for Compound 11c, the title Compound 198 (100% yield based on tri-TFA salt) was obtained. $^1$H-NMR (300 MHz, MeOH-d$_4$): δ 8.8 (s, 1H), 8.3 (s, 1H), 8.2 (s, 1H), 8.0 (m, 1H), 7.6-7.4 (m, 4H), 4.0 (br. m, 1H), 3.6 (m, 2H), 3.5-3.2 (m, 4H), 2.2 (m, 1H), 2.0 (m, 2H), 1.8 (m, 1H); MS: m/z 381.2 (M+H)$^+$.

Example 13

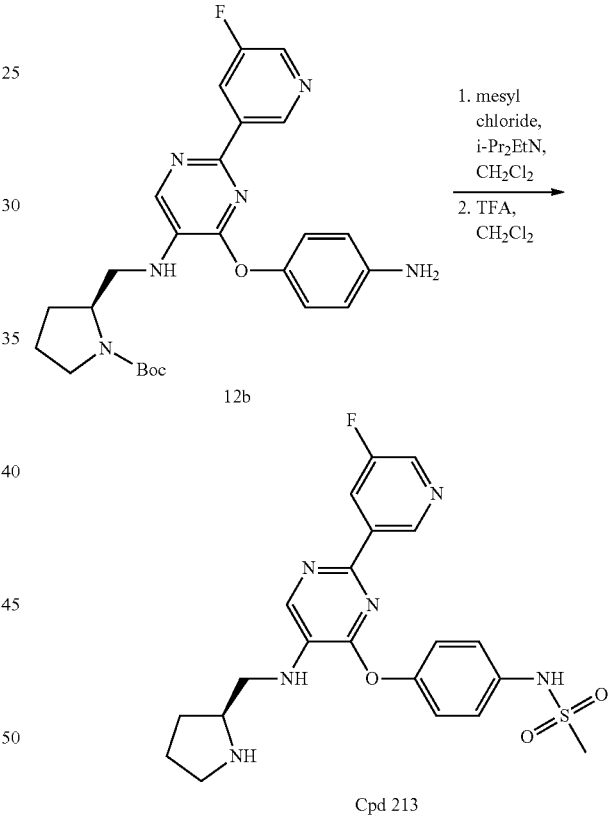

A. Cpd 213: N-(4-{2-(5-Fluoro-pyridin-3-yl)-5-[(pyrrolidin-2-(S)-ylmethyl)-amino]-pyrimidin-4-yloxy}-phenyl)-methanesulfonamide To a solution of Compound 12b (30 mg; 0.062 mmol) and i-Pr$_2$EtN (0.044 mL; 0.25 mmol) in CH$_2$Cl$_2$ (4 mL), cooled to 0° C., was added a solution of mesyl chloride (0.0044 mL; 0.062 mmol) in CH$_2$Cl$_2$ (2 mL) over 2 h. The reaction was then allowed to warm to room temperature and stirred at room temperature for 20 h. Water was added and the organic phase was isolated, dried over MgSO$_4$ and filtered, TFA (0.5 mL) was added to the filtrate. The mixture was stirred at room temperature for 1 h. The solvent was evaporated in vacuo. The residue was purified by reverse phase HPLC, eluting with a CH₃CN—H₂O gradient to afford Compound 213 (3.4 mg; 7% yield). ¹H-NMR (300 MHz, DMSO-d₆): δ 8.9 (m, 1H), 8.6 (d, 1H), 8.45 (m, 1H), 8.3 (m, 2H), 7.7 (d, 2H), 7.5 (m, 1H), 7.25 (d, 2H), 3.85 (m, 1H), 3.5 (m, 2H), 3.2 (m, 2H), 3.1-2.7 (m, 2H), 2.6 (s, 3H), 2.1 (m, 1H), 1.95 (m, 1H), 1.7 (m, 1H); MS: m/z 459.1 (M+H)⁺.

Following the procedure described above for Example 13 and substituting the appropriate reagents, starting materials and purification methods known to those skilled in the art, the following compounds of the present invention were prepared:

| Cpd | MS (M + H)⁺ | Cpd | MS (M + H)⁺ |
|-----|-------------|-----|-------------|
| 212 | 423.3 | 214 | 441.2 |
| 216 | 391.2 | 223 | 409.2 |

Example 14

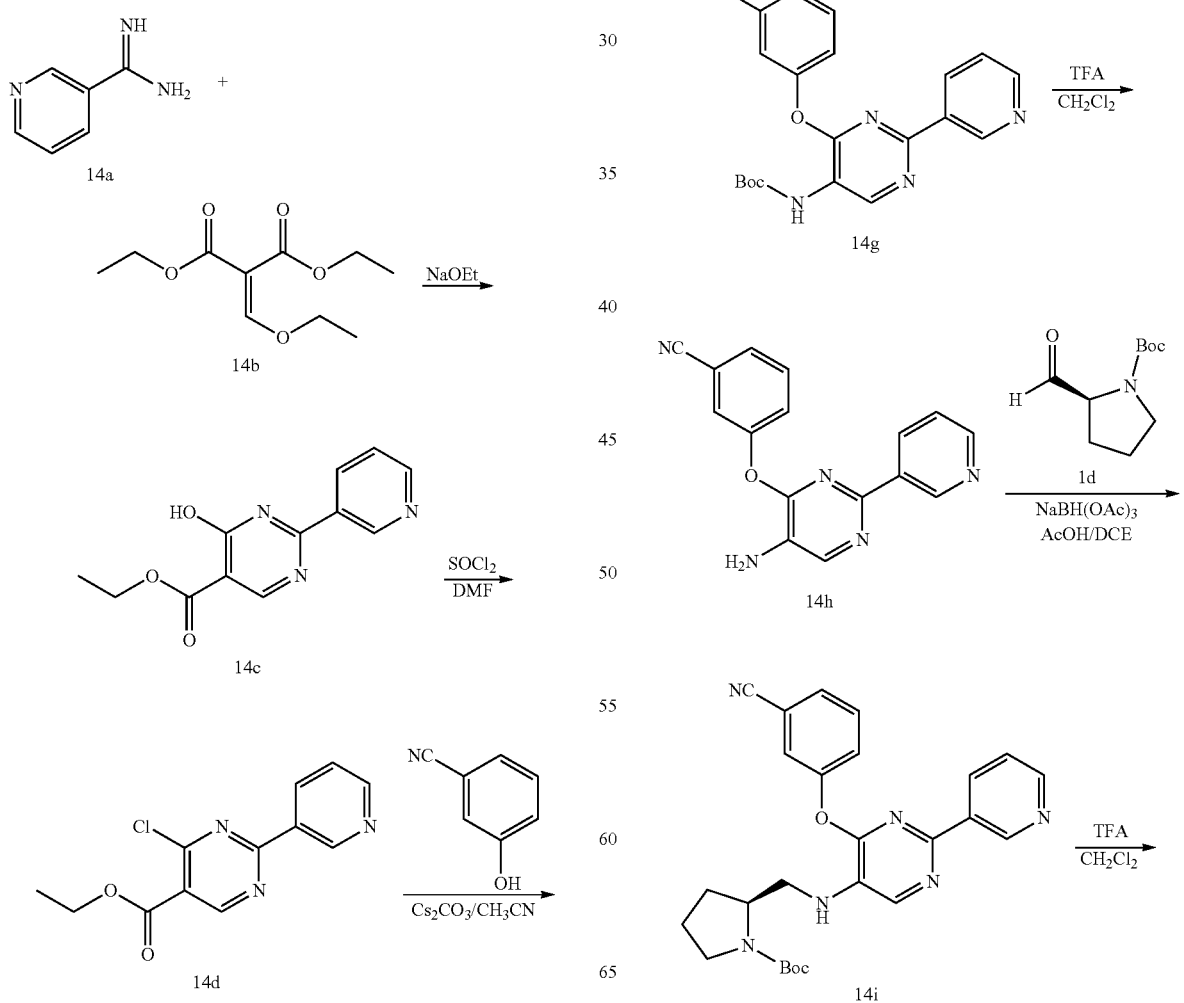

-continued

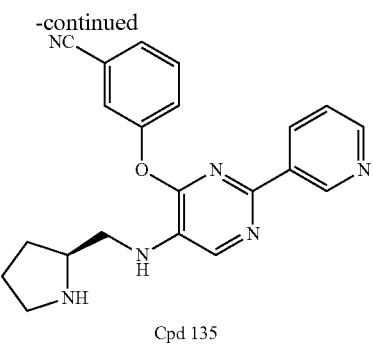

Cpd 135

A. 4-Hydroxy-2-pyridin-3-yl-pyrimidine-5-carboxylic acid ethyl ester (14c)

A suspension of Compound 14a (6.1 g; 38.64 mmol) in sodium ethoxide solution (21 wt. % in denatured ethanol) (100 mL) was stirred at room temperature for 10 min. To the mixture was added Compound 14b (7.81 mL; 38.65 mmol) at 0° C. The reaction was allowed to stir at room temperature for 5 h. Water (100 mL) was added to the reaction mixture, and the pH was adjusted to 5 with 2N HCl. The aqueous phase was extracted with $CH_2Cl_2$ (3×150 mL). The combined organic phases were dried over $MgSO_4$ and concentrated. To the residue was added $Et_2O$ (100 mL). The solid (Compound 14c) was collected by filtration and dried. $^1H$ NMR (300 MHz, $CDCl_3$): δ 9.80 (s, 1H), 9.10 (s, 1H), 7.75-8.90 (m, 2H), 7.50 (dd, 1H), 4.50 (q, 2H), 1.50 (t, 3H); MS: m/z 246.1 $(M+H)^+$.

B. 4-Chloro-2-pyridin-3-yl-pyrimidine-5-carboxylic acid ethyl ester (14d)

To a suspension of Compound 14c (5.05 g; 20.59 mmol) in DMF (70 mL) was added $SOCl_2$ (3 mL; 41.23 mmol) dropwise at room temperature. The reaction was stirred at room temperature for 30 min, then poured into an ice water slurry of $K_2CO_3$ (3.41 g). The resultant solid (Compound 14d) was collected by filtration and dried. $^1H$ NMR (300 MHz, $CDCl_3$): δ 9.70 (s, 1H), 9.20 (s, 1H), 7.70-8.85 (m, 2H), 7.50 (dd, 1H), 4.50 (q, 2H), 1.45 (t, 3H); MS: m/z 264.1 $(M+H)^+$.

C. 4-(3-Cyano-phenoxy)-2-pyridin-3-yl-pyrimidine-5-carboxylic acid ethyl ester (14e)

A mixture of Compound 14d (1.0 g; 3.79 mmol), 3-cyanophenol (0.587 g; 4.93 mmol) and $Cs_2CO_3$ (4.93 g; 15.13 mmol) in $CH_3CN$ (25 mL) was stirred at room temperature for 2 h. The suspension was poured into ice-water and extracted with $CH_2Cl_2$ (3×50 mL). The combined organic phases were dried over $MgSO_4$ and concentrated to afford Compound 14e. $^1H$ NMR (300 MHz, $CDCl_3$): δ 9.40 (s, 1H), 9.25 (s, 1H), 8.70 (d, 1H), 8.45 (m, 1H), 7.45-7.65 (m, 4H), 7.35 (m, 1H), 4.50 (q, 2H), 1.45 (t, 3H); MS: m/z 347.2 $(M+H)^+$.

D. 4-(3-Cyano-phenoxy)-2-pyridin-3-yl-pyrimidine-5-carboxylic acid (14f)

To a suspension of Compound 14e (1.06 g; 3.06 mmol) in EtOH (50 mL) was added 0.5N NaOH (9 mL; 4.5 mmol). The reaction was stirred at room temperature for 2 h. The pH of the reaction mixture was adjusted to 2 with 1N HCl. The resultant white solid was collected by filtration to afford Compound 14f. $^1H$ NMR (300 MHz, DMSO $d_6$): δ 9.21 (s, 1H), 9.18 (d, 1H), 8.70 (d, 1H), 8.35 (dd, 1H), 7.95 (s, 1H), 7.85 (dd, 1H), 7.75 (m, 2H), 7.50 (dd, 1H); MS: m/z 319.2 $(M+H)^+$.

E. [4-(3-Cyano-phenoxy)-2-pyridin-3-yl-pyrimidin-5-yl]carbamic acid tert-butyl ester (14g)

To a solution of $Et_3N$ (0.058 mL; 0.42 mmol) in $^tBuOH$ (9.35 mL) was added 4 Å molecular sieves (3 g) and the mixture was refluxed for 30 min under a $N_2$ atmosphere. Compound 14f (0.1 g; 0.31 mmol) and diphenylphosphorylazide (0.085 mL; 0.39 mmol) were added to the mixture and refluxed for 3 h under a $N_2$ atmosphere. The reaction mixture was allowed to cool to room temperature, filtered and concentrated. The resulting residue was suspended in EtOAc (10 mL) and washed with water (10 mL) and brine (10 mL), dried over $MgSO_4$ and concentrated. The crude product was purified by reverse phase HPLC to give Compound 14g. $^1H$ NMR (300 MHz, $CD_3OD$): δ 9.30 (s, 1H), 9.20 (s, 1H), 8.80 (d, 1H), 8.65 (d, 1H), 7.80 (dd, 1H), 7.70 (s, 1H), 7.65 (m, 3H), 1.50 (s, 9H); MS: m/z 390.3 $(M+H)^+$.

F. 3-(5-Amino-2-pyridin-3-yl-pyrimidin-4-yloxy)-benzonitrile (15h)

To a solution of Compound 14g (0.78 g; 2.0 mmol) in $CH_2Cl_2$ (20 mL) was added TFA (4 mL). The mixture was stirred at room temperature for 4 h. The solvent was evaporated under reduced pressure to afford Compound 14h. The crude product was used in the next reaction without further purification. MS: m/z 290.3 $(M+H)^+$.

G. 2-(S)-{[4-(3-Cyano-phenoxy)-2-pyridin-3-yl-pyrimidin-5-ylamino]-methyl}-pyrrolidine-1-carboxylic acid tert-butyl ester (14i)

To a suspension of Compound 14h (0.52 g; 1.8 mmol) and Compound 1d (0.505 mL; 2.69 mmol) in 1,2-dichloroethane (10 mL) was added acetic acid (0.103 mL; 1.8 mmol). The reaction was stirred at room temperature for 30 min. Sodium triacetoxyborohydride (0.46 g; 2.17 mmol) was added to the mixture. The mixture was stirred at room temperature for 20 h. Additional sodium triacetoxyborohydride (0.92 g; 4.34 mmol) was added to the mixture. The reaction was stirred at room temperature for 6 h, diluted with EtOAc (50 mL), and washed with $H_2O$ (2×20 mL). The organic layer was dried over $MgSO_4$ and concentrated. The crude product was purified by reverse phase HPLC to give Compound 14i. $^1H$ NMR (300 MHz, MeOH-$d_4$): δ 9.20 (s, 1H), 8.95 (d, 1H), 8.20 (d, 1H), 8.45 (s, 1H), 8.00 (dd, 1H), 7.65-7.8 (m, 4H), 4.20 (m, 1H), 3.3-3.6 (m, 4H), 1.9-2.1 (m, 4H), 1.5 (s, 9H); MS: m/z 473.4 $(M+H)^+$.

H. Cpd 135: 3-{2-Pyridin-3-yl-5-[(pyrrolidin-2-(S)-ylmethyl)-amino]-pyrimidin-4-yloxy}-benzonitrile To a solution of Compound 14i (0.05 g; 0.106 mmol) in $CH_2Cl_2$ (2 mL) was added TFA (0.4 mL). The mixture was stirred at room temperature for 4 h. The solvent was evaporated under reduced pressure. The crude product was purified by reverse phase HPLC to give Compound 135 as a TFA salt. $^1H$ NMR (300 MHz, MeOH-$d_4$): δ 9.20 (s, 1H), 8.95 (d, 1H), 8.75 (d, 1H), 8.35 (s, 1H), 8.00 (dd, 1H), 7.60-7.80 (m, 4H), 4.00 (m, 1H), 3.70 (m, 2H), 3.40 (m, 2H), 2.4 (m, 1H), 2.15 (m, 2H), 1.9 (m, 1H); MS: m/z 373.2 $(M+H)^+$.

Following the procedure described above for Example 14 and substituting the appropriate reagents, starting materials and purification methods known to those skilled in the art, the following compounds of the present invention were prepared:

| Cpd | MS (M + H)⁺ | Cpd | MS (M + H)⁺ |
|-----|-------------|-----|-------------|
| 136 | 373.3 | 137 | 391.3 |

Example 15

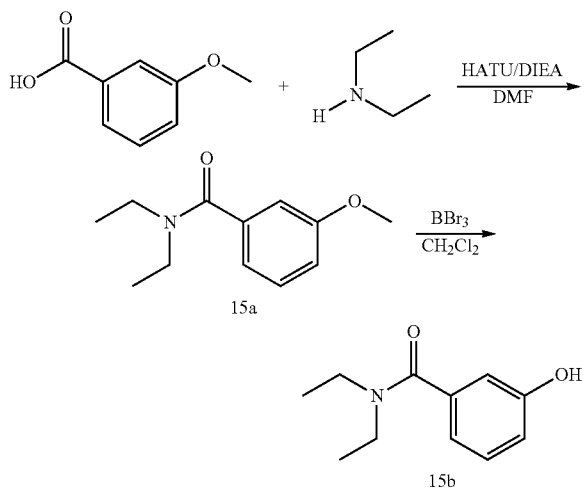

A. N,N-Diethyl-3-methoxy-benzamide (15a)

To a solution of m-anisic acid (0.5 g; 3.29 mmol) and HATU (1.4 g; 3.68 mmol) in DMF (5 mL) was added N,N-diisopropylethylamine (2 mL; 11.48 mmol). The reaction was stirred at room temperature for 30 min. Diethylamine (0.377 mL; 3.62 mmol) was added to the reaction. The mixture was stirred at room temperature for 1.5 d, diluted with $H_2O$ (5 mL), and extracted with EtOAc (2×5 mL). The organic layer was dried over $MgSO_4$ and concentrated to afford Compound 15a. The crude product was used in the next reaction without further purification. MS: m/z 208.2 (M+H)⁺.

B. N,N-Diethyl-3-hydroxy-benzamide (15b)

To a solution of Compound 15a (0.68 g; 3.28 mmol) in $CH_2Cl_2$ (50 mL) was added $BBr_3$ (1.0M in $CH_2Cl_2$) (16 mL; 16 mmol) dropwise at 0° C. The reaction was stirred at room temperature for 1 h. The mixture was quenched with saturated aqueous $NaHCO_3$. The organic layer was dried over $MgSO_4$ and concentrated to afford Compound 15b. The crude product was used in the next reaction without further purification. MS m/z 194.2 (M+H)⁺.

Following the procedure described above for Example 15 and substituting pyrrolidine for diethylamine in Procedure A, the Compound 15c was prepared:

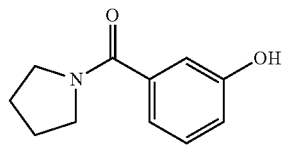

Following the procedure described above for Example 14, substituting Compound 15c for Compound 14c RIGHT?; and substituting the appropriate reagents and purification methods known to those skilled in the art, the following compounds of the present invention were prepared:

| Cpd | MS (M + H)⁺ | Cpd | MS (M + H)⁺ |
|-----|-------------|-----|-------------|
| 157 | 447.3 | 158 | 445.4 |

Example 16

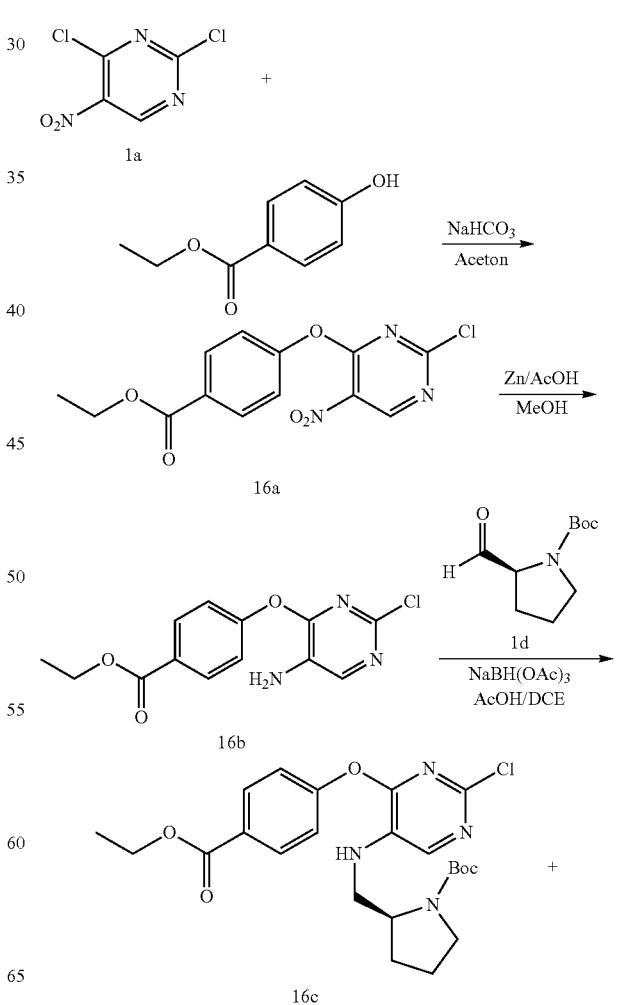

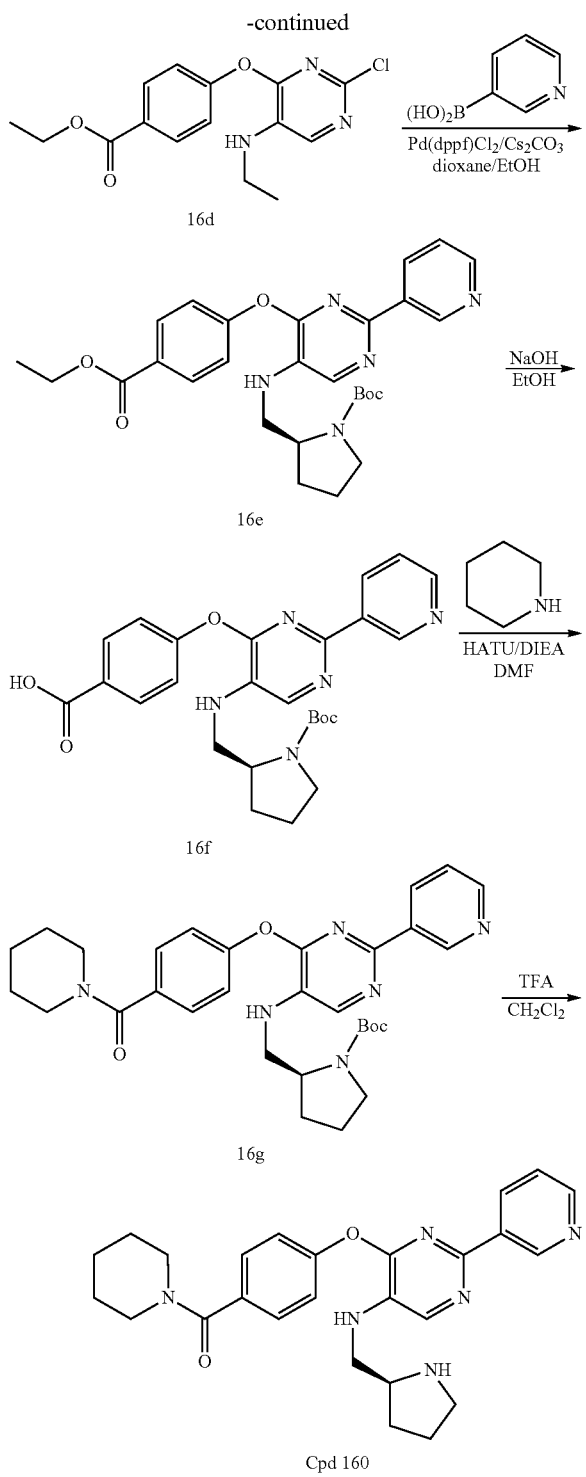

was extracted with EtOAc (2×20 mL). The organic layer was washed with brine and dried over MgSO$_4$ and concentrated. The crude product was purified by normal phase chromatography (SiO$_2$) to give Compound 16a. $^1$H NMR (300 MHz, CDCl$_3$): δ 9.20 (s, 1H), 8.20 (d, 2H), 7.25 (d, 2H), 4.45 (q, 2H), 1.4 (t, 3H); MS: m/z 324.1 (M+H)$^+$.

B. 4-(5-Amino-2-chloro-pyrimidin-4-yloxy)-benzoic acid ethyl ester (16b)

To a solution of Compound 16a (2.12 g; 6.55 mmol) in AcOH (15 mL) and CH$_3$OH (20 mL) was added Zn (2.57 g; 39.31 mmol) in portions at room temperature. The reaction mixture was stirred at room temperature for 6 h. The solid was collected by filtration and washed with CH$_3$OH. The filtrate was concentrated. The residue was quenched with aqueous NaOH (<1N) and adjusted to pH ~7, and extracted with EtOAc (2×20 mL). The organic layer was dried over MgSO$_4$ and concentrated. The crude product was purified by normal phase chromatography (SiO$_2$) to give Compound 16b. $^1$H NMR (300 MHz, CDCl$_3$): δ 8.15 (d, 2H), 7.95 (s, 1H), 7.25 (d, 2H), 4.45 (q, 2H), 1.4 (t, 3H); MS: m/z 294.1 (M+H)$^+$.

C. 2-(S)-{[2-Chloro-4-(4-ethoxycarbonyl-phenoxy)-pyrimidin-5-ylamino]-methyl}-pyrrolidine-1-carboxylic acid tert-butyl ester (16c) and 4-(2-Chloro-5-ethylamino-pyrimidin-4-yloxy)-benzoic acid ethyl ester (16d)

To a suspension of Compound 16b (0.82 g; 2.79 mmol) and Boc-L-prolinal (Compound 1d) (0.67 g; 3.36 mmol) in 1,2-dichloroethane (10 mL) was added acetic acid (0.16 mL, 2.79 mmol). The reaction was stirred at room temperature for 30 min. Sodium triacetoxyborohydride (0.89 g; 4.20 mmol) was added to the mixture. The mixture was stirred at room temperature for 20 h. Additional sodium triacetoxyborohydride (0.89 g; 4.20 mmol) was added to the mixture. The reaction was stirred at room temperature for 2 d, diluted with EtOAc (50 mL), and washed with H$_2$O (2×20 mL). The organic layer was dried over MgSO$_4$ and concentrated. The crude product was purified by normal phase chromatography (SiO$_2$) to give Compound 16c and Compound 16d. Compound 16c-MS: m/z 477.3 (M+H)$^+$. Compound 16d-MS: m/z 322.2 (M+H)$^+$.

D. 2-(S)-{[4-(4-Ethoxycarbonyl-phenoxy)-2-pyridin-3-yl-pyrimidin-5-ylamino]-methyl}-pyrrolidine-1-carboxylic acid tert-butyl ester (16e)

To a suspension of Compound 16c (0.76 g; 1.59 mmol), pyridin-3-yl boronic acid (0.235 g; 1.91 mmol) and Cs$_2$CO$_3$ (1.30 g; 3.99 mmol) in a dioxane (10 mL)/EtOH (2 mL) mixture, was added 1,1'-bis(diphenylphosphino)ferrocene palladium (II) chloride complex with dichloromethane (0.116 g; 0.159 mmol). The mixture was stirred at 80° C. for 4 h, and then cooled to room temperature. The solid was collected by filtration and washed with CH$_3$OH. The filtrate was concentrated. The crude product was purified by reverse phase HPLC to give Compound 16e. MS: m/z 520.3 (M+H)$^+$.

E. 2-(S)-{[4-(4-Carboxy-phenoxy)-2-pyridin-3-yl-pyrimidin-5-ylamino]-methyl}-pyrrolidine-1-carboxylic acid tert-butyl ester (16f)

To a suspension of Compound 16e (0.4 g; 0.77 mmol) in EtOH (10 mL) was added 0.5N NaOH (2.3 mL; 1.15 mmol). The reaction was stirred at room temperature for 3 h. Additional 0.5N NaOH (6 mL; 3 mmol) was added to the mixture.

A. 4-(2-Chloro-5-nitro-pyrimidin-4-yloxy)-benzoic acid ethyl ester (16a)

To a suspension of Compound 1a (2.0 g; 10.31 mmol) and 0.5N NaHCO$_3$ (20 mL; 10 mmol) in acetone (60 mL) was added a solution of 4-hydroxy-benzoic acid ethyl ester (1.71 g; 10.29 mmol) in acetone (20 mL) dropwise at 0° C. The mixture was stirred at 0° C. for 1 h. The reaction mixture was concentrated under reduced pressure. The resultant residue The reaction was stirred at room temperature for 3 h. The solution was adjusted to pH 2 with 1N HCl. The white solid was collected by filtration to afford Compound 16f. MS: m/z 492.3 (M+H)+.

F. 2-(S)-({4-[4-(Piperidine-1-carbonyl)-phenoxy]-2-pyridin-3-yl-pyrimidin-5-ylamino}-methyl)-pyrrolidine-1-carboxylic acid tert-butyl ester (16 g)

To a solution of Compound 16f (0.08 g; 0.16 mmol) and HATU (0.065 g; 0.17 mmol) in DMF (3 mL) was added N,N-diisopropylethylamine (0.115 mL; 0.66 mmol). The reaction was stirred at room temperature for 30 min. Piperidine (0.017 mL; 0.17 mmol) was added to the reaction. The mixture was stirred at room temperature for 1 h, poured into H$_2$O (3 mL), and extracted with EtOAc (2×5 mL). The organic layer was dried over MgSO$_4$ and concentrated to afford Compound 16g. The crude product was used in the next reaction without further purification. MS: m/z 559.3 (M+H)+.

G. Cpd 160: Piperidin-1-yl-(4-{2-pyridin-3-yl-5-[(pyrrolidin-2-(S)-ylmethyl)-amino]-pyrimidin-4-yloxy}-phenyl)-methanone To a solution of Compound 16g (0.089 g; 0.16 mmol) in CH$_2$Cl$_2$ (4 mL) was added TFA (0.8 mL). The mixture was stirred at room temperature for 4 h. The solvent was evaporated under reduced pressure. The crude product was purified by reverse phase HPLC to give Compound 160 as a TFA salt. $^1$H NMR (300 MHz, MeOH-d$_4$): δ 9.21 (s, 1H), 8.95 (d, 1H), 8.75 (d, 1H), 8.35 (s, 1H), 7.95 (dd, 1H), 7.55 (d, 2H), 7.40 (d, 2H), 4.05 (m, 1H), 3.6-3.85 (m, 4H), 3.3-3.55 (m, 4H), 2.35 (m, 1H), 2.20 (m, 2H), 1.9 (m, 1H), 1.55-1.85 (m, 6H); MS: m/z 459.3 (M+H)+.

Following the procedure described above for Example 16 and substituting the appropriate reagents, starting materials and purification methods known to those skilled in the art, the following compounds of the present invention were prepared:

| Cpd | MS (M + H)+ | Cpd | MS (M + H)+ |
|-----|-------------|-----|-------------|
| 161 | 461.2 | 162 | 474.3 |
| 166 | 445.4 | 167 | 459.3 |
| 168 | 461.4 | 169 | 474.3 |
| 170 | 465.3 | 171 | 463.4 |
| 172 | 477.3 | 173 | 479.3 |
| 174 | 492.3 | 175 | 447.3 |
|     |       | 176 | 463.4 |

Cpd 159

Deprotection of Compound 16f was performed using TFA/CH$_2$Cl$_2$ as described in Procedure G of Example 16 to afford Compound 159 as a TFA salt. MS: m/z 392.3 (M+H)+.

Cpd 163

The title compound was prepared in an analogous manner to Cpd 159, substituting 3-hydroxy-benzoic acid ethyl ester for 4-hydroxy-benzoic acid ethyl ester in Procedure A of Example 16. MS: m/z 392.3 (M+H)+.

Cpd 164

The title compound was prepared in an analogous manner to Cpd 159, substituting 3-hydroxy-benzoic acid ethyl ester for 4-hydroxy-benzoic acid ethyl ester in Procedure A and substituting 5-fluoropyridin-3-yl boronic acid for pyridin-3-yl boronic acid in Procedure D of Example 16. MS: m/z 410.2 (M+H)+.

Cpd 165

The title compound was prepared in an analogous manner to Cpd 159, substituting 5-fluoropyridin-3-yl boronic acid for pyridin-3-yl boronic acid in Procedure D of Example 16. MS: m/z 410.2 (M+H)+.

Example 17

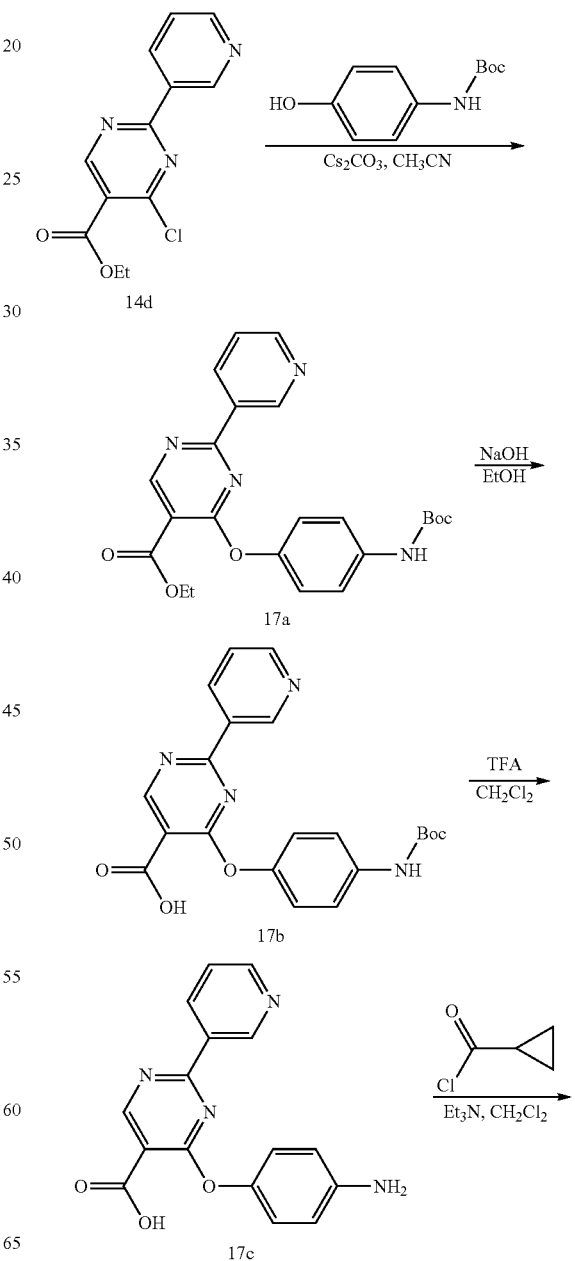

-continued

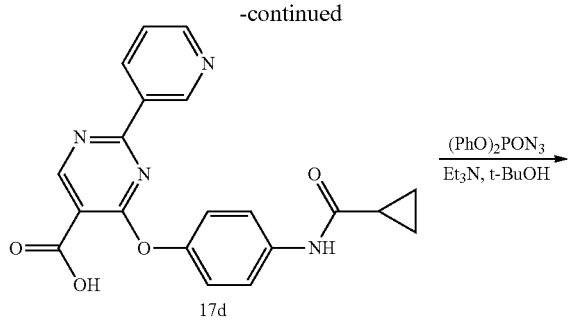

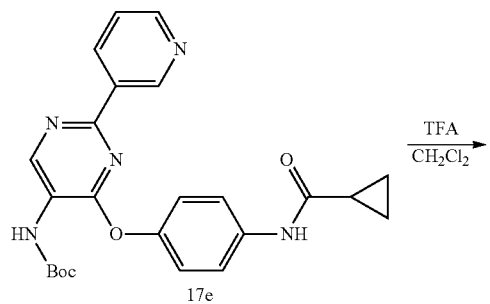

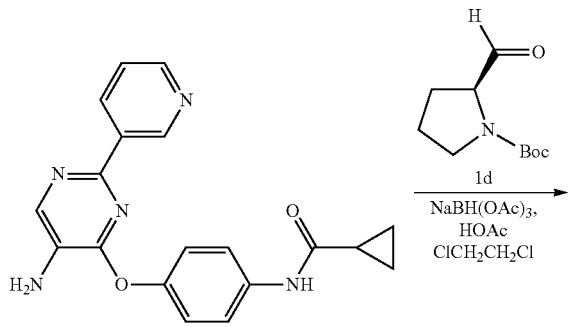

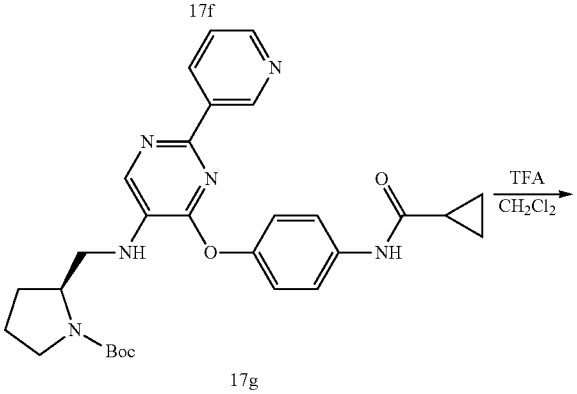

A. 4-(4-tert-Butoxycarbonylaminophenoxy)-2-pyridin-3-ylpyrimidine-5-carboxylic acid ethyl ester (17a)

Using an adaptation of the method described in Procedure C of Example 14, substituting (4-hydroxyphenyl)carbamic acid t-butyl ester for 3-cyanophenol, the title Compound 17a was obtained. MS: m/z 437.3 (M+H)$^+$.

B. 4-(4-tert-Butoxycarbonylaminophenoxy)-2-pyridin-3-ylpyrimidine-5-carboxylic acid (17b)

Using an adaptation of the method described in Procedure D of Example 14, substituting Compound 17a for Compound 14e, the title Compound 17b was obtained. MS: m/z 409.2 (M+H)$^+$.

C. 4-(4-Aminophenoxy)-2-pyridin-3-ylpyrimidine-5-carboxylic acid (17c)

To a solution of Compound 17b (1.5 g; 3.6 mmol) in CH$_2$Cl$_2$ (30 mL) was adde TFA (10 mL). The solution was stirred at room temperature for 1.5 h, and the solvent was evaporated in vacuo. The residue was triturated with Et$_2$O, collected the solid and dried to afford the title Compound 17c (2.25 g; 96% yield based on tri-TFA salt). MS: m/z 309.2 (M+H)$^+$.

D. 4-[4-(Cyclopropanecarbonylamino)phenoxy]-2-pyridin-3-ylpyrimidine-5-carboxylic acid (17d)

To a solution of Compound 17c (0.5 g; 1.6 mmol) in CH$_2$Cl$_2$ (6 mL) was added Et$_3$N (0.72 mL; 6.4 mmol) and cyclopropylcarbonyl chloride (0.19 mL; 2.1 mmol). The solution was stirred at room temperature for 1 h, then poured the reaction mixture into water. Filtered to collect the solid and dried to afford Compound 17d (410 mg; 68% yield). MS: m/z 376.1 (M+H)$^+$.

E. {4-[4-(Cyclopropanecarbonylamino)phenoxy]-2-pyridin-3-ylpyrimidin-5-yl}-carbamic acid tert-butyl ester (17e)

Using an adaptation of the method described in Procedure E of Example 14, substituting Compound 17d for Compound 14f, the title Compound 17e (16% yield) was obtained. MS: m/z 448.2 (M+H)$^+$.

F. Cyclopropanecarboxylic acid [4-(5-amino-2-pyridin-3-yl-pyrimidin-4-yloxy)-phenyl]amide (17f)

Using an adaptation of the method described in Procedure F of Example 14, substituting Compound 17e for Compound 14g, the title Compound 17f (78% yield) was obtained. The crude product was used in the next reaction without further purification. MS: m/z 347.3 (M+H)$^+$.

G. 2-(S)-({4-[4-(Cyclopropanecarbonyl-amino)-phenoxy]-2-pyridin-3-yl-pyrimidin-5-ylamino}-methyl)-pyrrolidine-1-carboxylic acid tert-butyl ester (17g)

Using an adaptation of the method described in Procedure G of Example 14, substituting Compound 17f for Compound 14h, the title Compound 17g was obtained. MS: m/z 531.3 (M+H)$^+$.

97

H. Cpd 138: Cyclopropanecarboxylic acid (4-{2-pyridin-3-yl-5-[(pyrrolidin-2-(S)-ylmethyl)-amino]-pyrimidin-4-yloxy}-phenyl)-amide Using an adaptation of the method described in Procedure H of Example 15, substituting Compound 17g for Compound 14i, the title Compound 138 (15% yield based on di-TFA salt) was obtained. $^1$H-NMR (300 MHz, DMSO-d$_6$): δ 8.6 (d, 2H), 8.5 (m, 1H), 8.3 (m, 2H), 7.7 (m, 2H), 7.5 (m, 1H), 7.25 (m, 2H), 6.3 (m, 1H), 3.9 (m, 1H), 3.5 (m, 2H), 3.2 (m, 2H) 3.1-2.8 (m, 2H), 2.15 (m, 1H), 1.9 (m, 2H), 1.8-1.6 (m, 3H), 0.9 (d, 2H); MS: m/z 431.3 (M+H)$^+$.

Example 18

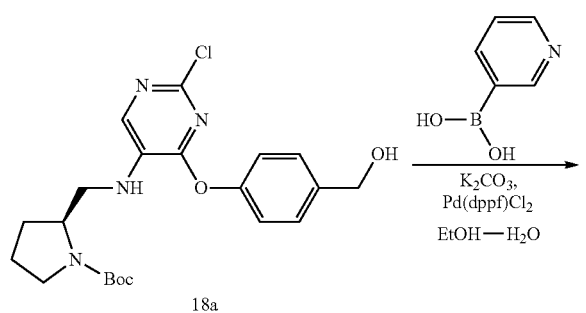

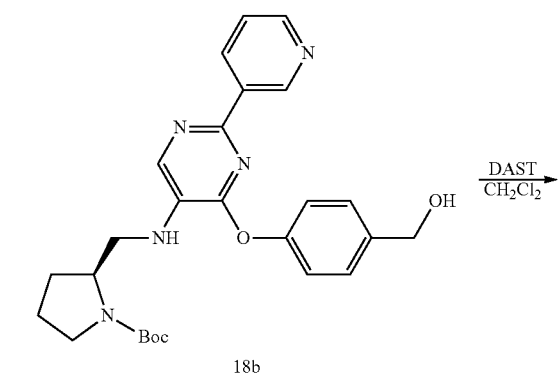

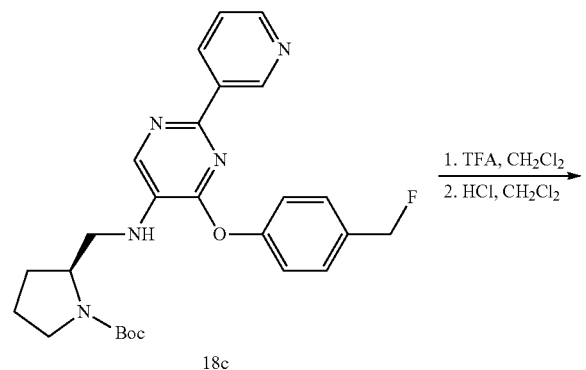

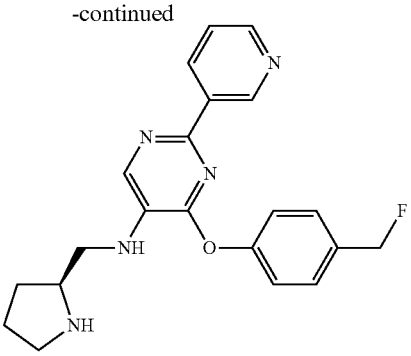

Cpd 217

A. 2-(S)-{[2-Chloro-4-(4-hydroxymethyl-phenoxy)-pyrimidin-5-ylamino]-methyl}-pyrrolidine-1-carboxylic acid tert-butyl ester (18a)

The title compound was prepared in a same manner to Compound 1e in Example 1. Using an adaptation of the method described in Procedures A-C, substituting 4-hydroxymethyl-phenol for 4-methoxyphenol in Procedure A, the title Compound 18a was obtained. MS: m/z 435.2 (M+H)$^+$.

B. 2-(S)-{[4-(4-Hydroxymethyl-phenoxy)-2-pyridin-3-yl-pyrimidin-5-ylamino]-methyl}-pyrrolidine-1-carboxylic acid tert-butyl ester (18b)

Using an adaptation of the method described in Procedure D of Example 1, substituting Compound 18a for Compound 1e and substituting pyridin-3-yl boronic acid for Compound 1f, the title Compound 18b (73% yield) was obtained. MS: m/z 478.2 (M+H)$^+$.

C. 2-(S)-{[4-(4-Fluoromethyl-phenoxy)-2-pyridin-3-yl-pyrimidin-5-ylamino]-methyl}-pyrrolidine-1-carboxylic acid tert-butyl ester (18c)

To a solution of (diethylamino)sulfur trifluoride (0.036 mL; 0.28 mmol) in CH$_2$Cl$_2$ (2 mL), cooled to −78° C., was added a solution of Compound 18b (100 mg; 0.21 mmol) in CH$_2$Cl$_2$ (1 mL). The reaction mixture was stirred at −78° C. for 20 min. The resultant mixture was partitioned between EtOAc and H$_2$O. The organic phase was washed with water and dried over Na$_2$SO$_4$. The mixture was filtered and the solvent removed under reduced pressure to give the crude material. The crude material was purified by flash column chromatography (SiO$_2$), eluting with a heptane-EtOAc gradient to afford Compound 18c (50 mg; 50% yield). MS: m/z 480.2 (M+H)$^+$.

D. Cpd 217: [4-(4-Fluoromethyl-phenoxy)-2-pyridin-3-yl-pyrimidin-5-yl]-pyrrolidin-2-(S)-ylmethyl-amine Using an adaptation of the method described in Procedure E of Example 1, substituting Compound 18c for Compound 1g, the title Compound 217 was obtained as a HCl salt. $^1$H-NMR (400 MHz, MeOH-d$_4$): δ 9.21 (br. s, 1H), 8.73-8.74 (m, 1H), 8.63 (br. s, 1H), 8.27-8.29 (m, 1H), 7.75 (br. s, 1H), 7.45-7.58 (m, 2H), 7.30-7.39 (m, 2H), 5.36-5.51 (m, 2H), 4.02-4.05 (m, 1H), 3.67-3.73 (m, 2H), 3.41-3.48 (m, 2H), 2.32-2.38 (m, 1H), 2.09-2.21 (m, 2H), 1.86-1.95 (m, 1H); MS: m/z 380.2 (M+H)⁺.

Following the procedure described above for Example 18 and substituting the appropriate reagents, starting materials and purification methods known to those skilled in the art, the following compound of the present invention was prepared:

| Cpd | MS (M + H)⁺ |
|---|---|
| 348 | 405.2 |

Example 19

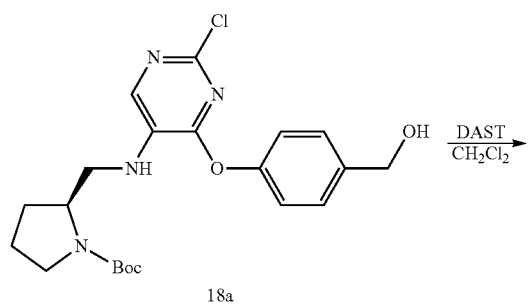
18a

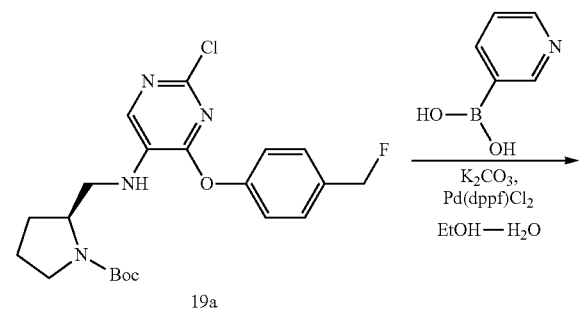
19a

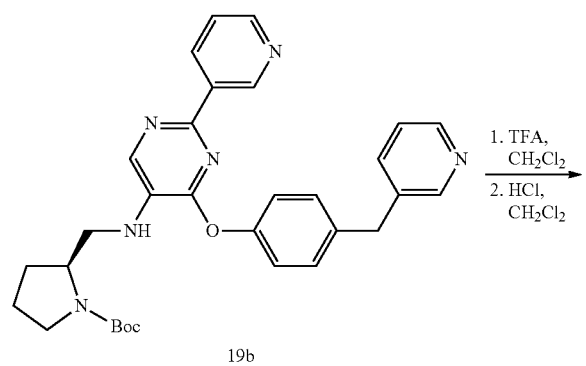
19b

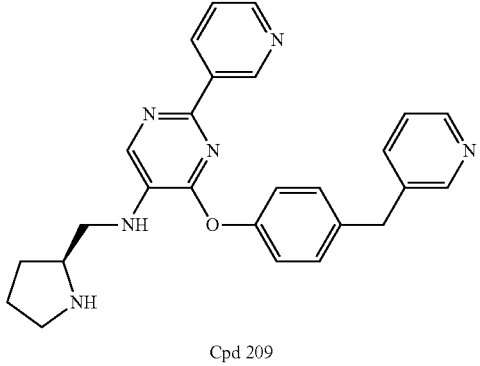
Cpd 209

A. 2-(S)-{[2-Chloro-4-(4-fluoromethyl-phenoxy)-pyrimidin-5-ylamino]-methyl}-pyrrolidine-1-carboxylic acid tert-butyl ester (19a)

Using an adaptation of the method described in Procedure C of Example 18, substituting Compound 18a for Compound 18b, the title Compound 19a (23% yield) was obtained. MS: m/z 437.2 (M+H)⁺.

B. 2-(S)-{[2-Pyridin-3-yl-4-(4-pyridin-3-ylmethyl-phenoxy)-pyrimidin-5-ylamino]-methyl}-pyrrolidine-1-carboxylic acid tert-butyl ester (19b)

Using an adaptation of the method described in Procedure D of Example 1, substituting Compound 19a for Compound 1e and substituting pyridin-3-yl boronic acid for Compound 1f, the title Compound 19b (22% yield) was obtained. ¹H-NMR (400 MHz, CDCl₃): δ 9.26 (s, 1H), 8.55 (d, 1H), 8.51 (dd, 2H), 8.32 (d, 1H), 8.01-8.06 (m, 1H), 7.53 (d, 1H), 7.18-7.27 (m, 6H), 5.78 (br. s, 0.7H), 4.85 (br. s, 0.3; H), 4.21-4.32 (m, 1H), 4.04 (s, 2H), 3.21-3.54 (m, 4H), 1.84-2.14 (m, 4H); MS: m/z 539.3 (M+H)⁺.

C. Cpd 209: [2-Pyridin-3-yl-4-(4-pyridin-3-ylmethyl-phenoxy)-pyrimidin-5-yl]-pyrrolidin-2-(S)-ylmethyl-amine Using an adaptation of the method described in Procedure E of Example 1, substituting Compound 19b for Compound 1g, the title Compound 209 was obtained as a HCl salt. ¹H-NMR (400 MHz, MeOH-d₄): δ 9.12 (br. s, 1H), 8.44-8.57 (m, 4H), 8.23 (s, 1H), 7.94 (d, 1H), 7.47-7.57 (m, 2H), 7.41 (d, 2H), 7.29 (d, 2H), 4.17 (s, 2H), 4.01-4.04 (m, 1H), 3.67-3.70 (m, 2H), 3.45-3.54 (m, 2H), 2.31-2.39 (m, 1H), 2.08-2.21 (m, 2H), 1.85-1.95 (m, 1H); MS: m/z 439.2 (M+H)⁺.

Example 20

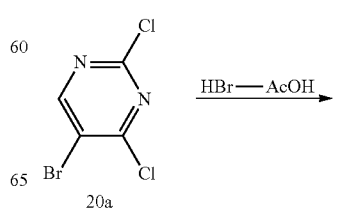
20a

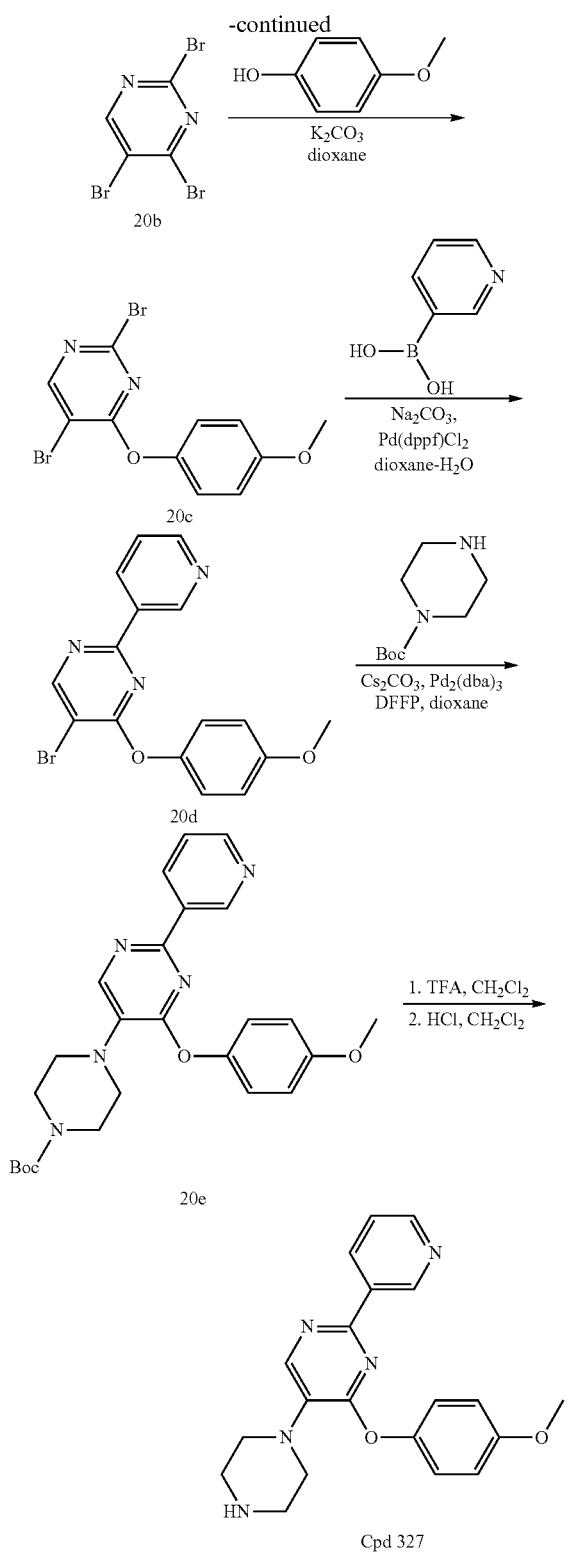

A. 2,4,5-Tribromo-pyrimidine (20b)

To a pressure vessel, a suspension of 2,4-dichloro-5-bromo-pyrimidine (Compound 20a) (3.0 g; 13.2 mmol) in HBr solution (33 wt % in AcOH) (35 mL) was heated at 50° C. for 4 h before cooling in an ice bath. The reaction mixture was poured into ice/water (2-fold volume) and was extracted with EtOAc. The organic phase was washed sequentially with $H_2O$ and brine, and dried over $Na_2SO_4$. The mixture was filtered and the solvent evaporated under reduced pressure to give the crude material. The crude material was recrystallized from EtOAc-hexanes to afford Compound 20b (3.75 g; 90% yield) as a yellow solid. $^1$H-NMR (400 MHz, $CDCl_3$): δ 8.58 (s, 1H); MS: m/z 314.8 (M+H)$^+$.

B. 2,5-Dibromo-4-(4-methoxy-phenoxy)-pyrimidine (26c)

A mixture of Compound 20b (0.39 g; 1.23 mmol), $K_2CO_3$ (0.25 g, 1.85 mmol) and 4-methoxy-phenol (0.15 g; 1.23 mmol) in dioxane (4 mL) was heated at 65° C. for 20 h. The reaction mixture was filtered and the filtrate was diluted with EtOAc and $H_2O$. The organic phase was washed sequentially with $H_2O$ and brine, and dried over $Na_2SO_4$. The mixture was filtered and the solvent evaporated under reduced pressure to give the crude material. Recrystallized the crude material from EtOAc-hexane to afford Compound 20c (0.42 g; 95% yield) as white solid. $^1$H-NMR (400 MHz, $CDCl_3$): δ 8.49 (s, 1H), 7.10 (d, 2H), 6.95 (d, 2H), 3.84 (s, 3H); MS: m/z 359.0 (M+H)$^+$.

C. 5-Bromo-4-(4-methoxy-phenoxy)-2-pyridin-3-yl-pyrimidine (20d)

Under argon pressure, a mixture of Compound 20c (2.27 g; 6.31 mmol), pyridine-3-boronic acid (853 mg; 6.94 mmol), $Na_2CO_3$ (1.34 g; 12.6 mmol) and [1,1'-Bis(diphenylphosphino)-ferrocene]dichloro-palladium(II) (258 mg, 0.32 mmol) in dioxane (32 mL) was stirred at room temperature for 5 min, and then D.I. water (8 mL) was added. The whole mixture was heated at 55° C. under argon pressure for 20 h. Diluted the resulted mixture with EtOAc, washed with saturated $NH_4Cl_{(aq)}$ and $H_2O$. The organic phase was washed sequentially with $H_2O$, and then dried over $Na_2SO_4$. The mixture was filtered and the filtrate was evaporated under reduced pressure to give the crude material. The crude material was purified by flash column chromatography ($SiO_2$), eluting with a heptane-EtOAc gradient to afford Compound 20d (1.44 g; 64% yield) as off-white solid. $^1$H-NMR (400 MHz, $CDCl_3$): δ 9.33 (dd, 1H), 8.77 (s, 1H), 8.64 (dd, 1H), 8.41 (dt, 1H), 7.32 (td, 1H), 7.16 (dd, 2H), 6.97 (dd, 2H), 3.87 (s, 3H); MS: m/z 358.0 (M+H)$^+$.

D. 4-[4-(4-Methoxy-phenoxy)-2-pyridin-3-yl-pyrimidin-5-yl]-piperazine-1-carboxylic acid tert-butyl ester (20e)

To a dry Schlenk tube was added a mixture of Compound 20d (100 mg; 0.28 mmol), piperazine-1-carboxylic acid tert-butyl ester (52 mg; 0.56 mmol), $Cs_2CO_3$ (227 mg; 0.70 mmol), (Diphenylphosphino)ferrocene (54 mg; 0.10 mmol), and Tris(dibenzylideneacetone)dipalladium(0) (25.6 mg; 0.028 mmol). Sealed the tube with a teflon-lined septum, evacuated, and refilled with argon. Added dioxane (0.3 mL; reaction conc. >0.75M) to the mixture via syringe. The mixture was heated at 95° C. for 3 h. Diluted the resulted mixture with EtOAc, washed with saturated $NH_4Cl_{(aq)}$ and $H_2O$. The organic phase was washed sequentially with $H_2O$, and then dried over $Na_2SO_4$. The mixture was filtered and the filtrate was evaporated under reduced pressure to give the crude material. The crude material was purified by flash column chromatography ($SiO_2$), eluting with a heptane-EtOAc gradient to afford Compound 20e (104 mg; 80% yield). $^1$H-NMR (400 MHz, CDCl₃): δ 9.28 (d, 1H), 8.58 (dd, 1H), 8.35 (dt, 1H), 8.22 (s, 1H), 7.29 (td, 1H), 7.14 (dd, 2H), 6.98 (dd, 2H), 3.87 (s, 3H), 3.66 (t, 4H), 3.25 (t, 4H), 1.56 (s, 9H); MS: m/z 464.2 (M+H)⁺.

E. Cpd 327: 4-(4-Methoxy-phenoxy)-5-piperazin-1-yl-2-pyridin-3-yl-pyrimidine Using an adaptation of the method described in Procedure E of Example 1, substituting Compound 20e for Compound 1g, the title Compound 327 was obtained as a HCl salt. Free base-¹H-NMR (400 MHz, CDCl₃): δ 9.28 (d, 1H), 8.57 (dd, 1H), 8.34 (dt, 1H), 8.23 (s, 1H), 7.28 (td, 1H), 7.15 (dd, 2H), 6.97 (dd, 2H), 3.87 (s, 3H), 3.28 (t, 4H), 3.11 (t, 4H); MS: m/z 364.2 (M+H)⁺.

Following the procedure described above for Example 20 and substituting the appropriate reagents, starting materials and purification methods known to those skilled in the art, the following compounds of the present invention were prepared:

| Cpd | MS (M + H)⁺ | Cpd | MS (M + H)⁺ |
|---|---|---|---|
| 324 | 363.2 | 325 | 389.2 |
| 326 | 389.2 | 199 | 403.2 |
| 328 | 389.2 | 329 | 403.2 |
| 207 | 403.2 | 208 | 403.2 |
| 329 | 403.2 | 331 | 389.2 |
| 215 | 389.2 | 332 | 403.2 |
| 333 | 403.2 | 334 | 403.2 |
| 336 | 378.0 | 224 | 364.0 |
| 225 | 392.0 | 226 | 350.0 |
| 305 | 392.0 | 236 | 378.0 |
| 338 | 401.0 | 237 | 364.0 |
| 339 | 364.0 | 341 | 410.0 |
| 340 | 350.0 | 342 | 394.0 |
| 245 | 408.0 | 344 | 403.0 |
| 343 | 403.0 | 246 | 408.0 |
| 345 | 403.0 | 252 | 424.2 |
| 346 | 408.0 | 347 | 424.0 |
| 254 | 424.0 | 255 | 410.0 |
| 348 | 410.0 | 256 | 394.0 |
| 349 | 394.0 | 257 | 378.0 |
| 258 | 392.2 | 259 | 392.0 |
| 350 | 438.0 | 351 | 378.0 |
| 352 | 378.0 | 261 | 378.0 |
| 354 | 378.0 | 355 | 392.2 |
| 356 | 378.0 | 358 | 392.2 |
| 296 | 352.0 | 267 | 392.2 |

Following the procedure described above for Example 20 and substituting the appropriate reagents, starting materials and purification methods known to those skilled in the art, the following compounds of the present invention were prepared as mixtures (contained 4 isomers).

| Cpd | MS (M + H)⁺ | Cpd | MS (M + H)⁺ |
|---|---|---|---|
| 306 | 392.0 | 312 | 438.0 |
| 309 | 422.2 | 315 | 406.2 |

Using purification methods known to those skilled in the art, the above mixtures of the present invention were further separated into their corresponding diastereoisomers and/or single stereoisomer.

| Cpd | stationary phase/order of elution off the column | MS (M + H)⁺ |
|---|---|---|
| 307 | C-18 (CH₃CN—H₂O)/first peak off column | 392.0 |
| 308 | C-18 (CH₃CN—H₂O)/first peak off column | 392.0 |
| 311 | CHIRALPAK ® AD ™ (50% methanol with 0.5% isopropylamine/50% Ethanol with 0.5% isopropylamine; flow rate: 1.0 mL/min)/first peak off column | 422.0 |
| 312 | CHIRALPAK ® AD ™ (50% methanol with 0.5% isopropylamine/50% Ethanol with 0.5% isopropylamine; flow rate: 1.0 mL/min)/second peak off column | 422.0 |
| 313 | CHIRALPAK ® AD ™ (50% methanol with 0.5% isopropylamine/50% Ethanol with 0.5% isopropylamine; flow rate: 1.0 mL/min)/third peak off column | 422.0 |
| 314 | CHIRALPAK ® AD ™ (50% methanol with 0.5% isopropylamine/50% Ethanol with 0.5% isopropylamine; flow rate: 1.0 mL/min)/fourth peak off column | 422.0 |
| 316 | CHIRALCEL ® OJ ™ (85% heptane/7.5% ethanol/7.5% ammonia sat. in methanol 7N, flow rate: 2.0 mL/min)/third peak off column | 438.2 |
| 317 | CHIRALCEL ® OJ ™ (85% heptane/7.5% ethanol/7.5% ammonia sat. in methanol 7N, flow rate: 2.0 mL/min)/fourth peak off column | 438.2 |
| 318 | CHIRALCEL ® OJ ™ (85% heptane/7.5% ethanol/7.5% ammonia sat. in methanol 7N, flow rate: 2.0 mL/min)/first peak off column | 438.2 |
| 319 | CHIRALCEL ® OJ ™ (85% heptane/7.5% ethanol/7.5% ammonia sat. in methanol 7N, flow rate: 2.0 mL/min)/second peak off column | 438.2 |
| 321 | CHIRALPAK ® AD ™ (20% IPA in hexane at 15 mL/min)/third peak off column | 392.2 |
| 322 | CHIRALPAK ® AD ™ (20% IPA in hexane at 15 mL/min)/fourth peak off column | 392.2 |
| 323 | CHIRALPAK ® AD ™ (20% IPA in hexane at 15 mL/min)/first peak off column | 392.2 |

²Using Boc-protected mixtures, chiral separations were performed to obtain the Boc-protected single isomers, which were then deprotected to give the example compounds.

Example 21

An Alternative Route for Preparing Compounds Described in Example 20

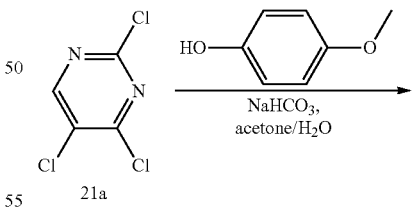

21a

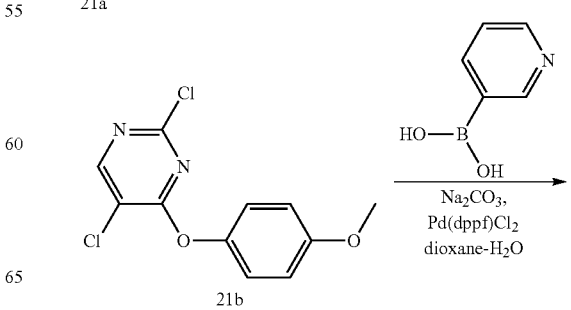

21b

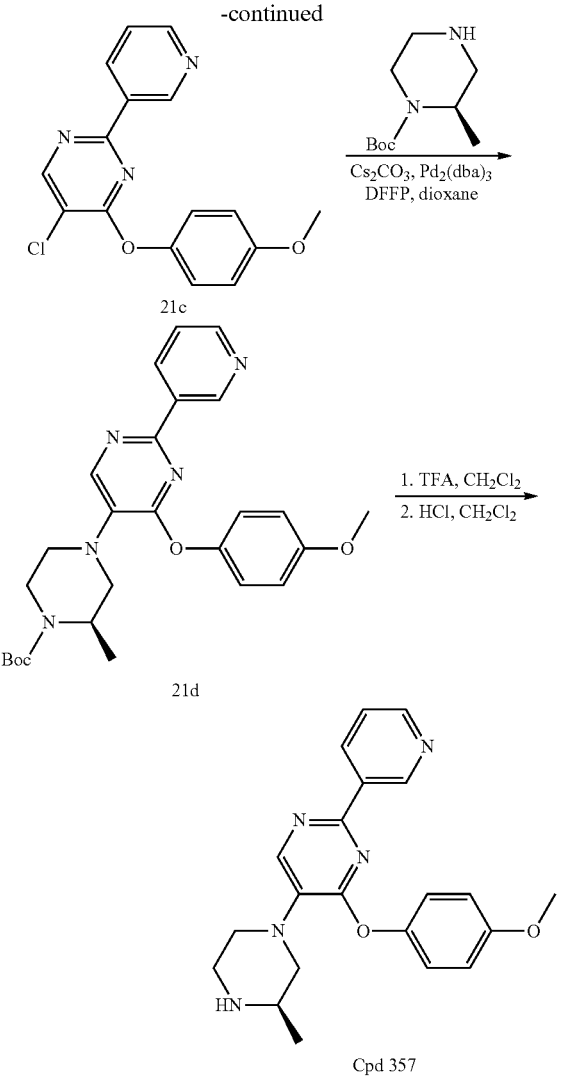

Na₂CO₃ (1.90 g; 17.96 mmol) and [1,1'-bis(diphenylphosphino)-ferrocene]dichloro-palladium(II) (370 mg, 0.45 mmol) in dioxane (35 mL) was stirred at room temperature for 5 min, and then deionized water (7 mL) was added. The mixture was heated at 75° C. under an argon atmosphere for 20 h. The resultant mixture was diluted with EtOAc, washed with saturated NH₄Cl (aq) and H₂O. The organic phase was washed sequentially with H₂O, and then dried over Na₂SO₄. The mixture was filtered and the filtrate was evaporated under reduced pressure to give the crude material. The crude material was purified by flash column chromatography (SiO₂), eluting with a heptane-EtOAc gradient to afford Compound 23c (2.10 g; 75% yield). $^1$H-NMR (400 MHz, CDCl₃): δ 9.34 (dd, 1H), 8.6 (s, 1H), 8.65 (dd, 1H), 8.42 (dt, 1H), 7.31-7.34 (m, 1H), 7.15-7.19 (m, 2H), 6.97-7.01 (m, 2H), 3.88 (s, 3H); MS: m/z 314.0 (M+H)⁺.

C. 4-[4-(4-Methoxy-phenoxy)-2-pyridin-3-yl-pyrimidin-5-yl]-2-(R)-methyl-piperazine-1-carboxylic acid tert-butyl ester (21d)

Using an adaptation of the method described in Procedure D of Example 22, substituting 2-(R)-methyl-piperazine-1-carboxylic acid tert-butyl ester for piperazine-1-carboxylic acid tert-butyl ester, the title Compound 23d was obtained. $^1$H-NMR (400 MHz, CDCl₃): δ 9.30 (br. s, 1H), 8.58 (br. s, 1H), 8.36 (d, 1H), 8.20 (s, 1H), 7.25-7.32 (m, 1H), 7.13-7.18 (m, 2H), 6.96-7.00 (m, 2H), 4.40 (br. s, 1H), 4.02-4.05 (m, 1H), 3.88 (s, 3H), 3.59-3.62 (m, 1H), 3.30-3.51 (m, 1H), 2.89-2.96 (m, 2H), 1.50 (s, 9H), 1.40 (d, 3H); MS: m/z 478.0 (M+H)⁺.

D. Cpd 357: 4-(4-Methoxy-phenoxy)-5-[3-(R)-methyl-piperazin-1-yl]-2-pyridin-3-yl-pyrimidine Using an adaptation of the method described in Procedure E of Example 1, substituting Compound 21d for Compound 1g, the title Compound 357 was obtained as a HCl salt. Free base-$^1$H-NMR (400 MHz, CDCl₃): δ 9.29 (d, 1H), 8.58 (dd, 1H), 8.36 (dt, 1H), 8.23 (s, 1H), 7.25-7.30 (m, 1H), 7.14-7.18 (m, 2H), 6.96-7.00 (m, 2H), 3.88 (s, 3H), 3.60-3.67 (m, 2H), 3.12-3.18 (m, 3H), 2.85-2.92 (m, 1H), 2.53-2.58 (m, 1H), 1.18 (d, 3H); MS: m/z 378.0 (M+H)⁺.

Following the procedure described above for Example 21 and substituting the appropriate reagents, starting materials and purification methods known to those skilled in the art, the following compounds of the present invention were prepared:

| Cpd | MS (M + H)⁺ | Cpd | MS (M + H)⁺ |
|-----|-------------|-----|-------------|
| 320 | 374.2 | 360 | 422.2 |
| 361 | 422.0 | | |

Cpd 320

The title compound was prepared in an analogous manner to Compound 21e of Example 21, substituting 4-cyclopropyl-phenol[4] for 4-methoxy-phenol in Procedure A, and substituting piperazine-1-carboxylic acid tert-butyl ester for 2-(R)-methyl-piperazine-1-carboxylic acid tert-butyl ester in Procedure C. $^1$H-NMR (400 MHz, MeOH-d₄): δ 9.11 (d, 1H), 8.49 (dd, 1H), 8.40 (dt, 1H), 8.29 (s, 1H), 7.42 (dd, 1H), A. 2,5-Dichloro-4-(4-methoxy-phenoxy)-pyrimidine (21b)

To a solution of Compound 21a (5 g; 27.26 mmol) in acetone (480 mL), cooled to 0° C., was added a solution of 4-methoxy-phenol (3.38 g; 27.26 mmol) in a mixture of 1 N NaHCO₃ (aq) (27.3 mL) and H₂O (120 mL), dropwise, by an additional funnel. Upon completion of the addition, the reaction mixture was allowed to warm to ambient temperature, and then stirred at room temperature for 3 h. The resultant mixture was concentrated in vacuo, and the resultant residue was diluted with EtOAc, then washed sequentially with 1 N NaOH (aq) and H₂O. The organic phase was washed sequentially with H₂O and brine, and dried over Na₂SO₄. The mixture was filtered and the filtrate concentrated under reduced pressure to give a crude material. The crude material was recrystallized from EtOAc-hexanes to afford Compound 21b (7.0 g; 94% yield). $^1$H-NMR (400 MHz, CDCl₃): δ 8.46 (s, 1H), 7.09-7.27 (m, 2H), 6.94-6.98 (m, 2H), 3.85 (s, 3H); MS: m/z 271.0 (M+H)⁺.

B. 5-Chloro-4-(4-methoxy-phenoxy)-2-pyridin-3-yl-pyrimidine (21c)

Under argon pressure, a mixture of Compound 21b (2.43 g; 8.98 mmol), pyridin-3-yl boronic acid (1.43 g; 11.67 mmol), 7.15-7.20 (m, 2H), 7.10-7.12 (m, 2H), 3.29-3.32 (m, 4H), 3.04-3.06 (m, 4H), 1.94-2.01 (m, 1H), 0.98-1.03 (m, 2H), 0.70-0.74 (m, 2H); MS: m/z 374.2 (M+H)+.

[4] 4-Cyclopropyl-phenol was prepared by the following synthetic scheme and procedure:

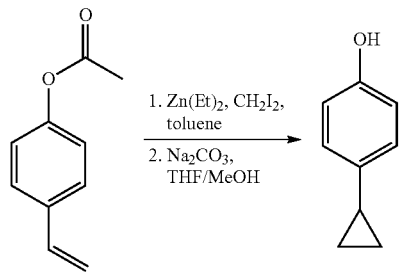

A. 4-Cyclopropyl-phenol

To a solution of diethylzinc (59 mL, 65.9 mmol) in toluene (80 mL) was added acetic acid 4-vinyl-phenyl ester (5 mL, 32.7 mmol) and diiodomethane (6.86 mL, 85 mmol). The resultant mixture was stirred at room temperature for 5 h, and then heated to reflux for 12 h. The reaction mixture was quenched with 2N HCl solution, the organic layer separated, washed with brine, dried over $Na_2SO_4$, and concentrated to afford a brown oil (4.5 g). The brown oil (4.5 g) was dissolved in MeOH/THF (20/20 mL), then treated with $Na_2CO_3$ (5.41 g, 51.1 mmol) at room temperature for 2 h. The reaction mixture was diluted with EtOAc, washed sequentially with saturated $NH_4Cl$ (aq) and $H_2O$, and extracted with EtOAc (3×). The organic extracts were combined, dried over $Na_2SO_4$ and concentrated under reduced pressure to afford the title compound (3.2 g; 94% yield), which was used directly without further purification.

Example 22

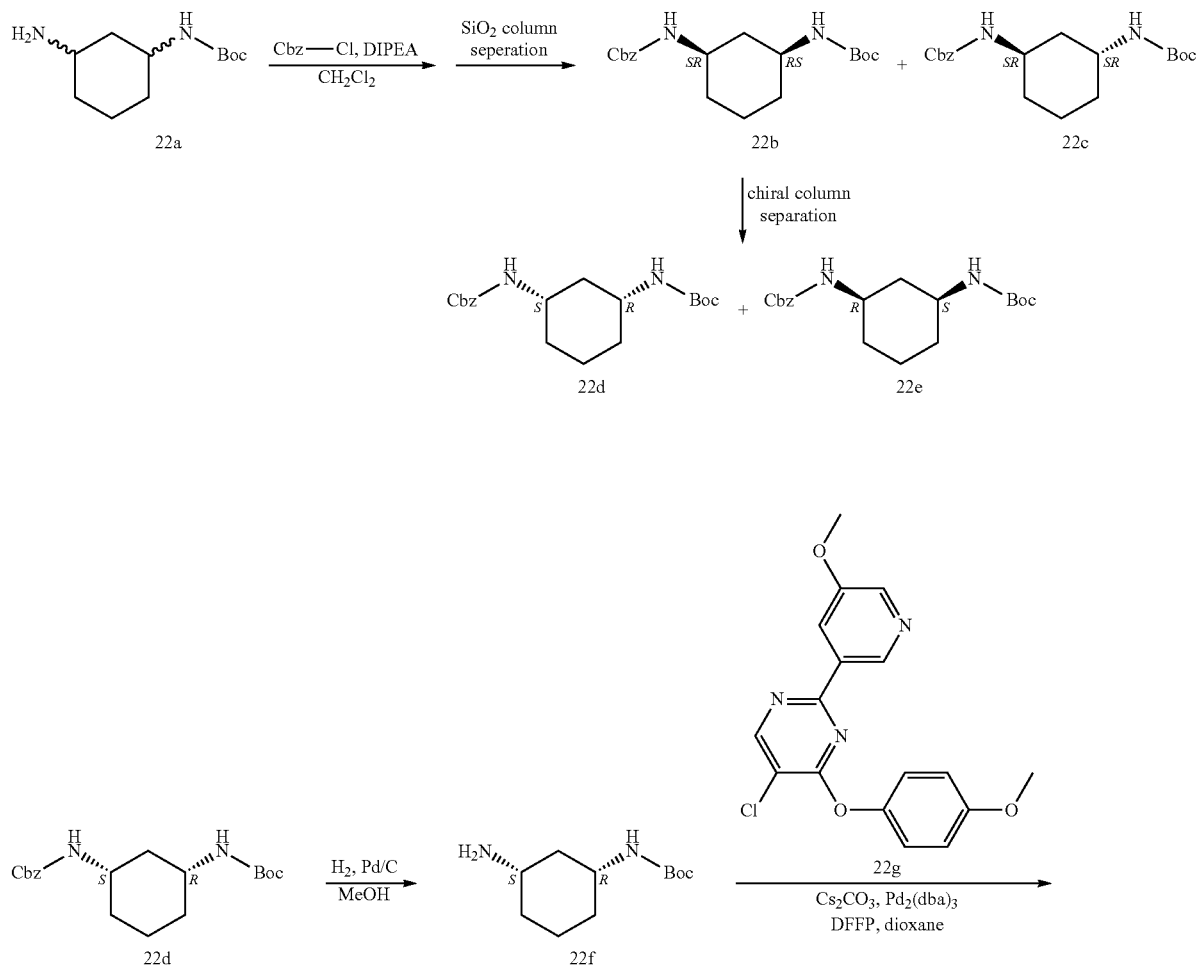

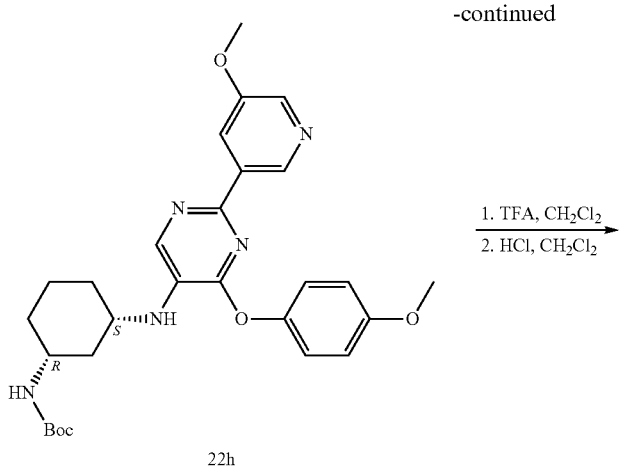

22h

1. TFA, CH₂Cl₂
2. HCl, CH₂Cl₂

Cpd 312

A. (3-Benzyloxycarbonylamino-cyclohexyl)-carbamic acid tert-butyl ester (22b, 22c)

To a mixture of (3-amino-cyclohexyl)-carbamic acid tert-butyl ester (22a) (1.5 g, 7 mmol) and benzyloxycarbonyl chloride (1.1 mL; 7.7 mmol) in CH₂Cl₂ (30 mL) at −20° C. was added diisopropylmethylamine (2.4 mL; 14 mmol) dropwise under argon atmosphere. The reaction mixture was stirred for 15 min at the same temperature, and it was allowed to warm to room temperature and stirred for an additional 2 h. The reaction mixture was diluted with CH₂Cl₂ and washed with brine. The organic phase was dried and concentrated to give a crude material. The crude material was purified by flash column chromatography (SiO₂), eluting with a heptane-EtOAc gradient to afford Compound 22b (second fraction; 1,3-cis racemic mixture) (1.8 g; 74% yield) and Compound 22c (first fraction; 1,3-trans racemic mixture). Compound 22b: ¹H-NMR (400 MHz, CDCl₃): δ 7.30-7.40 (m, 5H), 5.09 (s, 2H), 4.59 (br. s, 1H), 4.37 (br. s, 1H), 3.54 (br. s, 2H), 2.29-2.31 (m, 1H), 1.99 (br. s, 2H), 1.76-1.81 (m, 1H), 1.44 (s, 9H), 1.34-1.44 (m, 1H), 0.90-1.05 (m, 3H); MS: m/z 249.0 (M+H-Boc)⁺. Compound 22c: ¹H-NMR (400 MHz, CDCl₃): δ 7.30-7.40 (m, 5H), 5.09 (s, 2H), 4.78 (br. s, 1H), 4.56 (br. s, 1H), 3.77-3.85 (m, 2H), 1.68-1.79 (m, 4H), 1.53-1.62 (m, 2H), 1.38-1.49 (m, 2H), 1.45 (s, 9H); MS: m/z 249.0 (M+H-Boc)⁺.

B. [3-(S)-Benzyloxycarbonylamino-cyclohexyl]-1-(R)-carbamic acid tert-butyl ester (27d) and [3-(R)-Benzyloxycarbonylamino-cyclohexyl]-1-(S)-carbamic acid tert-butyl ester (22e)

Compound 22b (850 mg) was separated into two enantiomeric pure compounds, Compound 22d (340 mg; the first fraction) and Compound 22e (365 mg; the second fraction), by using CHIRALPAK® AD™ column (mobile phase: 9% isopropanol in hexanes; flow rate: 60 mL/min). Compound 22d: ¹H-NMR (400 MHz, CDCl₃): δ 7.30-7.39 (m, 5H), 5.09 (s, 2H), 4.60 (br. s, 1H), 4.38 (br. s, 1H), 3.54 (br. s, 2H), 2.28-2.31 (m, 1H), 1.99 (br. s, 2H), 1.75-1.81 (m, 1H), 1.44 (s, 9H), 1.34-1.44 (m, 1H), 0.89-1.05 (m, 3H); MS: m/z 249.0 (M+H-Boc)⁺. Compound 22e: ¹H-NMR (400 MHz, CDCl₃): δ 7.30-7.39 (m, 5H), 5.09 (s, 2H), 4.60 (br. s, 1H), 4.39 (br. s, 1H), 3.54 (br. s, 2H), 2.28-2.32 (m, 1H), 1.99 (br. s, 2H), 1.75-1.81 (m, 1H), 1.44 (s, 9H), 1.34-1.44 (m, 1H), 0.91-1.05 (m, 3H); MS: m/z 249.0 (M+H-Boc)⁺; [α]_D=−9.0 (c=1.2 in CHCl₃). The absolute stereochemistry of Compound 22e was determined by comparing the optical rotation of the synthetic (3R-Amino-cyclohexyl)-1S-carbamic acid tert-butyl ester[3] with the material from chiral HPLC separation.

[3] An alternative approach of synthesizing enantiomeric pure [3-(R)-Amino-cyclohexyl]-1-(S)-carbamic acid tert-butyl ester was described in the following scheme and procedure:

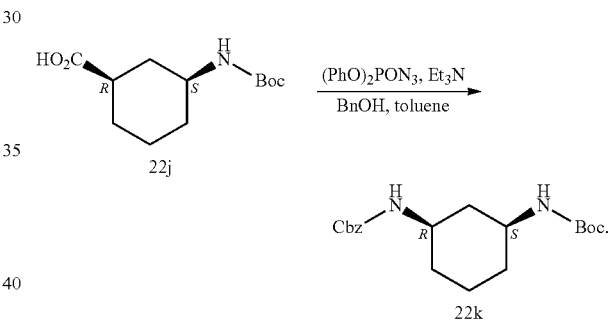

B1. [3-(R)-Amino-cyclohexyl]-1-(S)-carbamic acid tert-butyl ester (22k)

To a solution of Compound 22j (prepared according to the literature procedure described in *Bioorganic & Medicinal Chemistry* 2005, 13, 2509) (294 mg, 1.21 mmol) and Et₃N (0.185 mL, 1.33 mmol) in toluene (7 mL) was added (PhO)₂P(O)N₃ (0.29 mL, 1.34 mmol). The reaction mixture was heated to reflux for 1 h before BnOH (0.5 mL, 4.8 mmol) was added. The reaction was heated to reflux for another 7 h. The mixture was concentrated and purified by flash column chromatography (SiO₂, 30% EtOAc/heptane) to give Compound 22k (0.1 g; 24% yield). ¹H-NMR (400 MHz, CDCl₃): δ 7.35 (m, 5H), 5.08 (s, 2H), 4.67 (d, 1H), 4.42 (s, 1H), 3.53 (m, 2H), 2.29 (d, 1H), 1.97 (s, 2H), 1.75 (m, 1H), 1.43 (s, 9H), 1.39 (m, 1H), 0.98 (m, 3H); MS: m/z 371 (M+Na)⁺; [α]_D=−6.3 (c=1.1 in CHCl₃).

C. [3-(S)-Amino-cyclohexyl]-1-(R)-carbamic acid tert-butyl ester (22f)

A portion of 10% Pd/C (42 mg), Compound 22d (214 mg; 0.61 mmol) and MeOH (35 mL) was added to a Parr bottle.

111

The reaction mixture was shaken under a 40-psi $H_2$ atmosphere for 2 h. The resultant mixture was passed through a bed of diatomaceous earth and the filtrate was evaporated in vacuo to afford Compound 22f (90 mg) as a white solid. The compound was used in the next reaction without further purification. $^1$H-NMR (400 MHz, CDCl$_3$): δ 4.55-4.66 (m, 1H), 3.48-3.50 (m, 1H), 2.75-2.81 (m, 1H), 2.08-2.14 (m, 1H), 1.91-1.94 (m, 1H), 1.74-1.82 (m, 2H), 1.45 (s, 9H), 1.26-1.45 (m, 1H), 0.89-1.05 (m, 3H); MS: m/z 215.2 (M+H)$^+$.

D. 5-Chloro-4-(4-methoxy-phenoxy)-2-(5-methoxy-pyridin-3-yl)-pyrimidine (22g)

Compound 22g was prepared in an analogous manner to that of Compound 21c in Example 21, substituting 3-methoxy-5-(4,4,5,5-tetramethyl-[1,3,2]dioxaborolan-2-yl)-pyridine for pyridin-3-yl boronic acid in Procedure B of Example 23.

E. {3-(S)-[4-(4-Methoxy-phenoxy)-2-pyridin-3-yl-pyrimidin-5-ylamino]-cyclohexyl}-1-(R)-carbamic acid tert-butyl ester (22h)

To a dry Schlenk tube was added a mixture of Compound 22g (116 mg; 0.34 mmol)), Compound 22f (60 mg; 0.28 mmol), Cs$_2$CO$_3$ (182 mg; 0.56 mmol), (diphenylphosphino)ferrocene (54 mg; 0.10 mmol), and tris(dibenzylideneacetone)dipalladium(0) (26 mg; 0.028 mmol). The tube was sealed with a teflon-lined septum, evacuated, and refilled with argon. Dioxane (0.35 mL; reaction conc. >0.75M) was added to the mixture via syringe, and the mixture was heated at 95° C. for 3 h. The resultant mixture was diluted with EtOAc, washed with saturated NH$_4$Cl (aq) and H$_2$O. The organic phase was washed sequentially with H$_2$O, and then dried over Na$_2$SO$_4$. The mixture was filtered and the filtrate was concentrated under reduced pressure to give a crude material. The crude material was purified by flash column chromatography (SiO$_2$), eluting with a heptane-EtOAc gradient to afford Compound 22h (110 mg; 93% yield). $^1$H-NMR (400 MHz, CDCl$_3$): δ 8.84 (d, 1H), 8.24 (d, 1H), 8.01 (s, 1H), 7.89-7.90 (m, 1H), 7.14-7.18 (m, 1H), 6.94-6.98 (m, 2H), 4.48-4.50 (m, 1H), 4.23-4.25 (m, 1H), 3.86 (s, 6H), 3.62 (br. s, 1H), 3.43-3.51 (m, 1H), 2.52-2.55 (m, 1H), 2.20-2.23 (m, 1H), 2.04-2.07 (m, 1H), 1.89-1.94 (m, 1H), 1.46 (s, 9H), 1.41-1.46 (m, 1H), 1.08-1.21 (m, 3H); MS: m/z 522.2 (M+H)$^+$.

E. Cpd 312: N-[4-(4-Methoxy-phenoxy)-2-(5-methoxy-pyridin-3-yl)-pyrimidin-5-yl]-cyclohexane-(1R,3S)-1,3-diamine Using an adaptation of the method described in Procedure E of Example 1, substituting Compound 22h for Compound 1g, the title Compound 312 was obtained as a HCl salt (92 mg). Free base-$^1$H-NMR (400 MHz, CDCl$_3$): δ 8.86 (s, 1H), 8.24 (d, 1H), 7.99 (s, 1H), 7.88-7.89 (m, 1H), 7.16-7.19 (m, 2H), 6.95-6.98 (m, 2H), 4.44-4.46 (m, 1H), 3.87 (s, 3H), 3.86 (s, 3H), 3.43-3.51 (m, 1H), 2.89-2.95 (m, 1H), 2.34-2.37 (m, 1H), 2.15-2.19 (m, 1H), 1.88-1.95 (m, 2H), 1.41-1.51 (m, 3H), 1.10-1.26 (m, 3H); MS: m/z 422.0 (M+H)$^+$.

Following the procedure described above for Example 22 and substituting the appropriate reagents, starting materials and purification methods known to those skilled in the art, the following compounds of the present invention were prepared:

112

Cpd 311

The title compound was prepared in an analogous manner to Compound 312 of Example 22, substituting Compound 22e for Compound 22d in Procedure C. Free base-$^1$H-NMR (400 MHz, CDCl$_3$): δ 8.86 (d, 1H), 8.24 (d, 1H), 7.99 (s, 1H), 7.88-7.89 (m, 1H), 7.15-7.20 (m, 2H), 6.94-6.98 (m, 2H), 4.44-4.46 (m, 1H), 3.87 (s, 3H), 3.86 (s, 3H), 3.42-3.51 (m, 1H), 2.89-2.96 (m, 1H), 2.34-2.37 (m, 1H), 2.15-2.18 (m, 1H), 1.88-1.95 (m, 2H), 1.40-1.51 (m, 3H), 1.10-1.25 (m, 3H); MS: m/z 422.0 (M+H)$^+$.

Cpd 316

The title compound was prepared in an analogous manner to Compound 312 of Example 22, substituting 5-chloro-4-(4-methoxy-phenoxy)-2-(5-methylsulfanyl-pyridin-3-yl)-pyrimidine (prepared in a same manner to Compound 21c of Example 21, substituting 5-(methylthio)pyridine-3-boronic acid for pyridin-3-yl boronic acid in Procedure B) for Compound 22g in Procedure D. Free base-$^1$H-NMR (400 MHz, CDCl$_3$): δ 8.99 (d, 1H), 8.40 (d, 1H), 8.20-8.21 (m, 1H), 7.98 (s, 1H), 7.14-7.18 (m, 2H), 6.94-6.98 (m, 2H), 4.47-4.49 (m, 1H), 3.86 (s, 3H), 3.41-3.51 (m, 1H), 2.87-2.94 (m, 1H), 2.47 (s, 3H), 2.32-2.35 (m, 1H), 2.14-2.17 (m, 1H), 1.87-1.92 (m, 2H), 1.37-1.50 (m, 3H), 1.08-1.27 (m, 3H); MS: m/z 438.2 (M+H)$^+$.

Example 23

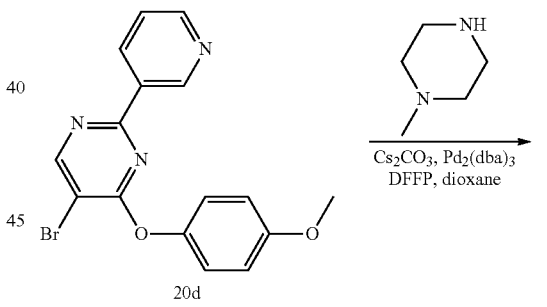

20d

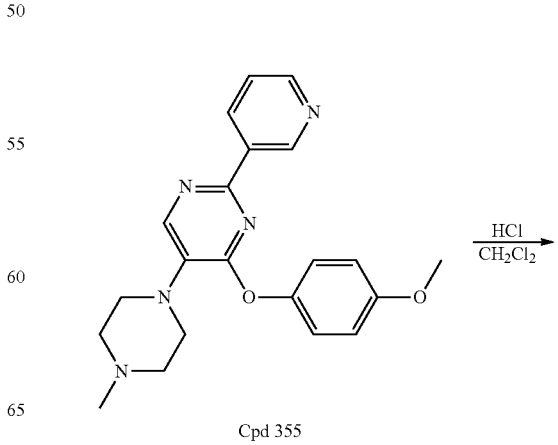

Cpd 355

113

-continued

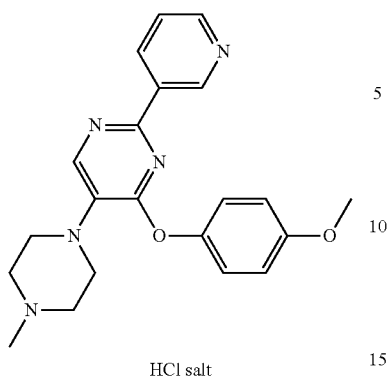

HCl salt

A. Cpd 355: 4-(4-Methoxy-phenoxy)-5-(4-methyl-piperazin-1-yl)-2-pyridin-3-yl-pyrimidine Using an adaptation of the method described in Procedure D of Example 22 check to see if this method is present in examples, substituting 1-methyl-piperazine for piperazine-1-carboxylic acid tert-butyl ester, the title Compound 355 was obtained as a free base. HCl salt-$^1$H-NMR (400 MHz, DMSO-$d_6$): δ 11.24 (br. s, 1H), 9.12 (d, 1H), 8.81 (dd, 1H), 8.64 (d, 1H), 8.54 (s, 1H), 7.87 (dd, 1H), 7.26-7.30 (m, 2H), 7.03-7.08 (m, 2H), 3.86-3.91 (m, 2H), 3.81 (s, 3H), 3.52-3.55 (m, 2H), 3.22-3.40 (m, 4H), 2.83 (d, 3H); MS: m/z 378.0 (M+H)$^+$.

Following the procedure described above for Example 23 and substituting the appropriate reagents, starting materials and purification methods known to those skilled in the art, the following compounds of the present invention were prepared:

| Cpd | MS (M + H)$^+$ |
|---|---|
| 297 | 352.0 |
| 359 | 392.3 |

Example 24

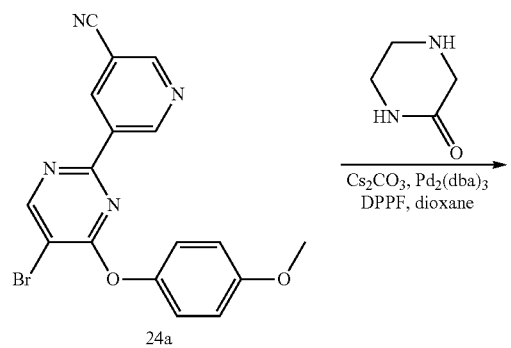

114

-continued

Cpd 335

A. 5-Bromo-2-(5-cyano-pyridin-3-yl)-4-(4-methoxy-phenoxy)-pyrimidine (24a)

Using an adaptation of the method described in Procedure C of Example 22, substituting 5-(4,4,5,5-tetramethyl-[1,3,2] dioxaborolan-2-yl)-nicotinonitrile for pyridin-3-yl boronic acid, the title Compound 24a was obtained as white powder. $^1$H-NMR (400 MHz, CDCl$_3$): δ 9.50 (d, 1H), 8.91 (d, 1H), 8.80 (s, 1H), 8.69 (t, 1H), 7.14 (d, 2H), 6.99 (d, 2H), 3.88 (s, 3H); MS: m/z 383.0 (M+H)$^+$.

B. Cpd 335: 5-[4-(4-Methoxy-phenoxy)-5-(3-oxo-piperazin-1-yl)-pyrimidin-2-yl]-nicotinonitrile Using an adaptation of the method described in Procedure D of Example 22, substituting Compound 24a for Compound 22d and substituting piperazin-2-one for piperazine-1-carboxylic acid tert-butyl ester, the title Compound 335 (10% yield) was obtained as a free base after purification by preparative TLC. $^1$H-NMR (400 MHz, CDCl$_3$): δ 9.44 (d, 1H), 8.84 (d, 1H), 8.63 (t, 1H), 8.24 (s, 1H), 7.12 (d, 2H), 6.98 (d, 2H), 6.03 (br. s, 1H), 4.04 (s, 2H), 3.88 (s, 3H), 3.61-3.64 (m, 4H); MS: m/z 403.0 (M+H)$^+$.

Example 25

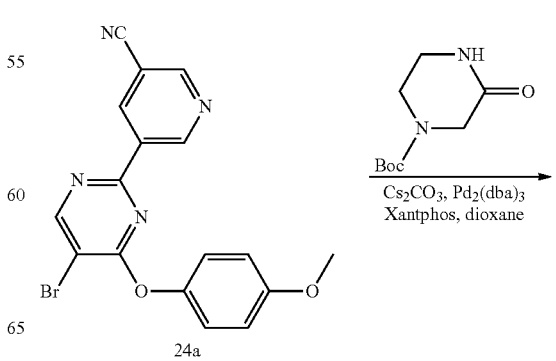

8.68 (s, 1H), 7.09 (d, 2H), 6.98 (d, 2H), 4.11 (br. s, 4H), 3.87 (s, 3H), 3.72 (br. s, 2H); MS: m/z 403.0 (M+H)$^+$.

Example 26

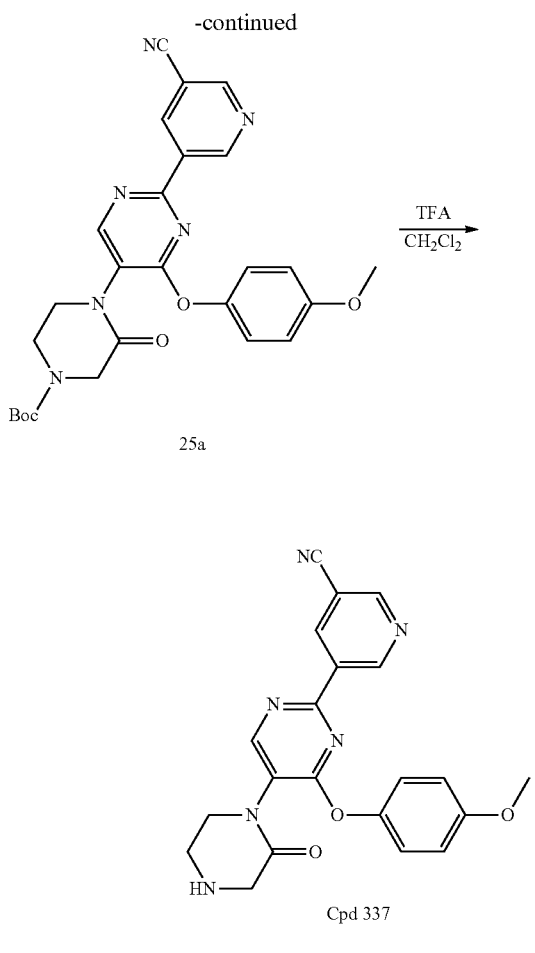

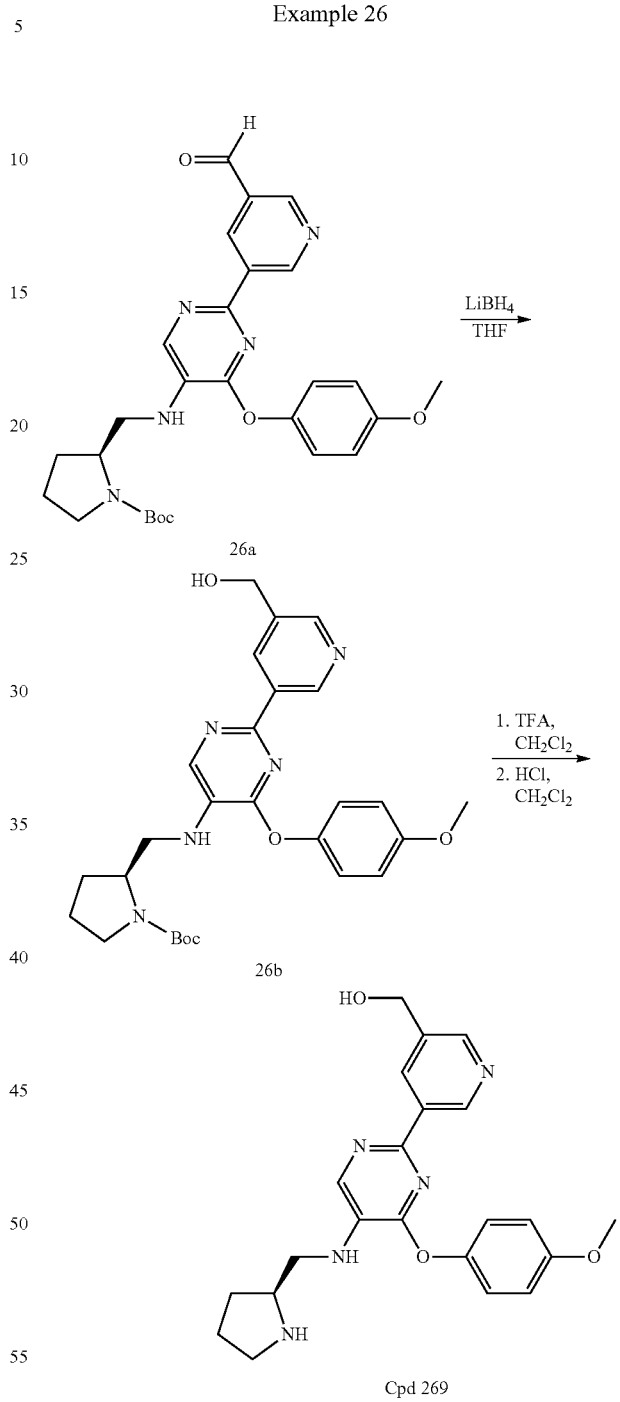

A. 4-[2-(5-Cyano-pyridin-3-yl)-4-(4-methoxy-phenoxy)-pyrimidin-5-yl]-3-oxo-piperazine-1-carboxylic acid tert-butyl ester (25a)

Using an adaptation of the method described in Procedure D of Example 22, substituting Compound 24a for Compound 22d, substituting 3-oxo-piperazine-1-carboxylic acid tert-butyl ester for piperazine-1-carboxylic acid tert-butyl ester and substituting Xantphos for (diphenylphosphino)ferrocene, the title Compound 25a (85% yield) was obtained. $^1$H-NMR (400 MHz, CDCl$_3$): δ 9.51 (d, 1H), 8.90 (d, 1H), 8.71 (t, 1H), 8.65 (s, 1H), 7.11 (d, 2H), 6.97 (d, 2H), 4.34 (s, 2H), 3.88 (s, 3H), 3.87-3.90 (m, 2H), 3.82-3.85 (m, 2H); MS: m/z 503.0 (M+H)$^+$.

B. Cpd 337: 5-[4-(4-Methoxy-phenoxy)-5-(2-oxo-piperazin-1-yl)-pyrimidin-2-yl]-nicotinonitrile To a solution of Compound 24a in CH$_2$Cl$_2$ (3 mL) was added TFA (1 mL). The reaction was stirred at room temperature for 3 h and the solvent was evaporated in vacuo to give the crude material. The crude material was purified by preparative TLC to afford Compound 337 as a TFA salt. $^1$H-NMR (400 MHz, CDCl$_3$): δ 9.52 (d, 1H), 8.93 (d, 1H), 8.74 (t, 1H),

A. 2-(S)-{[2-(5-Formyl-pyridin-3-yl)-4-(4-methoxy-phenoxy)-pyrimidin-5-ylamino]-methyl}-pyrrolidine-1-carboxylic acid tert-butyl ester (26a)

The title compound was prepared in an analogous manner to Compound 1g of Example 1, substituting 5-formylpyridin-3-yl boronic acid for Compound 1f in Procedure D.

B. 2-(S)-{[2-(5-Hydroxymethyl-pyridin-3-yl)-4-(4-methoxy-phenoxy)-pyrimidin-5-ylamino]-methyl}-pyrrolidine-1-carboxylic acid tert-butyl ester (26b)

To a solution of Compound 26a (200 mg, 0.40 mmol) in THF (5 mL) at 0° C. was added LiBH₄ solution (2.0 M in THF) (0.3 mL) dropwise. The reaction mixture was stirred at 0° C. for 0.5 h, then warmed to room temperature over 2 h. The resultant mixture was diluted with water. The mixture was extracted with EtOAc (3×), and the organic phases were combined, dried over Na₂SO₄, and concentrated under reduced pressure to give the crude material. The crude material was purified by flash column chromatography (SiO₂), eluting with a heptane-EtOAc gradient to afford Compound 26b (71.5 mg; 35% yield). $^1$H-NMR (400 MHz, CDCl₃): δ 9.00 (s, 1H), 8.43 (s, 1H), 8.39 (s, 1H), 7.80-7.94 (m, 1H), 7.13-7.16 (m, 2H), 6.91-6.94 (m, 2H), 5.83 (br. s, 0.6H), 5.06 (br. s, 0.4H), 4.71 (s, 2H), 4.18-4.26 (m, 1H), 3.84 (s, 3H), 3.86 (br. s, 0.6H), 3.50 (br. s, 0.4H), 3.37-3.40 (m, 2H), 3.15-3.20 (m, 2H), 2.06-2.15 (m, 1H), 1.90-1.98 (m, 2H), 1.77-1.86 (m, 1H), 1.43-1.49 (m, 9H); MS: m/z 508.2 (M+H)⁺.

C. Cpd 269: (5-{4-(4-Methoxy-phenoxy)-5-[(pyrrolidin-2-(S)-ylmethyl)-amino]-pyrimidin-2-yl}-pyridin-3-yl)-methanol To a solution of Compound 26b (71.5 mg) in dichloromethane (2 mL) was treated with TFA (1 mL) at room temperature for 2 h. The reaction mixture was adjusted to pH 12 with 1 N NaOH (aq). The resultant mixture was extracted with CH₂Cl₂ (3×). The organic extracts were combined, dried over Na₂SO₄, and concentrated under reduced pressure to give the free base (52 mg). The free base was dissolved in CH₂Cl₂ (2 mL), and treated with 1.0 M HCl in Et₂O (0.25 mL) at ambient temperature for 2 h. A solid was collected and dried by vacuum filtration to afford Compound 269 as a HCl salt. Free base-$^1$H-NMR (400 MHz, MeOH-d₄): δ 8.95-9.05 (m, 1H), 8.55-8.70 (m, 1H), 8.36-8.42 (m, 1H), 8.06-8.11 (m, 1H), 7.15-7.21 (m, 2H), 6.98-7.02 (m, 2H), 4.72 (s, 1H), 4.63 (s, 1H), 3.83 (d, 3H), 3.74-3.83 (m, 1H), 3.45-3.58 (m, 2H), 3.13-3.28 (m, 2H), 2.15-2.25 (m, 1H), 1.93-2.08 (m, 2H), 1.68-1.79 (m, 1H); MS: m/z 408.2 (M+H)⁺.

Example 27

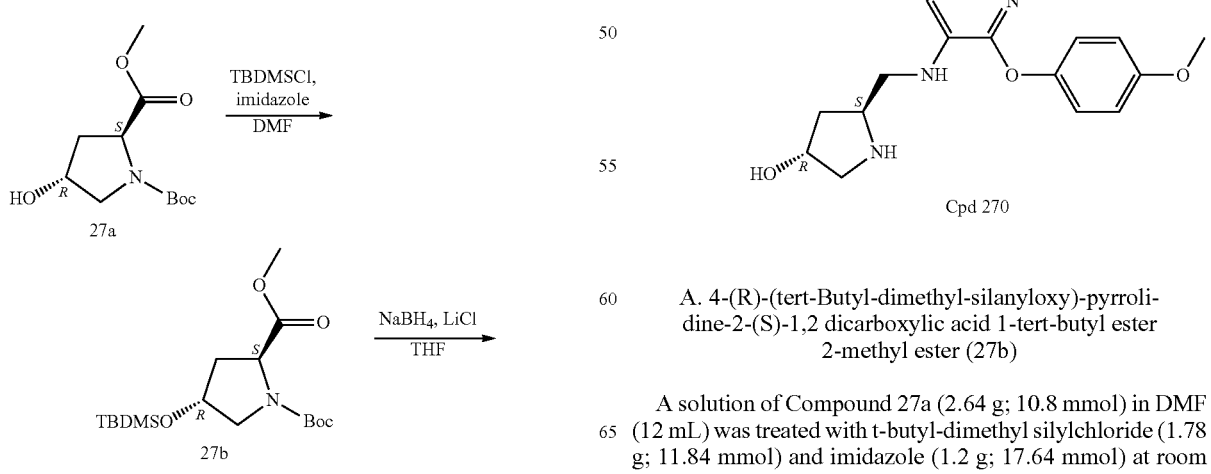

A. 4-(R)-(tert-Butyl-dimethyl-silanyloxy)-pyrrolidine-2-(S)-1,2 dicarboxylic acid 1-tert-butyl ester 2-methyl ester (27b)

A solution of Compound 27a (2.64 g; 10.8 mmol) in DMF (12 mL) was treated with t-butyl-dimethyl silylchloride (1.78 g; 11.84 mmol) and imidazole (1.2 g; 17.64 mmol) at room temperature for 2 h. The resultant mixture was concentrated in vacuuo and partitioned between EtOAc and H₂O. The organic phase was washed sequentially with 0.1 N HCl (aq), saturated NaHCO₃ (aq), and brine, and then dried over Na₂SO₄. The mixture was filtered and the filtrate was evaporated under reduced pressure to give the crude material. The crude material was purified by flash column chromatography (SiO₂), eluting with a heptane-EtOAc gradient to afford Compound 27b. $^1$H-NMR (400 MHz, CDCl₃): δ 4.32-4.45 (m, 2H), 3.74-3.75 (d, 3H), 3.58-3.64 (m, 1H), 3.32-3.43 (m, 1H), 2.16-2.19 (m, 1H), 2.00-2.06 (m, 1H), 1.42-1.47 (d, 9H), 0.88 (s, 9H), 0.07 (s, 6H). MS: m/z 360.2 (M+H)⁺.

B. 4-(R)-(tert-Butyl-dimethyl-silanyloxy)-2-(S)-hydroxymethyl-pyrrolidine-1-carboxylic acid tert-butyl ester (27c)

To a solution of Compound 27b (392 mg; 1.09 mmol) in THF/MeOH (3/3 mL) at 0° C. was added NaBH₄ (148 mg; 3.92 mmol) and LiCl (166 mg; 3.92 mmol). The reaction mixture was stirred at 0° C. for 0.5 h, then warmed to room temperature over 2 h. The resultant mixture was diluted with 0.5N HCl (aq). The mixture was extracted with EtOAc (3×), the organic extracts were combined, dried over Na₂SO₄, and concentrated under reduced pressure to give the crude material. The crude material was purified by flash column chromatography (SiO₂), eluting with a heptane-EtOAc gradient to afford Compound 27c (345 mg; 95% yield). $^1$H-NMR (400 MHz, CDCl₃): δ 4.90 (br. s, 1H), 4.28 (m, 1H), 4.10-4.16 (m, 1H), 3.69-3.72 (m, 1H), 3.53-3.57 (m, 1H), 3.43-3.46 (m, 1H), 3.33-3.37 (m, 1H), 1.94-1.98 (m, 1H), 1.53-1.63 (m, 1H), 1.48 (s, 9H), 0.88 (s, 9H), 0.07 (s, 6H); MS: m/z 332.2 (M+H)⁺.

C. 4-(R)-(tert-Butyl-dimethyl-silanyloxy)-2-(S)-formyl-pyrrolidine-1-carboxylic acid tert-butyl ester (27d)

To a solution of oxalyl chloride (0.16 mL; 1.785 mmol) in CH₂Cl₂ (2 mL) at −78° C. was added DMSO (0.25 mL; 3.55 mmol) dropwise and the mixture was stirred for 10 min. The mixture was then treated with a solution of Compound 27c (395 mg; 1.19 mmol) in CH₂Cl₂ (3 mL) dropwise and continually stirred for 20 min. To the resultant mixture was added Et₃N (0.5 mL; 3.55 mmol) dropwise and the mixture was stirred at −78° C. for 30 min. The mixture was allowed to warm to ambient temperature while continually stirring over 20 min. The reaction mixture was quenched with saturated NH₄Cl (aq), extracted with EtOAc, washed with water and brine; and the combined organic extracts were dried over Na₂SO₄, and concentrated under reduced pressure to give the crude material. The crude material was purified by flash column chromatography (SiO₂), eluting with a heptane-EtOAc gradient to afford Compound 27d (250 mg; 64% yield). $^1$H-NMR (400 MHz, CDCl₃): δ 9.44-9.57 (m, 1H), 4.20-4.39 (m, 1H), 3.35-3.57 (m, 1H), 1.89-2.09 (m, 1H), 1.44-1.49 (m, 9H), 0.88 (s, 9H), 0.08 (s, 6H); MS: m/z 330.2 (M+H)⁺.

D. 4-(R)-(tert-Butyl-dimethyl-silanyloxy)-2-(S)-{[2-chloro-4-(4-methoxy-phenoxy)-pyrimidin-5-ylamino]-methyl}-pyrrolidine-1-carboxylic acid tert-butyl ester (27e)

To a solution of Compound 1c (191 mg, 0.759 mmol) in 1,2-dichloroethane (4 mL) was added Compound 27d (250 mg; 0.759 mmol) and acetic acid (0.2 mL) at ambient temperature, and the mixture was stirred at room temperature for 1.5 h. The mixture was then treated with NaB(OAc)₃H (240 mg; 1.14 mmol) and continually stirred at room temperature for 4 h. The resultant mixture was diluted with CH₂Cl₂, then washed with saturated NaHCO₃ (aq) and water. The organic phase was washed sequentially with water and brine, and then dried over Na₂SO₄. The mixture was filtered and the filtrate was evaporated under reduced pressure to give the crude material. The crude material was purified by flash column chromatography (SiO₂), eluting with a heptane-EtOAc gradient to afford Compound 27e. $^1$H-NMR (400 MHz, CDCl₃): δ 7.70-7.75 (m, 1H), 7.10-7.13 (m, 2H), 6.94-7.01 (m, 2H), 5.79 (br. s, 0.6H), 4.73 (br. s, 0.4H), 4.30-4.39 (m, 2H), 3.84 (s, 3H), 3.12-3.69 (m, 4H), 2.06-2.16 (m, 1H), 1.80-1.87 (m, 1H), 1.45-1.48 (m, 9H), 0.88 (s, 9H), 0.08 (s, 6H); MS: m/z 565.2 (M+H)⁺.

E. 4-(R)-(tert-Butyl-dimethyl-silanyloxy)-2-{[4-(4-methoxy-phenoxy)-2-(S)-(pyridin-3-O-pyrimidin-5-ylamino]-methyl}-pyrrolidine-1-carboxylic acid tert-butyl ester (27f)

To a teflon-lined septum sealed Schlenk tube, a mixture of Compound 27e (130 mg; 0.23 mmol), pyridin-3-yl boronic acid (56.5 mg; 0.46 mmol), K₂CO₃ (64 mg; 0.46 mmol) and [1,1'-bis(diphenylphosphino)-ferrocene]dichloro-palladium (II) (11.3 mg, 0.014 mmol) in a mixture of ethanol (0.5 mL) and H₂O (0.1 mL) was added. The reaction mixture was irradiated in a microwave instrument at 130° C. for 30 min. The resultant mixture was diluted with EtOAc, then washed with saturated NH₄Cl (aq) and water. The organic phase was washed with H₂O, and then dried over Na₂SO₄. The mixture was filtered and the filtrate was evaporated under reduced pressure to give the crude material. The crude material was purified by flash column chromatography (SiO₂), eluting with a heptane-EtOAc gradient to afford Compound 27f (100 mg; 71% yield). $^1$H-NMR (400 MHz, CDCl₃): δ 9.27 (s, 1H), 8.52-8.53 (m, 1H), 8.33-8.35 (m, 1H), 7.99-8.02 (m, 1H), 7.26-7.28 (m, 1H), 7.13-7.19 (m, 2H), 6.95-6.97 (m, 2H), 5.77 (br. s, 0.6H), 4.84 (br. s, 0.4H), 4.35-4.42 (m, 2H), 3.87 (s, 3H), 3.28-3.69 (m, 4H), 2.12-2.18 (m, 1H), 1.86-1.91 (m, 1H), 1.47-1.51 (m, 9H), 0.88 (s, 9H), 0.08 (s, 6H); MS: m/z 608.1 (M+H)⁺.

F. Cpd 270: 5-(S)-{[4-(4-Methoxy-phenoxy)-2-(pyridin-3-yl)-pyrimidin-5-ylamino]-methyl}-pyrrolidin-3-(R)-ol Compound 27f (100 mg; 0.165 mmol) in trifluoroacetic acid (1 mL) was stirred at room temperature 20 h. The reaction mixture was adjusted to pH 12 by the addition of 1 N NaOH (aq). The resultant mixture was extracted with CH₂Cl₂ and H₂O. The organic phase was washed with H₂O and dried over Na₂SO₄. The mixture was then filtered, and the filtrate was concentrated under reduced pressure. The residue was dissolved in CH₂Cl₂ (3 mL), treated with 1.0 M HCl in Et₂O (0.33 mL; 0.33 mmol) at ambient temperature, and the reaction mixture was stirred for 20 h. The mixture was evaporated in vacuo, and the reside was triturated with Et₂O. A solid was collected and dried by vacuum filtration to afford Compound 270 (63 mg; 81% yield) as a HCl salt. Cpd 270 (free base) $^1$H-NMR (400 MHz, CDCl₃): δ 9.26 (d, 1H), 8.53 (dd, 1H), 8.32 (dt, 1H), 7.99 (s, 1H), 7.24-7.27 (m, 1H), 7.15-7.19 (m, 2H), 6.95-6.99 (m, 2H), 4.85-4.88 (m, 1H), 4.54-4.55 (m, 1H), 3.88 (s, 3H), 3.82-3.88 (m, 2H), 3.28-3.34 (m, 1H), 3.06-3.13 (m, 1H), 3.03-3.04 (m, 2H), 2.04-2.09 (m, 1H), 1.73-1.80 (m, 1H), 1.6 (br. s, 1H); MS: m/z 394.0 (M+H)⁺.

Following the procedure described above for Example 27 and substituting the appropriate reagents, starting materials and purification methods known to those skilled in the art, the following compounds of the present invention were prepared:

| Cpd | MS (M + H)⁺ | Cpd | MS (M + H)⁺ |
| --- | --- | --- | --- |
| 271 | 394.0 | 272 | 394.0 |

Example 28
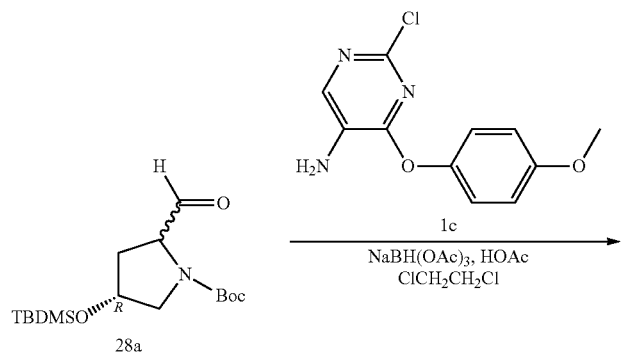
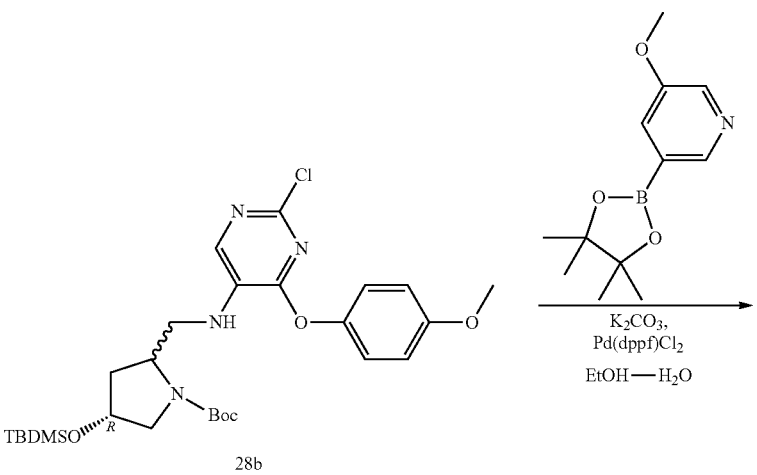
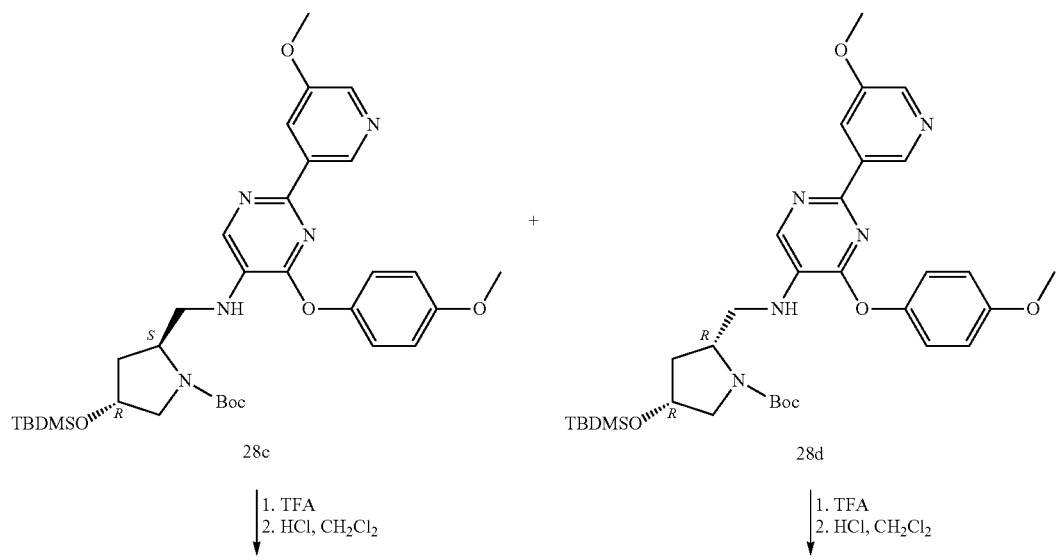

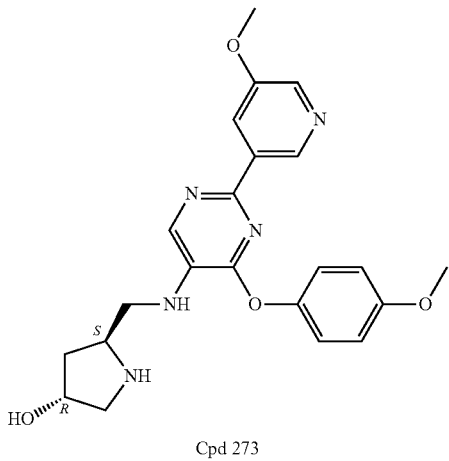

Cpd 273

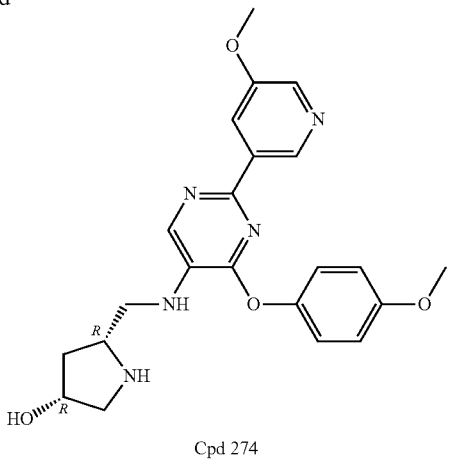

Cpd 274

A. 4-(R)-(tert-Butyl-dimethyl-silanyloxy)-2-{[2-chloro-4-(4-methoxy-phenoxy)-pyrimidin-5-ylamino]-methyl}-pyrrolidine-1-carboxylic acid tert-butyl ester (28b)

Using an adaptation of the method described in Procedure D of Example 27, substituting Compound 28a (commercially available) for Compound 27d, the title Compound 28b was obtained. $^1$H-NMR (400 MHz, CDCl$_3$): δ 7.70-7.75 (m, 1H), 7.06-7.13 (m, 2H), 6.91-6.95 (m, 2H), 5.74-5.79 (m, 0.6H), 4.73-4.82 (m, 0.4H), 4.38-4.44 (m, 2H), 3.83 (s, 3H), 3.12-3.69 (m, 4H), 2.10-2.24 (m, 1H), 1.78-1.88 (m, 1H), 1.44-1.48 (m, 9H), 0.88-0.92 (m, 9H), 0.08-0.10 (m, 6H); MS: m/z 565.0 (M+H)$^+$.

B. 4-(R)-(tert-Butyl-dimethyl-silanyloxy)-2-{[4-(4-methoxy-phenoxy)-2-(S)-(5-methoxy-pyridin-3-yl)-pyrimidin-5-ylamino]-methyl}-pyrrolidine-1-carboxylic acid tert-butyl ester (34c) and 4-(R)-(tert-Butyl-dimethyl-silanyloxy)-2-{[4-(4-methoxy-phenoxy)-2-(R)-(5-methoxy-pyridin-3-yl)-pyrimidin-5-ylamino]-methyl}-pyrrolidine-1-carboxylic acid tert-butyl ester (28d)

Using an adaptation of the method described in Procedure E of Example 27, substituting Compound 28b for Compound 27e and substituting 3-methoxy-5-(4,4,5,5-tetramethyl-[1,3,2]dioxaborolan-2-yl)-pyridine for pyridin-3-yl boronic acid, the title Compound 28c and Compound 28d were obtained separately after flash column chromatography (SiO$_2$). Compound 28c-$^1$H-NMR (400 MHz, CDCl$_3$): δ 8.87 (s, 1H), 8.24 (s, 1H), 7.98 (s, 1H), 7.89 (s, 1H), 7.13-7.20 (m, 2H), 6.94-6.96 (m, 2H), 5.78 (br. s, 0.6H), 4.86 (br. s, 0.4H), 4.34-4.42 (m, 2H), 3.86 (s, 6H), 3.29-3.51 (m, 4H), 2.12-2.18 (m, 1H), 1.86-1.94 (m, 1H), 1.47-1.51 (m, 9H), 0.87-0.89 (m, 9H), 0.08 (s, 6H); MS: m/z 638.2 (M+H)$^+$. Compound 28d-$^1$H-NMR (400 MHz, CDCl$_3$): δ 8.86 (br. s, 1H), 8.23 (br. s, 1H), 7.98-7.99 (m, 1H), 7.89 (s, 1H), 7.12-7.20 (m, 2H), 6.92-6.96 (m, 2H), 5.84 (br. s, 0.6H), 4.97 (br. s, 0.4H), 4.27-4.43 (m, 2H), 3.85 (s, 6H), 3.57-3.81 (m, 2H), 3.29-3.39 (m, 2H), 2.18-2.25 (m, 1H), 1.82-1.91 (m, 1H), 1.45-1.50 (m, 9H), 0.91-0.92 (m, 9H), 0.10-0.11 (m, 6H); MS: m/z 638.2 (M+H)$^+$.

C. Cpd 273: 5-(S)-{[4-(4-Methoxy-phenoxy)-2-(5-methoxy-pyridin-3-yl)-pyrimidin-5-ylamino]-methyl}-pyrrolidin-3-(R)-ol Using an adaptation of the method described in Procedure F of Example 27, substituting Compound 28c for Compound 27f, the title Compound 273 was obtained as a HCl salt. Cpd 273, free base-$^1$H-NMR (400 MHz, CDCl$_3$): δ 8.87 (d, 1H), 8.25 (d, 1H), 8.00 (s, 1H), 7.89 (dd, 1H), 7.16-7.20 (m, 2H), 6.94-6.98 (m, 2H), 4.83-4.86 (m, 1H), 4.53-4.55 (m, 1H), 3.87 (s, 3H), 3.86 (s, 3H), 3.79-3.87 (m, 1H), 3.26-3.32 (m, 1H), 3.04-3.11 (m, 1H), 3.01-3.02 (m, 2H), 2.02-2.08 (m, 1H), 1.72-1.79 (m, 1H), 1.25-1.27 (m, 1H); MS: m/z 424.0 (M+H)$^+$.

D. Cpd 274: 5-(R)-{[4-(4-Methoxy-phenoxy)-2-(5-methoxy-pyridin-3-yl)-pyrimidin-5-ylamino]-methyl}-pyrrolidin-3-(R)-ol Using an adaptation of the method described in Procedure F of Example 27, substituting Compound 28d for Compound 27f, the title Compound 274 was obtained as a HCl salt. Free base-$^1$H-NMR (400 MHz, CDCl$_3$): δ 8.85 (d, 1H), 8.24 (d, 1H), 7.99 (s, 1H), 7.88 (dd, 1H), 7.16-7.20 (m, 2H), 6.93-6.97 (m, 2H), 5.08-5.10 (m, 1H), 4.46-4.50 (m, 1H), 3.86 (s, 3H), 3.86 (s, 3H), 3.62-3.69 (m, 1H), 3.42-3.49 (m, 1H), 3.31-3.38 (m, 1H), 3.01-3.14 (m, 2H), 2.28-2.37 (m, 1H), 1.66-1.73 (m, 1H), 1.25-1.27 (m, 1H); MS: m/z 424.0 (M+H)$^+$.

Following the procedure described above for Example 28 and substituting the appropriate reagents, starting materials and purification methods known to those skilled in the art, the following compounds of the present invention were prepared:

Compounds 1 through 319, and 321 through 323 of Formula (I) in the table below were synthesized using the procedures described above.

TABLE 1

Formula (I)

| Cpd No | R₁ | R₂ | A—L— | a | L | Rₐ | Stereo Chem |
|---|---|---|---|---|---|---|---|
| 1 | 4-methoxy-phenyl | 4-methoxy-phenyl | a₁-L₁ | pyrrolidin-2-yl | methyl | H | 2S |
| 2 | phenyl | 4-methoxy-phenyl | a₁-L₁ | pyrrolidin-2-yl | methyl | H | 2S |
| 3 | 3-methoxy-phenyl | 4-methoxy-phenyl | a₁-L₁ | pyrrolidin-2-yl | methyl | H | 2S |
| 4 | 2-methoxy-phenyl | 4-methoxy-phenyl | a₁-L₁ | pyrrolidin-2-yl | methyl | H | 2S |
| 5 | naphth-1-yl | 4-methoxy-phenyl | a₁-L₁ | pyrrolidin-2-yl | methyl | H | 2S |
| 6 | naphth-2-yl | 4-methoxy-phenyl | a₁-L₁ | pyrrolidin-2-yl | methyl | H | 2S |
| 7 | pyridin-4-yl | 4-methoxy-phenyl | a₁-L₁ | pyrrolidin-2-yl | methyl | H | 2S |
| 8 | pyridin-3-yl | 4-methoxy-phenyl | a₁-L₁ | pyrrolidin-2-yl | methyl | H | 2S |
| 9 | thien-3-yl | 4-methoxy-phenyl | a₁-L₁ | pyrrolidin-2-yl | methyl | H | 2S |
| 10 | furan-3-yl | 4-methoxy-phenyl | a₁-L₁ | pyrrolidin-2-yl | methyl | H | 2S |
| 11 | pyridin-3-yl | 4-trifluoromethoxy-phenyl | a₁-L₁ | pyrrolidin-2-yl | methyl | H | 2S |
| 12 | pyridin-3-yl | 4-aminocarbonyl-phenyl | a₁-L₁ | pyrrolidin-2-yl | methyl | H | 2S |
| 13 | pyridin-3-yl | 4-methylcarbonylamino-phenyl | a₁-L₁ | pyrrolidin-2-yl | methyl | H | 2S |
| 14 | pyridin-3-yl | phenyl | a₁-L₁ | pyrrolidin-2-yl | methyl | H | 2S |
| 15 | 3-hydroxy-phenyl | 4-methoxy-phenyl | a₁-L₁ | pyrrolidin-2-yl | methyl | H | 2S |
| 16 | quinolin-5-yl | 4-methoxy-phenyl | a₁-L₁ | pyrrolidin-2-yl | methyl | H | 2S |
| 17 | quinolin-8-yl | 4-methoxy-phenyl | a₁-L₁ | pyrrolidin-2-yl | methyl | H | 2S |
| 18 | 2-methyl-quinolin-5-yl | 4-methoxy-phenyl | a₁-L₁ | pyrrolidin-2-yl | methyl | H | 2S |
| 19 | 4-biphenyl | 4-methoxy-phenyl | a₁-L₁ | pyrrolidin-2-yl | methyl | H | 2S |
| 20 | quinolin-3-yl | 4-methoxy-phenyl | a₁-L₁ | pyrrolidin-2-yl | methyl | H | 2S |
| 21 | dibenzothiophen-2-yl | 4-methoxy-phenyl | a₁-L₁ | pyrrolidin-2-yl | methyl | H | 2S |
| 22 | 6-methoxy-pyridin-3-yl | 4-methoxy-phenyl | a₁-L₁ | pyrrolidin-2-yl | methyl | H | 2S |
| 23 | pyrimidin-5-yl | 4-methoxy-phenyl | a₁-L₁ | pyrrolidin-2-yl | methyl | H | 2S |
| 24 | 2-fluoro-pyridin-3-yl | 4-methoxy-phenyl | a₁-L₁ | pyrrolidin-2-yl | methyl | H | 2S |
| 25 | 6-fluoro-pyridin-3-yl | 4-methoxy-phenyl | a₁-L₁ | pyrrolidin-2-yl | methyl | H | 2S |
| 26 | 2-methoxy-pyridin-3-yl | 4-methoxy-phenyl | a₁-L₁ | pyrrolidin-2-yl | methyl | H | 2S |
| 27 | 2,6-dihydroxypyrimidin-5-yl | 4-methoxy-phenyl | a₁-L₁ | pyrrolidin-2-yl | methyl | H | 2S |
| 28 | 3-cyano-phenyl | 4-methoxy-phenyl | a₁-L₁ | pyrrolidin-2-yl | methyl | H | 2S |
| 29 | 3-nitro-phenyl | 4-methoxy-phenyl | a₁-L₁ | pyrrolidin-2-yl | methyl | H | 2S |
| 30 | 3-aminocarbonyl-phenyl | 4-methoxy-phenyl | a₁-L₁ | pyrrolidin-2-yl | methyl | H | 2S |
| 31 | 3-N,N-diethylaminocarbonyl-phenyl | 4-methoxy-phenyl | a₁-L₁ | pyrrolidin-2-yl | methyl | H | 2S |
| 32 | 3-methanesulfonyl-phenyl | 4-methoxy-phenyl | a₁-L₁ | pyrrolidin-2-yl | methyl | H | 2S |
| 33 | 4-hydroxy-phenyl | 4-methoxy-phenyl | a₁-L₁ | pyrrolidin-2-yl | methyl | H | 2S |
| 34 | indol-5-yl | 4-methoxy-phenyl | a₁-L₁ | pyrrolidin-2-yl | methyl | H | 2S |
| 35 | 4H-[1,2,4]oxadiazol-5-on-3-yl | 4-methoxy-phenyl | a₁-L₁ | pyrrolidin-2-yl | methyl | H | 2S |
| 36 | pyridin-3-yl | 4-fluoro-phenyl | a₁-L₁ | pyrrolidin-2-yl | methyl | H | 2S |
| 37 | 6-methoxy-pyridin-3-yl | 4-fluoro-phenyl | a₁-L₁ | pyrrolidin-2-yl | methyl | H | 2S |
| 38 | 3-fluoro-phenyl | 4-methoxy-phenyl | a₁-L₁ | pyrrolidin-2-yl | methyl | H | 2S |
| 39 | 6-methoxy-pyridin-3-yl | 2-methoxy-phenyl | a₁-L₁ | pyrrolidin-2-yl | methyl | H | 2S |
| 40 | pyridin-3-yl | 2-methoxy-phenyl | a₁-L₁ | pyrrolidin-2-yl | methyl | H | 2S |
| 41 | 3-diethylamino-phenyl | 4-methoxy-phenyl | a₁-L₁ | pyrrolidin-2-yl | methyl | H | 2S |
| 42 | 3-methylcarbonylamino-phenyl | 4-methoxy-phenyl | a₁-L₁ | pyrrolidin-2-yl | methyl | H | 2S |
| 43 | 4-methylcarbonylamino-phenyl | 4-methoxy-phenyl | a₁-L₁ | pyrrolidin-2-yl | methyl | H | 2S |
| 44 | 6-methoxy-pyridin-3-yl | 4-amino-phenyl | a₁-L₁ | pyrrolidin-2-yl | methyl | H | 2S |
| 45 | 3-amino-phenyl | 4-methoxy-phenyl | a₁-L₁ | pyrrolidin-2-yl | methyl | H | 2S |
| 46 | pyridin-3-yl | 4-amino-phenyl | a₁-L₁ | pyrrolidin-2-yl | methyl | H | 2S |
| 47 | benzothiazol-2-yl | 4-methoxy-phenyl | a₁-L₁ | pyrrolidin-2-yl | methyl | H | 2S |
| 48 | thiazol-2-yl | 4-methoxy-phenyl | a₁-L₁ | pyrrolidin-2-yl | methyl | H | 2S |
| 49 | benzothiophen-2-yl | 4-methoxy-phenyl | a₁-L₁ | pyrrolidin-2-yl | methyl | H | 2S |

TABLE 1-continued

Formula (I)

| Cpd No | R₁ | R₂ | A—L— | a | L | Rₐ | Stereo Chem |
|---|---|---|---|---|---|---|---|
| 50 | 3-trifluoromethyl-phenyl | 4-methoxy-phenyl | a₁-L₁ | pyrrolidin-2-yl | methyl | H | 2S |
| 51 | 3-trifluoromethoxy-phenyl | 4-methoxy-phenyl | a₁-L₁ | pyrrolidin-2-yl | methyl | H | 2S |
| 52 | 2-methylthio-pyrimidin-5-yl | 4-methoxy-phenyl | a₁-L₁ | pyrrolidin-2-yl | methyl | H | 2S |
| 53 | 2-methoxy-pyrimidin-5-yl | 4-methoxy-phenyl | a₁-L₁ | pyrrolidin-2-yl | methyl | H | 2S |
| 54 | 5-fluoro-pyridin-3-yl | 4-methoxy-phenyl | a₁-L₁ | pyrrolidin-2-yl | methyl | H | 2S |
| 55 | 3,5-difluoro-phenyl | 4-methoxy-phenyl | a₁-L₁ | pyrrolidin-2-yl | methyl | H | 2S |
| 56 | 3,4-difluoro-phenyl | 4-methoxy-phenyl | a₁-L₁ | pyrrolidin-2-yl | methyl | H | 2S |
| 57 | 3,5-difluoro-4-hydroxymethyl-phenyl | 4-methoxy-phenyl | a₁-L₁ | pyrrolidin-2-yl | methyl | H | 2S |
| 58 | 2,4-dimethoxy-pyrimidin-5-yl | 4-methoxy-phenyl | a₁-L₁ | pyrrolidin-2-yl | methyl | H | 2S |
| 59 | 6-methoxy-pyridin-3-yl | 4-hydroxy-phenyl | a₁-L₁ | pyrrolidin-2-yl | methyl | H | 2S |
| 60 | 2-ethoxy-pyrimidin-5-yl | 4-methoxy-phenyl | a₁-L₁ | pyrrolidin-2-yl | methyl | H | 2S |
| 61 | pyrazol-5-yl | 4-methoxy-phenyl | a₁-L₁ | pyrrolidin-2-yl | methyl | H | 2S |
| 62 | 3,5-dimethyl-isoxazol-4-yl | 4-methoxy-phenyl | a₁-L₁ | pyrrolidin-2-yl | methyl | H | 2S |
| 63 | 2,3-dihydrobenzofuran-5-yl | 4-methoxy-phenyl | a₁-L₁ | pyrrolidin-2-yl | methyl | H | 2S |
| 64 | 3-fluoro-4-methoxy-phenyl | 4-methoxy-phenyl | a₁-L₁ | pyrrolidin-2-yl | methyl | H | 2S |
| 65 | pyrazol-4-yl | 4-methoxy-phenyl | a₁-L₁ | pyrrolidin-2-yl | methyl | H | 2S |
| 66 | 2-methylthio-pyrimidin-4-yl | 4-methoxy-phenyl | a₁-L₁ | pyrrolidin-2-yl | methyl | H | 2S |
| 67 | 1-methyl-pyrazol-4-yl | 4-methoxy-phenyl | a₁-L₁ | pyrrolidin-2-yl | methyl | H | 2S |
| 68 | 5-methoxy-pyridin-3-yl | 4-methoxy-phenyl | a₁-L₁ | pyrrolidin-2-yl | methyl | H | 2S |
| 69 | 5-cyano-pyridin-3-yl | 4-methoxy-phenyl | a₁-L₁ | pyrrolidin-2-yl | methyl | H | 2S |
| 70 | 3-fluoro-5-methoxy-phenyl | 4-methoxy-phenyl | a₁-L₁ | pyrrolidin-2-yl | methyl | H | 2S |
| 71 | 3-fluoro-5-methyl-phenyl | 4-methoxy-phenyl | a₁-L₁ | pyrrolidin-2-yl | methyl | H | 2S |
| 72 | 6-amino-pyridin-3-yl | 4-methoxy-phenyl | a₁-L₁ | pyrrolidin-2-yl | methyl | H | 2S |
| 73 | 5-fluoro-6-methoxy-pyridin-3-yl | 4-methoxy-phenyl | a₁-L₁ | pyrrolidin-2-yl | methyl | H | |
| 74 | 6-hydroxy-pyridin-3-yl | 4-methoxy-phenyl | a₁-L₁ | pyrrolidin-2-yl | methyl | H | 2S |
| 75 | 6-hydroxy-pyridin-3-yl | 4-hydroxy-phenyl | a₁-L₁ | pyrrolidin-2-yl | methyl | H | |
| 76 | quinoxalin-6-yl | 4-methoxy-phenyl | a₁-L₁ | pyrrolidin-2-yl | methyl | H | 2S |
| 77 | 1H-pyrrolo[2,3-b]pyridin-5-yl | 4-methoxy-phenyl | a₁-L₁ | pyrrolidin-2-yl | methyl | H | 2S |
| 78 | benzo[1,2,5]oxadiazol-5-yl | 4-methoxy-phenyl | a₁-L₁ | pyrrolidin-2-yl | methyl | H | 2S |
| 79 | pyrimidin-5-yl | 4-methoxy-phenyl | a₁-L₁ | 4,4-difluoro-pyrrolidin-2-yl | methyl | H | 2S |
| 80 | pyrimidin-5-yl | 4-methoxy-phenyl | a₁-L₁ | 4-fluoro-pyrrolidin-2-yl | methyl | H | 2S,4R |
| 81 | 2-amino-pyrimidin-5-yl | 4-methoxy-phenyl | a₁-L₁ | pyrrolidin-2-yl | methyl | H | 2S |
| 82 | 2-dimethylamino-pyrimidin-5-yl | 4-methoxy-phenyl | a₁-L₁ | pyrrolidin-2-yl | methyl | H | 2S |
| 83 | 2-(morpholin-4-yl)-pyrimidin-5-yl | 4-methoxy-phenyl | a₁-L₁ | pyrrolidin-2-yl | methyl | H | 2S |
| 84 | 2-(4-methyl-pyrazin-1-yl)-pyrimidin-5-yl | 4-methoxy-phenyl | a₁-L₁ | pyrrolidin-2-yl | methyl | H | 2S |
| 85 | pyrimidin-5-yl | benzothiazol-6-yl | a₁-L₁ | pyrrolidin-2-yl | methyl | H | 2S |
| 86 | 5-cyano-pyridin-3-yl | benzothiazol-6-yl | a₁-L₁ | pyrrolidin-2-yl | methyl | H | 2S |
| 87 | pyrimidin-5-yl | 2-methyl-benzoxazol-6-yl | a₁-L₁ | pyrrolidin-2-yl | methyl | H | 2S |
| 88 | 5-cyano-pyridin-3-yl | 2-methyl-benzoxazol-6-yl | a₁-L₁ | pyrrolidin-2-yl | methyl | H | 2S |
| 89 | pyrimidin-5-yl | 4-methoxy-phenyl | a₁-L₁ | 4-fluoro-pyrrolidin-2-yl | methyl | H | 2S,4S |

TABLE 1-continued

Formula (I)

| Cpd No | R$_1$ | R$_2$ | A—L— | a | L | R$_a$ | Stereo Chem |
|---|---|---|---|---|---|---|---|
| 90 | 5-cyano-pyridin-3-yl | 2-methyl-benzothiazol-6-yl | a$_1$-L$_1$ | pyrrolidin-2-yl | methyl | H | 2S |
| 91 | pyrimidin-5-yl | 2-methyl-benzothiazol-6-yl | a$_1$-L$_1$ | pyrrolidin-2-yl | methyl | H | 2S |
| 92 | 3,5-dimethyl-phenyl | 4-methoxy-phenyl | a$_1$-L$_1$ | pyrrolidin-2-yl | methyl | H | 2S |
| 93 | benzo[1,3]dioxol-5-yl | 4-methoxy-phenyl | a$_1$-L$_1$ | pyrrolidin-2-yl | methyl | H | 2S |
| 94 | 3,5-dichloro-phenyl | 4-methoxy-phenyl | a$_1$-L$_1$ | pyrrolidin-2-yl | methyl | H | 2S |
| 95 | 6-cyano-pyridin-3-yl | 4-methoxy-phenyl | a$_1$-L$_1$ | pyrrolidin-2-yl | methyl | H | 2S |
| 96 | 5-cyano-pyridin-3-yl | 3,5-difluoro-4-methoxy-phenyl | a$_1$-L$_1$ | pyrrolidin-2-yl | methyl | H | 2S |
| 97 | pyrimidin-5-yl | 3,5-difluoro-4-methoxy-phenyl | a$_1$-L$_1$ | pyrrolidin-2-yl | methyl | H | 2S |
| 98 | 5-cyano-pyridin-3-yl | 3-methoxy-phenyl | a$_1$-L$_1$ | pyrrolidin-2-yl | methyl | H | 2S |
| 99 | pyrimidin-5-yl | 3-methoxy-phenyl | a$_1$-L$_1$ | pyrrolidin-2-yl | methyl | H | 2S |
| 100 | pyridin-3-yl | 3-methoxy-phenyl | a$_1$-L$_1$ | pyrrolidin-2-yl | methyl | H | 2S |
| 101 | 5-cyano-pyridin-3-yl | 2,3-difluoro-4-methoxy-phenyl | a$_1$-L$_1$ | pyrrolidin-2-yl | methyl | H | 2S |
| 102 | 5-fluoro-pyridin-3-yl | 2,3-difluoro-4-methoxy-phenyl | a$_1$-L$_1$ | pyrrolidin-2-yl | methyl | H | 2S |
| 103 | pyrimidin-5-yl | 2,3-difluoro-4-methoxy-phenyl | a$_1$-L$_1$ | pyrrolidin-2-yl | methyl | H | 2S |
| 104 | 5-cyano-pyridin-3-yl | 4-ethoxy-phenyl | a$_1$-L$_1$ | pyrrolidin-2-yl | methyl | H | 2S |
| 105 | pyrimidin-5-yl | 4-ethoxy-phenyl | a$_1$-L$_1$ | pyrrolidin-2-yl | methyl | H | 2S |
| 106 | 5-fluoro-pyridin-3-yl | 4-ethoxy-phenyl | a$_1$-L$_1$ | pyrrolidin-2-yl | methyl | H | 2S |
| 107 | 5-methylthio-pyridin-3-yl | 4-methoxy-phenyl | a$_1$-L$_1$ | pyrrolidin-2-yl | methyl | H | 2S |
| 108 | 5-methanesulfonyl-pyridin-3-yl | 4-methoxy-phenyl | a$_1$-L$_1$ | pyrrolidin-2-yl | methyl | H | 2S |
| 109 | pyrimidin-5-yl | 4-methoxy-phenyl | a$_1$-L$_1$ | piperidin-3-yl | absent | H | racemic |
| 110 | 5-cyano-pyridin-3-yl | 4-difluoromethoxy-phenyl | a$_1$-L$_1$ | pyrrolidin-2-yl | methyl | H | 2S |
| 111 | pyrimidin-5-yl | 4-difluoromethoxy-phenyl | a$_1$-L$_1$ | pyrrolidin-2-yl | methyl | H | 2S |
| 112 | 5-fluoro-pyridin-3-yl | 4-difluoromethoxy-phenyl | a$_1$-L$_1$ | pyrrolidin-2-yl | methyl | H | 2S |
| 113 | 5-cyano-pyridin-3-yl | 4-n-propyloxy-phenyl | a$_1$-L$_1$ | pyrrolidin-2-yl | methyl | H | 2S |
| 114 | pyrimidin-5-yl | 4-n-propyloxy-phenyl | a$_1$-L$_1$ | pyrrolidin-2-yl | methyl | H | 2S |
| 115 | 5-fluoro-pyridin-3-yl | 4-n-propyloxy-phenyl | a$_1$-L$_1$ | pyrrolidin-2-yl | methyl | H | 2S |
| 117 | indol-4-yl | 4-methoxy-phenyl | a$_1$-L$_1$ | pyrrolidin-2-yl | methyl | H | 2S |
| 118 | indol-6-yl | 4-methoxy-phenyl | a$_1$-L$_1$ | pyrrolidin-2-yl | methyl | H | 2S |
| 119 | indol-7-yl | 4-methoxy-phenyl | a$_1$-L$_1$ | pyrrolidin-2-yl | methyl | H | 2S |
| 120 | pyrazin-2-yl | 4-methoxy-phenyl | a$_1$-L$_1$ | pyrrolidin-2-yl | methyl | H | 2S |
| 121 | 2-cyano-pyrimidin-5-yl | 4-methoxy-phenyl | a$_1$-L$_1$ | pyrrolidin-2-yl | methyl | H | 2S |
| 122 | 5-cyano-pyridin-3-yl | 4-(2,2,2-trifluoro-ethoxy)-phenyl | a$_1$-L$_1$ | pyrrolidin-2-yl | methyl | H | 2S |
| 123 | pyrimidin-5-yl | 4-(2,2,2-trifluoro-ethoxy)-phenyl | a$_1$-L$_1$ | pyrrolidin-2-yl | methyl | H | 2S |
| 124 | 5-fluoro-pyridin-3-yl | 4-(2,2,2-trifluoro-ethoxy)-phenyl | a$_1$-L$_1$ | pyrrolidin-2-yl | methyl | H | 2S |
| 125 | 5-cyano-pyridin-3-yl | 4-n-butoxy-phenyl | a$_1$-L$_1$ | pyrrolidin-2-yl | methyl | H | 2S |
| 126 | pyrimidin-5-yl | 4-n-butoxy-phenyl | a$_1$-L$_1$ | pyrrolidin-2-yl | methyl | H | 2S |
| 127 | 5-fluoro-pyridin-3-yl | 4-n-butoxy-phenyl | a$_1$-L$_1$ | pyrrolidin-2-yl | methyl | H | 2S |
| 128 | 5-fluoro-pyridin-3-yl | 4-chloro-phenyl | a$_1$-L$_1$ | pyrrolidin-2-yl | methyl | H | 2S |
| 129 | 5-cyano-pyridin-3-yl | 4-chloro-phenyl | a$_1$-L$_1$ | pyrrolidin-2-yl | methyl | H | 2S |
| 130 | pyrimidin-5-yl | 4-chloro-phenyl | a$_1$-L$_1$ | pyrrolidin-2-yl | methyl | H | 2S |
| 131 | 5-fluoro-pyridin-3-yl | 3-fluoro-4-methoxy-phenyl | a$_1$-L$_1$ | pyrrolidin-2-yl | methyl | H | 2S |
| 132 | 5-cyano-pyridin-3-yl | 3-fluoro-4-methoxy-phenyl | a$_1$-L$_1$ | pyrrolidin-2-yl | methyl | H | 2S |
| 133 | pyrimidin-5-yl | 3-fluoro-4-methoxy-phenyl | a$_1$-L$_1$ | pyrrolidin-2-yl | methyl | H | 2S |
| 134 | 5-cyano-pyridin-3-yl | 4-methoxy-phenyl | a$_1$-L$_1$ | 4-fluoro-pyrrolidin-2-yl | methyl | H | 2S,4R |
| 135 | pyridin-3-yl | 3-cyano-phenyl | a$_1$-L$_1$ | pyrrolidin-2-yl | methyl | H | 2S |
| 136 | pyridin-3-yl | 4-cyano-phenyl | a$_1$-L$_1$ | pyrrolidin-2-yl | methyl | H | 2S |
| 137 | pyridin-3-yl | 3-fluoro-4-cyano-phenyl | a$_1$-L$_1$ | pyrrolidin-2-yl | methyl | H | 2S |
| 138 | pyridin-3-yl | 4-cyclopropylcarbonylamino-phenyl | a$_1$-L$_1$ | pyrrolidin-2-yl | methyl | H | 2S |
| 139 | 5-cyano-pyridin-3-yl | 4-isopropyloxy-phenyl | a$_1$-L$_1$ | pyrrolidin-2-yl | methyl | H | 2S |
| 140 | pyrimidin-5-yl | 4-isopropyloxy-phenyl | a$_1$-L$_1$ | pyrrolidin-2-yl | methyl | H | 2S |
| 141 | pyridin-3-yl | 4-isopropyloxy-phenyl | a$_1$-L$_1$ | pyrrolidin-2-yl | methyl | H | 2S |
| 142 | 3-cyano-5-fluoro-phenyl | 4-methoxy-phenyl | a$_1$-L$_1$ | pyrrolidin-2-yl | methyl | H | 2S |

TABLE 1-continued

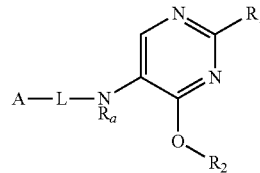

Formula (I)

| Cpd No | R₁ | R₂ | A—L— | a | L | Rₐ | Stereo Chem |
|---|---|---|---|---|---|---|---|
| 143 | 5-cyano-pyridin-3-yl | 4-hydroxymethyl-phenyl | a₁-L₁ | pyrrolidin-2-yl | methyl | H | 2S |
| 144 | pyrimidin-5-yl | 4-hydroxymethyl-phenyl | a₁-L₁ | pyrrolidin-2-yl | methyl | H | 2S |
| 145 | pyridin-3-yl | 4-hydroxymethyl-phenyl | a₁-L₁ | pyrrolidin-2-yl | methyl | H | 2S |
| 146 | 5-cyano-pyridin-3-yl | 4-fluoro-phenyl | a₁-L₁ | pyrrolidin-2-yl | methyl | H | 2S |
| 147 | 5-cyano-pyridin-3-yl | 4-methyl-phenyl | a₁-L₁ | pyrrolidin-2-yl | methyl | H | 2S |
| 148 | pyrimidin-5-yl | 4-methyl-phenyl | a₁-L₁ | pyrrolidin-2-yl | methyl | H | 2S |
| 149 | pyridin-3-yl | 4-methyl-phenyl | a₁-L₁ | pyrrolidin-2-yl | methyl | H | 2S |
| 150 | 5-cyano-pyridin-3-yl | 4-methylthio-phenyl | a₁-L₁ | pyrrolidin-2-yl | methyl | H | 2S |
| 151 | pyrimidin-5-yl | 4-methylthio-phenyl | a₁-L₁ | pyrrolidin-2-yl | methyl | H | 2S |
| 152 | pyridin-3-yl | 4-methylthio-phenyl | a₁-L₁ | pyrrolidin-2-yl | methyl | H | 2S |
| 153 | 5-cyano-pyridin-3-yl | 4-(methoxymethyl)-phenyl | a₁-L₁ | pyrrolidin-2-yl | methyl | H | 2S |
| 154 | pyrimidin-5-yl | 4-(methoxymethyl)-phenyl | a₁-L₁ | pyrrolidin-2-yl | methyl | H | 2S |
| 155 | pyridin-3-yl | 4-(methoxymethyl)-phenyl | a₁-L₁ | pyrrolidin-2-yl | methyl | H | 2S |
| 156 | pyrimidin-5-yl | 4-hydroxy-phenyl | a₁-L₁ | pyrrolidin-2-yl | methyl | H | 2S |
| 157 | pyridin-3-yl | 3-diethylaminocarbonyl-phenyl | a₁-L₁ | pyrrolidin-2-yl | methyl | H | 2S |
| 158 | pyridin-3-yl | 4-pyrrolidin-1-ylcarbonyl-phenyl | a₁-L₁ | pyrrolidin-2-yl | methyl | H | 2S |
| 159 | pyridin-3-yl | 4-carboxy-phenyl | a₁-L₁ | pyrrolidin-2-yl | methyl | H | 2S |
| 160 | pyridin-3-yl | 4-piperidin-1-ylcarbonyl-phenyl | a₁-L₁ | pyrrolidin-2-yl | methyl | H | 2S |
| 161 | pyridin-3-yl | 4-(morpholin-4-ylcarbonyl)-phenyl | a₁-L₁ | pyrrolidin-2-yl | methyl | H | 2S |
| 162 | pyridin-3-yl | 4-(4-methyl-piperazin-1-ylcarbonyl)-phenyl | a₁-L₁ | pyrrolidin-2-yl | methyl | H | 2S |
| 163 | pyridin-3-yl | 3-carboxy-phenyl | a₁-L₁ | pyrrolidin-2-yl | methyl | H | 2S |
| 164 | 5-fluoro-pyridin-3-yl | 3-carboxy-phenyl | a₁-L₁ | pyrrolidin-2-yl | methyl | H | 2S |
| 165 | 5-fluoro-pyridin-3-yl | 4-carboxy-phenyl | a₁-L₁ | pyrrolidin-2-yl | methyl | H | 2S |
| 166 | pyridin-3-yl | 3-(pyrrolidin-1-ylcarbonyl)-phenyl | a₁-L₁ | pyrrolidin-2-yl | methyl | H | 2S |
| 167 | pyridin-3-yl | 3-(piperidin-1-ylcarbonyl)-phenyl | a₁-L₁ | pyrrolidin-2-yl | methyl | H | 2S |
| 168 | pyridin-3-yl | 3-(morpholin-4-ylcarbonyl)-phenyl | a₁-L₁ | pyrrolidin-2-yl | methyl | H | 2S |
| 169 | pyridin-3-yl | 3-(4-methyl-piperazin-1-ylcarbonyl)-phenyl | a₁-L₁ | pyrrolidin-2-yl | methyl | H | 2S |
| 170 | 5-fluoro-pyridin-3-yl | 3-diethylaminocarbonyl-phenyl | a₁-L₁ | pyrrolidin-2-yl | methyl | H | 2S |
| 171 | 5-fluoro-pyridin-3-yl | 3-(pyrrolidin-1-ylcarbonyl)-phenyl | a₁-L₁ | pyrrolidin-2-yl | methyl | H | 2S |
| 172 | 5-fluoro-pyridin-3-yl | 3-(piperidin-1-ylcarbonyl)-phenyl | a₁-L₁ | pyrrolidin-2-yl | methyl | H | 2S |
| 173 | 5-fluoro-pyridin-3-yl | 3-(morpholin-4-ylcarbonyl)-phenyl | a₁-L₁ | pyrrolidin-2-yl | methyl | H | 2S |
| 174 | 5-fluoro-pyridin-3-yl | 3-(4-methyl-piperazin-1-ylcarbonyl)-phenyl | a₁-L₁ | pyrrolidin-2-yl | methyl | H | 2S |
| 175 | pyridin-3-yl | 4-diethylaminocarbonyl-phenyl | a₁-L₁ | pyrrolidin-2-yl | methyl | H | 2S |
| 176 | 5-fluoro-pyridin-3-yl | 4-(pyrrolidin-1-ylcarbonyl)-phenyl | a₁-L₁ | pyrrolidin-2-yl | methyl | H | 2S |
| 177 | pyridin-3-yl | 4-benzyloxycarbonylamino-phenyl | a₁-L₁ | pyrrolidin-2-yl | methyl | H | 2S |
| 178 | 5-fluoro-pyridin-3-yl | 4-methyl-phenyl | a₁-L₁ | pyrrolidin-2-yl | methyl | H | 2S |
| 179 | 5-cyano-pyridin-3-yl | 4-ethyl-phenyl | a₁-L₁ | pyrrolidin-2-yl | methyl | H | 2S |
| 180 | 5-chloro-pyridin-3-yl | 4-ethyl-phenyl | a₁-L₁ | pyrrolidin-2-yl | methyl | H | 2S |
| 181 | pyrimidin-5-yl | 4-methoxy-phenyl | a₁-L₁ | pyrrolidin-2-yl | methyl | —C(O)Me | 2S |
| 182 | 5-fluoro-pyridin-3-yl | 4-ethyl-phenyl | a₁-L₁ | pyrrolidin-2-yl | methyl | H | 2S |
| 183 | 5-cyano-pyridin-3-yl | 3-fluoro-4-methyl-phenyl | a₁-L₁ | pyrrolidin-2-yl | methyl | H | 2S |
| 184 | pyridin-3-yl | 4-ethyl-phenyl | a₁-L₁ | pyrrolidin-2-yl | methyl | H | 2S |
| 185 | 5-fluoro-pyridin-3-yl | 3-fluoro-4-methyl-phenyl | a₁-L₁ | pyrrolidin-2-yl | methyl | H | 2S |
| 186 | 5-chloro-pyridin-3-yl | 3-fluoro-4-methyl-phenyl | a₁-L₁ | pyrrolidin-2-yl | methyl | H | 2S |
| 187 | pyridin-3-yl | 3-fluoro-4-methyl-phenyl | a₁-L₁ | pyrrolidin-2-yl | methyl | H | 2S |
| 188 | pyridin-3-yl | 3-benzyloxycarbonylamino-phenyl | a₁-L₁ | pyrrolidin-2-yl | methyl | H | 2S |
| 189 | 5-cyano-pyridin-3-yl | 2,3-difluoro-4-methyl-phenyl | a₁-L₁ | pyrrolidin-2-yl | methyl | H | 2S |

TABLE 1-continued

Formula (I)

| Cpd No | R₁ | R₂ | A—L— | a | L | R_a | Stereo Chem |
|---|---|---|---|---|---|---|---|
| 190 | 5-chloro-pyridin-3-yl | 2,3-difluoro-4-methyl-phenyl | a₁-L₁ | pyrrolidin-2-yl | methyl | H | 2S |
| 191 | 5-fluoro-pyridin-3-yl | 2,3-difluoro-4-methyl-phenyl | a₁-L₁ | pyrrolidin-2-yl | methyl | H | 2S |
| 192 | pyridin-3-yl | 2,3-difluoro-4-methyl-phenyl | a₁-L₁ | pyrrolidin-2-yl | methyl | H | 2S |
| 193 | 5-fluoro-pyridin-3-yl | 4-methoxy-phenyl | a₁-L₁ | 4-fluoro-pyrrolidin-2-yl | methyl | H | 2S,4R |
| 194 | 5-chloro-pyridin-3-yl | 4-methoxy-phenyl | a₁-L₁ | 4-fluoro-pyrrolidin-2-yl | methyl | H | 2S,4R |
| 195 | 5-cyano-pyridin-3-yl | 4-ethyl-phenyl | a₁-L₁ | 4-fluoro-pyrrolidin-2-yl | methyl | H | 2S,4R |
| 196 | pyridin-3-yl | 4-methoxy-phenyl | a₁-L₁ | 4-fluoro-pyrrolidin-2-yl | methyl | H | 2S,4R |
| 197 | 5-fluoro-pyridin-3-yl | 4-benzyloxycarbonylamino-phenyl | a₁-L₁ | pyrrolidin-2-yl | methyl | H | 2S |
| 198 | 5-fluoro-pyridin-3-yl | 4-amino-phenyl | a₁-L₁ | pyrrolidin-2-yl | methyl | H | 2S |
| 199 | 5-cyano-pyridin-3-yl | 4-methoxy-phenyl | a₁-L₁ | piperidin-3-yl | absent | H | 3S |
| 200 | 5-cyano-pyridin-3-yl | 3-methyl-phenyl | a₁-L₁ | pyrrolidin-2-yl | methyl | H | 2S |
| 201 | 5-chloro-pyridin-3-yl | 3-methyl-phenyl | a₁-L₁ | pyrrolidin-2-yl | methyl | H | 2S |
| 202 | 5-fluoro-pyridin-3-yl | 3-methyl-phenyl | a₁-L₁ | pyrrolidin-2-yl | methyl | H | 2S |
| 203 | pyridin-3-yl | 3-methyl-phenyl | a₁-L₁ | pyrrolidin-2-yl | methyl | H | 2S |
| 204 | 5-cyano-pyridin-3-yl | 3-methyl-4-methoxy-phenyl | a₁-L₁ | pyrrolidin-2-yl | methyl | H | 2S |
| 205 | 5-fluoro-pyridin-3-yl | 3-methyl-4-methoxy-phenyl | a₁-L₁ | pyrrolidin-2-yl | methyl | H | 2S |
| 206 | 5-cyano-pyridin-3-yl | 4-fluoromethyl-phenyl | a₁-L₁ | pyrrolidin-2-yl | methyl | H | 2S |
| 207 | 5-cyano-pyridin-3-yl | 4-methoxy-phenyl | a₁-L₁ | piperidin-3-yl | absent | H | 3S |
| 208 | 5-cyano-pyridin-3-yl | 4-methoxy-phenyl | a₁-L₁ | piperidin-4-yl | absent | H | |
| 209 | pyridin-3-yl | 4-(pyridin-3-ylmethyl)-phenyl | a₁-L₁ | pyrrolidin-2-yl | methyl | H | 2S |
| 210 | 5-chloro-pyridin-3-yl | 3-methyl-4-methoxy-phenyl | a₁-L₁ | pyrrolidin-2-yl | methyl | H | 2S |
| 211 | pyridin-3-yl | 3-methyl-4-methoxy-phenyl | a₁-L₁ | pyrrolidin-2-yl | methyl | H | 2S |
| 212 | 5-fluoro-pyridin-3-yl | 4-(methylcarbonylamino)-phenyl | a₁-L₁ | pyrrolidin-2-yl | methyl | H | 2S |
| 213 | 5-fluoro-pyridin-3-yl | 4-methanesulfonylamino-phenyl | a₁-L₁ | pyrrolidin-2-yl | methyl | H | 2S |
| 214 | pyridin-3-yl | 4-methanesulfonylamino-phenyl | a₁-L₁ | pyrrolidin-2-yl | methyl | H | 2S |
| 215 | 5-cyano-pyridin-3-yl | 4-methoxy-phenyl | a₁-L₁ | azetidin-3-yl | methyl | H | |
| 216 | pyridin-3-yl | 4-formamido-phenyl | a₁-L₁ | pyrrolidin-2-yl | methyl | H | 2S |
| 217 | pyridin-3-yl | 4-fluoromethyl-phenyl | a₁-L₁ | pyrrolidin-2-yl | methyl | H | 2S |
| 218 | 5-cyano-pyridin-3-yl | 3-methyl-4-fluoro-phenyl | a₁-L₁ | pyrrolidin-2-yl | methyl | H | 2S |
| 219 | 5-fluoro-pyridin-3-yl | 3-methyl-4-fluoro-phenyl | a₁-L₁ | pyrrolidin-2-yl | methyl | H | 2S |
| 220 | 5-cyano-pyridin-3-yl | 4-trifluoromethyl-phenyl | a₁-L₁ | pyrrolidin-2-yl | methyl | H | 2S |
| 221 | 5-fluoro-pyridin-3-yl | 4-trifluoromethyl-phenyl | a₁-L₁ | pyrrolidin-2-yl | methyl | H | 2S |
| 222 | 5-fluoro-pyridin-3-yl | 4-methanesulfonyl-phenyl | a₁-L₁ | pyrrolidin-2-yl | methyl | H | 2S |
| 223 | 5-fluoro-pyridin-3-yl | 4-formamido-phenyl | a₁-L₁ | pyrrolidin-2-yl | methyl | H | 2S |
| 224 | pyridin-3-yl | 4-methoxy-phenyl | a₁-L₁ | pyrrolidin-3-yl | absent | H | 3R |
| 225 | pyridin-3-yl | 4-methoxy-phenyl | a₁-L₁ | piperidin-2-yl | methyl | H | 2S |
| 226 | pyridin-3-yl | 4-methoxy-phenyl | a₁-L₁ | azetidin-3-yl | absent | H | |
| 227 | 5-chloro-pyridin-3-yl | 2-methyl-phenyl | a₁-L₁ | pyrrolidin-2-yl | methyl | H | 2S |
| 228 | 5-cyano-pyridin-3-yl | 3-methylcarbonyloxy-phenyl | a₁-L₁ | pyrrolidin-2-yl | methyl | H | 2S |
| 229 | 5-chloro-pyridin-3-yl | 2-chloro-phenyl | a₁-L₁ | pyrrolidin-2-yl | methyl | H | 2S |
| 230 | 5-cyano-pyridin-3-yl | 2-chloro-phenyl | a₁-L₁ | pyrrolidin-2-yl | methyl | H | 2S |
| 231 | 5-cyano-pyridin-3-yl | 3-hydroxy-phenyl | a₁-L₁ | pyrrolidin-2-yl | methyl | H | 2S |
| 232 | 5-methoxy-pyridin-3-yl | 2-chloro-phenyl | a₁-L₁ | pyrrolidin-2-yl | methyl | H | 2S |
| 233 | 5-methylthio-pyridin-3-y | 2-chloro-phenyl | a₁-L₁ | pyrrolidin-2-yl | methyl | H | 2S |
| 234 | 5-methylthio-pyridin-3-y | 4-methoxy-phenyl | a₁-L₁ | 4-fluoro-pyrrolidin-2-yl | methyl | H | 2S,4R |
| 235 | 5-methoxy-pyridin-3-yl | 4-methoxy-phenyl | a₁-L₁ | 4-fluoro-pyrrolidin-2-yl | methyl | H | 2S,4R |
| 236 | pyridin-3-yl | 4-methoxy-phenyl | a₁-L₁ | piperidin-3-yl | absent | H | 3S |
| 237 | pyridin-3-yl | 4-methoxy-phenyl | a₁-L₁ | pyrrolidin-3-yl | absent | H | 3S |
| 238 | 5-methyl-pyridin-3-yl | 4-methoxy-phenyl | a₁-L₁ | 4-fluoro-pyrrolidin-2-yl | methyl | H | 2S,4R |

TABLE 1-continued

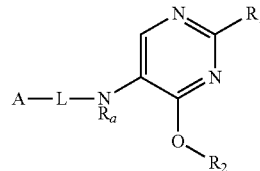

Formula (I)

| Cpd No | R₁ | R₂ | A—L— | a | L | $R_a$ | Stereo Chem |
|---|---|---|---|---|---|---|---|
| 239 | 5-methyl-pyridin-3-yl | 4-methoxy-phenyl | $a_1$-$L_1$ | 4-fluoro-pyrrolidin-2-yl | methyl | H | 2S,4S |
| 240 | 5-methoxy-pyridin-3-yl | 4-methoxy-phenyl | $a_1$-$L_1$ | 4-fluoro-pyrrolidin-2-yl | methyl | H | 2S,4S |
| 241 | 5-methylthio-pyridin-3-yl | 4-(2-methoxy-ethoxy)-phenyl | $a_1$-$L_1$ | pyrrolidin-2-yl | methyl | H | 2S |
| 242 | 5-methyl-pyridin-3-yl | 4-(2-methoxy-ethoxy)-phenyl | $a_1$-$L_1$ | pyrrolidin-2-yl | methyl | H | 2S |
| 243 | 5-methoxy-pyridin-3-yl | 4-(2-methoxy-ethoxy)-phenyl | $a_1$-$L_1$ | pyrrolidin-2-yl | methyl | H | 2S |
| 244 | pyridin-3-yl | 4-(2-methoxy-ethoxy)-phenyl | $a_1$-$L_1$ | pyrrolidin-2-yl | methyl | H | 2S |
| 245 | 5-methoxy-pyridin-3-yl | 4-methoxy-phenyl | $a_1$-$L_1$ | piperidin-3-yl | absent | H | 3S |
| 246 | 5-methoxy-pyridin-3-yl | 4-methoxy-phenyl | $a_1$-$L_1$ | piperidin-3-yl | absent | H | 3R |
| 247 | 5-methoxy-pyridin-3-yl | 4-methoxy-phenyl | $a_1$-$L_1$ | piperidin-3-yl | absent | H | 3S |
| 248 | 5-methylthio-pyridin-3-yl | 3-methylcarbonyloxy-phenyl | $a_1$-$L_1$ | pyrrolidin-2-yl | methyl | H | 2S |
| 249 | 5-methoxy-pyridin-3-yl | 3-hydroxy-phenyl | $a_1$-$L_1$ | pyrrolidin-2-yl | methyl | H | 2S |
| 250 | 5-methoxy-pyridin-3-yl | 3-methylcarbonyloxy-phenyl | $a_1$-$L_1$ | pyrrolidin-2-yl | methyl | H | 2S |
| 251 | 5-methyl-pyridin-3-yl | 3-methylcarbonyloxy-phenyl | $a_1$-$L_1$ | pyrrolidin-2-yl | methyl | H | 2S |
| 252 | 5-methylthio-pyridin-3-yl | 4-methoxy-phenyl | $a_1$-$L_1$ | piperidin-3-yl | absent | H | 3S |
| 253 | 5-methyl-pyridin-3-yl | 4-methoxyphenyl | $a_1$-$L_1$ | pyrrolidin-2-yl | methyl | H | 2S |
| 254 | 5-methylthiopyridin-3-yl | 4-methoxyphenyl | $a_1$-$L_1$ | piperidin-3-yl | absent | H | 3R |
| 255 | 5-methylthiopyridin-3-yl | 4-methoxyphenyl | $a_1$-$L_1$ | pyrrolidin-3-yl | absent | H | 3S |
| 256 | 5-methoxypyridin-3-yl | 4-methoxyphenyl | $a_1$-$L_1$ | pyrrolidin-3-yl | absent | H | 3S |
| 257 | 5-methyl-pyridin-3-yl | 4-methoxyphenyl | $a_1$-$L_1$ | pyrrolidin-3-yl | absent | H | 3S |
| 258 | 5-methyl-pyridin-3-yl | 4-methoxyphenyl | $a_1$-$L_1$ | piperidin-3-yl | absent | H | 3R |
| 259 | 5-methyl-pyridin-3-yl | 4-methoxyphenyl | $a_1$-$L_1$ | piperidin-3-yl | absent | H | 3S |
| 260 | 5-methyl-pyridin-3-yl | 4-fluoromethoxyphenyl | $a_1$-$L_1$ | pyrrolidin-2-yl | methyl | H | 2S |
| 261 | pyridin-3-yl | 4-methoxyphenyl | $a_1$-$L_1$ | piperidin-3-yl | absent | H | 3R |
| 262 | 6-fluoro-5-methylpyridin-3-yl | 4-methoxyphenyl | $a_1$-$L_1$ | pyrrolidin-2-yl | methyl | H | 2S |
| 263 | 2,5-dimethyl-pyridin-3-yl | 4-methoxyphenyl | a1-$L_1$ | pyrrolidin-2-yl | methyl | H | 2S |
| 264 | 6'-chloro-3,5'-dimethyl-[2,3']bipyridinyl-5-yl | 4-methoxyphenyl | $a_1$-$L_1$ | pyrrolidin-2-yl | methyl | H | 2S |
| 265 | 6-chloro-4-methyl pyridin-3-yl | 4-methoxyphenyl | $a_1$-$L_1$ | pyrrolidin-2-yl | methyl | H | 2S |
| 266 | 6-chloro-5-methyl-pyridin-3-yl | 4-methoxyphenyl | $a_1$-$L_1$ | pyrrolidin-2-yl | methyl | H | 2S |
| 267 | pyridin-3-yl | 4-methoxyphenyl | $a_1$-$L_1$ | piperidin-2-yl | methyl | H | 2R |
| 268 | 2-chloro-5-methylpyridin-3-yl | 4-methoxyphenyl | $a_1$-$L_1$ | pyrrolidin-2-yl | methyl | H | 2S |
| 269 | 5-hydroxymethyl-pyridin-3-yl | 4-methoxyphenyl | $a_1$-$L_1$ | pyrrolidin-2-yl | methyl | H | 2S |
| 270 | pyridin-3-yl | 4-methoxyphenyl | $a_1$-$L_1$ | 4-hydroxy-pyrrolidin-2-yl | methyl | H | trans 2S,4R |
| 271 | pyridin-3-yl | 4-methoxyphenyl | a1-$L_1$ | 4-hydroxy pyrrolidin-2-yl | methyl | H | cis 2R,4R |
| 272 | pyridin-3-yl | 4-methoxyphenyl | $a_1$-$L_1$ | 4-hydroxy-pyrrolidin-2-yl | methyl | H | cis 2S,4S |
| 273 | 5-methoxypyridin-3-yl | 4-methoxyphenyl | $a_1$-$L_1$ | 4-hydroxy-pyrrolidin-2-yl | methyl | H | trans 2S,4R |
| 274 | 5-methoxypyridin-3-yl | 4-methoxyphenyl | $a_1$-$L_1$ | 4-hydroxy-pyrrolidin-2-yl | methyl | H | cis 2R,4R |
| 275 | 5-cyano-pyridin-3-yl | 4-methoxy-phenyl | $a_2$-$L_2$ | morpholin-2-yl | methyl | H | racemic |
| 276 | 5-fluoro-pyridin-3-yl | 4-methoxy-phenyl | $a_2$-$L_2$ | morpholin-2-yl | methyl | H | |
| 277 | pyrimidin-5-yl | 4-methoxy-phenyl | $a_2$-$L_2$ | morpholin-2-yl | methyl | H | |
| 278 | pyrimidin-5-yl | 4-methoxy-phenyl | $a_2$-$L_2$ | morpholin-3-yl | methyl | H | racemic |
| 279 | 5-cyano-pyridin-3-yl | 4-methoxy-phenyl | $a_2$-$L_2$ | morpholin-3-yl | methyl | H | racemic |
| 280 | 5-cyano-pyridin-3-yl | 4-methoxy-phenyl | $a_2$-$L_2$ | morpholin-3-yl | methyl | H | 3S |

TABLE 1-continued

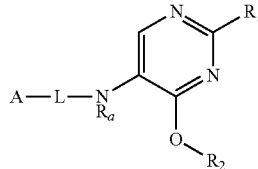

Formula (I)

| Cpd No | R₁ | R₂ | A—L— | a | L | Rₐ | Stereo Chem |
|---|---|---|---|---|---|---|---|
| 281 | 5-fluoro-pyridin-3-yl | 4-methoxy-phenyl | a₂-L₂ | morpholin-3-yl | methyl | H | 3S |
| 282 | pyridin-3-yl | 4-methoxy-phenyl | a₂-L₂ | morpholin-3-yl | methyl | H | 3S |
| 283 | 5-cyano-pyridin-3-yl | 4-methoxy-phenyl | a₃-L₃ | imidazol-2-yl | methylene | H | |
| 284 | 5-cyano-pyridin-3-yl | 4-methoxy-phenyl | a₃-L₃ | 3H-imidazol-4-yl | methylene | H | |
| 285 | 5-cyano-pyridin-3-yl | 4-methoxy-phenyl | a₃-L₃ | 5-methyl-3H-imidazol-4-yl | methyl | H | 0 |
| 286 | 5-cyano-pyridin-3-yl | 4-methoxy-phenyl | a₃-L₃ | 3-methyl-3H-imidazol-4-yl | methyl | H | 0 |
| 287 | 5-cyano-pyridin-3-yl | 4-methoxy-phenyl | a₃-L₃ | 2-ethyl-5-methyl-3H-imidazol-4-yl | methyl | H | |
| 288 | pyridin-3-yl | 4-methoxy-phenyl | a₃-L₃ | 3H-imidazol-4-yl | methyl | H | |
| 289 | 5-methylthio-pyridin-3-yl | 4-methoxy-phenyl | a₃-L₃ | 3H-imidazol-4-yl | methyl | H | |
| 290 | 5-methoxy-pyridin-3-yl | 4-methoxy-phenyl | a₃-L₃ | 3H-imidazol-4-yl | methyl | H | |
| 291 | 5-methyl-pyridin-3-yl | 4-methoxy-phenyl | a₃-L₃ | 3H-imidazol-4-yl | methyl | H | |
| 292 | 5-cyano-pyridin-3-yl | 4-methoxy-phenyl | a₄-L₄ | 2-amino | propyl | H | 2S |
| 293 | 5-cyano-pyridin-3-yl | 4-methoxy-phenyl | a₄-L₄ | 2-amino | ethyl | H | |
| 294 | 5-cyano-pyridin-3-yl | 4-methoxy-phenyl | a₄-L₄ | 2-amino | 4-methyl-pentyl | H | 2S |
| 295 | pyrimidin-5-yl | 4-methoxy-phenyl | a₄-L₄ | 2-amino | 4-methyl-pentyl | H | 2S |
| 296 | 5-methyl-pyridin-3-yl | 4-methoxyphenyl | a₄-L₄ | 2-amino | ethyl | H | |
| 297 | pyridin-3-yl | 4-methoxyphenyl | a₄-L₄ | 2-methylamino | ethyl | H | |
| 298 | 5-cyano-pyridin-3-yl | 4-methoxy-phenyl | a₅-L₅ | 4-aminocyclohexyl | absent | H | cis/trans mixture |
| 299 | 5-cyano-pyridin-3-yl | 4-methoxy-phenyl | a₅-L₅ | 2-aminocyclohexyl | methyl | H | 2S,1R |
| 300 | pyrimidin-5-yl | 4-methoxy-phenyl | a₅-L₅ | 2-aminocyclohexyl | methyl | H | 2S,1R |
| 301 | 5-cyano-pyridin-3-yl | 4-methoxy-phenyl | a₅-L₅ | 3-aminocyclobutyl | methyl | H | trans |
| 302 | pyrimidin-5-yl | 4-methoxy-phenyl | a₅-L₅ | 3-aminocyclobutyl | methyl | H | trans |
| 303 | 5-cyano-pyridin-3-yl | 4-methoxy-phenyl | a₅-L₅ | 3-aminocyclobutyl | absent | H | cis/trans mixture |
| 304 | pyrimidin-5-yl | 4-methoxy-phenyl | a₅-L₅ | 3-aminocyclobutyl | absent | H | cis/trans mixture |
| 305 | pyridin-3-yl | 4-methoxy-phenyl | a₅-L₅ | 4-aminocyclohexyl | absent | H | cis |
| 306 | pyridin-3-yl | 4-methoxy-phenyl | a₅-L₅ | 3-aminocyclohexyl | absent | H | Racemic, mixture of cis/trans |
| 307 | pyridin-3-yl | 4-methoxy-phenyl | a₅-L₅ | 3-aminocyclohexyl | absent | H | 1RS,3SR (racemic cis) |
| 308 | pyridin-3-yl | 4-methoxy-phenyl | a₅-L₅ | 2-aminocyclohexyl | absent | H | 1RS,2SR (racemic single stereoisomer, unknown cis/trans) |
| 309 | 5-methoxy-pyridin-3-yl | 4-methoxy-phenyl | a₅-L₅ | 3-aminocyclohexyl | absent | H | Racemic, mixture of cis/trans |
| 310 | 5-methylthiopyridin-3-yl | 4-methoxyphenyl | a₅-L₅ | 3-aminocyclohexyl | absent | H | Racemic, mixture of cis/trans |
| 311 | 5-methoxypyridin-3-yl | 4-methoxyphenyl | a₅-L₅ | 3-aminocyclohexyl | absent | H | cis 1R,3S |
| 312 | 5-methoxypyridin-3-yl | 4-methoxyphenyl | a₅-L₅ | 3-aminocyclohexyl | absent | H | cis 1S,3R |
| 313 | 5-methoxypyridin-3-yl | 4-methoxyphenyl | a₅-L₅ | 3-aminocyclohexyl | absent | H | trans, one enant. Absolute unknown |
| 314 | 5-methoxypyridin-3-yl | 4-methoxyphenyl | a₅-L₅ | 3-aminocyclohexyl | absent | H | trans, one enant., absolute unknown |

TABLE 1-continued

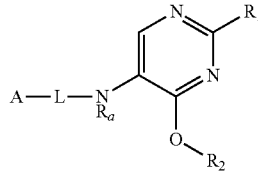

Formula (I)

| Cpd No | R₁ | R₂ | A—L— | a | L | Rₐ | Stereo Chem |
|---|---|---|---|---|---|---|---|
| 315 | 5-methyl-pyridin-3-yl | 4-methoxyphenyl | a₅-L₅ | 3-aminocyclohexyl | absent | H | Racemic, mixture of cis/trans |
| 316 | 5-methylthiopyridin-3-yl | 4-methoxyphenyl | a₅-L₅ | 3-aminocyclohexyl | absent | H | cis 1S,3R |
| 317 | 5-methylthiopyridin-3-yl | 4-methoxyphenyl | a₅-L₅ | 3-aminocyclohexyl | absent | H | cis 1R,3S |
| 318 | 5-methylthiopyridin-3-yl | 4-methoxyphenyl | a₅-L₅ | 3-aminocyclohexyl | absent | H | trans, one enant., absolute unknown |
| 319 | 5-methylthiopyridin-3-yl | 4-methoxyphenyl | a₅-L₅ | 3-aminocyclohexyl | absent | H | trans, one enant., absolute unknown |
| 321 | pyridin-3-yl | 4-methoxyphenyl | a₅-L₅ | 3-aminocyclohexyl | absent | H | cis 1S,3R |
| 322 | pyridin-3-yl | 4-methoxyphenyl | a₅-L₅ | 3-aminocyclohexyl | absent | H | cis 1R,3S |
| 323 | pyridin-3-yl | 4-methoxyphenyl | a₅-L₅ | 3-aminocyclohexyl | absent | H | trans, one enant., absolute unknown |

Compounds 320, and 324 through 361 of Formula (I), in the table below were synthesized using the procedures described above.

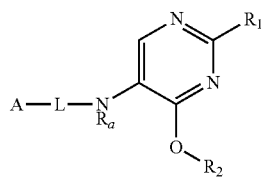

Formula (I)

| Cpd No | R₁ | R₂ | A—L— and Rₐ are taken to form | Stereo chem |
|---|---|---|---|---|
| 320 | pyridin-3-yl | 4-cyclopropyl-phenyl | piperazin-1-yl | |
| 324 | phenyl | 4-methoxy-phenyl | piperazin-1-yl | |
| 325 | 5-cyano-pyridin-3-yl | 4-methoxy-phenyl | piperazin-1-yl | |
| 326 | 5-cyano-pyridin-3-yl | 4-methoxy-phenyl | 3-amino pyrrolidin-1-yl | 3R |
| 327 | pyridin-3-yl | 4-methoxy-phenyl | piperazin-1-yl | |
| 328 | 5-cyano-pyridin-3-yl | 4-methoxy-phenyl | 3-amino pyrrolidin-1-yl | 3S |
| 329 | 5-cyano-pyridin-3-yl | 4-methoxy-phenyl | 3-amino piperidin-1-yl | 3S |
| 330 | 5-cyano-pyridin-3-yl | 4-methoxy-phenyl | 3-amino piperidin-1-yl | 3R |
| 331 | 5-cyano-pyridin-3-yl | 4-methoxy-phenyl | 3-aminomethyl azetidin-1-yl | |
| 332 | 5-cyano-pyridin-3-yl | 4-methoxy-phenyl | 2-aminomethyl pyrrolidin-1-yl | 2R |
| 333 | 5-cyano-pyridin-3-yl | 4-methoxy-phenyl | 4-amino piperidin-1-yl | |
| 334 | 5-cyano-pyridin-3-yl | 4-methoxy-phenyl | 2-aminomethyl pyrrolidin-1-yl | 2R |
| 335 | 5-cyano-pyridin-3-yl | 4-methoxy-phenyl | 3-oxopiperazin-1-yl | |
| 336 | pyridin-3-yl | 4-methoxy-phenyl | [1,4]diazepan-1-yl | |
| 337 | 5-cyano-pyridin-3-yl | 4-methoxy-phenyl | 2-oxopiperazin-1-yl | |
| 338 | 5-cyano-pyridin-3-yl | 4-methoxy-phenyl | 3,6-diaza-bicyclo[3.1.1] hept-3-ylamino | |
| 339 | pyridin-3-yl | 4-methoxy-phenyl | 3-amino pyrrolidin-1-yl | 3R |
| 340 | pyridin-3-yl | 4-methoxy-phenyl | 3-amino-azetidin-1-yl | |

-continued

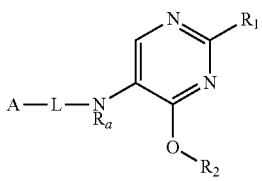

Formula (I)

| Cpd No | $R_1$ | $R_2$ | A—L— and $R_a$ are taken to form | Stereo chem |
|---|---|---|---|---|
| 341 | 5-methylthio-pyridin-3-y | 4-methoxy-phenyl | piperazin-1-yl | |
| 342 | 5-methoxy-pyridin-3-yl | 4-methoxy-phenyl | piperazin-1-yl | |
| 343 | 5-cyano-pyridin-3-yl | 4-methoxy-phenyl | 3-methyl-piperazin-1-yl | racemic |
| 344 | 5-cyano-pyridin-3-yl | 4-methoxy-phenyl | 2-methyl-piperazin-1-yl | 2R |
| 345 | 5-cyano-pyridin-3-yl | 4-methoxy-phenyl | 2-methyl-piperazin-1-yl | 2S |
| 346 | 5-methoxy-pyridin-3-yl | 4-methoxy-phenyl | [1,4]-diazepan-1-yl | |
| 347 | 5-methylthio pyridin-3-yl | 4-methoxy phenyl | [1,4]-diazepan-1-yl | |
| 348 | 5-methylthio pyridin-3-yl | 4-methoxy phenyl | 3-amino-pyrrolidin-1-yl | 3R |
| 349 | 5-methoxy pyridin-3-yl | 4-methoxy phenyl | 3-amino-pyrrolidin-1-yl | 3R |
| 350 | 5-methylthio pyridin-3-yl | 4-methoxy phenyl | 3,3-dimethyl-piperazin-1-yl | |
| 351 | 5-methyl-pyridin-3-yl | 4-methoxy phenyl | piperazin-1-yl | |
| 352 | 5-methyl-pyridin-3-yl | 4-methoxy phenyl | 3-amino-pyrrolidin-1-yl | 3R |
| 353 | pyridin-3-yl | 4-methoxy phenyl | 4-methyl-piperazin-1-yl | |
| 354 | pyridin-3-yl | 4-methoxy phenyl | 2-methyl-piperazin-1-yl | 2S |
| 355 | pyridin-3-yl | 4-methoxy phenyl | 3,3-dimethyl-piperazin-1-yl | |
| 356 | pyridin-3-yl | 4-methoxy phenyl | 3-methyl-piperazin-1-yl | 3S |
| 357 | pyridin-3-yl | 4-methoxy phenyl | 3-methyl-piperazin-1-yl | 3R |
| 358 | 5-methyl-pyridin-3-yl | 4-methoxy phenyl | [1,4]diazepan-1-yl | |
| 359 | pyridin-3-yl | 4-methoxy phenyl | 3,5-dimethyl-piperazin-1-yl | cis |
| 360 | 5-methoxy pyridin-3-yl | 4-methoxy phenyl | 2-ethyl-piperazin-1-yl | 2S |
| 361 | 5-methoxy pyridin-3-yl | 4-methoxy phenyl | 3-ethyl-piperazin-1-yl | 3R |

BIOLOGICAL EXAMPLES

In Vitro Assays

Example 1

NG108-15, 24-Well Delta Opioid Receptor Binding Assay

Methods: NG108-15 cell membranes were purchased from Applied Cell Sciences (Rockville, Md.). 5 mg/mL of membrane protein was suspended in 10 mM TRIS-HCl pH 7.2, 2 mM EDTA, 10% sucrose. With several brief pulses from a Polytron homogenizer, each vial was homogenized in 5 mls of 50 mM Tris Buffer, pH 7.4. The homogenate was diluted in 50 mM Tris Buffer containing 5 mM $MgCl_2$ to 330 ug/ml in the working solution for a final concentration of 133 ug/well. This particulate preparation was used for the 24-well delta opioid binding assay.

Following incubation with the delta selective peptide ligand ~0.2 nM [$^3$H]Naltrindole at 25° C. for 2.5 h in a 24-well plate with total volume of 1 mL, the plate contents were filtered through a UniFilter24, GF/B. This plate was presoaked in 0.3% PEI and filtered through a 24-well Harvester. The UniFilter24 was rinsed three times with 2 mL of 10 mM HEPES (pH 7.4), and dried in an oven at 37° C. for 1.5 hours. To each well, was added 150 uL of Scint0 (PerkinElmer, Cat#6013611). The plates were then read on a TopCount.

Analysis: The data from the scintillation counter were used to calculate either the % inhibition compared to control binding (when only a single concentration of test compound was evaluated) or a $K_i$ value (when a range of concentrations was tested). Non-specific binding (N.S.-1 mM Naloxone) is used as the negative control, while the Total Binding (T.B.-Membrane and ligand only) is used as the positive control. If one concentration is screened, the % inhibition is calculated as (cpms of total binding minus cpms of compound) divided by (cpms of T.B.minus cpms of N.S). The triplicate % Inhibitions are averaged and reported. If multiple concentrations are generated, the values are analyzed using the one-site binding non-linear regression program in Prism to determine Ki values. The bottom and top values are globally shared. The triplicate K is are then averaged and reported.

The data obtained are shown in Table 2, below.

Example 2

Rat Brain Delta Opioid Receptor Binding Assay

Procedure: Male, Wistar rats (150-250 g, VAF, Charles River, Kingston, N.Y.) were killed by $CO_2$, and their brains were removed and placed immediately in ice cold Tris HCl buffer (50 mM, pH 7.4). The forebrains were separated from the remainder of the brain by a coronal transection, beginning dorsally at the colliculi and passing ventrally through the midbrain-pontine junction. After dissection, the forebrains were homogenized in Tris buffer in a Teflon®-glass homogenizer. The homogenate was diluted to a concentration of 1 g of forebrain tissue per 80 mL Tris and centrifuged at 39,000×g for 10 min. The pellet was resuspended in the same volume of Tris buffer containing 5 mM $MgCl_2$ with several brief pulses from a Polytron homogenizer. This particulate preparation was used for the delta opioid binding assays. Following incubation with the delta selective peptide ligand ~4 nM [$^3$H]DPDPE or 0.25 nM [$^3$H]naltrindole at 25° C. for 2.5 h in a 96-well plate with total volume of 1 mL, the plate contents were filtered through Wallac filtermat B sheets on a Tomtec 96-well harvester. The filters were rinsed three times with 2 mL of 10 mM HEPES (pH 7.4), and dried in a 650 W microwave oven for 1.75 min twice. To each sample area 2×50 µL of Betaplate Scint scintillation fluid (LKB) was added and the radioactivity was quantified on a LKB (Wallac) 1205 BetaPlate liquid scintillation counter.

Analysis: The data from the scintillation counter were used to calculate either the % inhibition compared to control binding (when only a single concentration of test compound was evaluated) or a $K_i$ value (when a range of concentrations was tested). Percent inhibition was calculated as: [(total dpm-test compound dpm)/(total dpm-nonspecific dpm)]*100. Kd and Ki values were calculated using GraphPad PRISM data analysis program. The data obtained are shown in Table 2, below.

Example 3

Rat Brain Mu Opioid Receptor Binding Assay

Procedure: Male, Wistar rats (150-250 g, VAF, Charles River, Kingston, N.Y.) were killed by $CO_2$, and their brains were removed and placed immediately in ice cold Tris HCl buffer (50 mM, pH 7.4). The forebrains were separated from the remainder of the brain by a coronal transection, beginning dorsally at the colliculi and passing ventrally through the midbrain-pontine junction. After dissection, the forebrains were homogenized in Tris buffer in a Teflon®-glass homogenizer. The homogenate was diluted to a concentration of 1 g of forebrain tissue per 80 mL Tris and centrifuged at 39,000×g for 10 min. The pellet was resuspended in the same volume of Tris buffer containing 5 mM $MgCl_2$ with several brief pulses from a Polytron homogenizer. This particulate preparation was used for the mu opioid binding assays. Following incubation with the mu selective peptide ligand, ~0.8 nM [$^3$H]DAMGO, at 25° C. for 2.5 h in a 96-well plate with total assay volume of 1 mL, the plate contents were filtered through Wallac filtermat B sheets on a Tomtec 96-well harvester. The filters were rinsed three times with 2 mL of 10 mM HEPES (pH 7.4), and dried in a 650 W microwave oven for 1.75 min twice. To each sample area 2×40 µL of Betaplate Scint scintillation fluid (LKB) was added and the radioactivity was quantifed on a LKB (Wallac) 1205 BetaPlate liquid scintillation counter.

Analysis: The data from the scintillation counter was used to calculate either the % inhibition compared to control binding (when only a single concentration of test compound was evaluated) or a $K_i$ value (when a range of concentrations was tested). Percent inhibition was calculated as: [(total dpm-test compound dpm)/(total dpm-nonspecific dpm)]*100. Kd and Ki values were calculated using GraphPad PRISM data analysis program. The data obtained are shown in Table 2, below.

TABLE 2

Delta and Mu Opioid Receptor Binding Data

| Cpd No. | δ-binding NG108 cell membrane $K_i$ (µM) | δ-binding (DPDPE ligand) $K_i$ (µM) | δ-binding (Naltrindole ligand) $K_i$ (µM) | µ-binding $K_i$ (µM) |
|---|---|---|---|---|
| 1 | | 0.363 | | 3.228 |
| 2 | | 0.020 | 0.033 | 3.387, 3.139 |
| 3 | | 0.142 | | 2.345 |
| 4 | | 2.217 | | >10 |
| 5 | | | 0.157 | >10 |
| 6 | | | 0.116 | 9.007 |
| 7 | | | 0.013 | 2.169 |
| 8 | | | 0.00619 | 0.0428 |
| 9 | | | 0.001 | 2.968 |
| 10 | | | 0.034 | 2.000 |
| 11 | | | 0.005 | 3.083 |
| 12 | | | 0.018 | 4.516 |
| 13 | | | 0.002 | 5.568 |
| 14 | | | 0.001 | 1.731 |
| 15 | | | 0.0001 | 0.416 |
| 16 | | | 0.014 | 1.317 |
| 17 | | | 0.030 | 3.081 |
| 18 | | | 0.172 | 2.237 |
| 19 | | | 0.201 | 8.084 |
| 20 | | | 0.00493 | 0.146 |
| 21 | | | 0.201 | 2.387 |
| 22 | | | 0.000909 | 1.100 |
| 23 | | | 0.00125 | 0.214 |
| 24 | | | 0.001 | 1.064 |
| 25 | | | 0.000308 | 0.616 |
| 26 | | | 0.008 | 4.049 |
| 27 | | | 2.569 | 15.549 |
| 28 | | | 0.00610 | 0.295 |
| 29 | | | 0.086 | 2.663 |
| 30 | | | 0.003 | 1.087 |
| 31 | | | 0.031 | 0.837 |
| 32 | | | 0.0126 | 0.0641 |
| 33 | | | 0.029 | 0.029 |
| 34 | | | 0.015 | 0.015 |
| 35 | | | 0.184 | 0.184 |
| 36 | | | 0.003 | 4.769 |
| 37 | | | 0.010 | >10 |
| 38 | | | 0.001 | 4.906 |
| 39 | | | 0.067 | 8.991 |
| 40 | | | 0.093 | 7.642 |
| 41 | | | 0.041 | 1.529 |
| 42 | | | 0.016 | 1.230 |
| 43 | | | 0.004 | 0.523 |
| 44 | | | 0.004 | 2.693 |
| 45 | | | 0.011 | 0.812 |
| 46 | | | 0.027 | 3.550 |
| 47 | | | 0.006 | 1.126 |
| 48 | | | 0.024 | 0.862 |
| 49 | | | 0.103 | 3.563 |
| 50 | | | 0.055 | 0.597 |
| 51 | | | 0.022 | 1.026 |
| 52 | | | 0.0004 | 0.539 |
| 53 | | | 0.0002 | 0.591 |
| 54 | 0.000188 | | 0.00033 | 0.2172 |
| 55 | | | 0.021 | 2.046 |
| 56 | | | 0.015 | 1.944 |
| 57 | | | 0.011 | 0.113 |
| 58 | | | 0.004 | 0.640 |
| 59 | 0.00154 | | 0.000954 | 1.610 |
| 60 | | | 0.014 | 1.523 |
| 61 | | | 0.259 | 3.988 |
| 62 | | | 0.544 | 1.915 |
| 63 | | | 0.037 | 0.633 |
| 64 | | | 0.008 | 0.466 |
| 65 | | | 0.003 | 0.555 |
| 66 | | | 0.010 | 0.390 |
| 67 | | | 0.001 | 1.561 |
| 68 | | | 0.002 | 0.465 |
| 69 | 0.000139 | | 0.0041 | 0.196 |
| 70 | | | 0.047 | 2.253 |
| 72 | | | 0.002 | 0.732 |
| 73 | | | 0.003 | 1.102 |
| 74 | | | 0.026 | 1.062 |
| 75 | | | 0.036 | 5.117 |
| 76 | | | 0.111 | 0.333 |
| 77 | | | 0.154 | 0.313 |
| 78 | | | 0.075 | 1.878 |
| 79 | | | 0.095 | >10 |
| 80 | | | 0.002 | 0.106 |
| 81 | | | 0.355 | 0.569 |
| 82 | | | 0.028 | 1.050 |
| 83 | | | 0.014 | 0.673 |
| 84 | | | 0.016 | 0.338 |
| 85 | | | 0.002 | >10 |
| 86 | | | 0.002 | 1.176 |
| 87 | | | 0.072 | |
| 88 | | | 0.014 | |
| 89 | | | 0.010 | |
| 90 | | | 0.009 | |
| 91 | | | 0.022 | |
| 92 | | | 0.035 | |
| 93 | | | 0.008 | 0.554 |
| 94 | | | 0.143 | |
| 95 | | | 0.011 | |
| 96 | | | 0.035 | |
| 97 | | | 0.039 | |
| 98 | | | 0.003 | 0.102 |
| 99 | | | 0.059 | |

TABLE 2-continued

Delta and Mu Opioid Receptor Binding Data

| Cpd No. | δ-binding NG108 cell membrane $K_i$ (μM) | δ-binding (DPDPE ligand) $K_i$ (μM) | δ-binding (Naltrindole ligand) $K_i$ (μM) | μ-binding $K_i$ (μM) |
|---|---|---|---|---|
| 100 | | | 0.033 | |
| 101 | | | 0.007 | 0.058 |
| 102 | | | 0.003 | |
| 103 | | | 0.011 | |
| 104 | | | 0.008 | 0.190 |
| 105 | | | 0.003 | 0.421 |
| 106 | | | 0.006 | 0.042 |
| 107 | | | 0.001 | 0.039 |
| 108 | | | 0.107 | |
| 109 | | | 0.001 | 0.522 |
| 110 | | | 0.033 | 1.071 |
| 111 | | | 0.009 | |
| 112 | | | 0.006 | |
| 113 | | | 0.045 | 1.433 |
| 114 | | | 0.008 | |
| 115 | | | 0.052 | |
| 117 | | | 0.157 | |
| 118 | | | 0.155 | |
| 119 | | | 4.018 | |
| 120 | | | 0.104 | |
| 121 | | | 0.020 | 0.379 |
| 122 | | | 0.122 | |
| 123 | 0.0004 | | | |
| 124 | 0.0003 | | 0.126 | |
| 125 | | | 0.078 | |
| 126 | | | 0.565 | |
| 127 | | | 0.224 | |
| 128 | 0.0004 | | | |
| 129 | 0.0003 | | | |
| 130 | 0.002 | | | |
| 131 | 0.0002 | | | |
| 132 | 0.0004 | | | 0.061 |
| 133 | 0.0004 | | | |
| 134 | 4.8084e−005 | | | 0.027 |
| 135 | 0.002 | | | |
| 136 | 0.007 | | | |
| 137 | 0.009 | | | |
| 138 | 0.004 | | | |
| 139 | 0.002 | | | |
| 140 | 0.008 | | | |
| 141 | 0.003 | | | |
| 142 | 0.0002 | | | |
| 143 | 0.001 | | | |
| 144 | 0.007 | | | |
| 145 | 0.005 | | | |
| 146 | 0.0004 | | | |
| 147 | 0.0004 | | | 0.438 |
| 148 | 0.001 | | | |
| 149 | 0.001 | | | |
| 150 | 0.0003 | | | |
| 151 | 0.001 | | | |
| 152 | 0.0004 | | | |
| 153 | 0.001 | | | |
| 154 | 0.009 | | | |
| 155 | 0.005 | | | |
| 156 | 0.001 | | | |
| 157 | 0.040 | | | |
| 158 | 1.604 | | | |
| 159 | 4.452 | | | |
| 160 | 0.338 | | | |
| 161 | 0.795 | | | |
| 162 | 0.852 | | | |
| 163 | 6.386 | | | |
| 164 | 2.283 | | | |
| 165 | 3.765 | | | |
| 166 | 0.027 | | | |
| 167 | 0.021 | | | |
| 168 | 0.050 | | | |
| 169 | 0.033 | | | |
| 275 | | | 0.046 | |
| 276 | | | 0.227 | |
| 277 | | | 0.032 | |
| 278 | 0.00164 | | 0.999 | |
| 279 | | | 0.005 | |
| 280 | | | 0.006 | |
| 281 | 0.001 | | | |
| 282 | 0.001 | | | |
| 292 | | | 0.002 | |
| 293 | | | 0.008 | |
| 294 | 0.006 | | | |
| 295 | 0.064 | | | |
| 298 | | | 0.004 | |
| 299 | | | 0.023 | 0.222 |
| 300 | | | 0.021 | |
| 301 | 0.0005 | | | 0.658 |
| 302 | 0.001 | | | |
| 304 | 0.002 | | | |

*When compounds were tested more than once, the values have been reported as averages of their individual experiments.

Example 4

[$^{35}$S]GTPγS Binding Assay in NG108-15 Cell Membranes (Delta Opioid Functional Assay)-200 nM Screen Methods: NG108-15 cell membranes were purchased from Applied Cell Sciences (Rockville, Md.). 5 mg/mL of membrane protein was suspended in 10 mM TRIS-HCl pH 7.2, 2 mM EDTA, 10% sucrose. Membranes were maintained at 4-8° C. A 1 mL volume of membranes was added into 10 mL cold binding assay buffer. The assay buffer contained 50 mM Tris, pH 7.6, 5 mM MgCl$_2$, 100 mM NaCl, 1 mM DTT and 1 mM EGTA. The membrane suspension was homogenized twice with a Polytron, and centrifuged at 3000 rpm for 10 min. The supernatant was then centrifuged at 18,000 rpm for 20 min. Ten mL assay buffer was added into the pellet containing tube. The pellet and buffer were mixed with a Polytron.

Incubation procedure: The pellet membranes (75 μg/mL) were preincubated with SPA (10 mg/mL) at 25° C. for 45 min in the assay buffer. The SPA (5 mg/mL) coupled with membranes (37.5 μg/mL) was then incubated with 0.1 nM [$^{35}$S]GTPγS in the same Tris buffer containing 100 μM GDP in total volume of 200 μL. 200 nM of receptor agonists was used to stimulate [$^{35}$S]-GTPγS binding. The basal binding was tested in the absence of agonists and non-specific binding was tested in the presence of 10 μM unlabeled GTPγS. The data were analyzed on a Packard Top Count and are shown in Table 3, below.

DATA

% of Basal=(stimulated−non specific)*100/(basal−non specific).

Relative Efficacy of a compound at 200 nM=(% of Basal of test compound at 200 nM)/(Calculated Max of SNC80 dose response. Curve in prism).

Example 5

[$^{35}$S]GTPγS Binding Assays in CHO-hMOR Cell Membranes (Mu Opioid Functional Assay)

Methods: CHO-hMOR cell membranes can be purchased from Receptor Biology, Inc. (Baltimore, Md.). About 10 mg/mL of membrane protein can be suspended in 10 mM TRIS-HCl pH 7.2, 2 mM EDTA, 10% sucrose, and the suspension kept on ice. A 1 mL volume of membranes can be added to 15 mL cold binding assay buffer containing 50 mM HEPES, pH 7.6, 5 mM MgCl$_2$, 100 mM NaCl, 1 mM DTT and 1 mM EDTA. The membrane suspension can be homogenized with a Polytron and centrifuged at 3,000 rpm for 10 min. The supernatant can then be centrifuged at 18,000 rpm for 20 min. The pellet can be resuspended in 10 mL assay buffer with a Polytron. The membranes can be preincubated with wheat germ agglutinin coated SPA beads (Amersham) at 25° C. for 45 min in the assay buffer. The SPA bead (5 mg/mL) coupled membranes (10 μg/mL) can be then incubated with 0.5 nM [$^{35}$S]GTPγS in the assay buffer. The basal binding can be that taking place in the absence of added test compound; this unmodulated binding can be considered as 100%, with agonist stimulated binding rising to levels significantly above this value. A range of concentrations of receptor agonist can be used to stimulate [$^{35}$S]GTPγS binding. Both basal and non-specific binding can be tested in the absence of agonist; non-specific binding determination included 10 μM unlabeled GTPγS.

Compounds can be tested for function as antagonists by evaluating their potential to inhibit agonist-stimulated GTPγS binding. Radioactivity can be quantified on a Packard Top-Count. The following parameters can be calculated:

$$\% \text{ stimulation} = \frac{(\text{test compound } cpm - \text{non-specific } cpm)}{(\text{basal } cpm - \text{non-specific } cpm)} \times 100$$

$$\% \text{ inhibition} = \frac{(\% \text{ stimulation by 1 μM } DAMGO - \% \text{ stimulation by test compound})}{(\% \text{ stimulation by 1 μM } DAMGO - 100)} \times 100$$

EC$_{50}$ values can be calculated using GraphPad Prism and are shown in Table 3, below.

TABLE 3

Delta and Mu Opioid Receptor Functional Data

| Cpd No. | GTPγS δ-RelEfficacy @200 nM | GTPγS δ-opioid receptor EC$_{50}$ (μM) | GTPγS δ-opioid receptor Rel Efficacy | GTPγS δ-opioid receptor % Inh @10 μM | GTPγS μ-opioid receptor EC$_{50}$ (μM) | GTPγS μ-opioid receptor % Inh @10 μM |
|---|---|---|---|---|---|---|
| 2 | | 0.430; 0.069 | 0.733 | 5.790 | | |
| 5 | | 0.164 | 0.803 | 18.100 | | |
| 7 | | 0.436 | 0.912 | 17.066 | | |
| 8 | | 0.0681 | 0.848 | 23.626 | | 2.480 |
| 9 | | 1.262 | 0.873 | 27.407 | | |
| 10 | | 1.164 | 0.769 | 24.400 | | |
| 11 | | 0.419 | 0.818 | 11.561 | | |
| 12 | | >10 | | 45.032 | | |
| 13 | | 0.319 | 0.563 | 31.369 | | |
| 14 | | 0.313 | 0.782 | 15.795 | | |
| 15 | | 0.128 | 0.503 | 55.234 | | |
| 16 | | 0.030 | 0.928 | 25.532 | | |
| 17 | | 1.734 | 0.704 | 16.178 | | |
| 20 | | 0.0162 | 0.912 | 33.681 | | |
| 22 | | 0.0393 | 0.977 | 20.485 | | |
| 23 | | 0.0416 | 1.0000 | 17.675 | >10 | 13.505 |
| 24 | | 0.048 | 0.733 | 46.235 | | |
| 25 | | 0.0821 | 0.946 | 23.384 | | |
| 26 | | 0.069 | 0.681 | 5.443 | | |
| 28 | | 0.00810 | 0.989 | 4.3964 | | |
| 30 | | 0.025 | 0.842 | 20.615 | | |
| 31 | | 0.189 | 0.996 | 8.195 | | |
| 32 | | 0.0336 | 1.0345 | 12.011 | | |
| 33 | | 0.074 | 0.828 | 11.792 | | |
| 34 | | 0.216 | 0.911 | 24.781 | | |
| 36 | | 1.489 | 0.565 | 12.801 | | |
| 37 | | 3.072 | 0.882 | 18.665 | | |
| 38 | | 0.154 | 0.795 | 9.115 | | |
| 39 | | 0.370 | 0.882 | 1.000 | | |
| 40 | | 0.023 | 0.521 | 1.000 | | |
| 41 | | 0.350 | 0.821 | 8.514 | | |
| 42 | | 0.182 | 0.771 | 20.416 | | |
| 43 | | 0.138 | 0.831 | 16.944 | | |
| 44 | | 0.539 | 0.780 | 9.315 | | |
| 45 | | 0.128 | 0.883 | 1.000 | | |
| 46 | | 0.097 | 0.708 | 1.000 | | |
| 47 | | 0.055 | 0.987 | 1.000 | | |
| 48 | | 0.076 | 0.659 | 4.336 | | |
| 50 | | 0.198 | 0.961 | 9.284 | | |
| 51 | | 0.159 | 0.899 | 1.000 | | |
| 52 | | 0.008 | 1.037 | 1.000 | | |
| 53 | | 0.074 | 0.870 | 14.421 | | |
| 54 | | 0.046 | 0.976 | 1.444 | >10 | 15.716 |
| 55 | | 0.151 | 0.855 | 18.315 | | |
| 56 | | 0.536 | 0.909 | 26.261 | | |
| 57 | | 0.032 | 0.828 | 9.212 | | |

TABLE 3-continued

Delta and Mu Opioid Receptor Functional Data

| Cpd No. | GTPγS δ-RelEfficacy @200 nM | GTPγS δ-opioid receptor EC$_{50}$ (μM) | GTPγS δ-opioid receptor Rel Efficacy | GTPγS δ-opioid receptor % Inh @10 μM | GTPγS μ-opioid receptor EC$_{50}$ (μM) | GTPγS μ-opioid receptor % Inh @10 μM |
|---|---|---|---|---|---|---|
| 58 | | 1.514 | 0.823 | 12.772 | | |
| 59 | | 0.433 | 1.0063 | 1.478 | | |
| 60 | | 0.089 | 0.926 | 3.735 | | |
| 63 | | 0.693 | 0.993 | | | |
| 64 | | 0.088 | 0.830 | 12.034 | | |
| 65 | | 0.339 | 0.824 | | | |
| 66 | | 0.568 | 0.760 | 5.771 | | |
| 67 | | 0.194 | 0.944 | | | |
| 68 | | 0.031 | 0.912 | | | 11.460 |
| 69 | | 0.0085 | 1.004 | | >10 | 22.837 |
| 72 | | 0.105 | 0.905 | 15.204 | | |
| 73 | | 0.059 | 0.956 | | | |
| 74 | | 0.856 | 0.868 | 2.367 | | |
| 80 | | 0.113 | 1.049 | | | |
| 85 | | >10 | | | | |
| 86 | | 0.386 | 0.633 | | | |
| 88 | | 0.478 | 0.538 | | | |
| 89 | | 1.315 | 0.963 | | | |
| 90 | | 0.923 | 1.045 | | | |
| 91 | | >10 | | | | |
| 92 | | 0.470 | 1.183 | | | |
| 93 | | 0.072 | 1.115 | | | |
| 95 | | 0.708 | 1.025 | | | |
| 96 | | 0.749 | 0.942 | | | |
| 97 | | 7.119 | 1.128 | | | |
| 98 | | 0.106 | 1.060 | | | |
| 99 | | 0.939 | 1.007 | | | |
| 100 | | 1.625 | 1.019 | | | |
| 101 | | 0.103 | 1.096 | | >10 | 16.560 |
| 102 | | 0.255 | 0.989 | | | |
| 103 | | 0.311 | 1.066 | | | |
| 104 | | 0.018 | 0.921 | | | |
| 105 | | 0.146 | 1.099 | | | |
| 106 | | 0.027 | 1.019 | | >10 | 16.954 |
| 107 | 1.046 | 0.0213 | 0.957 | | 5.100 | 4.050 |
| 109 | | 0.057 | 1.102 | | | |
| 110 | | 0.081 | 0.986 | | | |
| 111 | | 0.491 | 1.031 | | | |
| 112 | | 0.330 | 1.082 | | | |
| 113 | | 0.075 | 1.104 | | | |
| 114 | | 0.306 | 1.088 | | | |
| 115 | | 2.710 | 1.039 | | | |
| 120 | | | | | | |
| 121 | | 0.019 | 1.010 | | | |
| 122 | | | | | | |
| 123 | 0.653 | 0.057 | 1.124 | | | |
| 128 | | 0.453 | 1.144 | | | |
| 129 | 0.633 | 0.0551 | 0.976 | | | |
| 130 | 0.245 | | | | | |
| 131 | 0.819 | 0.076 | 1.063 | | | |
| 132 | | 0.015 | 1.042 | | 9.277 | 9.396 |
| 133 | 0.755 | 0.028 | 1.041 | | | |
| 134 | | 0.004 | 1.087 | | 2.785 | 1.000 |
| 135 | | 1.383 | 1.023 | | | |
| 136 | | 9.005 | 0.789 | | | |
| 137 | | >10 | | | | |
| 138 | | 1.340 | 0.882 | | | |
| 139 | | 2.266 | 1.118 | | | |
| 140 | 0.137 | | | | | |
| 141 | 0.149 | | | | | |
| 142 | 0.931 | 0.029 | 1.006 | | | |
| 143 | | 0.690 | 1.066 | | | |
| 144 | 0.191 | | | | | |
| 145 | | 4.024 | 1.180 | | | |
| 146 | | 0.387 | 1.197 | | | |
| 147 | | 0.051 | 1.077 | | | |
| 148 | 0.411 | 0.158 | 1.052 | | | |
| 149 | 0.403 | 0.236 | 1.026 | | | |
| 150 | 0.801 | 0.033 | 1.093 | | | |
| 151 | 0.704 | 0.119 | 1.121 | | | |
| 152 | 0.607 | 0.070 | 1.083 | | | |
| 153 | 0.454 | 0.193 | 1.120 | | | |

TABLE 3-continued

Delta and Mu Opioid Receptor Functional Data

| Cpd No. | GTPγS δ-RelEfficacy @200 nM | GTPγS δ-opioid receptor $EC_{50}$ (μM) | GTPγS δ-opioid receptor Rel Efficacy | GTPγS δ-opioid receptor % Inh @10 μM | GTPγS μ-opioid receptor $EC_{50}$ (μM) | GTPγS μ-opioid receptor % Inh @10 μM |
|---|---|---|---|---|---|---|
| 154 | 0.164 | | | | | |
| 155 | 0.170 | | | | | |
| 156 | | 0.177 | 0.967 | | | |
| 157 | 0.213 | | | | | |
| 166 | 0.169 | | | | | |
| 167 | 0.328 | | | | | |
| 168 | 0.300 | | | | | |
| 170 | 0.176 | | | | | |
| 171 | 0.257 | | | | | |
| 172 | 0.246 | | | | | |
| 173 | 0.249 | | | | | |
| 174 | 0.205 | | | | | |
| 175 | 0.005 | | | | | |
| 176 | 0.112 | | | | | |
| 177 | 0.511 | 0.255 | 1.389 | | | |
| 178 | 0.578 | 0.300 | 1.239 | | | |
| 179 | 0.601 | 0.119 | 1.182 | | | |
| 180 | 0.250 | | | | | |
| 181 | 0.139 | | | | | |
| 182 | 0.470 | 0.377 | 1.065 | | | |
| 183 | 0.723 | 0.091 | 1.091 | | | |
| 184 | 0.497 | 0.418 | 1.271 | | | |
| 185 | 0.447 | 0.101 | 1.014 | | | |
| 186 | 0.466 | 0.331 | 1.113 | | | |
| 187 | 0.497 | 0.160 | 1.104 | | | |
| 188 | 0.779 | 0.219 | 1.950 | | | |
| 189 | 0.375 | | | | | |
| 190 | 0.222 | | | | | |
| 191 | 0.410 | | | | | |
| 192 | 0.135 | | | | | |
| 193 | 0.801 | 0.032 | 1.090 | | | |
| 194 | 0.665 | 0.022 | 1.034 | | | |
| 195 | 0.477 | 0.194 | 1.119 | | | |
| 196 | 0.800 | 0.0693 | 1.146 | | | |
| 197 | 0.411 | 0.145 | 1.289 | | | |
| 198 | 0.513 | 0.118 | 1.050 | | | |
| 199 | 0.615 | 0.033 | 1.140 | | | |
| 200 | 0.289 | | | | | |
| 201 | 0.148 | | | | | |
| 202 | 0.122 | | | | | |
| 203 | 0.096 | | | | | |
| 204 | 0.911 | 0.026 | 0.982 | | | |
| 205 | 0.609 | 0.044 | 1.178 | | | |
| 206 | 0.292 | | | | | |
| 207 | 0.963 | 0.002 | 1.047 | | | |
| 208 | 0.398 | | | | | |
| 209 | 0.002 | | | | | |
| 210 | 0.730 | 0.044 | 1.150 | | | |
| 211 | 0.814 | 0.106 | 1.050 | | | |
| 212 | 0.161 | | | | | |
| 212 | 0.658 | 0.029 | 0.994 | | | |
| 213 | 0.079 | | | | | |
| 214 | 0.115 | | | | | |
| 215 | 0.674 | 0.128 | 1.002 | | | |
| 216 | 0.406 | 0.494 | 0.969 | | | |
| 217 | 0.480 | 0.612 | 0.882 | | | |
| 218 | 0.642 | 0.353 | 0.960 | | | |
| 219 | 0.475 | >1 | | | | |
| 220 | 0.457 | 0.454 | 0.890 | | | |
| 221 | 0.324 | | | | | |
| 222 | 0.284 | | | | | |

TABLE 3-continued

Delta and Mu Opioid Receptor Functional Data

| Cpd No. | GTPγS δ-RelEfficacy @200 nM | GTPγS δ-opioid receptor EC$_{50}$ (μM) | GTPγS δ-opioid receptor Rel Efficacy | GTPγS δ-opioid receptor % Inh @10 μM | GTPγS μ-opioid receptor EC$_{50}$ (μM) | GTPγS μ-opioid receptor % Inh @10 μM |
|---|---|---|---|---|---|---|
| 223 | 0.802 | 0.152 | 0.986 | | | |
| 224 | 0.460 | 0.214 | 1.104 | | | |
| 225 | 0.260 | 0.483 | 0.718 | | | |
| 226 | 0.320 | | | | | |
| 227 | 0.480 | 0.246 | 1.093 | | | |
| 228 | 1.039 | 0.006 | 1.082 | | | |
| 229 | 0.715 | 0.061 | 0.890 | | | |
| 230 | 0.847 | | | | | |
| 231 | 1.159 | 0.005 | 1.113 | | | |
| 232 | 0.679 | 0.143 | 1.021 | | | |
| 233 | 0.549 | | | | | |
| 234 | 0.847 | 0.034 | 0.987 | | | 7.287 |
| 235 | 0.962 | 0.00733 | 0.953 | | | |
| 236 | 1.026 | 0.0170 | 1.042 | | | 6.203 |
| 237 | | | | | | 3.524 |
| 238 | | 0.008 | 0.966 | | | |
| 239 | 0.348 | | | | | |
| 240 | 0.376 | | | | | |
| 241 | 0.381 | | | | | |
| 242 | 0.413 | | | | | |
| 243 | 0.433 | | | | | |
| 244 | 0.354 | | | | | |
| 245 | | 0.0127 | 1.095 | | | 4.259 |
| 246 | | 0.078 | 1.043 | | | |
| 248 | 0.754 | 0.047 | 1.084 | | | |
| 249 | 1.000 | 0.011 | 0.940 | | | |
| 250 | 0.912 | 0.026 | 1.022 | | | |
| 251 | 0.955 | 0.015 | 1.145 | | | |
| 252 | | 0.025 | 1.007 | | | 2.480 |
| 253 | | 0.0168 | 0.997 | | | |
| 254 | | 0.151 | 0.928 | | | |
| 255 | | 0.0464 | 0.997 | | | 17.090 |
| 256 | | 0.034 | 1.004 | | | 6.203 |
| 257 | | 0.095 | 0.830 | | | |
| 258 | | 0.075 | 0.835 | | | |
| 259 | | 0.0749 | 1.030 | | | |
| 260 | | 0.300 | 0.937 | | | |
| 261 | | 0.241 | 0.979 | | | |
| 262 | | 0.037 | 0.957 | | | |
| 263 | | 0.027 | 0.869 | | | |
| 264 | | 0.120 | 1.036 | | | |
| 265 | | 0.053 | 1.024 | | | |
| 266 | | 0.018 | 1.041 | | | |
| 267 | | 0.121 | 0.920 | | | |
| 268 | | 0.081 | 1.023 | | | |
| 269 | | 0.053 | 0.984 | | | |
| 270 | | 0.197 | 0.820 | | | |
| 271 | | 0.185 | 0.745 | | | |
| 272 | | >1 | | | | |
| 273 | | 0.026 | 1.001 | | | |
| 274 | | 0.286 | 0.863 | | | |
| 275 | | 0.922 | 1.024 | | | |
| 276 | | | | | | |
| 277 | | 1.092 | 1.012 | | | |
| 278 | 0.263 | | | | | |
| 279 | | 0.170 | 1.004 | | | |
| 280 | | 0.181 | 0.998 | | | |
| 281 | 0.221 | | | | | |
| 282 | 0.349 | | | | | |
| 284 | 0.600 | 0.055 | 0.609 | | | |
| 285 | 0.730 | 0.027 | 0.782 | | | |
| 286 | 0.1 | | | | | |

TABLE 3-continued

Delta and Mu Opioid Receptor Functional Data

| Cpd No. | GTPγS δ-RelEfficacy @200 nM | GTPγS δ-opioid receptor EC$_{50}$ (μM) | GTPγS δ-opioid receptor Rel Efficacy | GTPγS δ-opioid receptor % Inh @10 μM | GTPγS μ-opioid receptor EC$_{50}$ (μM) | GTPγS μ-opioid receptor % Inh @10 μM |
|---|---|---|---|---|---|---|
| 287 | 0.640 | | | | | |
| 288 | 0.428 | | | | | |
| 289 | 0.402 | | | | | |
| 290 | 0.398 | | | | | |
| 291 | 0.303 | | | | | |
| 292 | | 0.363 | 0.958 | | | |
| 293 | | 0.317 | 0.975 | | | |
| 294 | | >10 | | | | |
| 296 | | 0.429 | 0.938 | | | |
| 297 | | 0.424 | 0.820 | | | |
| 298 | | 0.087 | 1.012 | | | |
| 299 | | 0.129 | 0.840 | | | |
| 300 | | 1.052 | 0.968 | | | |
| 301 | | 0.087 | 1.085 | | | |
| 302 | 0.393 | | | | | |
| 303 | 0.622 | 0.114 | 1.047 | | | |
| 304 | 0.228 | | | | | |
| 305 | 0.780 | 0.090 | 1.081 | | | |
| 306 | 0.910 | 0.031 | 1.127 | | | |
| 307 | 0.880 | 0.011 | 1.191 | | | |
| 308 | 0.140 | | | | | |
| 309 | | 0.035 | 1.162 | | | |
| 310 | | 0.031 | 1.042 | | | |
| 311 | | 0.0987 | 0.936 | | | |
| 312 | | 0.00435 | 1.007 | | | |
| 313 | | 0.131 | 1.033 | | | |
| 314 | | 0.206 | 0.840 | | | |
| 315 | | 0.042 | 1.019 | | | |
| 316 | | 0.00338 | 0.977 | | | |
| 317 | | >1 | | | | |
| 318 | | | 0.539 | | | |
| 319 | | 0.112 | 0.871 | | | |
| 320 | | 0.191 | 0.918 | | | |
| 321 | | 0.005 | 1.022 | | | |
| 322 | | 0.196 | 0.960 | | | |
| 323 | | 0.060 | 0.988 | | | |
| 324 | 0.519 | 0.428 | 1.045 | | | |
| 325 | 0.866 | 0.011 | 1.042 | | | |
| 326 | 0.744 | 0.032 | 1.104 | | | |
| 327 | 0.471 | 0.0527 | 1.037 | | | 4.259 |
| 328 | 0.377 | | | | | |
| 329 | 0.475 | 0.138 | 1.006 | | | |
| 330 | 0.547 | 0.051 | 0.894 | | | |
| 331 | 0.764 | 0.108 | 0.928 | | | |
| 332 | 0.393 | | | | | |
| 333 | 0.664 | 0.118 | 1.116 | | | |
| 334 | 0.423 | | | | | |
| 335 | 0.050 | | | | | |
| 336 | 0.830 | 0.0502 | 1.009 | | | 17.090 |
| 338 | 0.723 | 0.197 | 0.956 | | | |
| 339 | 0.641 | | | | | |
| 341 | | 0.041 | 0.788 | | | 0.000 |
| 342 | | 0.0439 | 1.020 | | | |
| 343 | 0.985 | 0.001 | 1.105 | | 1.977 | 7.287 |
| 344 | 0.808 | 0.047 | 1.089 | | | |
| 345 | 0.989 | 0.001 | 1.089 | | 1.934 | 0.000 |
| 346 | | 0.0470 | 1.031 | | | |
| 347 | | 0.069 | 0.898 | | | −0.404 |
| 348 | | 0.101 | 0.689 | | | |
| 349 | | 0.082 | 0.929 | | | 0.000 |
| 350 | | 0.083 | 1.079 | | | |
| 351 | | 0.0249 | 1.036 | | | |
| 351 | | 0.034 | 1.056 | | | |
| 352 | | 0.079 | 0.967 | | | |
| 353 | | 0.270 | 0.651 | | | |

TABLE 3-continued

Delta and Mu Opioid Receptor Functional Data

| Cpd No. | GTPγS δ-RelEfficacy @200 nM | GTPγS δ-opioid receptor EC$_{50}$ (μM) | GTPγS δ-opioid receptor Rel Efficacy | GTPγS δ-opioid receptor % Inh @10 μM | GTPγS μ-opioid receptor EC$_{50}$ (μM) | GTPγS μ-opioid receptor % Inh @10 μM |
|---|---|---|---|---|---|---|
| 354 | | 0.026 | 1.050 | | | |
| 355 | | 0.022 | 1.002 | | 0.243 | 0.000 |
| 356 | | 0.031 | 1.030 | | | |
| 357 | | 0.005 | 0.929 | | 1.831 | 11.460 |
| 358 | | 0.0242 | 0.978 | | | |
| 359 | | 0.034 | 0.709 | | | |
| 360 | | 0.013 | 1.015 | | | |
| 361 | | 0.070 | 0.962 | | | |

*When compounds were tested more than once, the values have been reported as averages of their individual experiments.

In Vivo Assays

Example 6

CFA-Induced Paw Radiant Heat Hypersensitivity

Each rat was placed in a test chamber on a warm glass surface and allowed to acclimate for approximately 10 min. A radiant thermal stimulus (beam of light) was then focused through the glass onto the plantar surface of each hind paw in turn. The thermal stimulus was automatically shut off by a photoelectric relay when the paw was moved or when the cut-off time was reached (20 sec for radiant heat at ~5 amps). An initial (baseline) response latency to the thermal stimulus was recorded for each animal prior to the injection of complete Freund's adjuvant (CFA). Twenty-four hours following intraplantar CFA injection, the response latency of the animal to the thermal stimulus was then re-evaluated and compared to the animal's baseline response time. Only rats that exhibited at least a 25% reduction in response latency (i.e., were hyperalgesic) were included in further analysis. Immediately following the post-CFA latency assessment, test compound or vehicle (usually Solutol, hydroxypropyl methylcellulose HPMC, hydroxypropyl beta-cyclodextrin HPRCD, or PEG-400) was administered i.p. or p.o. to rats. Post-compound treatment withdrawal latencies were assessed at fixed time intervals, typically 30, 60, 100, 120, 180, and 300 min. The percent reversal (% R) of hypersenstivitiy was calculated according to the following formula:

% reversal=[(treatment response−post CFA response)]/[(baseline response−post CFA response)]×100.

Results are expressed as an average of % reversal values for individual animals, +/−SEM (Standard Error of the Mean).

ED$_{50}$ values and associated statistics were calculated with PharmTools Pro software (The McCary Group Inc., Schnecksville. PA).

TABLE 4

Time-course studies: The term "Algos" denotes a study run at a contract lab under the same conditions as internal studies)

| Cpd | dose (mg/kg) | vehicle | route of admin. | no. of animals | last time point (min) | maximum % reversal @ time (min) | +/− SEM |
|---|---|---|---|---|---|---|---|
| 8 | 30 | 0.5% HPMC | p.o. | 6 | 100 | 49.0 | 16.4 |
| 8 | 100 | 0.5% HPMC | p.o. | 6 | 100 | 64.8 | 10.0 |
| 8 | 100 | 0.5% HPMC | p.o. | 7 | 180 | 12.5 @ 30' | 54.6 |
| | | | | | | 46.5 @ 60' | 34.0 |
| 8 | 100 | 0.5% HPMC | p.o. | 9 | 180 | 27.7 @ 30' | 17.6 |
| 8 Algos | 100 | 0.5% HPMC | p.o. | 10 | 180 | 75.1 @ 180' | 17.2 |
| 23 | 100 | 0.5% HPMC | p.o. | 8 | 240 | 75.8 @ 120' | 17.6 |
| 23 | 100 | 0.5% HPMC | p.o. | 8 | 120 | 23.1 @ 120' | 19.1 |
| 23 | 100 | 0.5% HPMC | p.o. | 10 | 180 | 76.8 @ 120' | 21.3 |
| 54 | 100 | 0.5% HPMC | p.o. | 8 | 120 | 17.8 @ 60' | 14.1 |
| 54 | 100 | 0.5% HPMC | p.o. | 8 | 180 | 32.7 @ 180' | 8.9 |
| 69 | 100 | 0.5% HPMC | p.o. | 8 | 60 | 10.1 @ 60' | 6.7 |
| 69 | 100 | 0.5% HPMC | p.o. | 8 | 180 | 55.7 @ 60' | 16.7 |
| 69 Algos | 100 | 0.5% HPMC | p.o. | 8 | 180 | 65.4 @ 180' | 15.8 |
| 107 | 100 | 0.5% HPMC | p.o. | 9 | 240 | 52.8 @ 120' | 17.3 |
| 235 | 30 | 0.5% HPMC | p.o. | 9 | 240 | 43.7 @ 60' | 20.1 |
| 238 | 30 | 0.5% HPMC | p.o. | 9 | 240 | 39.5 @ 60' | 18.4 |
| 253 | 30 | 0.5% HPMC | p.o. | 9 | 240 | 75.9 @ 60' | 11.9 |
| 327 | 30 | 0.5% HPMC | p.o. | 9 | 240 | 101.8 @ 60' | 28.2 |
| 336 | 30 | 0.5% HPMC | p.o. | 9 | 120 | 23.4 @ 30' | 12.6 |

TABLE 4-continued

Time-course studies: The term "Algos" denotes a study run at a contract lab under the same conditions as internal studies)

| Cpd | dose (mg/kg) | vehicle | route of admin. | no. of animals | last time point (min) | maximum % reversal @ time (min) | +/− SEM |
|---|---|---|---|---|---|---|---|
| 346 | 30 | 0.5% HPMC | p.o. | 8 | 120 | 37.0 @ 30' | 27.1 |
| 351 | 30 | 0.5% HPMC | p.o. | 8 | 120 | 9.8 @ 30' | 10.3 |
| 354 | 30 | 0.5% HPMC | p.o. | 9 | 120 | 24.7 @ 60' | 5.4 |

TABLE 5

Dose-response studies:

| Cpd | doses (mg/kg) | vehicle | route of admin. | no. of animals | time point (min) | $ED_{50}$ (mg/kg) | SEM |
|---|---|---|---|---|---|---|---|
| 23 | 10, 30, 100, 300 | 0.5% HPMC | p.o. | 8 | 120 | 35.35 | 18.2 |
| 107 | 10, 30, 100, 300 | 0.5% HPMC | p.o. | 8 | 120 | 32.0 | 8.0 |
| 327 | 3, 10, 30 | 20% HPβCD | p.o. | 8 | 60 | 14.3 | 3.1 |

Example 7

Mouse Graded Abdominal Irritant Test (GrAIT)

Test compound or vehicle was administered s.c. to mice. Following the pretreatment time, an i.p. injection of 0.6% of acetic acid in 0.5 mL was administered. Five min after acetic acid administration, mice were placed into clear chambers and were continuously observed for 5 min. Behavioral responses including twisting and elongation of the body that extended through the hindlimbs were counted and averaged for the group of animals over the observation period.

TABLE 6

| Cpd | dose (mg/kg) | vehicle | route of admin. | no. of animals | Pre-treatment (min) | # abdominal stretches (vehicle) | # abdominal stretches (compound) |
|---|---|---|---|---|---|---|---|
| 8 | 30 | 10% Solutol | s.c. | 10 | 30 | 20.8 | 18.9 |
| 20 | 30 | 10% Solutol | s.c. | 10 | 30 | 14.1 | 19.8 |
| 22 | 30 | 10% Solutol | s.c. | 10 | 30 | 19.8 | 16.0 |
| 22 | 30 | 10% Solutol | s.c. | 10 | 30 | 13.0 | 18.6 |
| 22 | 100 | 10% Solutol | s.c. | 10 | 30 | 19.8 | 17.4 |
| 22 | 300 | 10% Solutol | s.c. | 10 | 30 | 19.8 | 20.3 |
| 23 | 30 | 10% Solutol | s.c. | 10 | 30 | 13.6 | 16.7 |
| 24 | 30 | 10% Solutol | s.c. | 10 | 30 | 15.5 | 16.9 |
| 25 | 30 | 10% Solutol | s.c. | 10 | 30 | 15.5 | 12.3 |
| 26 | 30 | 10% Solutol | s.c. | 10 | 30 | 13.6 | 16.7 |

We claim:

1. A method for treating mild to severe pain in a subject in need thereof, comprising administering to the subject a therapeutically effective amount of a compound of Formula 1

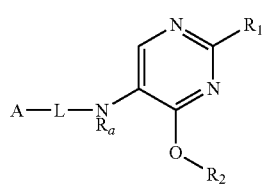

Formula I wherein $R_1$ is selected from the group consisting of i) phenyl optionally substituted with one to two substituents independently selected from the group consisting of $C_{1-4}$alkyl, $C_{2-4}$alkenyl, $C_{2-4}$alkynyl, $C_{1-4}$alkoxy, $C_{1-4}$alkylthio, hydroxy, chloro, and fluoro; in addition, phenyl is optionally substituted with a single amino, $C_{1-4}$alkylamino, di($C_{1-4}$alkyl)amino, di($C_{1-4}$alkyl)aminocarbonyl, $C_{1-4}$alkylaminocarbonyl, hydroxy($C_{1-4}$)alkyl, aminocarbonyl, $C_{1-4}$alkylcarbonylamino, $C_{1-4}$alkoxycarbonylamino, ureido, $C_{1-4}$alkylureido, di($C_{1-4}$alkyl)ureido, cyano, trifluoromethoxy, $C_{1-4}$alkylsulfonyl, nitro, trifluoromethyl, bromo, piperazin-1-yl optionally substituted with 4-$C_{1-4}$alkyl, morpholin-4-yl, phenyl, formamido, or pyridinyl substituent;

and wherein the phenyl and pyridinyl substituents of the $R_1$-phenyl are each optionally substituted with one substituent selected from the group consisting of $C_{1-4}$alkyl, $C_{1-4}$alkoxy, $C_{1-4}$alkylthio, fluoro, chloro, cyano, amino, and hydroxy;

ii) pyrimidinyl optionally substituted with one to two substituents independently selected from the group consisting of $C_{1-4}$alkyl, $C_{1-4}$alkoxy, $C_{1-4}$alkylthio, and hydroxy; in addition, pyrimidinyl is optionally substituted with a single amino, $C_{1-4}$alkylamino, di($C_{1-4}$alkyl) amino, di($C_{1-4}$alkyl)aminocarbonyl, $C_{1-4}$alkylaminocarbonyl, hydroxy($C_{1-4}$)alkyl, aminocarbonyl, $C_{1-4}$alkylcarbonylamino, $C_{1-4}$alkoxycarbonylamino, ureido, $C_{1-4}$alkylureido, di($C_{1-4}$alkyl)ureido, cyano, trifluoromethoxy, $C_{1-4}$alkylsulfonyl, nitro, trifluoromethyl, bromo, piperazin-1-yl optionally substituted with 4-$C_{1-4}$alkyl, morpholin-4-yl, formamido, pyrrol-1-yl, phenyl, pyridinyl or piperidin-1-yl substituent;

and wherein the phenyl and pyridinyl substituents of the $R_1$-pyrimidinyl are each optionally substituted with one substituent selected from the group consisting of $C_{1-4}$alkyl, $C_{1-4}$alkoxy, $C_{1-4}$alkylthio, fluoro, chloro, cyano, amino, and hydroxy;

iii) pyridinyl optionally substituted with one to two substituents independently selected form the group consisting of $C_{1-4}$alkyl, $C_{1-4}$alkoxy, $C_{1-4}$alkylthio, hydroxy, fluoro, chloro, and cyano; in addition, pyridinyl is optionally substituted with a single hydroxymethyl, amino, $C_{1-4}$alkylamino, di($C_{1-4}$alkyl)amino, $C_{1-4}$alkylsulfonyl, aminocarbonyl, $C_{1-4}$alkylaminocarbonyl, di($C_{1-4}$alkyl)aminocarbonyl, $C_{1-4}$alkylcarbonylamino, $C_{1-4}$alkoxyaminocarbonyl, ureido, $C_{1-4}$alkylureido, di($C_{1-4}$alkyl)ureido, piperazin-1-yl, morpholin-4-yl, phenyl, or pyridinyl;

and, wherein the phenyl and pyridinyl substituents of the $R_1$-pyridinyl are optionally independently substituted with one to two substituents selected from the group consisting of $C_{1-4}$alkyl, $C_{1-4}$alkoxy, $C_{1-4}$alkylthio, fluoro, chloro, cyano, amino, and hydroxy;

and iv) a G-substituent selected from the group consisting of naphthyl, pyrazolyl, thienyl, benzothiazolyl, benzimidazolyl, quinolinyl, indolyl, thiazolyl, furanyl, dihydrobenzofuranyl, pyrazinyl, isoquinolinyl, quinoxalinyl, quinazolinyl, isoxazolyl, oxazolyl, pyrrolopyridinyl, benzo[1,3]dioxol-5-yl, benzo[1,2,5]oxadiazolyl, dibenzothiophenyl, 4H-[1,2,4]oxadiazol-5-on-yl, benzothiophenyl, indazolyl, and 2,3-dihydrobenzo[1,4]dioxinyl;

wherein G is optionally independently substituted with one to two substituents selected from the group consisting of $C_{1-4}$alkyl, $C_{1-4}$alkoxy, fluoro, chloro, bromo, cyano, $C_{1-4}$alkylcarbonyl, amino, $C_{1-4}$alkylamino, and di($C_{1-4}$alkyl)amino;

$R_2$ is (i) phenyl optionally substituted with one to three substituents independently selected from the group consisting of $C_{1-4}$alkyl, $C_{1-4}$alkoxy, $C_{1-4}$alkylthio, fluoro, chloro, and hydroxy; in addition, phenyl of $R_2$ is optionally substituted with a single amino, $C_{1-4}$alkylamino, di($C_{1-4}$alkyl)amino, fluoromethyl, difluoromethyl, trifluoromethyl, fluoromethoxy, difluoromethoxy, trifluoromethoxy, formamidino, aminocarbonyl, $C_{1-4}$alkylaminocarbonyl, di($C_{1-4}$)alkylaminocarbonyl, $C_{1-4}$alkylcarbonylamino, 2,2,2-trifluoroethoxy, cyano, $C_{3-7}$cycloalkylcarbonylamino, hydroxy($C_{1-4}$)alkyl, $C_{1-4}$alkoxy($C_{1-4}$)alkyl, $C_{1-4}$alkoxy-($C_{1-4}$)alkoxy, $C_{1-4}$alkylcarbonyloxy, $C_{1-4}$alkylsulfonylamino, $C_{1-4}$alkylsulfonyl, pyridinyl($C_{1-4}$)alkyl, benzyloxycarbonylamino, 4-methyl-piperazin-1-ylcarbonyl, pyrrolidin-1-ylcarbonyl, carboxy, piperidin-1-ylcarbonyl, morpholin-4-ylcarbonyl, $C_{3-7}$cycloalkyl, $C_{3-7}$cycloalkyl-($C_{1-3}$)alkyl, or $C_{3-7}$cycloalkyl-($C_{1-3}$)alkoxy substituent;

(ii) 1,2-dihydrobenzofuranyl; provided that 1,2-dihydrobenzofuranyl is bound to O of Formula (I) at the benzo portion of the ring; and wherein the benzo portion of 1,2-dihydrobenzofuranyl is optionally independently substituted with one to two substituents selected from the group consisting of $C_{1-4}$alkyl, fluoro, chloro, bromo, cyano, $C_{1-4}$alkylcarbonyl, amino, $C_{1-4}$alkylamino, and di($C_{1-4}$alkylamino;

or (iii) heteroaryl selected from the group consisting of benzothiazolyl, benzooxazolyl, pyridinyl, pyrimidinyl, indazolyl, quinolinyl, quinazolinyl, benzimidazolyl, pyrazinyl, triazinyl, benzothiophenyl, benzofuranyl, and isoquinolinyl;

wherein heteroaryl of $R_2$ is optionally independently substituted with one to two substituents selected from the group consisting of $C_{1-4}$alkyl, fluoro, chloro, bromo, cyano, $C_{1-4}$alkylcarbonyl, amino, $C_{1-4}$alkylamino, and di($C_{1-4}$alkylamino;

A-L- is selected from the group consisting of $a_1$-$L_1$-; $a_2$-$L_2$-; $a_3$-$L_3$-; $a_4$-$L_4$-; and $a_5$-$L_5$-; wherein $L_1$ is absent or $C_{1-4}$alkyl;

$a_1$ is bound through a carbon atom to $L_1$ and is selected from the group consisting of i) pyrrolidinyl optionally substituted at carbon with $C_{1-4}$alkyl, amino, $C_{1-4}$alkylamino, di($C_{1-4}$alkyl)amino, aminomethyl, hydroxy, cyano, $C_{1-4}$alkoxy, $C_{1-4}$alkoxycarbonyl, or one to two fluoro substituents; and wherein pyrrolidinyl is optionally substituted at nitrogen with $C_{1-4}$alkyl, phenyl($C_{1-4}$)alkyl, $C_{1-4}$alkylcarbonyl, $C_{1-4}$alkoxycarbonyl, or phenyl($C_{1-4}$)alkoxycarbonyl;

ii) piperidinyl optionally substituted with $C_{1-4}$alkyl, phenyl, amino, $C_{1-4}$alkylamino, di($C_{1-4}$alkyl)amino, aminomethyl, hydroxy, cyano, $C_{1-4}$alkoxy, $C_{1-4}$alkoxycarbonyl, phenyl($C_{1-4}$)alkyl, $C_{1-4}$alkylcarbonyl, or phenyl($C_{1-4}$)alkoxycarbonyl;

and iii) azetidinyl optionally substituted with 3-amino, 3-hydroxy, 3-$C_{1-4}$alkoxy, $C_{1-4}$alkyl, or aminomethyl;

provided that when $L_1$ is absent, $a_1$ is attached to N($R_a$) via a carbon atom other than that which is alpha to a nitrogen atom of $a_1$;

and provided that when $a_1$ is substituted with a substituent containing an oxygen or nitrogen radical as a point of attachment to $a_1$, the substitution is at a carbon atom other than that alpha to a nitrogen atom of $a_1$;

$L_2$ is $C_{1-4}$alkyl;

$a_2$ is bound through a carbon atom to $L_2$ and is selected from the group consisting of i) piperazinyl optionally substituted at carbon with $C_{1-4}$alkyl, aminomethyl, cyano, or $C_{1-4}$alkoxycarbonyl; and wherein piperazinyl is optionally substituted at nitrogen with $C_{1-4}$alkyl, phenyl($C_{1-4}$)alkyl, $C_{1-4}$alkylcarbonyl, $C_{1-4}$alkoxycarbonyl, or phenyl($C_{1-4}$)alkoxycarbonyl;

and iii) morpholinyl optionally independently substituted with phenyl($C_{1-4}$)alkyl or one to two $C_{1-4}$alkyl substituents;

$L_3$ is methylene;

$a_3$ is imidazolyl optionally independently substituted with one to two $C_{1-4}$alkyl substituents;

$L_4$ is ($C_{2-6}$)alkyl; and when $L_4$ is $C_{3-6}$alkyl, $L_4$ is optionally substituted with chloro, hydroxy or $C_{1-4}$alkoxy; provided that the chloro, hydroxy, and $C_{1-4}$alkoxy substituents are not alpha to a nitrogen-bearing carbon atom;

$a_4$ is selected from the group consisting of amino and $C_{1-4}$alkylamino;

provided that $a_4$ is attached at a carbon atom other than that alpha to N($R_a$);

$L_5$ is absent or $C_{1-4}$alkyl;

$a_5$ is $C_{3-7}$cycloalkyl substituted with $R_B$; wherein $R_B$ is selected from the group consisting of amino, $C_{1-4}$alkylamino, di($C_{1-4}$alkyl)amino, aminomethyl, $C_{1-4}$alkylamino-methyl, and di($C_{1-4}$alkyl)amino-methyl;

provided that when $R_B$ contains a nitrogen radical as the point of attachment to $C_{3-7}$cycloalkyl, the attachment is at a carbon atom other than that alpha to N($R_a$);

or,

A-L- is taken with $R_a$ and the nitrogen atom to which they are both attached to form a nitrogen-bound heterocyclyl selected from the group consisting of i) pyrrolidinyl wherein pyrrolidinyl is optionally substituted with $C_{1-4}$alkyl, amino, $C_{1-4}$alkylamino, di($C_{1-4}$alkyl)amino, aminomethyl, cyano, $C_{1-4}$alkoxy, $C_{1-4}$alkoxycarbonyl, or phenyl;

ii) piperazinyl optionally substituted with 4-$C_{1-4}$alkyl; and wherein piperazinyl is optionally independently substituted at carbon with one to two $C_{1-4}$alkyl substituents, 2-oxo, 3-oxo, trifluoromethyl, aminomethyl, or hydroxymethyl iii) piperidinyl optionally substituted with one to two $C_{1-4}$alkyl substituents, amino, $C_{1-4}$alkylamino, di($C_{1-4}$alkyl)amino, aminomethyl, hydroxy, cyano, $C_{1-4}$alkoxy, $C_{1-4}$alkoxycarbonyl, phenyl, phenyl($C_{1-4}$alkyl, or one to two fluoro substituents;

and, wherein the phenyl and the phenyl portion of phenyl ($C_{1-4}$)alkyl are optionally substituted with $C_{1-4}$alkyl, $C_{1-4}$alkoxy, $C_{1-4}$alkylthio, fluoro, chloro, cyano, amino, or hydroxy;

iv) azetidinyl optionally substituted with 3-amino or 3-aminomethyl;

v) [1,4]diazepan-1-yl optionally substituted with one to two $C_{1-4}$alkyl substituents;

and vi) 3,6-diazoabicyclo[3.1.1]hept-3-yl optionally substituted with one to two $C_{1-4}$alkyl substituents;

$R_a$ is hydrogen or $C_{1-4}$alkylcarbonyl;

provided that a compound of Formula (I) is other than a compound selected from the group consisting of a compound wherein $R_1$ is 4-fluoro-phenyl, $R_2$ is 4-methoxy-phenyl, A-L- is $a_1$-$L_1$, $a_1$ is (S)-pyrrolidin-2-yl, $L_1$ is methyl, $R_a$ is H, and X is O;

a compound wherein $R_1$ is pyrimidin-5-yl, $R_2$ is 4-methoxy-phenyl, A-L- is $a_2$-$L_2$, $a_2$ is (S)-morpholin-3-yl, $L_2$ is methyl, $R_a$ is H, and X is O; a compound wherein $R_1$ is 5-fluoro-pyridin-3-yl, $R_2$ is 4-(piperidin-1-ylcarbonyl)-phenyl, A-L- is $a_1$-$L_1$, $a_1$ is (S)-pyrrolidin-2-yl, $L_1$ is methyl, $R_a$ is H, and X is O;

a compound wherein $R_1$ is 5-fluoro-pyridin-3-yl, $R_2$ is 4-(4-methyl-piperazin-1-ylcarbonyl)-phenyl, A-L- is $a_1$-$L_1$, $a_1$ is (S)-pyrrolidin-2-yl, $L_1$ is methyl, $R_a$ is H, and X is O;

a compound wherein $R_1$ is 5-cyano-pyridin-3-yl, $R_2$ is 2-methyl-phenyl, A-L- is $a_1$-$L_1$, $a_1$ is (S)-pyrrolidin-2-yl, $L_1$ is methyl, $R_a$ is H, and X is O;

a compound wherein $R_1$ is pyridin-3-yl, $R_2$ is 4-methoxy-phenyl, A-L- is $a_5$-$L_5$, $a_5$ is cyclohexyl, $L_5$ is absent, $R_B$ is 2-amino, $R_a$ is H, and X is O;

and a compound wherein $R_1$ is 5-fluoro-pyridin-3-yl, $R_2$ is 4-diethylaminocarbonyl-phenyl, A-L- is $a_1$-$L_1$, $a_1$ is (S)-pyrrolidin-2-yl, $L_1$ is methyl, $R_a$ is H, and X is O;

and enantiomers, diastereomers, and pharmaceutically acceptable salts thereof.

2. The method of claim 1 wherein the mild to severe pain is due to a disease or condition selected from the group consisting of osteoarthritis, rheumatoid arthritis, fibromyalgia, migraine, headache, toothache, burn, sunburn, snake bite, spider bite, insect sting, neurogenic bladder, benign prostatic hypertrophy, interstitial cystitis, rhinitis, contact dermatitis/hypersensitivity, itch, eczema, pharyngitis, mucositis, enteritis, cellulites, causalgia, sciatic neuritis, mandibular joint neuralgia, peripheral neuritis, polyneuritis, stump pain, phantom limb pain, post operative ileus, cholecystitis, postmastectomy pain syndrome, oral neuropathic pain, Charcot's pain, reflex sympathetic dystrophy, Guillain Barre syndrome, meralgia paresthetica, burning mouth syndrome, cluster headache, migraine headache, peripheral neuropathy, bilateral peripheral neuropathy, diabetic neuropathy, optic neuritis, postfebrile neuritis, migrating neuritis, segmental neuritis, Gombault's neuritis, neuronitis, cervicobrachial neuralgia, cranial neuralgia, geniculate neuralgia, glossopharyngial neuralgia, migrainous neuralgia, idiopathic neuralgia, intercostals neuralgia, mammary neuralgia, Morton's neuralgia, nasociliary neuralgia, occipital neuralgia, red neuralgia, Sluder's neuralgia, splenopalatine neuralgia, supraorbital neuralgia, vidian neuralgia, inflammatory bowel disease, irritable bowel syndrome, sinus headache, tension headache, labor, childbirth, menstrual cramps, and cancer.

3. The method of claim 1 wherein the pain is selected from the group consisting of inflammatory pain, centrally mediated pain, peripherally mediated pain, visceral pain, structural related pain, cancer pain, soft tissue injury related pain, progressive disease related pain, neuropathic pain and acute pain from acute injury, acute pain from trauma, acute pain from surgery, chronic pain from headache, chronic pain from neuropathic conditions, chronic pain from post stroke conditions and chronic pain from migraine.

* * * * *